(12) United States Patent
Nishimiya et al.

(10) Patent No.: US 12,024,547 B2
(45) Date of Patent: *Jul. 2, 2024

(54) KLK5 INHIBITORY PEPTIDE

(71) Applicant: DAIICHI SANKYO COMPANY, LIMITED, Tokyo (JP)

(72) Inventors: Daisuke Nishimiya, Sumida-ku (JP); Hidenori Yano, Ota-ku (JP); Hidenori Takahashi, Ota-ku (JP); Shinji Yamaguchi, Shinagawa-ku (JP); Shiho Ofuchi, Shinagawa-ku (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 107 days.

This patent is subject to a terminal disclaimer.

(21) Appl. No.: 17/707,857

(22) Filed: Mar. 29, 2022

(65) Prior Publication Data

US 2022/0306725 A1   Sep. 29, 2022

Related U.S. Application Data

(63) Continuation of application No. 17/326,280, filed on May 20, 2021, now Pat. No. 11,292,828, which is a continuation of application No. 17/064,543, filed on Oct. 6, 2020, now abandoned, which is a continuation of application No. PCT/JP2019/043384, filed on Nov. 6, 2019.

(30) Foreign Application Priority Data

Nov. 7, 2018 (JP) .................................. 2018-209729

(51) Int. Cl.
*A61K 38/57* (2006.01)
*A61K 38/55* (2006.01)
*C07K 14/81* (2006.01)
*C07K 19/00* (2006.01)
*A61K 38/00* (2006.01)

(52) U.S. Cl.
CPC .............. *C07K 14/81* (2013.01); *A61K 38/55* (2013.01); *A61K 38/57* (2013.01); *C07K 14/811* (2013.01); *C07K 14/8135* (2013.01); *A61K 38/00* (2013.01); *C07K 2319/30* (2013.01)

(58) Field of Classification Search
CPC ...... A61K 38/55; A61K 38/57; C07K 14/811; C07K 14/8135; C07K 2319/00
See application file for complete search history.

(56) References Cited

U.S. PATENT DOCUMENTS

| 9,987,328 B2 | 6/2018 | Zeitler et al. | |
|---|---|---|---|
| 11,292,828 B2 * | 4/2022 | Nishimiya | A61P 29/00 |
| 2011/0183924 A1 | 7/2011 | Mintz et al. | |
| 2018/0142038 A1 | 5/2018 | Brown et al. | |
| 2019/0078160 A1 | 3/2019 | Dressen et al. | |
| 2020/0377573 A1 | 12/2020 | Nishimiya et al. | |
| 2021/0032313 A1 | 2/2021 | Nishimiya et al. | |

FOREIGN PATENT DOCUMENTS

| EP | 3 878 469 A1 | 9/2021 | |
|---|---|---|---|
| JP | 2018-511300 A | 4/2018 | |
| RU | 2 580 038 C2 | 4/2016 | |
| WO | 2014/024914 A1 | 2/2014 | |
| WO | 2017123401 | 7/2017 | |
| WO | WO-2017123401 A1 * | 7/2017 | ............ A61K 31/37 |
| WO | 2018/1117244 A1 | 6/2018 | |
| WO | 2018117244 | 6/2018 | |
| WO | 2019/049933 A1 | 3/2019 | |
| WO | 2020/095922 A1 | 5/2020 | |

OTHER PUBLICATIONS

Office Action dated Aug. 5, 2022, issued in corresponding Canadian Application No. 3,118,707, filed Nov. 6, 2019, 8 pages.
Chen, T. et al., Identification of Trypsin-Inhibitory Site and Structure Determination of Human SPINK2 Serine Proteinase Inhibitor, Proteins 77:209-219, 2009.
International Search Report dated Feb. 4, 2020, issued in corresponding Application No. PCT/JP2019/043384, filed Nov. 6, 2019, 4 pages.
Japanese Office Action dated Jan. 7, 2021, issued in corresponding Application No. JP 2018-209729, filed Nov. 7, 2018, 12 pages.
Kantyka, T., et al., "Inhibition of kallikrein-related peptidases by the serine protease inhibitor of Kazal-type 6," Peptides: Elsevier 32: 1187-1192, 2011.
Kherraf, Z., et al., "SPINK2 deficiency causes infertility by inducing sperm defects in heterozygotes and azoospermia in homozygotes," EMBO Molecular Medicine 9(8): 1132-1149, May 2017.
Nishimiya, D., et al., "A Protein Scaffold, Engineered SPINK2, for Generation of Inhibitors With High Affinity and Specificity Against Target Proteases," Scientific Reports, 9:11436, 11 pages, 2019.
Pending Claims from corresponding Application No. JP 2018-209729, filed Nov. 7, 2018, 12 pages (for Information purposes).
Notice of Allowance dated Mar. 16, 2021, from prior U.S. Appl. No. 17/064,543, filed Oct. 6, 2020, 10 pages.

(Continued)

*Primary Examiner* — Jeffrey E. Russel
(74) *Attorney, Agent, or Firm* — Christensen O'Connor Johnson Kindness PLLC

(57) ABSTRACT

SPINK2 mutant peptide conjugates are provided that inhibit KLK5. The KLK5 inhibitory peptide conjugates are Fc fusion peptides in which, in certain embodiments, the Fc region of the fusion peptides are the Fc region of human IgG1 or a fragment thereof. The KLK5 inhibitory peptide conjugates include an amino acid sequence of one of SEQ ID NOs: 34, 36, 38, 40, 42, 44, 46, 48, 96, 50, 52, 54, 56, 58, or 60. Pharmaceutical compositions that include the KLK5 inhibitory peptide conjugates useful for treating KLK5-related diseases are also provided.

23 Claims, 51 Drawing Sheets

Specification includes a Sequence Listing.

(56) References Cited

OTHER PUBLICATIONS

Written Opinion dated Feb. 4, 2020, issued in corresponding Application No. PCT/JP2019/043384, filed Nov. 6, 2019, 8 pages.
Notice of Allowance dated Feb. 23, 2022, from prior U.S. Appl. No. 17/326,280, filed May 20, 2021, 5 pages.
Kherraf, Z. et al., "SPINK2 deficiency causes infertility by inducing sperm defects in heterozygotes and azoospermia in homozygotes," EMBO Molecular Medicine, May 29, 2017, vol. 9, No. 8, p. 1132-1149.
Office Action dated Jun. 14, 2023, issued in corresponding Japanese Application No. 2022-101377, filed Jun. 23, 2022, 7 pages.
Russian Office Action and Search Report as dated Aug. 11, 2023, issued in corresponding Russian Application No. 2021115961, filed Nov. 6, 2019, 23 pages.
Baylot, V., et al., TCTP Has a Crucial Role in the Different Stages of Prostate Cancer Malignant Progression, Results Probl Cell Differ, 2017, vol. 64 , pp. 255-261.
Badri, H., et al., "Optimization of radiation dosing schedules for proneural glioblastoma," J Math Bio, 2016, vol. 72, N. 5, pp. 1301-1336.
Kuznetsova, E.A., Parenthesis in Text of Legal Document as a Linguo-Cognitive Phenomenon [in Russian], Vestnik Series: Russian Philology, 2015, N3, pp. 37-43.
Singer, M., et al., Genes and Genomes, Moscow, "Mir", 1998, vol. 1, p. 63-64.
Mariuzza, R.A., The structural basis of antigen-antibody recognition, Ann. Rev. Biophys. Biophys. Chem., 1987, vol. 16, pp. 139-159.
Colman, P.M., "Effects of amino acid sequence changes on antibody-antigen interactions," Research in Immunology, 1994, vol. 145, Issue 1, pp. 33-36.
Roitt, I., et al., Immunology, Moscow , "Mir", 2000, p. 110-111.
Rudikoff, S., et al., "Single amino acid substation altering antigen-binding specificity," Immunology, 1982, vol. 78, pp. 1979-1983.
Extended European Search Report dated Jul. 14, 2022, issued in Application No. EP 19882000.3, filed Nov. 6, 2019, 8 pages.
Colombian Office Action dated Dec. 28, 2023 as issued in corresponding Colombian Application No. NC2021/0007354, filed Nov. 6, 2019, 33 pages.
Taiwanese Office Action dated Nov. 16, 2023 as issued in Taiwanese Application No. 11221144070, 16 pages.

\* cited by examiner

| | | |
|---|---|---|
| hKLK5 | 1 | IINGSDCDMHTQPWQAALLRPNQ-LYCGAVLVHPQWVLITAAHCRKKVFRVRLGHYSISP 59 |
| hKLK7 | 1 | IIDGAPCARGSHPWQVALLSGNQ-LHCGGVLVNERWVLTAAHCKMNEYTVHLGSDTLG- 57 |
| hKLK14 | 1 | IIGGHTCTRSSQPWQAALLAGPRRRFLCGGALLSGQWVITAAHCGRPILQVALGKHNLR- 59 |

| | | |
|---|---|---|
| hKLK5 | 60 | VYESGQMFQGVKSIPHPQYSHPGTSNDLMLIKLNRRIRPTKDVRPINVSHCPSAGTKC 119 |
| hKLK7 | 58 | --DRRAQRIKASKSFRHPGYSTQTHVNDLMLVKLNSQARLSSMVKKVRLPSRCEPPGTTC 115 |
| hKLK14 | 60 | RWEATQQVLRVVRQVTHPNYNSRTHDNDIMLLQLQQPARIGRAVRPIEVTQACASPGTSC 119 |

| | | |
|---|---|---|
| hKLK5 | 120 | LVSGWGTTKSPQVHFPKVLQCLNISVLSQKRCEDAYPRQIDDTMFCAGDKAGR-DSCQGD 178 |
| hKLK7 | 116 | TVSGWGTTSPDVTFPSDMCVDVKLISPQDCTKVYKDLLENSMLCAGIPDSKKNACNGD 175 |
| hKLK14 | 120 | RVSGWGTISSPIARYPASLQCVNINISPDEVCQKAYPRTITPGIVCAGVPQGGKDSCQGD 179 |

| | | |
|---|---|---|
| hKLK5 | 179 | SGGPLVCNGSLQGLVSWGDYPCARPNRPGVYINLCKFTKWIQETIQANS 227 |
| hKLK7 | 176 | SGGPLVCRGTLQGLVSWGTFPCGQPNDPGVYTQVCKFTKWINDTMKKHR 224 |
| hKLK14 | 180 | SGGPLVCRGQLQGLVSWGMERCALPGYPGVYTNLCKYVRSWIEETMRDK- 227 |

*FIG. 1*

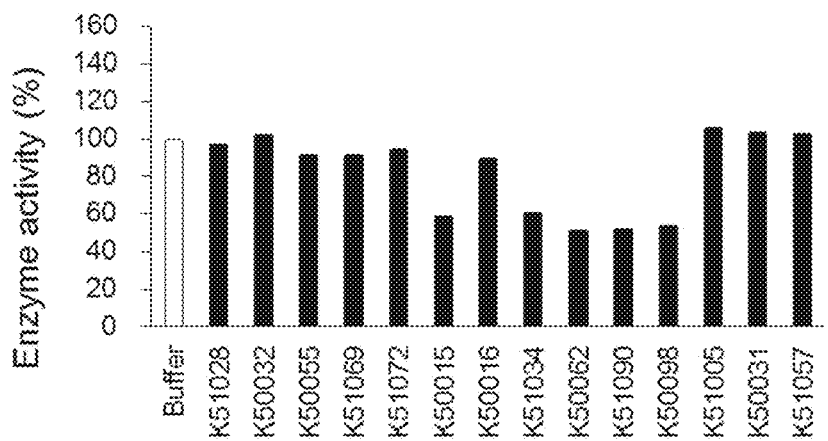
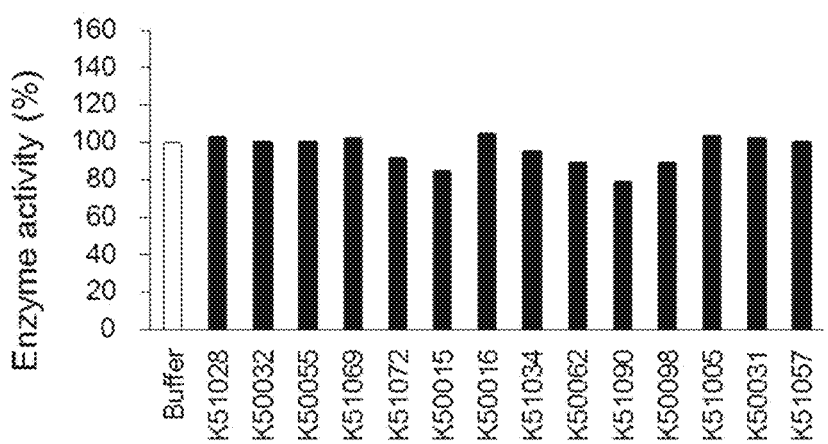
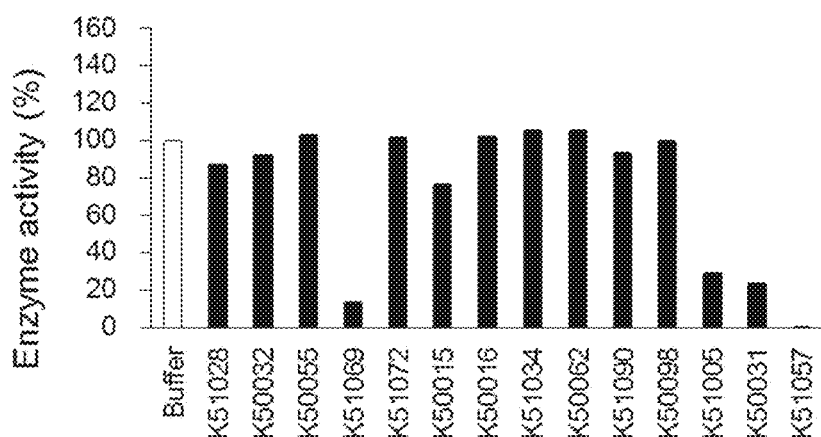
FIG. 3A

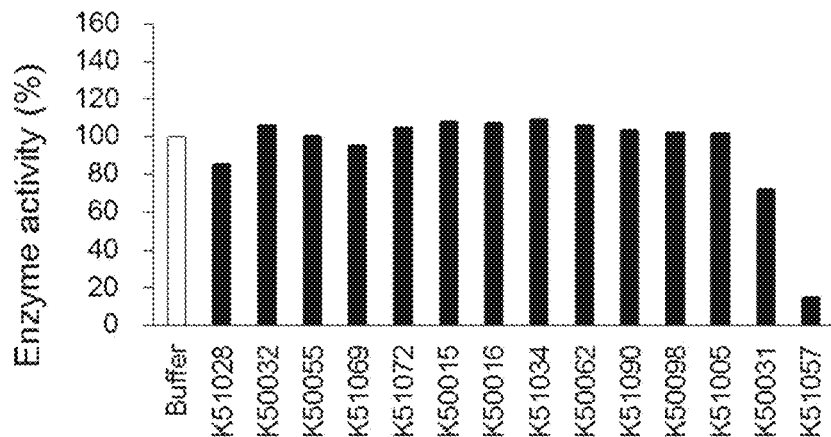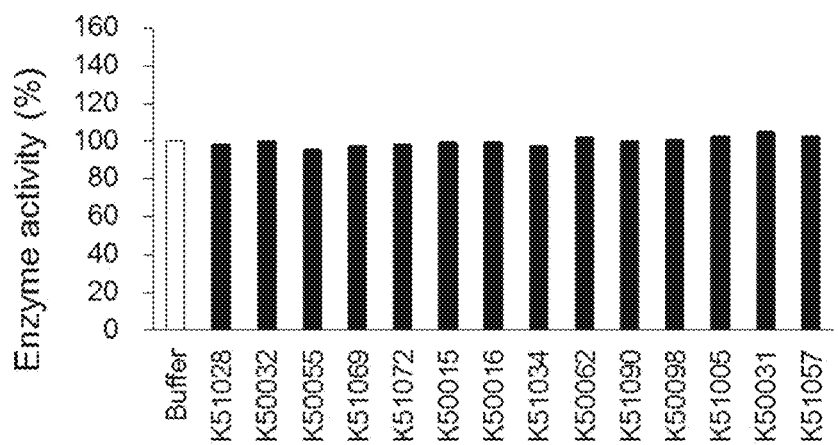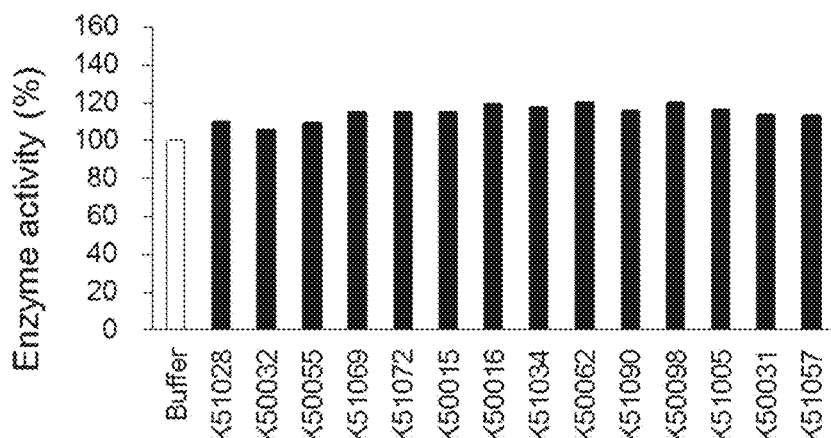
FIG. 3B

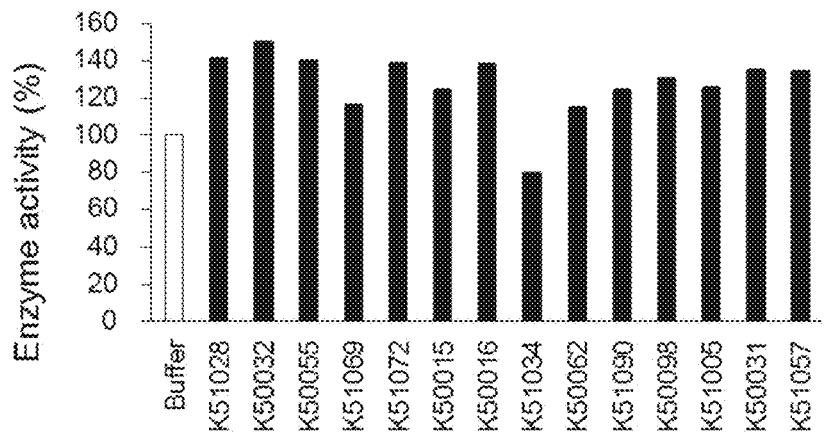
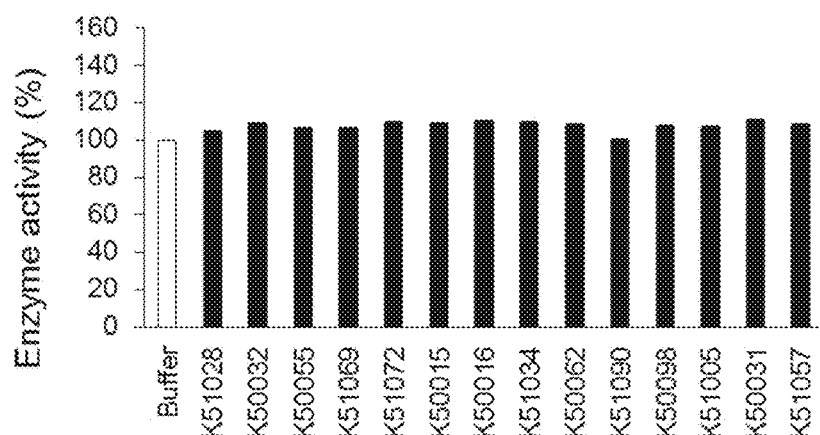
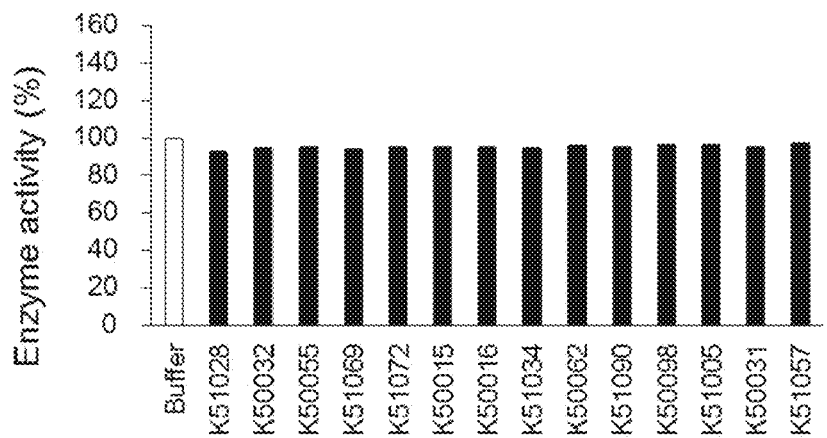
*FIG. 3C*

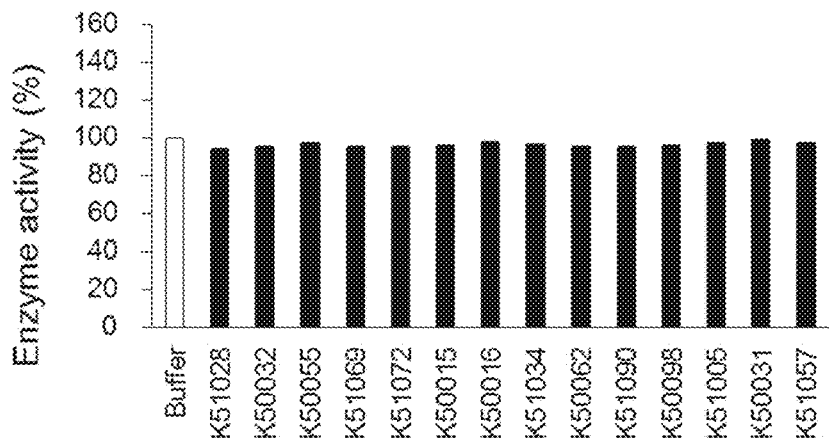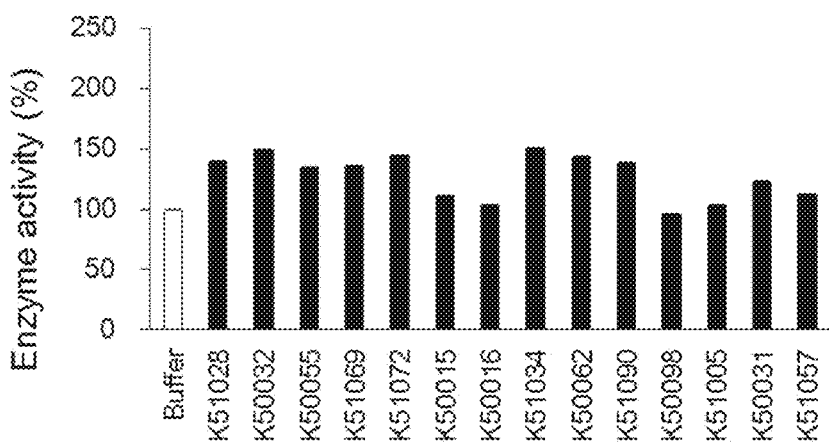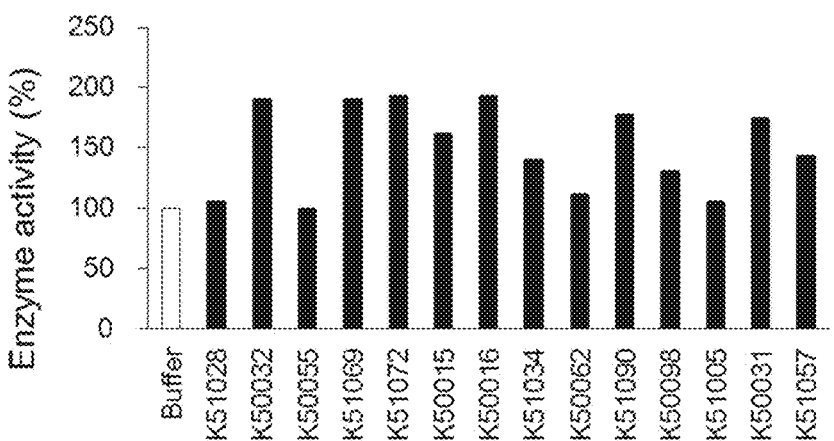
FIG. 3D

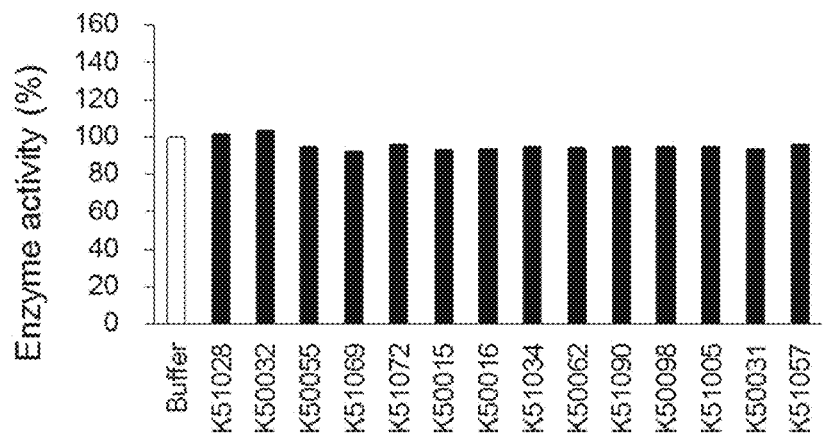
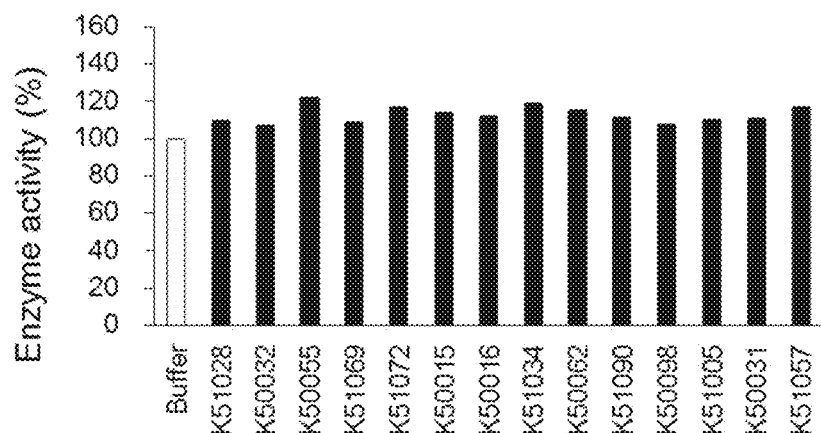
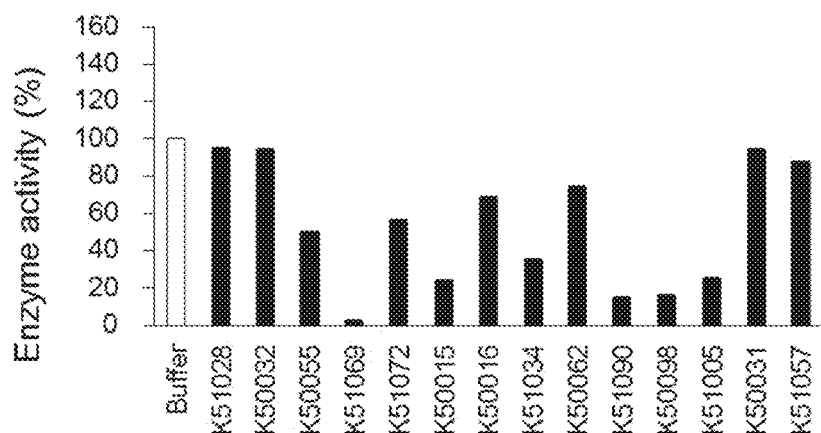
*FIG. 3F*

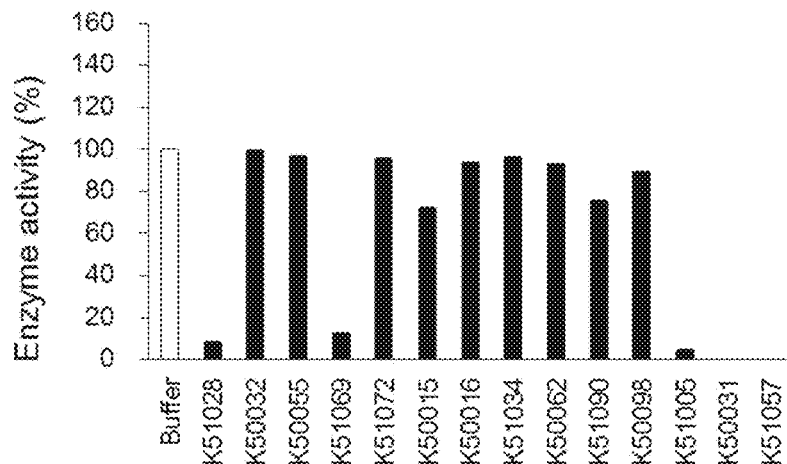
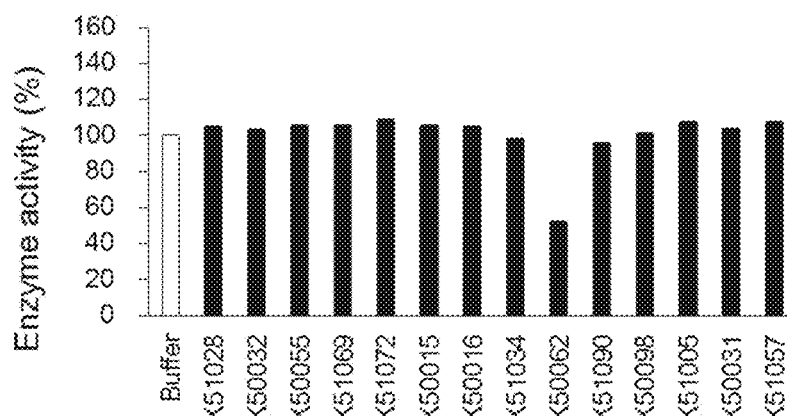
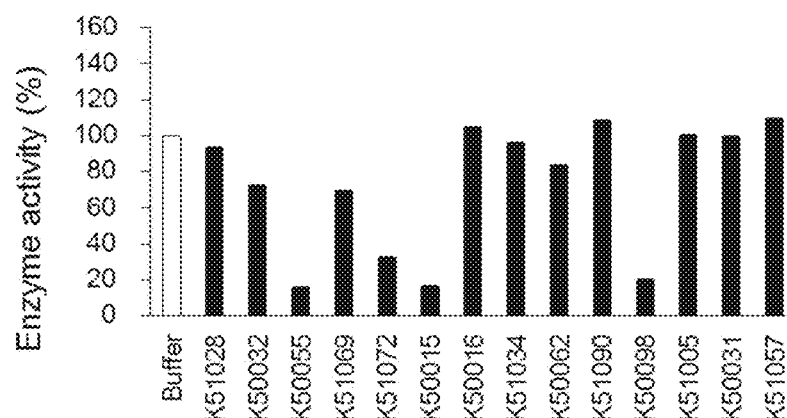
FIG. 3G

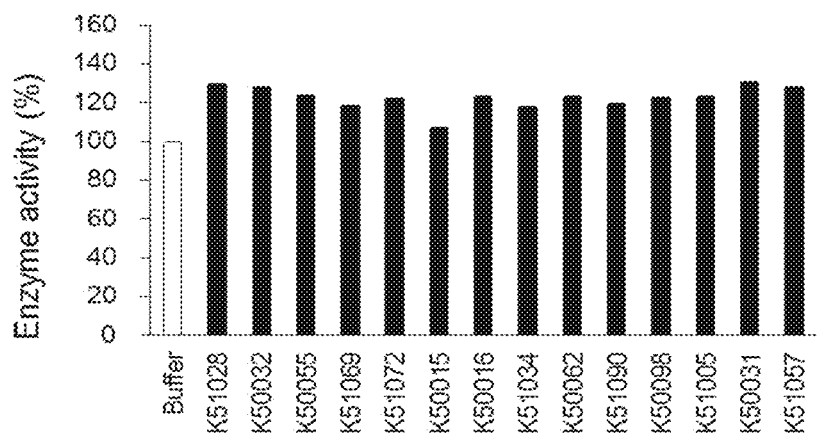
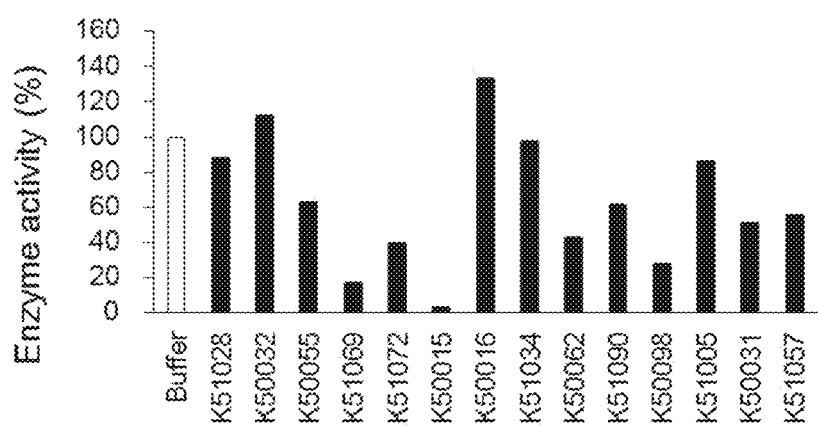
FIG. 3H

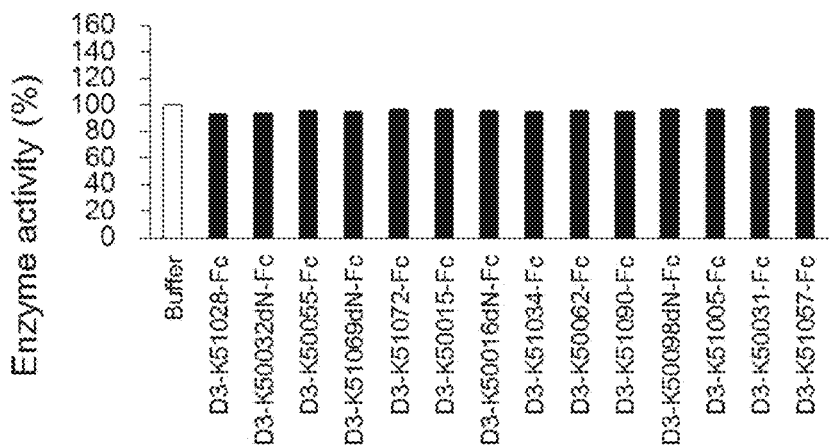
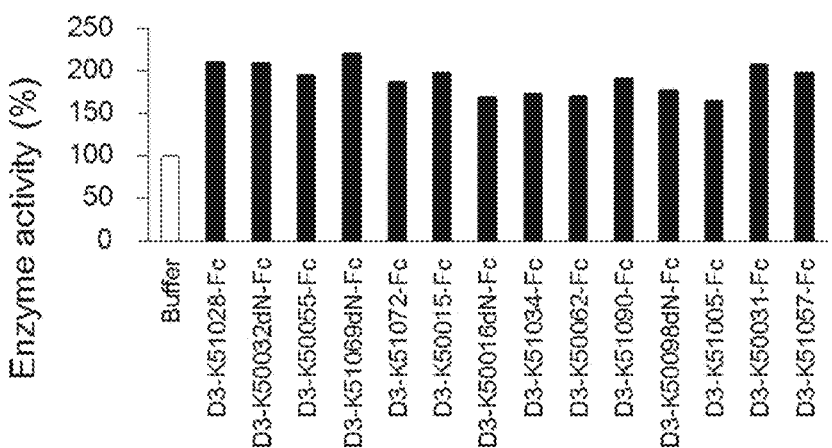
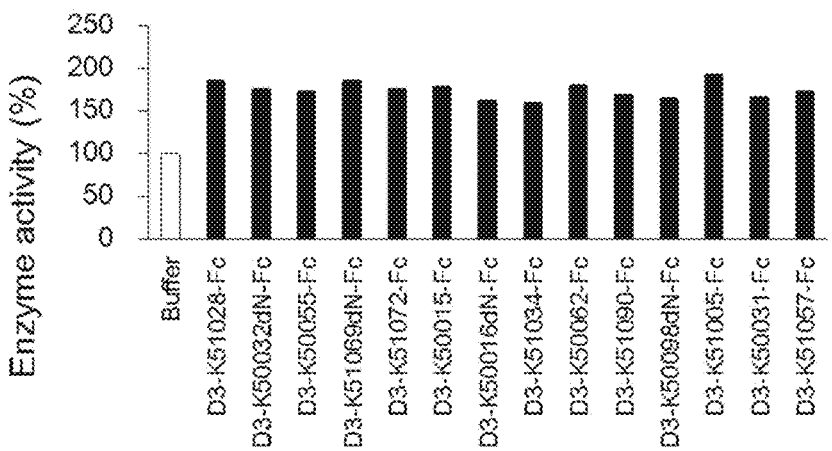
FIG. 6D

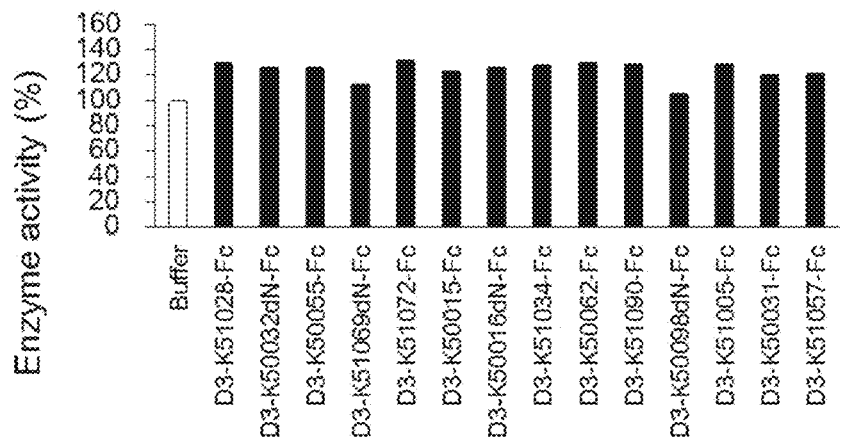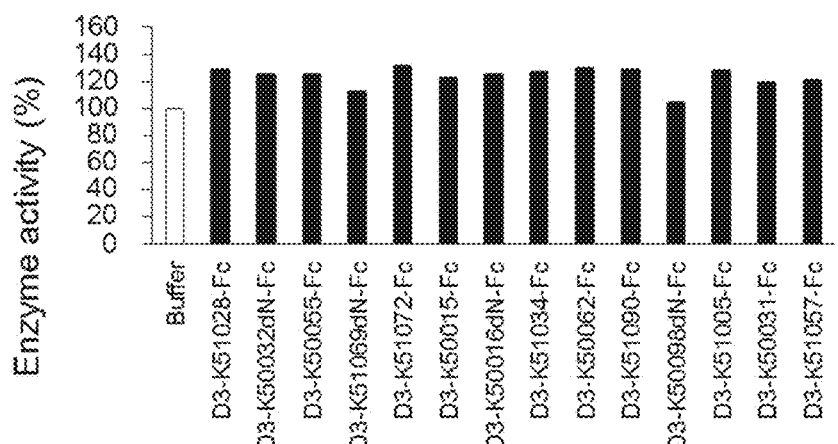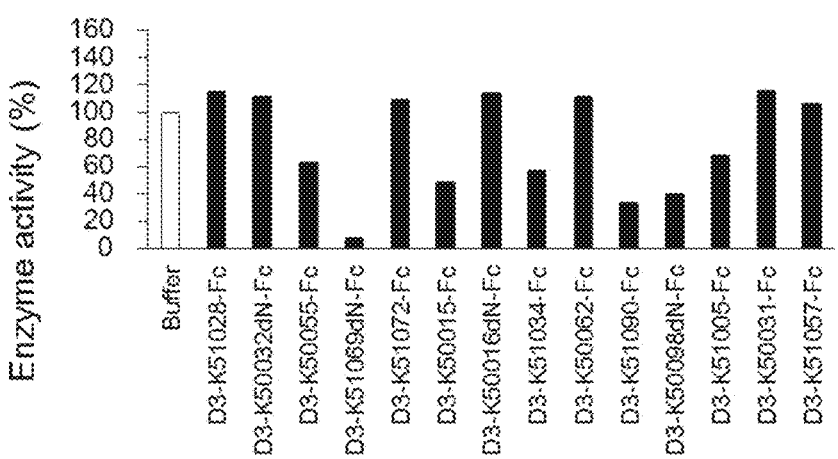
*FIG. 6F*

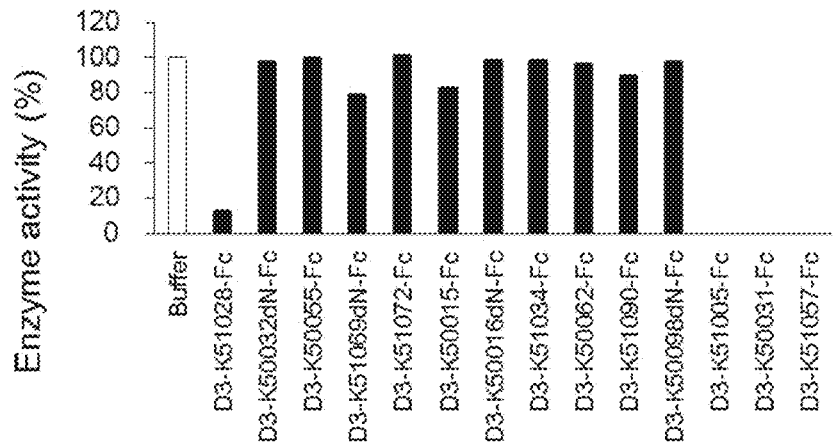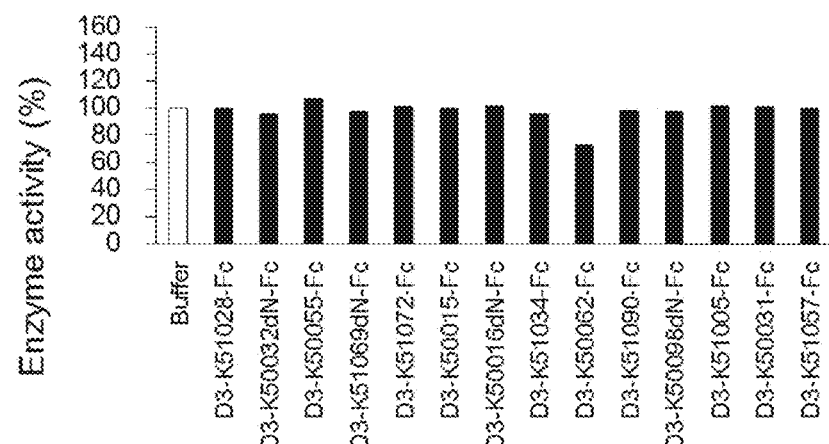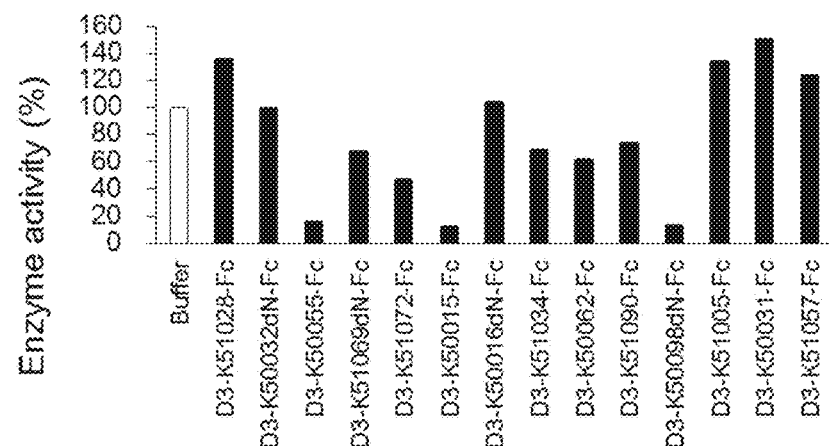
*FIG. 6G*

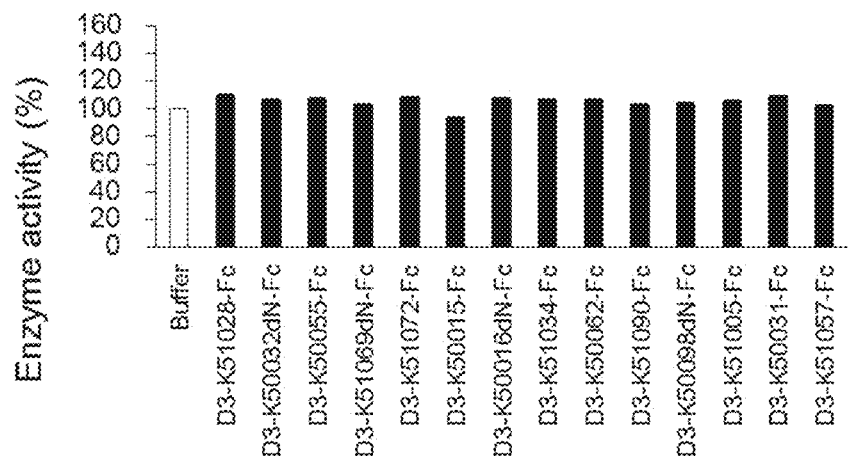
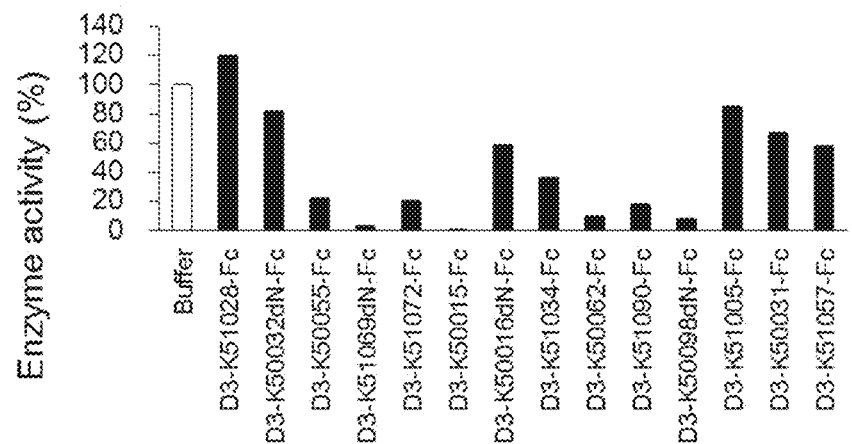
*FIG. 6H*

```
human_SPINK2      1  PQFGLFSKYRTP-NCSQYR----CPRHFNDVCGSDYSTYANECTLCMKIREGGHN  53
hSP5_D8_E490-G551 1  ------EAAKEI--CSEFRDQVRNGTLICTREHNPVRGPDGKMHGNKCAMCASVFKLEEE  52
hSP5_D9_E561-K622 1  ------EAVQEL--CSEYRHYVRNGRLPCTRENDPIEGLDGKIHGNTCSMCEAFFQQEAK  52
hSPINK9           1  --IECAKQTKQMVDCSHYKKLPPGQQRFCHHMYDPICESDGKTYKNDGFFCSKVKTDGT  58 human_SPINK2      54 IKIIRNGPC-                                                  62
hSP5_D8_E490-G551 53 EKKNDKEEKG                                                  62
hSP5_D9_E561-K622 53 EKERAEPRAK                                                  62
hSPINK9           59 LKFVHFGKC-                                                  67
```

FIG. 8

Amino acid sequence of human SPINK2
DPQFGLFSKYRTPNCSQYRLPGCPRHFNPVCGSDMSTYANECTLCMKIREGGHNI
KIIRNGPC (SEQ ID NO: 1)

*FIG. 9*

Amino acid sequence of human KLK5
IINGSDCDMHTQPWQAALLLRPNQLYCGAVLVHPQWLLTAAHCRKKVFRVRLGHY
SLSPVYESGQQMFQGVKSIPHPGYSHPGHSNDLMLIKLNRRIRPTKDVRPINVSSH
CPSAGTKCLVSGWGTTKSPQVHFPKVLQCLNISVLSQKRCEDAYPRQIDDTMFCA
GDKAGRDSCQGDSGGPVVCNGSLQGLVSWGDYPCARPNRPGVYTNLCKFTKWI
QETIQANS (SEQ ID NO: 2)

*FIG. 10*

Amino acid sequence of human KLK7
IIDGAPCARGSHPWQVALLSGNQLHCGGVLVNERWVLTAAHCKMNEYTVHLGS
DTLGDRRAQRIKASKSFRHPGYSTQTHVNDLMLVKLNSQARLSSMVKKVRLPSR
CEPPGTTCTVSGWGTTTSPDVTFPSDLMCVDVKLISPQDCTKVYKDLLENSMLC
AGIPDSKKNACNGDSGGPLVCRGTLQGLVSWGTFPCGQPNDPGVYTQVCKFTK
WINDTMKKHR (SEQ ID NO: 3)

*FIG. 11*

Amino acid sequence of human KLK14
IIGGHTCTRSSQPWQAALLAGPRRRFLCGGALLSGQWVITAAHCGRPILQVALGK
HNLRRWEATQQVLRVVRQVTHPNYNSRTHDNDLMLLQLQQPARIGRAVRPIEVT
QACASPGTSCRVSGWGTISSPIARYPASLQCVNINISPDEVCQKAYPRTITPGMV
CAGVPQGGKDSCQGDSGGPLVCRGQLQGLVSWGMERCALPGYPGVYTNLCK
YRSWIEETMRDK (SEQ ID NO: 4)

*FIG. 12*

Nucleotide sequence of KLK5 inhibitory peptide K50032
GGCCCGCAGTTTGGTCTGTTTAGCAAATATCGTACCCCGAATTGTCTGAACTGG
ACTGACCATCAGTGTGAACGTGACTACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 5)

*FIG. 13*

Amino acid sequence of KLK5 inhibitory peptide K50032
GPQFGLFSKYRTPNCLNWTDHQCERDYDPVCGSDMSTYANECTLCMKIREGGHN
IKIIRNGPCGG (SEQ ID NO: 6)

*FIG. 14*

Nucleotide sequence of KLK5 inhibitory peptide K50055
GGCCCGCAGTTTGGTCTGTTTAGCAAATATCGTACCCCGAATTGTGCTAACACT
ATGAAACAGGACTGTACTCGTGAATACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 7)

*FIG. 15*

Amino acid sequence of KLK5 inhibitory peptide K50055
GPQFGLFSKYRTPNCANTMKQDCTREYDPVCGSDMSTYANECTLCMKIREGGHN
IKIIRNGPCGG (SEQ ID NO: 8)

*FIG. 16*

Nucleotide sequence of KLK5 inhibitory peptide K51072
GGCCCGCAGTTTGGTCTGTTTAGCAAATATCGTACCCCGAATTGTCAGGAAGA
CATGACTGAATACTGTGCTCGTGACTTCGACCCGGTTTGTGGTAGCGATATGA
GCACCTATGCAAATGAATGTACCCTGTGCATGAAAATTCGTGAAGGTGGCCATA
ATATTAAAATTATTCGCAATGGTCCGTGCGGCGGCTAA (SEQ ID NO: 9)

*FIG. 17*

Amino acid sequence of KLK5 inhibitory peptide K51072
GPQFGLFSKYRTPNCQEDMTEYCARDFDPVCGSDMSTYANECTLCMKIREGGHNI
KIIRNGPCGG (SEQ ID NO: 10)

*FIG. 18*

Nucleotide sequence of KLK5 inhibitory peptide K50016
GGCCCGCAGTTTGGTCTGTTTAGCAAATATCGTACCCCGAATTGTTCTCAGTGG
CAGTACTCTTCTTGTGACCGTGTTTACGACCCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 11)

*FIG. 19*

Amino acid sequence of KLK5 inhibitory peptide K50016
GPQFGLFSKYRTPNCSQWQYSSCDRVYDPVCGSDMSTYANECTLCMKIREGGHN
IKIIRNGPCGG (SEQ ID NO: 12)

*FIG. 20*

Nucleotide sequence of KLK5 inhibitory peptide K51034
GGCCCGCAGTTTGGTCTGTTTAGCAAATATCGTACCCCGAATTGTGGTCGTTAC
ACTACTGGTGGTTGTAACAAAGAATACGAACCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 13)

*FIG. 21*

Amino acid sequence of KLK5 inhibitory peptide K51034
GPQFGLFSKYRTPNCGRYTTGGCNKEYEPVCGSDMSTYANECTLCMKIREGGHN
IKIIRNGPCGG (SEQ ID NO: 14)

*FIG. 22*

Nucleotide sequence of KLK5 inhibitory peptide K50062
GGCCCGCAGTTTGGTCTGTTTAGCAAATATCGTACCCCGAATTGTCAGCAGTAC
CGTGAACTGGGTTGTGGTCGTCAGTACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 15)

*FIG. 23*

Amino acid sequence of KLK5 inhibitory peptide K50062
GPQFGLFSKYRTPNCQQYRELGCGRQYDPVCGSDMSTYANECTLCMKIREGGHN
IKIIRNGPCGG (SEQ ID NO: 16)

*FIG. 24*

Nucleotide sequence of KLK5 inhibitory peptide K51090
GGCCCGCAATTTGGTCTGTTTAGCAAATATCGTACCCCGAATTGTGACGAAATC
GGTAAATACGGTTGTGGTCGTTCTTACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 17)

*FIG. 25*

Amino acid sequence of KLK5 inhibitory peptide K51090
GPQFGLFSKYRTPNCDEIGKYGCGRSYDPVCGSDMSTYANECTLCMKIREGGHNI
KIIRNGPCGG (SEQ ID NO: 18)

FIG. 26

Nucleotide sequence of KLK5 inhibitory peptide K50098
GGCCCGCAGTTTGGTCTGTTTAGCAAATATCGTACCCCGAATTGTACTTCTCAG
ACTCTGGGTTCTTGTTCTCGTGAATACGACCCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 19)

FIG. 27

Amino acid sequence of KLK5 inhibitory peptide K50098
GPQFGLFSKYRTPNCTSQTLGSCSREYDPVCGSDMSTYANECTLCMKIREGGHNI
KIIRNGPCGG (SEQ ID NO: 20)

FIG. 28

Nucleotide sequence of the KLK5/KLK7 inhibitory peptide K51028
GGCCCGCAGTTTGGTCTGTTTAGCAAATATCGTACCCCGAATTGTTACCAGTAC
CGTTCTAAAGGTTGTACTCATGAATACGACCCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 21)

FIG. 29

Amino acid sequence of the KLK5/KLK7 inhibitory peptide K51028
GPQFGLFSKYRTPNCYQYRSKGCTHEYDPVCGSDMSTYANECTLCMKIREGGHN
IKIIRNGPCGG (SEQ ID NO: 22)

FIG. 30

Nucleotide sequence of the KLK5/KLK7 inhibitory peptide K51005
GGCCCGCAGTTTGGTCTGTTTAGCAAATATCGTACCCCGAATTGTATGCAGCAT
GCTCGTCAGGGTTGTCATTACGACTACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 23)

FIG. 31

Amino acid sequence of the KLK5/KLK7 inhibitory peptide K51005
GPQFGLFSKYRTPNCMQHARQGCHYDYDPVCGSDMSTYANECTLCMKIREGGH
NIKIIRNGPCGG (SEQ ID NO: 24)

FIG. 32

Nucleotide sequence of the KLK5/KLK7 inhibitory peptide K50031
GGCCCGCAGTTTGGTCTGTTTAGCAAATATCGTACCCCGAATTGTGGTGAATAC
AAAGGTCGTGGTTGTTACTACCATTACGACCCGGTTTGTGGTAGCGATATGAG
CACCTATGCAAATGAATGTACCCTGTGCATGAAAATTCGTGAAGGTGGCCATAA
TATTAAAATTATTCGCAATGGTCCGTGCGGCGGCTAA (SEQ ID NO: 25)

FIG. 33

Amino acid sequence of the KLK5/KLK7 inhibitory peptide K50031
GPQFGLFSKYRTPNCGEYKGRGCYYHYDPVCGSDMSTYANECTLCMKIREGGHNI
KIIRNGPCGG (SEQ ID NO: 26)

FIG. 34

Nucleotide sequence of the KLK5/KLK7 inhibitory peptide K51057
GGCCCGCAGTTTGGTCTGTTTAGCAAATATCGTACCCCGAATTGTGGTACTATG
CAGGGTTCTGGTTGTACTTACCATTACGAACCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 27)

FIG. 35

Amino acid sequence of the KLK5/KLK7 inhibitory peptide K51057
GPQFGLFSKYRTPNCGTMQGSGCTYHYEPVCGSDMSTYANECTLCMKIREGGH
NIKIIRNGPCGG (SEQ ID NO: 28)

FIG. 36

Nucleotide sequence of the KLK5/KLK14 inhibitory peptide K51069
GGCCCGCAGTTTGGTCTGTTTAGCAAATATCGTACCCCGAATTGTTCTCAGGTT
GTTGAAACTTACTGTAACCGTGACTACGACCCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 29)

FIG. 37

Amino acid sequence of the KLK5/KLK14 inhibitory peptide K51069
GPQFGLFSKYRTPNCSQVVETYCNRDYDPVCGSDMSTYANECTLCMKIREGGHNI
KIIRNGPCGG (SEQ ID NO: 30)

FIG. 38

Nucleotide sequence of the KLK5/KLK14 inhibitory peptide K50015
GGCCCGCAGTTTGGTCTGTTTAGCAAATATCGTACCCCGAATTGTTACGACACT
ACTACTCATTACTGTTCTCGTGAATACGACCCGGTTTGTGGTAGCGATATGAGC
ACCTATGCAAATGAATGTACCCTGTGCATGAAAATTCGTGAAGGTGGCCATAAT
ATTAAAATTATTCGCAATGGTCCGTGCGGCGGCTAA (SEQ ID NO: 31)

FIG. 39

Amino acid sequence of the KLK5/KLK14 inhibitory peptide K50015
GPQFGLFSKYRTPNCYDTTTHYCSREYDPVCGSDMSTYANECTLCMKIREGGHNI
KIIRNGPCGG (SEQ ID NO: 32)

FIG. 40

Nucleotide sequence of KLK5 inhibitory peptide Fc conjugate D3-K50032dN-Fc
GATGACGACGGCCCTCAGTTCGGCCTGTTCAGCAAGTACAGAACCCCTAACTG
CCTGCAGTGGACTGACCATCAGTGTGAACGTGACTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCTG
CGACAAGACCCACACCTGTCCCCCTTGTCCTGCCCCCGAACTGCTGGGAGGAC
CTAGCGTGTTCCTGTTCCCCCCAAAGCCCAAGGACACCCTGATGATCAGCCGG
ACCCCCGAAGTGACCTGCGTGGTGGTGGATGTGTCCACGAGGACCCTGAAGT
GAAGTTCAATTGGTACGTGGACGGCGTGGAAGTGCACAACGCCAAGACCAAGC
CTAGAGAGGAACAGTACAACTCCACCTACCGGGTGGTGTCTGTGCTGACAGTG
CTGCATCAGGACTGGCTGAACGGCAAGAGTACAAGTGCAAGGTGTCCAACAA
GGCCCTGCCTGCCCCATCGAGAAAACCATCAGCAAGGCCAAGGGCCAGCCC
CGCGAACCCCAGGTGTACACACTGCCCCCTAGCCGGGAAGAGATGACCAAGAA
CCAGGTGTCCCTGACCTGTCTCGTGAAAGGCTTCTACCCAGCGACATTGCCG
TGGAATGGGAGAGCAACGGCCAGCCCGAGAACAACTACAAGACCACCCCCCCT
GTGCTGGACAGCGACGGCTCATTCTTCCTGTACAGCAAGCTGACCGTGGACAA
GAGCCGGTGGCAGCAGGGCAACGTGTTCAGCTGCAGCGTGATGCACGAGGCC
CTGCACAACCACTACACCCAGAAGTCCCTGAGCCTGAGCCCCGGCAAATGA
(SEQ ID NO: 33)

FIG. 41

Amino acid sequence of KLK5 inhibitory peptide Fc conjugate D3-K50032dN-Fc
DDDGPQFGLFSKYRTPNCLQWTDHQCERDYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 34)

*FIG. 42*

Nucleotide sequence of KLK5 inhibitory peptide Fc conjugate D3-K50055-Fc
GATGACGACGGCCCTCAGTTCGGCCTGTTCAGCAAGTACAGAACCCCTAACTG
CGCTAACACTATGAAACAGGACTGTACTCGTGAATACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAGAGTACAAGTGCAAGGTGTCCAA
CAAGGCCCTGCCTGCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAAA
TGA (SEQ ID NO: 35)

*FIG. 43*

Amino acid sequence of KLK5 inhibitory peptide Fc conjugate D3-K50055-Fc
DDDGPQFGLFSKYRTPNCANTMKQDCTREYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 36)

*FIG. 44*

Nucleotide sequence of KLK5 inhibitory peptide Fc conjugate D3-K51072-Fc
GATGACGACGGCCCTCAGTTCGGCCTGTTCAGCAAGTACAGAACCCCTAACTG
CCAGGAAGACATGACTGAATACTGTGCTCGTGACTTCGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAA
ATGA (SEQ ID NO: 37)

FIG. 45

Amino acid sequence of KLK5 inhibitory peptide Fc conjugate D3-K51072-Fc
DDDGPQFGLFSKYRTPNCQEDMTEYCARDFDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 38)

FIG. 46

Nucleotide sequence of KLK5 inhibitory peptide Fc conjugate D3-K50016dN-Fc
GATGACGACGGCCCTCAGTTCGGCCTGTTCAGCAAGTACAGAACCCCTAACTG
CGGCCAGTGGCAGTACTCTTCTTGTGACCGTGTTTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAA
ATGA (SEQ ID NO: 39)

FIG. 47

Amino acid sequence of KLK5 inhibitory peptide Fc conjugate D3-K50016dN-Fc
DDDGPQFGLFSKYRTPNCGQWQYSSCDRVYDPVCGSDMSTYANECTLCMKIRE
GGHNIKIIRNGPCEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFS
CSVMHEALHNHYTQKSLSLSPGK (SEQ ID NO: 40)

FIG. 48

Nucleotide sequence of KLK5 inhibitory peptide Fc conjugate D3-K51034-Fc
GATGACGACGGCCCTCAGTTCGGCCTGTTCAGCAAGTACAGAACCCCTAACTG
CGGTCGTTACACTACTGGTGGTTGTAACAAAGAATACGAACCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACC
AAGCCTAGAGAGGAACAGTACAACTCCACCTACCGGGTGGTGTCTGTGCTGAC
AGTGCTGCATCAGGACTGGCTGAACGGCAAAGAGTACAAGTGCAAGGTGTCC
AACAAGGCCCTGCCTGCCCCATCGAGAAAACCATCAGCAAGGCCAAGGGCC
AGCCCCGCGAACCCCAGGTGTACACACTGCCCCCTAGCCGGGAAGAGATGAC
CAAGAACCAGGTGTCCCTGACCTGTCTCGTGAAAGGCTTCTACCCAGCGACA
TTGCCGTGGAATGGGAGAGCAACGGCCAGCCCGAGAACAACTACAAGACCAC
CCCCCCTGTGCTGGACAGCGACGGCTCATTCTTCCTGTACAGCAAGCTGACC
GTGGACAAGAGCCGGTGGCAGCAGGGCAACGTGTTCAGCTGCAGCGTGATGC
ACGAGGCCCTGCACAACCACTACACCCAGAAGTCCCTGAGCCTGAGCCCCGG
CAAATGA (SEQ ID NO: 41)

FIG. 49

Amino acid sequence of KLK5 inhibitory peptide Fc conjugate D3-K51034-Fc
DDDGPQFGLFSKYRTPNCGRYTTGGCNKEYEPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 42)

FIG. 50

Nucleotide sequence of KLK5 inhibitory peptide Fc conjugate D3-K50062-Fc
GATGACGACGGCCCTCAGTTCGGCCTGTTCAGCAAGTACAGAACCCCTAACTG
CCAGCAGTACCGTGAACTGGGTTGTGGTCGTCAGTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAA
ATGA (SEQ ID NO: 43)

FIG. 51

Amino acid sequence of KLK5 inhibitory peptide Fc conjugate D3-K50062-Fc
DDDGPQFGLFSKYRTPNCQQYRELGCGRQYDPVCGSDMSTYANECTLCMKIRE
GGHNIKIIRNGPCEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVF
SCSVMHEALHNHYTQKSLSLSPGK (SEQ ID NO: 44)

FIG. 52

Nucleotide sequence of KLK5 inhibitory peptide Fc conjugate D3-K51090-Fc
GATGACGACGGCCCTCAGTTCGGCCTGTTCAGCAAGTACAGAACCCCTAACTG
CGACGAAATCGGTAAATACGGTTGTGGTCGTTCTTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCTGCGAACCCAAGAGCTG
CGACAAGACCCACACCTGTCCCCCTTGTCCTGCCCCGAACTGCTGGGAGGAC
CTAGCGTGTTCCTGTTCCCCCCAAAGCCCAAGGACACCCTGATGATCAGCCGG
ACCCCCGAAGTGACCTGCGTGGTGGTGGATGTGTCCCACGAGGACCCTGAAGT
GAAGTTCAATTGGTACGTGGACGGCGTGGAAGTGCACAACGCCAAGACCAAGC
CTAGAGAGGAACAGTACAACTCCACCTACCGGGTGGTGTCTGTGCTGACAGTG
CTGCATCAGGACTGGCTGAACGGCAAAGAGTACAAGTGCAAGGTGTCCAACAA
GGCCCTGCCTGCCCCCATCGAGAAAACCATCAGCAAGGCCAAGGGCCAGCCC
CGCGAACCCCAGGTGTACACTGCCCCCTAGCCGGGAAGAGATGACCAAGAA
CCAGGTGTCCCTGACCTGTCTCGTGAAAGGCTTCTACCCCAGCGACATTGCCG
TGGAATGGGAGAGCAACGGCCAGCCCGAGAACAACTACAAGACCACCCCCCT
GTGCTGGACAGCGACGGCTCATTCTTCCTGTACAGCAAGCTGACCGTGGACAA
GAGCCGGTGGCAGCAGGGCAACGTGTTCAGCTGCAGCGTGATGCACGAGGCC
CTGCACAACCACTACACCCAGAAGTCCCTGAGCCTGAGCCCCGGCAAATGA
(SEQ ID NO: 45)

*FIG. 53*

Amino acid sequence of KLK5 inhibitory peptide Fc conjugate D3-K51090-Fc
DDDGPQFGLFSKYRTPNCDEIGKYGCGRSYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 46)

*FIG. 54*

Nucleotide sequence of KLK5 inhibitory peptide Fc conjugate D3-K50098dN-Fc
GATGACGACGGCCCTCAGTTCGGCCTGTTCAGCAAGTACAGAACCCCTAACTG
CGGCTCTCAGACTCTGGGTTCTTGTTCTCGTGAATACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAAA
TGA (SEQ ID NO: 47)

FIG. 55

Amino acid sequence of KLK5 inhibitory peptide Fc conjugate D3-K50098dN-Fc
DDDGPQFGLFSKYRTPNCGSQTLGSCSREYDPVCGSDMSTYANECTLCMKIREG
GHNIKIIRNGPCEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCS
VMHEALHNHYTQKSLSLSPGK (SEQ ID NO: 48)

FIG. 56

Nucleotide sequence of the KLK5/KLK7 inhibitory peptide Fc conjugate D3-K51028-Fc
GATGACGACGGCCCTCAGTTCGGCCTGTTCAGCAAGTACAGAACCCCTAACTG
CTACCAGTACAGAAGCAAGGGCTGCACCCACGAGTACGATCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAAACCATCAGCAAGGCCAAGGGCCAG
CCCCGCGAACCCCAGGTGTACACTGCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAA
ATGA (SEQ ID NO: 49)

FIG. 57

Amino acid sequence of the KLK5/KLK7 inhibitory peptide Fc conjugate D3-K51028-Fc
DDDGPQFGLFSKYRTPNCYQYRSKGCTHEYDPVCGSDMSTYANECTLCMKIREG
GHNIKIIRNGPCEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCS
VMHEALHNHYTQKSLSLSPGK (SEQ ID NO: 50)

FIG. 58

Nucleotide sequence of the KLK5/KLK7 inhibitory peptide Fc conjugate D3-K51005-Fc GATGACGACGGCCCTCAGTTCGGCCTGTTCAGCAAGTACAGAACCCCTAACTG
CATGCAGCATGCTCGTCAGGGTTGTCATTACGACTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAAA
TGA (SEQ ID NO: 51)

*FIG. 59*

Amino acid sequence of the KLK5/KLK7 inhibitory peptide Fc conjugate D3-K51005-Fc DDDGPQFGLFSKYRTPNCMQHARQGCHYDYDPVCGSDMSTYANECTLCMKIRE
GGHNIKIIRNGPCEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFS
CSVMHEALHNHYTQKSLSLSPGK (SEQ ID NO: 52)

*FIG. 60*

Nucleotide sequence of the KLK5/KLK7 inhibitory peptide Fc conjugate D3-K50031-Fc GATGACGACGGCCCTCAGTTCGGCCTGTTCAGCAAGTACAGAACCCCTAACTG
CGGTGAATACAAAGGTCGTGGTTGTTACTACCATTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCTGCGAACCCAAGAGCT
GCGACAAGACCCACACCTGTCCCCCTTGTCCTGCCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAA
ATGA (SEQ ID NO: 53)

FIG. 61

Amino acid sequence of the KLK5/KLK7 inhibitory peptide Fc conjugate D3-K50031-Fc DDDGPQFGLFSKYRTPNCGEYKGRGCYYHYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 54)

FIG. 62

Nucleotide sequence of the KLK5/KLK7 inhibitory peptide Fc conjugate D3-K51057-Fc GATGACGACGGCCCTCAGTTCGGCCTGTTCAGCAAGTACAGAACCCCTAACTG
CGGTACTATGCAGGGTTCTGGTTGTACTTACCATTACGAACCTGTGTGCGGCAG
CGACATGAGCACCTACGCCAATGAGTGCACCCTGTGCATGAAGATCAGAGAAG
GCGGCCACAACATCAAGATCATCCGGAATGGCCCCTGCGAACCCAAGAGCTGC
GACAAGACCCACACCTGTCCCCTTGTCCTGCCCCGAACTGCTGGGAGGACC
TAGCGTGTTCCTGTTCCCCCCAAAGCCCAAGGACACCCTGATGATCAGCCGGA
CCCCCGAAGTGACCTGCGTGGTGGTGGATGTGTCCACGAGGACCCTGAAGT
GAAGTTCAATTGGTACGTGGACGGCGTGGAAGTGCACAACGCCAAGACCAAGC
CTAGAGAGGAACAGTACAACTCCACCTACCGGGTGGTGTCTGTGCTGACAGTG
CTGCATCAGGACTGGCTGAACGGCAAGAGTACAAGTGCAAGGTGTCCAACAA
GGCCCTGCCTGCCCCCATCGAGAAAACCATCAGCAAGGCCAAGGGCCAGCCC
CGCGAACCCCAGGTGTACACACTGCCCCCTAGCCGGGAAGAGATGACCAAGAA
CCAGGTGTCCCTGACCTGTCTCGTGAAAGGCTTCTACCCCAGCGACATTGCCG
TGGAATGGGAGAGCAACGGCCAGCCCGAGAACAACTACAAGACCACCCCCCT
GTGCTGGACAGCGACGGCTCATTCTTCCTGTACAGCAAGCTGACCGTGGACAA
GAGCCGGTGGCAGCAGGGCAACGTGTTCAGCTGCAGCGTGATGCACGAGGCC
CTGCACAACCACTACACCCAGAAGTCCCTGAGCCTGAGCCCCGGCAAATGA
(SEQ ID NO: 55)

*FIG. 63*

Amino acid sequence of the KLK5/KLK7 inhibitory peptide Fc conjugate D3-K51057-Fc DDDGPQFGLFSKYRTPNCGTMQGSGCTYHYEPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 56)

*FIG. 64*

Nucleotide sequence of the KLK5/KLK14 inhibitory peptide Fc conjugate D3-K51069dN-Fc
GATGACGACGGCCCTCAGTTCGGCCTGTTCAGCAAGTACAGAACCCCTAACTG
CGGCCAGGTTGTTGAAACTTACTGTAACCGTGACTACGACCCTGTGTGCGGCA
GCGACATGAGCACCTACGCCAATGAGTGCACCCTGTGCATGAAGATCAGAGAA
GGCGGCCACAACATCAAGATCATCCGGAATGGCCCCTGCGAACCCAAGAGCT
GCGACAAGACCCACACCTGTCCCCCTTGTCCTGCCCCCGAACTGCTGGGAGG
ACCTAGCGTGTTCCTGTTCCCCCCAAAGCCCAAGGACACCCTGATGATCAGCC
GGACCCCCGAAGTGACCTGCGTGGTGGTGGATGTGTCCACGAGGACCCTGA
AGTGAAGTTCAATTGGTACGTGGACGGCGTGGAAGTGCACAACGCCAAGACCA
AGCCTAGAGAGGAACAGTACAACTCCACCTACCGGGTGGTGTCTGTGCTGACA
GTGCTGCATCAGGACTGGCTGAACGGCAAAGAGTACAAGTGCAAGGTGTCCAA
CAAGGCCCTGCCTGCCCCCATCGAGAAAACCATCAGCAAGGCCAAGGGCCAG
CCCCGCGAACCCCAGGTGTACACACTGCCCCCTAGCCGGGAAGAGATGACCA
AGAACCAGGTGTCCCTGACCTGTCTCGTGAAAGGCTTCTACCCCAGCGACATT
GCCGTGGAATGGGAGAGCAACGGCCAGCCCGAGAACAACTACAAGACCACCC
CCCTGTGCTGGACAGCGACGGCTCATTCTTCCTGTACAGCAAGCTGACCGTG
GACAAGAGCCGGTGGCAGCAGGGCAACGTGTTCAGCTGCAGCGTGATGCACG
AGGCCCTGCACAACCACTACACCCAGAAGTCCCTGAGCCTGAGCCCCGGCAAA
TGA (SEQ ID NO: 57)

FIG. 65

Amino acid sequence of the KLK5/KLK14 inhibitory peptide Fc conjugate D3-K51069dN-Fc
DDDGPQFGLFSKYRTPNCGQVVETYCNRDYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 58)

FIG. 66

Nucleotide sequence of the KLK5/KLK14 inhibitory peptide Fc conjugate D3-K50015-Fc GATGACGACGGCCCTCAGTTCGGCCTGTTCAGCAAGTACAGAACCCCTAACTG
CTACGACACTACTACTCATTACTGTTCTCGTGAATACGACCCTGTGTGCGGCAG
CGACATGAGCACCTACGCCAATGAGTGCACCCTGTGCATGAAGATCAGAGAAG
GCGGCCACAACATCAAGATCATCCGGAATGGCCCCTGCGAACCCAAGAGCTG
CGACAAGACCCACACCTGTCCCCCTTGTCCTGCCCCCGAACTGCTGGGAGGA
CCTAGCGTGTTCTGTTCCCCCAAAGCCCAAGGACACCTGATGATCAGCCG
GACCCCCGAAGTGACCTGCGTGGTGGTGGATGTGTCCACGAGGACCCTGAA
GTGAAGTTCAATTGGTACGTGGACGGCGTGGAAGTGCACAACGCCAAGACCAA
GCCTAGAGAGGAACAGTACAACTCCACCTACCGGGTGGTGTCTGTGCTGACAG
TGCTGCATCAGGACTGGCTGAACGGCAAGAGTACAAGTGCAAGGTGTCCAAC
AAGGCCCTGCCTGCCCCATCGAGAAAACCATCAGCAAGGCCAAGGGCCAGC
CCCGCGAACCCCAGGTGTACACTGCCCCCTAGCCGGGAAGAGATGACCAA
GAACCAGGTGTCCCTGACCTGTCTCGTGAAAGGCTTCTACCCCAGCGACATTG
CCGTGGAATGGGAGAGCAACGGCCAGCCCGAGAACAACTACAAGACCACCCC
CCCTGTGCTGGACAGCGACGGCTCATTCTTCCTGTACAGCAAGCTGACCGTGG
ACAAGAGCCGGTGGCAGCAGGGCAACGTGTTCAGCTGCAGCGTGATGCACGA
GGCCCTGCACAACCACTACACCCAGAAGTCCCTGAGCCTGAGCCCCGGCAAAT
GA (SEQ ID NO: 59)

FIG. 67

Amino acid sequence of the KLK5/KLK14 inhibitory peptide Fc conjugate D3-K50015-Fc DDDGPQFGLFSKYRTPNCYDTTTHYCSREYDPVCGSDMSTYANECTLCMKIREG
GHNIKIIRNGPCEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSC
SVMHEALHNHYTQKSLSLSPGK (SEQ ID NO: 60)

FIG. 68

Formula of SPINK2 mutant peptide
GPQFGLFSKYRTPNCX$_1$X$_2$X$_3$X$_4$X$_5$X$_6$X$_7$CX$_8$X$_9$X$_{10}$X$_{11}$X$_{12}$PVCGSDMSTYANECTLCMK
IREGGHNIKIIRNGPC (SEQ ID NO: 61)

*FIG. 69*

Nucleotide sequence of primer 1
AAAAGGATCCCTGGACAAACGTGGCCCGCAGTTTGGTCTGTTTAG
(SEQ ID NO: 62)

*FIG. 70*

Nucleotide sequence of primer 2
AAAACTCGAGTTAGCCGCCGCACGGACCATTGCGAATAA (SEQ ID NO: 63)

*FIG. 71*

Nucleotide sequence of primer 3
GGCGATTATAAAGATGACGATGATAAACACCATCACCACCATC (SEQ ID NO: 64)

*FIG. 72*

Nucleotide sequence of primer 4
GTTTAAACTCAATGATGGTGGTGATGGTGTTTATCATCGTCAT (SEQ ID NO: 65)

*FIG. 73*

Nucleotide sequence of primer 5
AAAATCTAGAGCCGCCACCATGGCCACAGCTAGACCCCCT (SEQ ID NO: 66)

*FIG. 74*

Nucleotide sequence of primer 6
CGTCATCTTTATAATCGCCGCTGTTGGCCTGGATGGTTTCCTG (SEQ ID NO: 67)

*FIG. 75*

Nucleotide sequence of primer 7
AAAATCTAGAGCCGCCACCATGGCCAGATCTCTGCTGCTGCCC (SEQ ID NO: 68)

FIG. 76

Nucleotide sequence of primer 8
CGTCATCTTTATAATCGCCCGGTGTTTCTTCATGGTGTCGTT (SEQ ID NO: 69)

FIG. 77

Nucleotide sequence of primer 9
AAAATCTAGAGCCGCCACCATGTTCCTCCTCCTCACCGCCCTC (SEQ ID NO: 70)

FIG. 78

Nucleotide sequence of primer 10
CGTCATCTTTATAATCGCCCTTGTCGCGCATGGTCTCCTCGAT (SEQ ID NO: 71)

FIG. 79

Nucleotide sequence of primer 11
AAAAGTTTAAACTCAATGATGGTGGTGATGGTGT (SEQ ID NO: 72)

FIG. 80

Nucleotide sequence of primer 12
AAAATCTAGAGCCGCCACCATGGGAGTGTGGCTGCTGAGCCTG
(SEQ ID NO: 73)

FIG. 81

Nucleotide sequence of primer 13
AAAAGTTTAAACTCAATGATGGTGGTGATGGTGCCGGTGGGTCTTCATGGTTTCCATG (SEQ ID NO: 74)

FIG. 82

Nucleotide sequence of primer 14
AAAATCTAGAGCCGCCACCATGTTTCTGCTGCTGATCATCCTG (SEQ ID NO: 75)

FIG. 83

Nucleotide sequence of primer 15
AAAAGTTTAAACTCAATGATGGTGGTGATGGTGGTTGCTCTGCATGGTCCGCTGAA (SEQ ID NO: 76)

FIG. 84

Amino acid sequence in KLK7 substrate peptide
Arg-Pro-Lys-Pro-Val-Glu-Nval-Trp-Arg-Lys (SEQ ID NO: 77)

FIG. 85

Amino acid sequence in chymotrypsin, chymase substrate peptide
Leu-Leu-Val-Tyr (SEQ ID NO: 78)

FIG. 86

Amino acid sequence in neutrophil elastase substrate peptide
Ala-Ala-Pro-Val (SEQ ID NO: 79)

FIG. 87

Amino acid sequence in protein C substrate peptide
Leu-Ser-Thr-Arg (SEQ ID NO: 80)

FIG. 88

Nucleotide sequence of primer 16
AGATGGGTGTTGTCTGATGACGACGGCCCTCAGTTCGGCCTGTTC (SEQ ID NO: 81)

FIG. 89

Nucleotide sequence of primer 17
GCAGGGGCCATTCCGGAT (SEQ ID NO: 82)

FIG. 90

Nucleotide sequence of primer 18
AAAATCTAGAGCCGCCACCATGAAGCACCTGTGGTTCTTTCTGCTGCT
(SEQ ID NO: 83)

FIG. 91

Nucleotide sequence of primer 19
AGACAACACCCATCTAGGAGCGGCCACCAGCAGCAGAAAGAACC
(SEQ ID NO: 84)

FIG. 92

Nucleotide sequence of primer 20
ATCCGGAATGGCCCCTGCGAACCCAAGAGCTGCGAC (SEQ ID NO: 85)

FIG. 93

Nucleotide sequence of primer 21
AAAAGTTTAAACTCATTTGCCGGGGCTCAG (SEQ ID NO: 86)

FIG. 94

Amino acid sequence of Fc of human IgG1
EPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHY
TQKSLSLSPGK (SEQ ID NO: 87)

FIG. 95

Amino acid sequence of D8 of human SPINK5 (E490-G551)
EAAKEICSEFRDQVRNGTLICTREHNPVRGPDGKMHGNKCAMCASVFKLEEEEKK
NDKEEKG (SEQ ID NO: 88)

FIG. 96

Amino acid sequence of D9 of human SPINK5 (E561-K622)
EAVQELCSEYRHYVRNGRLPCTRENDPIEGLDGKIHGNTCSMCEAFFQQEAKEKE
RAEPRAK (SEQ ID NO: 89)

FIG. 97

Amino acid sequence of human SPINK9
IECAKQTKQMVDCSHYKKLPPGQQRFCHHMYDPICGSDGKTYKNDCFFCSKVKKT
DGTLKFVHFGKC (SEQ ID NO: 90)

FIG. 98

Amino acid sequence of mouse KLK5
RIVNGSDCQKDAQPWQGALLLGPNKLYCGAVLISPQWLLTAAHCRKPVFRIRLGH
HSMSPVYESGQQMFQGIKSIPHPGYSHPGHSNDLMLIKMNRKIRDSHSVKPVEIAC
DCATEGTRCMVSGWGTTSSSHNNFPKVLQCLNITVLSEERCKNSYPGQIDKTMFC
AGDEEGRDSCQGDSGGPVVCNGKLQGLVSWGDFPCAQRNRPGVYTNLCEFVK
WIKDTMNSN (SEQ ID NO: 91)

FIG. 99

Amino acid sequence of mouse KLK7
RIIDGYKCKEGSHPWQVALLKGNQLHCGGVLVDKYWVLTAAHCKMGQYQVQLGS
DKIGDQSAQKIKATKSFRHPGYSTKTHVNDIMLVRLDEPVKMSSKVEAVQLPEHCE
PPGTSCTVSGWGTTTSPDVTFPSDLMCSDVKLISSRECKKVYKDLLGKTMLCAGIP
DSKTNTCNGDSGGPLVCNDTLQGLVSWGTYPCGQPNDPGVYTQVCKYKRWVME
TMKTHR (SEQ ID NO: 92)

FIG. 100

Amino acid sequence of mouse KLK14
IIGGYRCVRNSQPWQVALQAGPGHRFLCGGVLLSDQWVITAAHCARPILHVALGK
HNIRRWEATQQVVRVARQVPHPQYQPQAHDNDLMLLKLQKKVRLGRAVKTISVAS
SCASPGTPCRVSGWGTIASPIARYPTALQCVNVNIMSEQACHRAYPGIITSGMVCA
GVPEGGKDSCQGDSGGPLVCGGQLQGLVSWGMERCAMPGYPGVYANLCNYHS
WIQRTMQSN (SEQ ID NO: 93)

FIG. 101

Nucleotide sequence of primer 22
AGATGGGTGTTGTCTGACGGCCCTCAGTTCGGCCTGTTC (SEQ ID NO: 94)

FIG. 104

Nucleotide sequence of KLK5 inhibitory peptide Fc conjugate D1-K50055-Fc
GACGGCCCTCAGTTCGGCCTGTTCAGCAAGTACAGAACCCCTAACTGCGCTAA
CACTATGAAACAGGACTGTACTCGTGAATACGACCCTGTGTGCGGCAGCGACAT
GAGCACCTACGCCAATGAGTGCACCCTGTGCATGAAGATCAGAGAAGGCGGCC
ACAACATCAAGATCATCCGGAATGGCCCTGCGAACCCAAGAGCTGCGACAAG
ACCCACACCTGTCCCCCTTGTCCTGCCCCGAACTGCTGGGAGGACCTAGCGT
GTTCCTGTTCCCCCCAAAGCCCAAGGACACCCTGATGATCAGCCGGACCCCCG
AAGTGACCTGCGTGGTGGTGGATGTGTCCCACGAGGACCCTGAAGTGAAGTTC
AATTGGTACGTGGACGGCGTGGAAGTGCACAACGCCAAGACCAAGCCTAGAGA
GGAACAGTACAACTCCACCTACCGGGTGGTGTCTGTGCTGACAGTGCTGCATC
AGGACTGGCTGAACGGCAAAGAGTACAAGTGCAAGGTGTCCAACAAGGCCCTG
CCTGCCCCCATCGAGAAAACCATCAGCAAGGCCAAGGCCAGCCCCGCGAAC
CCCAGGTGTACACACTGCCCCCTAGCCGGGAAGAGATGACCAAGAACCAGGTG
TCCCTGACCTGTCTCGTGAAAGGCTTCTACCCCAGCGACATTGCCGTGGAATG
GGAGAGCAACGGCCAGCCCGAGAACAACTACAAGACCACCCCCCCTGTGCTG
GACAGCGACGGCTCATTCTTCCTGTACAGCAAGCTGACCGTGGACAAGAGCCG
GTGGCAGCAGGGCAACGTGTTCAGCTGCAGCGTGATGCACGAGGCCCTGCAC
AACCACTACACCCAGAAGTCCCTGAGCCTGAGCCCCGGCAAATGA
(SEQ ID NO: 95)

FIG. 105

Amino acid sequence of KLK5 inhibitory peptide Fc conjugate D1-K50055-Fc
DGPQFGLFSKYRTPNCANTMKQDCTREYDPVCGSDMSTYANECTLCMKIREGGH
NIKIIRNGPCEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSV
MHEALHNHYTQKSLSLSPGK (SEQ ID NO: 96)

FIG. 106

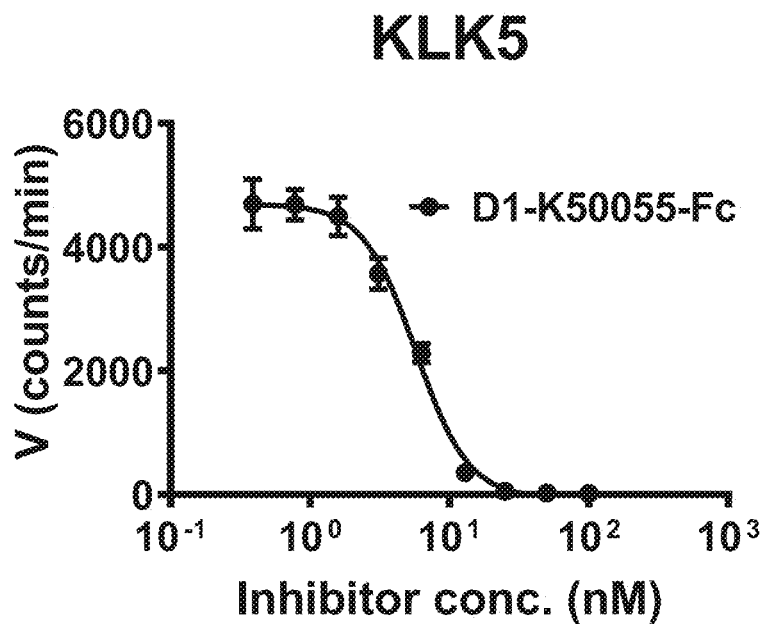
FIG. 107A
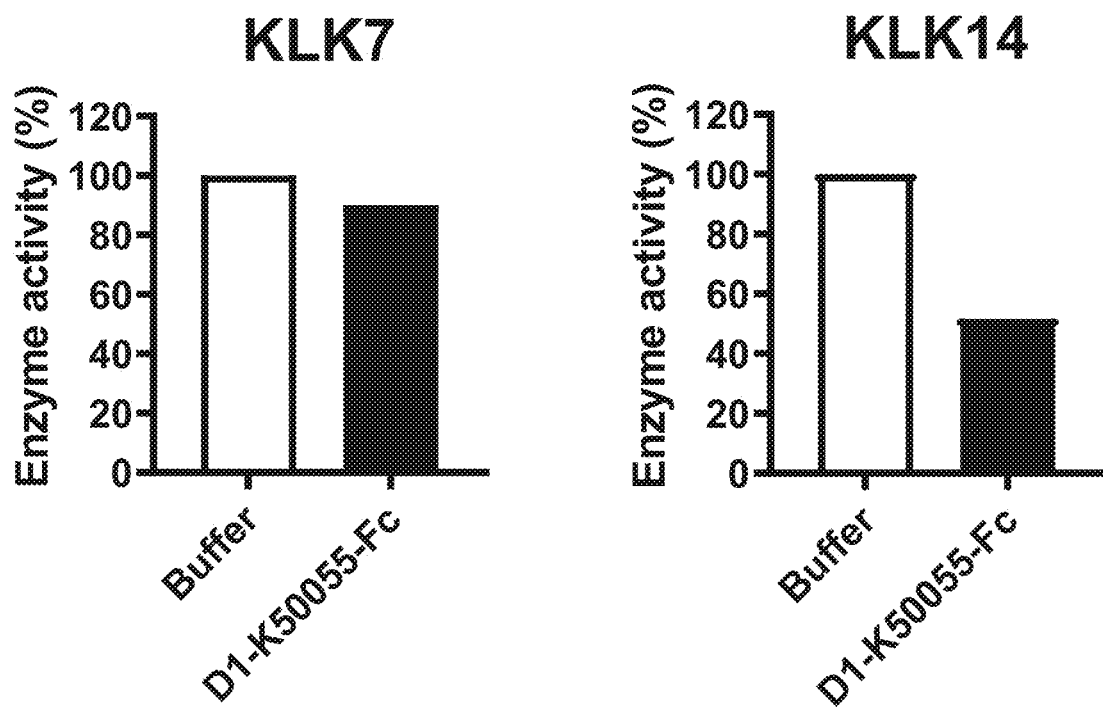
FIG. 107B
FIG. 107C

```
                       SEQUENCE LISTING

<160> NUMBER OF SEQ ID NOS: 101

<210> SEQ ID NO 1
<211> LENGTH: 63
<212> TYPE: PRT
<213> ORGANISM: Homo sapiens

<400> SEQUENCE: 1

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 2
<211> LENGTH: 227
<212> TYPE: PRT
<213> ORGANISM: Homo sapiens

<400> SEQUENCE: 2

Ile Ile Asn Gly Ser Asp Cys Asp Met His Thr Gln Pro Trp Gln Ala
1               5                   10                  15

Ala Leu Leu Leu Arg Pro Asn Gln Leu Tyr Cys Gly Ala Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
    50                  55                  60

Gln Gln Met Phe Gln Gly Val Lys Ser Ile Pro His Pro Gly Tyr Ser
65                  70                  75                  80

His Pro Gly His Ser Asn Asp Leu Met Leu Ile Lys Leu Asn Arg Arg
                85                  90                  95

Ile Arg Pro Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Lys
        115                 120                 125

Ser Pro Gln Val His Phe Pro Lys Val Leu Gln Cys Leu Asn Ile Ser
    130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Lys Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Arg Pro Asn Arg Pro Gly Val
        195                 200                 205

Tyr Thr Asn Leu Cys Lys Phe Thr Lys Trp Ile Gln Glu Thr Ile Gln
    210                 215                 220

Ala Asn Ser
```

225

<210> SEQ ID NO 3
<211> LENGTH: 224
<212> TYPE: PRT
<213> ORGANISM: Homo sapiens

<400> SEQUENCE: 3

Ile Ile Asp Gly Ala Pro Cys Ala Arg Gly Ser His Pro Trp Gln Val
1               5                   10                  15

Ala Leu Leu Ser Gly Asn Gln Leu His Cys Gly Gly Val Leu Val Asn
            20                  25                  30

Glu Arg Trp Val Leu Thr Ala Ala His Cys Lys Met Asn Glu Tyr Thr
        35                  40                  45

Val His Leu Gly Ser Asp Thr Leu Gly Asp Arg Arg Ala Gln Arg Ile
    50                  55                  60

Lys Ala Ser Lys Ser Phe Arg His Pro Gly Tyr Ser Thr Gln Thr His
65                  70                  75                  80

Val Asn Asp Leu Met Leu Val Lys Leu Asn Ser Gln Ala Arg Leu Ser
                85                  90                  95

Ser Met Val Lys Lys Val Arg Leu Pro Ser Arg Cys Glu Pro Pro Gly
            100                 105                 110

Thr Thr Cys Thr Val Ser Gly Trp Gly Thr Thr Thr Ser Pro Asp Val
        115                 120                 125

Thr Phe Pro Ser Asp Leu Met Cys Val Asp Val Lys Leu Ile Ser Pro
    130                 135                 140

Gln Asp Cys Thr Lys Val Tyr Lys Asp Leu Leu Glu Asn Ser Met Leu
145                 150                 155                 160

Cys Ala Gly Ile Pro Asp Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Met Lys Lys His Arg
    210                 215                 220

<210> SEQ ID NO 4
<211> LENGTH: 227
<212> TYPE: PRT
<213> ORGANISM: Homo sapiens

<400> SEQUENCE: 4

Ile Ile Gly Gly His Thr Cys Thr Arg Ser Ser Gln Pro Trp Gln Ala
1               5                   10                  15

Ala Leu Leu Ala Gly Pro Arg Arg Phe Leu Cys Gly Gly Ala Leu
            20                  25                  30

Leu Ser Gly Gln Trp Val Ile Thr Ala Ala His Cys Gly Arg Pro Ile
        35                  40                  45

Leu Gln Val Ala Leu Gly Lys His Asn Leu Arg Arg Trp Glu Ala Thr
    50                  55                  60

Gln Gln Val Leu Arg Val Val Arg Gln Val Thr His Pro Asn Tyr Asn
65                  70                  75                  80

Ser Arg Thr His Asp Asn Asp Leu Met Leu Leu Gln Leu Gln Pro
                85                  90                  95

Ala Arg Ile Gly Arg Ala Val Arg Pro Ile Glu Val Thr Gln Ala Cys

```
                100               105                 110
Ala Ser Pro Gly Thr Ser Cys Arg Val Ser Gly Trp Gly Thr Ile Ser
        115                 120                 125

Ser Pro Ile Ala Arg Tyr Pro Ala Ser Leu Gln Cys Val Asn Ile Asn
    130                 135                 140

Ile Ser Pro Asp Glu Val Cys Gln Lys Ala Tyr Pro Arg Thr Ile Thr
145                 150                 155                 160

Pro Gly Met Val Cys Ala Gly Val Pro Gln Gly Gly Lys Asp Ser Cys
                165                 170                 175

Gln Gly Asp Ser Gly Gly Pro Leu Val Cys Arg Gly Gln Leu Gln Gly
            180                 185                 190

Leu Val Ser Trp Gly Met Glu Arg Cys Ala Leu Pro Gly Tyr Pro Gly
        195                 200                 205

Val Tyr Thr Asn Leu Cys Lys Tyr Arg Ser Trp Ile Glu Glu Thr Met
    210                 215                 220

Arg Asp Lys
225

<210> SEQ ID NO 5
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 5 ggc ccg cag ttt ggt ctg ttt agc aaa tat cgt acc ccg aat tgt ctg    48
Gly Pro Gln Phe Gly Leu Phe Ser Lys Tyr Arg Thr Pro Asn Cys Leu
1               5                   10                  15 aac tgg act gac cat cag tgt gaa cgt gac tac gac ccg gtt tgt ggt    96
Asn Trp Thr Asp His Gln Cys Glu Arg Asp Tyr Asp Pro Val Cys Gly
            20                  25                  30 agc gat atg agc acc tat gca aat gaa tgt acc ctg tgc atg aaa att   144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc   192
Arg Glu Gly Gly His Asn Ile Lys Ile Ile Arg Asn Gly Pro Cys Gly
    50                  55                  60 ggc taa                                                            198
Gly
65

<210> SEQ ID NO 6
<211> LENGTH: 65
<212> TYPE: PRT
<213> ORGANISM: Artificial Sequence
<220> FEATURE:
<223> OTHER INFORMATION: Synthetic Construct

<400> SEQUENCE: 6

Gly Pro Gln Phe Gly Leu Phe Ser Lys Tyr Arg Thr Pro Asn Cys Leu
1               5                   10                  15

Asn Trp Thr Asp His Gln Cys Glu Arg Asp Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
```

```
                50                  55                  60
Gly
65

<210> SEQ ID NO 7
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 7 ggc ccg cag ttt ggt ctg ttt agc aaa tat cgt acc ccg aat tgt gct      48
Gly Pro Gln Phe Gly Leu Phe Ser Lys Tyr Arg Thr Pro Asn Cys Ala
1               5                   10                  15 aac act atg aaa cag gac tgt act cgt gaa tac gac ccg gtt tgt ggt      96
Asn Thr Met Lys Gln Asp Cys Thr Arg Glu Tyr Asp Pro Val Cys Gly
            20                  25                  30 agc gat atg agc acc tat gca aat gaa tgt acc ctg tgc atg aaa att     144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc     192
Arg Glu Gly Gly His Asn Ile Lys Ile Ile Arg Asn Gly Pro Cys Gly
    50                  55                  60 ggc taa                                                              198
Gly
65

<210> SEQ ID NO 8
<211> LENGTH: 65
<212> TYPE: PRT
<213> ORGANISM: Artificial Sequence
<220> FEATURE:
<223> OTHER INFORMATION: Synthetic Construct

<400> SEQUENCE: 8

Gly Pro Gln Phe Gly Leu Phe Ser Lys Tyr Arg Thr Pro Asn Cys Ala
1               5                   10                  15

Asn Thr Met Lys Gln Asp Cys Thr Arg Glu Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 9
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 9 ggc ccg cag ttt ggt ctg ttt agc aaa tat cgt acc ccg aat tgt cag      48
Gly Pro Gln Phe Gly Leu Phe Ser Lys Tyr Arg Thr Pro Asn Cys Gln
1               5                   10                  15
```

```
gaa gac atg act gaa tac tgt gct cgt gac ttc gac ccg gtt tgt ggt         96
Glu Asp Met Thr Glu Tyr Cys Ala Arg Asp Phe Asp Pro Val Cys Gly
             20                  25                  30 agc gat atg agc acc tat gca aat gaa tgt acc ctg tgc atg aaa att        144
Ser Asp Met Ser Thr Tyr Ala Asn Glu Cys Thr Leu Cys Met Lys Ile
         35                  40                  45 cgt gaa ggt ggc cat aat att aaa att att cgc aat ggt ccg tgc ggc        192
Arg Glu Gly Gly His Asn Ile Lys Ile Ile Arg Asn Gly Pro Cys Gly
     50                  55                  60 ggc taa                                                                 198
Gly
65

<210> SEQ ID NO 10
<211> LENGTH: 65
<212> TYPE: PRT
<213> ORGANISM: Artificial Sequence
<220> FEATURE:
<223> OTHER INFORMATION: Synthetic Construct

<400> SEQUENCE: 10

Gly Pro Gln Phe Gly Leu Phe Ser Lys Tyr Arg Thr Pro Asn Cys Gln
1               5                   10                  15

Glu Asp Met Thr Glu Tyr Cys Ala Arg Asp Phe Asp Pro Val Cys Gly
             20                  25                  30

Ser Asp Met Ser Thr Tyr Ala Asn Glu Cys Thr Leu Cys Met Lys Ile
         35                  40                  45

Arg Glu Gly Gly His Asn Ile Lys Ile Ile Arg Asn Gly Pro Cys Gly
     50                  55                  60

Gly
65

<210> SEQ ID NO 11
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 11 ggc ccg cag ttt ggt ctg ttt agc aaa tat cgt acc ccg aat tgt tct         48
Gly Pro Gln Phe Gly Leu Phe Ser Lys Tyr Arg Thr Pro Asn Cys Ser
1               5                   10                  15 cag tgg cag tac tct tct tgt gac cgt gtt tac gac ccg gtt tgt ggt         96
Gln Trp Gln Tyr Ser Ser Cys Asp Arg Val Tyr Asp Pro Val Cys Gly
             20                  25                  30 agc gat atg agc acc tat gca aat gaa tgt acc ctg tgc atg aaa att        144
Ser Asp Met Ser Thr Tyr Ala Asn Glu Cys Thr Leu Cys Met Lys Ile
         35                  40                  45 cgt gaa ggt ggc cat aat att aaa att att cgc aat ggt ccg tgc ggc        192
Arg Glu Gly Gly His Asn Ile Lys Ile Ile Arg Asn Gly Pro Cys Gly
     50                  55                  60 ggc taa                                                                 198
Gly
65

<210> SEQ ID NO 12
<211> LENGTH: 65
<212> TYPE: PRT
```

```
<213> ORGANISM: Artificial Sequence
<220> FEATURE:
<223> OTHER INFORMATION: Synthetic Construct

<400> SEQUENCE: 12

Gly Pro Gln Phe Gly Leu Phe Ser Lys Tyr Arg Thr Pro Asn Cys Ser
1               5                   10                  15

Gln Trp Gln Tyr Ser Ser Cys Asp Arg Val Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 13
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 13 ggc ccg cag ttt ggt ctg ttt agc aaa tat cgt acc ccg aat tgt ggt        48
Gly Pro Gln Phe Gly Leu Phe Ser Lys Tyr Arg Thr Pro Asn Cys Gly
1               5                   10                  15 cgt tac act act ggt ggt tgt aac aaa gaa tac gaa ccg gtt tgt ggt        96
Arg Tyr Thr Thr Gly Gly Cys Asn Lys Glu Tyr Glu Pro Val Cys Gly
            20                  25                  30 agc gat atg agc acc tat gca aat gaa tgt acc ctg tgc atg aaa att       144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc       192
Arg Glu Gly Gly His Asn Ile Lys Ile Ile Arg Asn Gly Pro Cys Gly
    50                  55                  60 ggc taa                                                                198
Gly
65

<210> SEQ ID NO 14
<211> LENGTH: 65
<212> TYPE: PRT
<213> ORGANISM: Artificial Sequence
<220> FEATURE:
<223> OTHER INFORMATION: Synthetic Construct

<400> SEQUENCE: 14

Gly Pro Gln Phe Gly Leu Phe Ser Lys Tyr Arg Thr Pro Asn Cys Gly
1               5                   10                  15

Arg Tyr Thr Thr Gly Gly Cys Asn Lys Glu Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 15
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 15

```
ggc ccg cag ttt ggt ctg ttt agc aaa tat cgt acc ccg aat tgt cag      48
Gly Pro Gln Phe Gly Leu Phe Ser Lys Tyr Arg Thr Pro Asn Cys Gln
1               5                   10                  15 cag tac cgt gaa ctg ggt tgt ggt cgt cag tac gac ccg gtt tgt ggt      96
Gln Tyr Arg Glu Leu Gly Cys Gly Arg Gln Tyr Asp Pro Val Cys Gly
            20                  25                  30 agc gat atg agc acc tat gca aat gaa tgt acc ctg tgc atg aaa att     144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc     192
Arg Glu Gly Gly His Asn Ile Lys Ile Ile Arg Asn Gly Pro Cys Gly
    50                  55                  60 ggc taa                                                              198
Gly
65
```

<210> SEQ ID NO 16
<211> LENGTH: 65
<212> TYPE: PRT
<213> ORGANISM: Artificial Sequence
<220> FEATURE:
<223> OTHER INFORMATION: Synthetic Construct

<400> SEQUENCE: 16

```
Gly Pro Gln Phe Gly Leu Phe Ser Lys Tyr Arg Thr Pro Asn Cys Gln
1               5                   10                  15

Gln Tyr Arg Glu Leu Gly Cys Gly Arg Gln Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 17
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 17

```
ggc ccg caa ttt ggt ctg ttt agc aaa tat cgt acc ccg aat tgt gac      48
Gly Pro Gln Phe Gly Leu Phe Ser Lys Tyr Arg Thr Pro Asn Cys Asp
1               5                   10                  15 gaa atc ggt aaa tac ggt tgt ggt cgt tct tac gac ccg gtt tgt ggt      96
Glu Ile Gly Lys Tyr Gly Cys Gly Arg Ser Tyr Asp Pro Val Cys Gly
            20                  25                  30
```

```
agc gat atg agc acc tat gca aat gaa tgt acc ctg tgc atg aaa att    144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc    192
Arg Glu Gly Gly His Asn Ile Lys Ile Ile Arg Asn Gly Pro Cys Gly
50                  55                  60 ggc taa                                                            198
Gly
65

<210> SEQ ID NO 18
<211> LENGTH: 65
<212> TYPE: PRT
<213> ORGANISM: Artificial Sequence
<220> FEATURE:
<223> OTHER INFORMATION: Synthetic Construct

<400> SEQUENCE: 18

Gly Pro Gln Phe Gly Leu Phe Ser Lys Tyr Arg Thr Pro Asn Cys Asp
1               5                   10                  15

Glu Ile Gly Lys Tyr Gly Cys Gly Arg Ser Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 19
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 19 ggc ccg cag ttt ggt ctg ttt agc aaa tat cgt acc ccg aat tgt act    48
Gly Pro Gln Phe Gly Leu Phe Ser Lys Tyr Arg Thr Pro Asn Cys Thr
1               5                   10                  15 tct cag act ctg ggt tct tgt tct cgt gaa tac gac ccg gtt tgt ggt    96
Ser Gln Thr Leu Gly Ser Cys Ser Arg Glu Tyr Asp Pro Val Cys Gly
            20                  25                  30 agc gat atg agc acc tat gca aat gaa tgt acc ctg tgc atg aaa att    144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc    192
Arg Glu Gly Gly His Asn Ile Lys Ile Ile Arg Asn Gly Pro Cys Gly
    50                  55                  60 ggc taa                                                            198
Gly
65

<210> SEQ ID NO 20
<211> LENGTH: 65
<212> TYPE: PRT
<213> ORGANISM: Artificial Sequence
<220> FEATURE:
<223> OTHER INFORMATION: Synthetic Construct

<400> SEQUENCE: 20
```

```
Gly Pro Gln Phe Gly Leu Phe Ser Lys Tyr Arg Thr Pro Asn Cys Thr
1               5                   10                  15

Ser Gln Thr Leu Gly Ser Cys Ser Arg Glu Tyr Asp Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys Gly
    50                  55                  60

Gly
65

<210> SEQ ID NO 21
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 21 ggc ccg cag ttt ggt ctg ttt agc aaa tat cgt acc ccg aat tgt tac    48
Gly Pro Gln Phe Gly Leu Phe Ser Lys Tyr Arg Thr Pro Asn Cys Tyr
1               5                   10                  15 cag tac cgt tct aaa ggt tgt act cat gaa tac gac ccg gtt tgt ggt    96
Gln Tyr Arg Ser Lys Gly Cys Thr His Glu Tyr Asp Pro Val Cys Gly
            20                  25                  30 agc gat atg agc acc tat gca aat gaa tgt acc ctg tgc atg aaa att   144
Ser Asp Met Ser Thr Tyr Ala Asn Glu Cys Thr Leu Cys Met Lys Ile
            35                  40                  45 cgt gaa ggt ggc cat aat att aaa att att cgc aat ggt ccg tgc ggc   192
Arg Glu Gly Gly His Asn Ile Lys Ile Ile Arg Asn Gly Pro Cys Gly
    50                  55                  60 ggc taa                                                             198
Gly
65

<210> SEQ ID NO 22
<211> LENGTH: 65
<212> TYPE: PRT
<213> ORGANISM: Artificial Sequence
<220> FEATURE:
<223> OTHER INFORMATION: Synthetic Construct

<400> SEQUENCE: 22

Gly Pro Gln Phe Gly Leu Phe Ser Lys Tyr Arg Thr Pro Asn Cys Tyr
1               5                   10                  15

Gln Tyr Arg Ser Lys Gly Cys Thr His Glu Tyr Asp Pro Val Cys Gly
            20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys Gly
    50                  55                  60

Gly
65

<210> SEQ ID NO 23
<211> LENGTH: 198
<212> TYPE: DNA
<213> ORGANISM: Artificial Sequence
```

```
<220> FEATURE:
<223> OTHER INFORMATION: binder
<220> FEATURE:
<221> NAME/KEY: CDS
<222> LOCATION: (1)..(198)

<400> SEQUENCE: 23 ggc ccg cag ttt ggt ctg ttt agc aaa tat cgt acc ccg aat tgt atg      48
Gly Pro Gln Phe Gly Leu Phe Ser Lys Tyr Arg Thr Pro Asn Cys Met
1               5                   10                  15 cag cat gct cgt cag ggt tgt cat tac gac tac gac ccg gtt tgt ggt      96
Gln His Ala Arg Gln Gly Cys His Tyr Asp Tyr Asp Pro Val Cys Gly
                20                  25                  30 agc gat atg agc acc tat gca aat gaa tgt acc ctg tgc atg aaa att     144
Ser Asp Met Ser Thr Tyr Ala Asn Glu Cys Thr Leu Cys Met Lys Ile
            35                  40                  45 cgt gaa ggt ggc cat aat att aaa att att cgc aat ggt ccg tgc ggc     192
Arg Glu Gly Gly His Asn Ile Lys Ile Ile Arg Asn Gly Pro Cys Gly
50                  55                  60 ggc taa                                                              198
Gly
65

<210> SEQ ID NO 24
<211> LENGTH: 65
<212> TYPE: PRT
<213> ORGANISM: Artificial Sequence
<220> FEATURE:
<223> OTHER INFORMATION: Synthetic Construct

<400> SEQUENCE: 24

Gly Pro Gln Phe Gly Leu Phe Ser Lys Tyr Arg Thr Pro Asn Cys Met
1               5                   10                  15

Gln His Ala Arg Gln Gly Cys His Tyr Asp Tyr Asp Pro Val Cys Gly
                20                  25                  30

Ser Asp Met Ser Thr Tyr Ala Asn Glu Cys Thr Leu Cys Met Lys Ile
            35                  40                  45

Arg Glu Gly Gly His Asn Ile Lys Ile Ile Arg Asn Gly Pro Cys Gly
    50                  55                  60

Gly
65

<210> SEQ ID NO 25
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 25 ggc ccg cag ttt ggt ctg ttt agc aaa tat cgt acc ccg aat tgt ggt      48
Gly Pro Gln Phe Gly Leu Phe Ser Lys Tyr Arg Thr Pro Asn Cys Gly
1               5                   10                  15 gaa tac aaa ggt cgt ggt tgt tac tac cat tac gac ccg gtt tgt ggt      96
Glu Tyr Lys Gly Arg Gly Cys Tyr Tyr His Tyr Asp Pro Val Cys Gly
                20                  25                  30 agc gat atg agc acc tat gca aat gaa tgt acc ctg tgc atg aaa att     144
Ser Asp Met Ser Thr Tyr Ala Asn Glu Cys Thr Leu Cys Met Lys Ile
            35                  40                  45 cgt gaa ggt ggc cat aat att aaa att att cgc aat ggt ccg tgc ggc     192
```

```
Arg Glu Gly Gly His Asn Ile Lys Ile Ile Arg Asn Gly Pro Cys Gly
    50                  55                  60 ggc taa                                                           198
Gly
65
```

<210> SEQ ID NO 26
<211> LENGTH: 65
<212> TYPE: PRT
<213> ORGANISM: Artificial Sequence
<220> FEATURE:
<223> OTHER INFORMATION: Synthetic Construct

<400> SEQUENCE: 26

```
Gly Pro Gln Phe Gly Leu Phe Ser Lys Tyr Arg Thr Pro Asn Cys Gly
1               5                   10                  15

Glu Tyr Lys Gly Arg Gly Cys Tyr Tyr His Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 27
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 27

```
ggc ccg cag ttt ggt ctg ttt agc aaa tat cgt acc ccg aat tgt ggt    48
Gly Pro Gln Phe Gly Leu Phe Ser Lys Tyr Arg Thr Pro Asn Cys Gly
1               5                   10                  15 act atg cag ggt tct ggt tgt act tac cat tac gaa ccg gtt tgt ggt    96
Thr Met Gln Gly Ser Gly Cys Thr Tyr His Tyr Glu Pro Val Cys Gly
            20                  25                  30 agc gat atg agc acc tat gca aat gaa tgt acc ctg tgc atg aaa att   144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc   192
Arg Glu Gly Gly His Asn Ile Lys Ile Ile Arg Asn Gly Pro Cys Gly
    50                  55                  60 ggc taa                                                           198
Gly
65
```

<210> SEQ ID NO 28
<211> LENGTH: 65
<212> TYPE: PRT
<213> ORGANISM: Artificial Sequence
<220> FEATURE:
<223> OTHER INFORMATION: Synthetic Construct

<400> SEQUENCE: 28

```
Gly Pro Gln Phe Gly Leu Phe Ser Lys Tyr Arg Thr Pro Asn Cys Gly
1               5                   10                  15

Thr Met Gln Gly Ser Gly Cys Thr Tyr His Tyr Glu Pro Val Cys Gly
```

```
                        20                  25                  30

Ser Asp Met Ser Thr Tyr Ala Asn Glu Cys Thr Leu Cys Met Lys Ile
         35                  40                  45

Arg Glu Gly Gly His Asn Ile Lys Ile Ile Arg Asn Gly Pro Cys Gly
     50                  55                  60

Gly
65

<210> SEQ ID NO 29
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)

<400> SEQUENCE: 29 ggc ccg cag ttt ggt ctg ttt agc aaa tat cgt acc ccg aat tgt tct      48
Gly Pro Gln Phe Gly Leu Phe Ser Lys Tyr Arg Thr Pro Asn Cys Ser
1               5                   10                  15 cag gtt gtt gaa act tac tgt aac cgt gac tac gac ccg gtt tgt ggt      96
Gln Val Val Glu Thr Tyr Cys Asn Arg Asp Tyr Asp Pro Val Cys Gly
            20                  25                  30 agc gat atg agc acc tat gca aat gaa tgt acc ctg tgc atg aaa att     144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc     192
Arg Glu Gly Gly His Asn Ile Lys Ile Ile Arg Asn Gly Pro Cys Gly
    50                  55                  60 ggc taa                                                              198
Gly
65

<210> SEQ ID NO 30
<211> LENGTH: 65
<212> TYPE: PRT
<213> ORGANISM: Artificial Sequence
<220> FEATURE:
<223> OTHER INFORMATION: Synthetic Construct

<400> SEQUENCE: 30

Gly Pro Gln Phe Gly Leu Phe Ser Lys Tyr Arg Thr Pro Asn Cys Ser
1               5                   10                  15

Gln Val Val Glu Thr Tyr Cys Asn Arg Asp Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 31
<211> LENGTH: 198
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(198)
```

<400> SEQUENCE: 31

```
ggc ccg cag ttt ggt ctg ttt agc aaa tat cgt acc ccg aat tgt tac     48
Gly Pro Gln Phe Gly Leu Phe Ser Lys Tyr Arg Thr Pro Asn Cys Tyr
1               5                   10                  15 gac act act act cat tac tgt tct cgt gaa tac gac ccg gtt tgt ggt     96
Asp Thr Thr Thr His Tyr Cys Ser Arg Glu Tyr Asp Pro Val Cys Gly
            20                  25                  30 agc gat atg agc acc tat gca aat gaa tgt acc ctg tgc atg aaa att    144
Ser Asp Met Ser Thr Tyr Ala Asn Glu Cys Thr Leu Cys Met Lys Ile
        35                  40                  45 cgt gaa ggt ggc cat aat att aaa att att cgc aat ggt ccg tgc ggc    192
Arg Glu Gly Gly His Asn Ile Lys Ile Ile Arg Asn Gly Pro Cys Gly
    50                  55                  60 ggc taa                                                            198
Gly
65
```

<210> SEQ ID NO 32
<211> LENGTH: 65
<212> TYPE: PRT
<213> ORGANISM: Artificial Sequence
<220> FEATURE:
<223> OTHER INFORMATION: Synthetic Construct

<400> SEQUENCE: 32

```
Gly Pro Gln Phe Gly Leu Phe Ser Lys Tyr Arg Thr Pro Asn Cys Tyr
1               5                   10                  15

Asp Thr Thr Thr His Tyr Cys Ser Arg Glu Tyr Asp Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 33
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 33

```
gat gac gac ggc cct cag ttc ggc ctg ttc agc aag tac aga acc cct     48
Asp Asp Asp Gly Pro Gln Phe Gly Leu Phe Ser Lys Tyr Arg Thr Pro
1               5                   10                  15 aac tgc ctg cag tgg act gac cat cag tgt gaa cgt gac tac gac cct     96
Asn Cys Leu Gln Trp Thr Asp His Gln Cys Glu Arg Asp Tyr Asp Pro
            20                  25                  30 gtg tgc ggc agc gac atg agc acc tac gcc aat gag tgc acc ctg tgc    144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc    192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt    240
Pro Cys Glu Pro Lys Ser Cys Asp Lys Thr His Thr Cys Pro Pro Cys
```

```
                65                  70                  75                  80
cct gcc ccc gaa ctg ctg gga gga cct agc gtg ttc ctg ttc ccc cca        288
Pro Ala Pro Glu Leu Leu Gly Gly Pro Ser Val Phe Leu Phe Pro Pro
                    85                  90                  95 aag ccc aag gac acc ctg atg atc agc cgg acc ccc gaa gtg acc tgc        336
Lys Pro Lys Asp Thr Leu Met Ile Ser Arg Thr Pro Glu Val Thr Cys
                    100                 105                 110 gtg gtg gtg gat gtg tcc cac gag gac cct gaa gtg aag ttc aat tgg        384
Val Val Val Asp Val Ser His Glu Asp Pro Glu Val Lys Phe Asn Trp
                    115                 120                 125 tac gtg gac ggc gtg gaa gtg cac aac gcc aag acc aag cct aga gag        432
Tyr Val Asp Gly Val Glu Val His Asn Ala Lys Thr Lys Pro Arg Glu
                    130                 135                 140 gaa cag tac aac tcc acc tac cgg gtg gtg tct gtg ctg aca gtg ctg        480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac        528
His Gln Asp Trp Leu Asn Gly Lys Glu Tyr Lys Cys Lys Val Ser Asn
                    165                 170                 175 aag gcc ctg cct gcc ccc atc gag aaa acc atc agc aag gcc aag ggc        576
Lys Ala Leu Pro Ala Pro Ile Glu Lys Thr Ile Ser Lys Ala Lys Gly
                    180                 185                 190 cag ccc cgc gaa ccc cag gtg tac aca ctg ccc cct agc cgg gaa gag        624
Gln Pro Arg Glu Pro Gln Val Tyr Thr Leu Pro Pro Ser Arg Glu Glu
                    195                 200                 205 atg acc aag aac cag gtg tcc ctg acc tgt ctc gtg aaa ggc ttc tac        672
Met Thr Lys Asn Gln Val Ser Leu Thr Cys Leu Val Lys Gly Phe Tyr
                    210                 215                 220 ccc agc gac att gcc gtg gaa tgg gag agc aac ggc cag ccc gag aac        720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc        768
Asn Tyr Lys Thr Thr Pro Pro Val Leu Asp Ser Asp Gly Ser Phe Phe
                    245                 250                 255 ctg tac agc aag ctg acc gtg gac aag agc cgg tgg cag cag ggc aac        816
Leu Tyr Ser Lys Leu Thr Val Asp Lys Ser Arg Trp Gln Gln Gly Asn
                    260                 265                 270 gtg ttc agc tgc agc gtg atg cac gag gcc ctg cac aac cac tac acc        864
Val Phe Ser Cys Ser Val Met His Glu Ala Leu His Asn His Tyr Thr
                    275                 280                 285 cag aag tcc ctg agc ctg agc ccc ggc aaa tga                             897
Gln Lys Ser Leu Ser Leu Ser Pro Gly Lys
                    290                 295
```

<210> SEQ ID NO 34
<211> LENGTH: 298
<212> TYPE: PRT
<213> ORGANISM: Artificial Sequence
<220> FEATURE:
<223> OTHER INFORMATION: Synthetic Construct

<400> SEQUENCE: 34

```
Asp Asp Asp Gly Pro Gln Phe Gly Leu Phe Ser Lys Tyr Arg Thr Pro
1               5                   10                  15

Asn Cys Leu Gln Trp Thr Asp His Gln Cys Glu Arg Asp Tyr Asp Pro
                20                  25                  30

Val Cys Gly Ser Asp Met Ser Thr Tyr Ala Asn Glu Cys Thr Leu Cys
            35                  40                  45

Met Lys Ile Arg Glu Gly Gly His Asn Ile Lys Ile Ile Arg Asn Gly
        50                  55                  60
```

```
Pro Cys Glu Pro Lys Ser Cys Asp Lys Thr His Thr Cys Pro Pro Cys
 65                  70                  75                  80

Pro Ala Pro Glu Leu Leu Gly Gly Pro Ser Val Phe Leu Phe Pro Pro
                 85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 35
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 35 gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc gct aac act atg aaa cag gac tgt act cgt gaa tac gac cct      96
Asn Cys Ala Asn Thr Met Lys Gln Asp Cys Thr Arg Glu Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80
```

| | | | | | | | | | | | | | | | |
|---|---|---|---|---|---|---|---|---|---|---|---|---|---|---|---|
| cct | gcc | ccc | gaa | ctg | ctg | gga | gga | cct | agc | gtg | ttc | ctg | ttc | ccc | cca | 288 |
| Pro | Ala | Pro | Glu | Leu | Leu | Gly | Gly | Pro | Ser | Val | Phe | Leu | Phe | Pro | Pro | |
| | | | | 85 | | | | 90 | | | | | 95 | | | |
| aag | ccc | aag | gac | acc | ctg | atg | atc | agc | cgg | acc | ccc | gaa | gtg | acc | tgc | 336 |
| Lys | Pro | Lys | Asp | Thr | Leu | Met | Ile | Ser | Arg | Thr | Pro | Glu | Val | Thr | Cys | |
| | | | 100 | | | | | 105 | | | | | 110 | | | |
| gtg | gtg | gtg | gat | gtg | tcc | cac | gag | gac | cct | gaa | gtg | aag | ttc | aat | tgg | 384 |
| Val | Val | Val | Asp | Val | Ser | His | Glu | Asp | Pro | Glu | Val | Lys | Phe | Asn | Trp | |
| | | 115 | | | | | 120 | | | | | 125 | | | | |
| tac | gtg | gac | ggc | gtg | gaa | gtg | cac | aac | gcc | aag | acc | aag | cct | aga | gag | 432 |
| Tyr | Val | Asp | Gly | Val | Glu | Val | His | Asn | Ala | Lys | Thr | Lys | Pro | Arg | Glu | |
| | 130 | | | | | 135 | | | | | 140 | | | | | |
| gaa | cag | tac | aac | tcc | acc | tac | cgg | gtg | gtg | tct | gtg | ctg | aca | gtg | ctg | 480 |
| Glu | Gln | Tyr | Asn | Ser | Thr | Tyr | Arg | Val | Val | Ser | Val | Leu | Thr | Val | Leu | |
| 145 | | | | | 150 | | | | | 155 | | | | | 160 | |
| cat | cag | gac | tgg | ctg | aac | ggc | aaa | gag | tac | aag | tgc | aag | gtg | tcc | aac | 528 |
| His | Gln | Asp | Trp | Leu | Asn | Gly | Lys | Glu | Tyr | Lys | Cys | Lys | Val | Ser | Asn | |
| | | | | 165 | | | | 170 | | | | | 175 | | | |
| aag | gcc | ctg | cct | gcc | ccc | atc | gag | aaa | acc | atc | agc | aag | gcc | aag | ggc | 576 |
| Lys | Ala | Leu | Pro | Ala | Pro | Ile | Glu | Lys | Thr | Ile | Ser | Lys | Ala | Lys | Gly | |
| | | | 180 | | | | | 185 | | | | | 190 | | | |
| cag | ccc | cgc | gaa | ccc | cag | gtg | tac | aca | ctg | ccc | cct | agc | cgg | gaa | gag | 624 |
| Gln | Pro | Arg | Glu | Pro | Gln | Val | Tyr | Thr | Leu | Pro | Pro | Ser | Arg | Glu | Glu | |
| | | 195 | | | | | 200 | | | | | 205 | | | | |
| atg | acc | aag | aac | cag | gtg | tcc | ctg | acc | tgt | ctc | gtg | aaa | ggc | ttc | tac | 672 |
| Met | Thr | Lys | Asn | Gln | Val | Ser | Leu | Thr | Cys | Leu | Val | Lys | Gly | Phe | Tyr | |
| | 210 | | | | | 215 | | | | | 220 | | | | | |
| ccc | agc | gac | att | gcc | gtg | gaa | tgg | gag | agc | aac | ggc | cag | ccc | gag | aac | 720 |
| Pro | Ser | Asp | Ile | Ala | Val | Glu | Trp | Glu | Ser | Asn | Gly | Gln | Pro | Glu | Asn | |
| 225 | | | | | 230 | | | | | 235 | | | | | 240 | |
| aac | tac | aag | acc | acc | ccc | cct | gtg | ctg | gac | agc | gac | ggc | tca | ttc | ttc | 768 |
| Asn | Tyr | Lys | Thr | Thr | Pro | Pro | Val | Leu | Asp | Ser | Asp | Gly | Ser | Phe | Phe | |
| | | | | 245 | | | | 250 | | | | | 255 | | | |
| ctg | tac | agc | aag | ctg | acc | gtg | gac | aag | agc | cgg | tgg | cag | cag | ggc | aac | 816 |
| Leu | Tyr | Ser | Lys | Leu | Thr | Val | Asp | Lys | Ser | Arg | Trp | Gln | Gln | Gly | Asn | |
| | | | 260 | | | | | 265 | | | | | 270 | | | |
| gtg | ttc | agc | tgc | agc | gtg | atg | cac | gag | gcc | ctg | cac | aac | cac | tac | acc | 864 |
| Val | Phe | Ser | Cys | Ser | Val | Met | His | Glu | Ala | Leu | His | Asn | His | Tyr | Thr | |
| | | 275 | | | | | 280 | | | | | 285 | | | | |
| cag | aag | tcc | ctg | agc | ctg | agc | ccc | ggc | aaa | tga | | | | | | 897 |
| Gln | Lys | Ser | Leu | Ser | Leu | Ser | Pro | Gly | Lys | | | | | | | |
| | 290 | | | | | 295 | | | | | | | | | | |

<210> SEQ ID NO 36
<211> LENGTH: 298
<212> TYPE: PRT
<213> ORGANISM: Artificial Sequence
<220> FEATURE:
<223> OTHER INFORMATION: Synthetic Construct

<400> SEQUENCE: 36

Asp Asp Asp Gly Pro Gln Phe Gly Leu Phe Ser Lys Tyr Arg Thr Pro
1               5                   10                  15

Asn Cys Ala Asn Thr Met Lys Gln Asp Cys Thr Arg Glu Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys

```
                65                  70                  75                  80
Pro Ala Pro Glu Leu Leu Gly Gly Pro Ser Val Phe Leu Phe Pro Pro
                    85                  90                  95

Lys Pro Lys Asp Thr Leu Met Ile Ser Arg Thr Pro Glu Val Thr Cys
                100                 105                 110

Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
        130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
                180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
        210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
                260                 265                 270

Val Phe Ser Cys Ser Val Met His Glu Ala Leu His Asn His Tyr Thr
            275                 280                 285

Gln Lys Ser Leu Ser Leu Ser Pro Gly Lys
        290                 295

<210> SEQ ID NO 37
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 37 gat gac gac ggc cct cag ttc ggc ctg ttc agc aag tac aga acc cct        48
Asp Asp Asp Gly Pro Gln Phe Gly Leu Phe Ser Lys Tyr Arg Thr Pro
1               5                   10                  15 aac tgc cag gaa gac atg act gaa tac tgt gct cgt gac ttc gac cct        96
Asn Cys Gln Glu Asp Met Thr Glu Tyr Cys Ala Arg Asp Phe Asp Pro
                20                  25                  30 gtg tgc ggc agc gac atg agc acc tac gcc aat gag tgc acc ctg tgc       144
Val Cys Gly Ser Asp Met Ser Thr Tyr Ala Asn Glu Cys Thr Leu Cys
            35                  40                  45 atg aag atc aga gaa ggc ggc cac aac atc aag atc atc cgg aat ggc       192
Met Lys Ile Arg Glu Gly Gly His Asn Ile Lys Ile Ile Arg Asn Gly
        50                  55                  60 ccc tgc gaa ccc aag agc tgc gac aag acc cac acc tgt ccc cct tgt       240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca       288
Pro Ala Pro Glu Leu Leu Gly Gly Pro Ser Val Phe Leu Phe Pro Pro
```

```
                    85                  90                  95
aag ccc aag gac acc ctg atg atc agc cgg acc ccc gaa gtg acc tgc     336
Lys Pro Lys Asp Thr Leu Met Ile Ser Arg Thr Pro Glu Val Thr Cys
        100                 105                 110 gtg gtg gtg gat gtg tcc cac gag gac cct gaa gtg aag ttc aat tgg     384
Val Val Val Asp Val Ser His Glu Asp Pro Glu Val Lys Phe Asn Trp
    115                 120                 125 tac gtg gac ggc gtg gaa gtg cac aac gcc aag acc aag cct aga gag     432
Tyr Val Asp Gly Val Glu Val His Asn Ala Lys Thr Lys Pro Arg Glu
130                 135                 140 gaa cag tac aac tcc acc tac cgg gtg gtg tct gtg ctg aca gtg ctg     480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac     528
His Gln Asp Trp Leu Asn Gly Lys Glu Tyr Lys Cys Lys Val Ser Asn
            165                 170                 175 aag gcc ctg cct gcc ccc atc gag aaa acc atc agc aag gcc aag ggc     576
Lys Ala Leu Pro Ala Pro Ile Glu Lys Thr Ile Ser Lys Ala Lys Gly
        180                 185                 190 cag ccc cgc gaa ccc cag gtg tac aca ctg ccc cct agc cgg gaa gag     624
Gln Pro Arg Glu Pro Gln Val Tyr Thr Leu Pro Pro Ser Arg Glu Glu
    195                 200                 205 atg acc aag aac cag gtg tcc ctg acc tgt ctc gtg aaa ggc ttc tac     672
Met Thr Lys Asn Gln Val Ser Leu Thr Cys Leu Val Lys Gly Phe Tyr
210                 215                 220 ccc agc gac att gcc gtg gaa tgg gag agc aac ggc cag ccc gag aac     720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc     768
Asn Tyr Lys Thr Thr Pro Pro Val Leu Asp Ser Asp Gly Ser Phe Phe
            245                 250                 255 ctg tac agc aag ctg acc gtg gac aag agc cgg tgg cag cag ggc aac     816
Leu Tyr Ser Lys Leu Thr Val Asp Lys Ser Arg Trp Gln Gln Gly Asn
        260                 265                 270 gtg ttc agc tgc agc gtg atg cac gag gcc ctg cac aac cac tac acc     864
Val Phe Ser Cys Ser Val Met His Glu Ala Leu His Asn His Tyr Thr
    275                 280                 285 cag aag tcc ctg agc ctg agc ccc ggc aaa tga                         897
Gln Lys Ser Leu Ser Leu Ser Pro Gly Lys
290                 295

<210> SEQ ID NO 38
<211> LENGTH: 298
<212> TYPE: PRT
<213> ORGANISM: Artificial Sequence
<220> FEATURE:
<223> OTHER INFORMATION: Synthetic Construct

<400> SEQUENCE: 38

Asp Asp Asp Gly Pro Gln Phe Gly Leu Phe Ser Lys Tyr Arg Thr Pro
1               5                   10                  15

Asn Cys Gln Glu Asp Met Thr Glu Tyr Cys Ala Arg Asp Phe Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80
```

```
Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 39
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 39 gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc ggc cag tgg cag tac tct tct tgt gac cgt gtt tac gac cct      96
Asn Cys Gly Gln Trp Gln Tyr Ser Ser Cys Asp Arg Val Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95
```

```
aag ccc aag gac acc ctg atg atc agc cgg acc ccc gaa gtg acc tgc      336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg      384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag      432
Tyr Val Asp Gly Val Glu Val His Asn Ala Lys Thr Lys Pro Arg Glu
    130                 135                 140 gaa cag tac aac tcc acc tac cgg gtg gtg tct gtg ctg aca gtg ctg      480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac      528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc      576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag      624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac      672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac      720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc      768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac      816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc      864
Val Phe Ser Cys Ser Val Met His Glu Ala Leu His Asn His Tyr Thr
        275                 280                 285 cag aag tcc ctg agc ctg agc ccc ggc aaa tga                          897
Gln Lys Ser Leu Ser Leu Ser Pro Gly Lys
    290                 295

<210> SEQ ID NO 40
<211> LENGTH: 298
<212> TYPE: PRT
<213> ORGANISM: Artificial Sequence
<220> FEATURE:
<223> OTHER INFORMATION: Synthetic Construct

<400> SEQUENCE: 40

Asp Asp Asp Gly Pro Gln Phe Gly Leu Phe Ser Lys Tyr Arg Thr Pro
1               5                   10                  15

Asn Cys Gly Gln Trp Gln Tyr Ser Ser Cys Asp Arg Val Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95
```

```
Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
            130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
            210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
            290                 295

<210> SEQ ID NO 41
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 41 gat gac gac ggc cct cag ttc ggc ctg ttc agc aag tac aga acc cct     48
Asp Asp Asp Gly Pro Gln Phe Gly Leu Phe Ser Lys Tyr Arg Thr Pro
1               5                   10                  15 aac tgc ggt cgt tac act act ggt ggt tgt aac aaa gaa tac gaa cct     96
Asn Cys Gly Arg Tyr Thr Thr Gly Gly Cys Asn Lys Glu Tyr Glu Pro
            20                  25                  30 gtg tgc ggc agc gac atg agc acc tac gcc aat gag tgc acc ctg tgc    144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc    192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt    240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca    288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc    336
Lys Pro Lys Asp Thr Leu Met Ile Ser Arg Thr Pro Glu Val Thr Cys
            100                 105                 110
```

```
        100                 105                 110
gtg gtg gtg gat gtg tcc cac gag gac cct gaa gtg aag ttc aat tgg      384
Val Val Val Asp Val Ser His Glu Asp Pro Glu Val Lys Phe Asn Trp
            115                 120                 125 tac gtg gac ggc gtg gaa gtg cac aac gcc aag acc aag cct aga gag      432
Tyr Val Asp Gly Val Glu Val His Asn Ala Lys Thr Lys Pro Arg Glu
130                 135                 140 gaa cag tac aac tcc acc tac cgg gtg gtg tct gtg ctg aca gtg ctg      480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac      528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc      576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag      624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac      672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac      720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc      768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac      816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc      864
Val Phe Ser Cys Ser Val Met His Glu Ala Leu His Asn His Tyr Thr
        275                 280                 285 cag aag tcc ctg agc ctg agc ccc ggc aaa tga                          897
Gln Lys Ser Leu Ser Leu Ser Pro Gly Lys
    290                 295

<210> SEQ ID NO 42
<211> LENGTH: 298
<212> TYPE: PRT
<213> ORGANISM: Artificial Sequence
<220> FEATURE:
<223> OTHER INFORMATION: Synthetic Construct

<400> SEQUENCE: 42

Asp Asp Asp Gly Pro Gln Phe Gly Leu Phe Ser Lys Tyr Arg Thr Pro
1               5                   10                  15

Asn Cys Gly Arg Tyr Thr Thr Gly Gly Cys Asn Lys Glu Tyr Glu Pro
            20                  25                  30

Val Cys Gly Ser Asp Met Ser Tyr Ala Asn Glu Cys Thr Leu Cys
        35                  40                  45

Met Lys Ile Arg Glu Gly Gly His Asn Ile Lys Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
```

```
                    100                 105                 110
Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
        130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 43
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 43 gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc cag cag tac cgt gaa ctg ggt tgt ggt cgt cag tac gac cct      96
Asn Cys Gln Gln Tyr Arg Glu Leu Gly Cys Gly Arg Gln Tyr Asp Pro
                20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
            35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
        50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc     336
Lys Pro Lys Asp Thr Leu Met Ile Ser Arg Thr Pro Glu Val Thr Cys
            100                 105                 110
```

```
gtg gtg gtg gat gtg tcc cac gag gac cct gaa gtg aag ttc aat tgg      384
Val Val Val Asp Val Ser His Glu Asp Pro Glu Val Lys Phe Asn Trp
            115                 120                 125 tac gtg gac ggc gtg gaa gtg cac aac gcc aag acc aag cct aga gag      432
Tyr Val Asp Gly Val Glu Val His Asn Ala Lys Thr Lys Pro Arg Glu
        130                 135                 140 gaa cag tac aac tcc acc tac cgg gtg gtg tct gtg ctg aca gtg ctg      480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac      528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc      576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag      624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac      672
Met Thr Lys Asn Gln Val Ser Leu Thr Cys Leu Val Lys Gly Phe Tyr
210                 215                 220 ccc agc gac att gcc gtg gaa tgg gag agc aac ggc cag ccc gag aac      720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc      768
Asn Tyr Lys Thr Thr Pro Pro Val Leu Asp Ser Asp Gly Ser Phe Phe
            245                 250                 255 ctg tac agc aag ctg acc gtg gac aag agc cgg tgg cag cag ggc aac      816
Leu Tyr Ser Lys Leu Thr Val Asp Lys Ser Arg Trp Gln Gln Gly Asn
        260                 265                 270 gtg ttc agc tgc agc gtg atg cac gag gcc ctg cac aac cac tac acc      864
Val Phe Ser Cys Ser Val Met His Glu Ala Leu His Asn His Tyr Thr
    275                 280                 285 cag aag tcc ctg agc ctg agc ccc ggc aaa tga                          897
Gln Lys Ser Leu Ser Leu Ser Pro Gly Lys
290                 295
```

<210> SEQ ID NO 44
<211> LENGTH: 298
<212> TYPE: PRT
<213> ORGANISM: Artificial Sequence
<220> FEATURE:
<223> OTHER INFORMATION: Synthetic Construct

<400> SEQUENCE: 44

```
Asp Asp Asp Gly Pro Gln Phe Gly Leu Phe Ser Lys Tyr Arg Thr Pro
1               5                   10                  15

Asn Cys Gln Gln Tyr Arg Glu Leu Gly Cys Gly Arg Gln Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110
```

-continued

```
Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

```
<210> SEQ ID NO 45
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 45
```

```
gat gac gac ggc cct cag ttc ggc ctg ttc agc aag tac aga acc cct    48
Asp Asp Asp Gly Pro Gln Phe Gly Leu Phe Ser Lys Tyr Arg Thr Pro
1               5                   10                  15 aac tgc gac gaa atc ggt aaa tac ggt tgt ggt cgt tct tac gac cct    96
Asn Cys Asp Glu Ile Gly Lys Tyr Gly Cys Gly Arg Ser Tyr Asp Pro
                20                  25                  30 gtg tgc ggc agc gac atg agc acc tac gcc aat gag tgc acc ctg tgc   144
Val Cys Gly Ser Asp Met Ser Thr Tyr Ala Asn Glu Cys Thr Leu Cys
            35                  40                  45 atg aag atc aga gaa ggc ggc cac aac atc aag atc atc cgg aat ggc   192
Met Lys Ile Arg Glu Gly Gly His Asn Ile Lys Ile Ile Arg Asn Gly
        50                  55                  60 ccc tgc gaa ccc aag agc tgc gac aag acc cac acc tgt ccc cct tgt   240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca   288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc   336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg   384
Val Val Val Asp Val Ser His Glu Asp Pro Glu Val Lys Phe Asn Trp
```

```
                115                 120                 125
tac gtg gac ggc gtg gaa gtg cac aac gcc aag acc aag cct aga gag      432
Tyr Val Asp Gly Val Glu Val His Asn Ala Lys Thr Lys Pro Arg Glu
    130                 135                 140 gaa cag tac aac tcc acc tac cgg gtg gtg tct gtg ctg aca gtg ctg      480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac      528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc      576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag      624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac      672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac      720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc      768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac      816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc      864
Val Phe Ser Cys Ser Val Met His Glu Ala Leu His Asn His Tyr Thr
        275                 280                 285 cag aag tcc ctg agc ctg agc ccc ggc aaa tga                          897
Gln Lys Ser Leu Ser Leu Ser Pro Gly Lys
    290                 295
```

<210> SEQ ID NO 46
<211> LENGTH: 298
<212> TYPE: PRT
<213> ORGANISM: Artificial Sequence
<220> FEATURE:
<223> OTHER INFORMATION: Synthetic Construct

<400> SEQUENCE: 46

```
Asp Asp Asp Gly Pro Gln Phe Gly Leu Phe Ser Lys Tyr Arg Thr Pro
1               5                   10                  15

Asn Cys Asp Glu Ile Gly Lys Tyr Gly Cys Gly Arg Ser Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125
```

```
Tyr Val Asp Gly Val Glu Val His Asn Ala Lys Thr Lys Pro Arg Glu
        130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

<210> SEQ ID NO 47
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 47

```
gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc ggc tct cag act ctg ggt tct tgt tct cgt gaa tac gac cct      96
Asn Cys Gly Ser Gln Thr Leu Gly Ser Cys Ser Arg Glu Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc     336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg     384
Val Val Val Asp Val Ser His Glu Asp Pro Glu Val Lys Phe Asn Trp
        115                 120                 125
```

```
tac gtg gac ggc gtg gaa gtg cac aac gcc aag acc aag cct aga gag       432
Tyr Val Asp Gly Val Glu Val His Asn Ala Lys Thr Lys Pro Arg Glu
130                 135                 140 gaa cag tac aac tcc acc tac cgg gtg gtg tct gtg ctg aca gtg ctg       480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac       528
His Gln Asp Trp Leu Asn Gly Lys Glu Tyr Lys Cys Lys Val Ser Asn
            165                 170                 175 aag gcc ctg cct gcc ccc atc gag aaa acc atc agc aag gcc aag ggc       576
Lys Ala Leu Pro Ala Pro Ile Glu Lys Thr Ile Ser Lys Ala Lys Gly
                180                 185                 190 cag ccc cgc gaa ccc cag gtg tac aca ctg ccc cct agc cgg gaa gag       624
Gln Pro Arg Glu Pro Gln Val Tyr Thr Leu Pro Pro Ser Arg Glu Glu
            195                 200                 205 atg acc aag aac cag gtg tcc ctg acc tgt ctc gtg aaa ggc ttc tac       672
Met Thr Lys Asn Gln Val Ser Leu Thr Cys Leu Val Lys Gly Phe Tyr
210                 215                 220 ccc agc gac att gcc gtg gaa tgg gag agc aac ggc cag ccc gag aac       720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc       768
Asn Tyr Lys Thr Thr Pro Pro Val Leu Asp Ser Asp Gly Ser Phe Phe
            245                 250                 255 ctg tac agc aag ctg acc gtg gac aag agc cgg tgg cag cag ggc aac       816
Leu Tyr Ser Lys Leu Thr Val Asp Lys Ser Arg Trp Gln Gln Gly Asn
                260                 265                 270 gtg ttc agc tgc agc gtg atg cac gag gcc ctg cac aac cac tac acc       864
Val Phe Ser Cys Ser Val Met His Glu Ala Leu His Asn His Tyr Thr
            275                 280                 285 cag aag tcc ctg agc ctg agc ccc ggc aaa tga                           897
Gln Lys Ser Leu Ser Leu Ser Pro Gly Lys
                290                 295

<210> SEQ ID NO 48
<211> LENGTH: 298
<212> TYPE: PRT
<213> ORGANISM: Artificial Sequence
<220> FEATURE:
<223> OTHER INFORMATION: Synthetic Construct

<400> SEQUENCE: 48

Asp Asp Asp Gly Pro Gln Phe Gly Leu Phe Ser Lys Tyr Arg Thr Pro
1               5                   10                  15

Asn Cys Gly Ser Gln Thr Leu Gly Ser Cys Ser Arg Glu Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
```

```
                130                 135                 140
Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

```
<210> SEQ ID NO 49
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 49 gat gac gac ggc cct cag ttc ggc ctg ttc agc aag tac aga acc cct    48
Asp Asp Asp Gly Pro Gln Phe Gly Leu Phe Ser Lys Tyr Arg Thr Pro
1               5                   10                  15 aac tgc tac cag tac aga agc aag ggc tgc acc cac gag tac gat cct    96
Asn Cys Tyr Gln Tyr Arg Ser Lys Gly Cys Thr His Glu Tyr Asp Pro
                20                  25                  30 gtg tgc ggc agc gac atg agc acc tac gcc aat gag tgc acc ctg tgc   144
Val Cys Gly Ser Asp Met Ser Thr Tyr Ala Asn Glu Cys Thr Leu Cys
            35                  40                  45 atg aag atc aga gaa ggc ggc cac aac atc aag atc atc cgg aat ggc   192
Met Lys Ile Arg Glu Gly Gly His Asn Ile Lys Ile Ile Arg Asn Gly
        50                  55                  60 ccc tgc gaa ccc aag agc tgc gac aag acc cac acc tgt ccc cct tgt   240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca   288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc   336
Lys Pro Lys Asp Thr Leu Met Ile Ser Arg Thr Pro Glu Val Thr Cys
                100                 105                 110 gtg gtg gtg gat gtg tcc cac gag gac cct gaa gtg aag ttc aat tgg   384
Val Val Val Asp Val Ser His Glu Asp Pro Glu Val Lys Phe Asn Trp
            115                 120                 125 tac gtg gac ggc gtg gaa gtg cac aac gcc aag acc aag cct aga gag   432
Tyr Val Asp Gly Val Glu Val His Asn Ala Lys Thr Lys Pro Arg Glu
```

```
                            130                 135                 140
gaa cag tac aac tcc acc tac cgg gtg gtg tct gtg ctg aca gtg ctg         480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac         528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc         576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag         624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac         672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac         720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc         768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac         816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc         864
Val Phe Ser Cys Ser Val Met His Glu Ala Leu His Asn His Tyr Thr
        275                 280                 285 cag aag tcc ctg agc ctg agc ccc ggc aaa tga                             897
Gln Lys Ser Leu Ser Leu Ser Pro Gly Lys
    290                 295

<210> SEQ ID NO 50
<211> LENGTH: 298
<212> TYPE: PRT
<213> ORGANISM: Artificial Sequence
<220> FEATURE:
<223> OTHER INFORMATION: Synthetic Construct

<400> SEQUENCE: 50

Asp Asp Asp Gly Pro Gln Phe Gly Leu Phe Ser Lys Tyr Arg Thr Pro
1               5                   10                  15

Asn Cys Tyr Gln Tyr Arg Ser Lys Gly Cys Thr His Glu Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140
```

```
Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
            165                 170                 175

Lys Ala Leu Pro Ala Pro Ile Glu Lys Thr Ile Ser Lys Ala Lys Gly
        180                 185                 190

Gln Pro Arg Glu Pro Gln Val Tyr Thr Leu Pro Pro Ser Arg Glu Glu
    195                 200                 205

Met Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

<210> SEQ ID NO 51
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 51

```
gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc atg cag cat gct cgt cag ggt tgt cat tac gac tac gac cct      96
Asn Cys Met Gln His Ala Arg Gln Gly Cys His Tyr Asp Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc     336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg     384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag     432
Tyr Val Asp Gly Val Glu Val His Asn Ala Lys Thr Lys Pro Arg Glu
    130                 135                 140
```

-continued

| | | |
|---|---|---|
| gaa cag tac aac tcc acc tac cgg gtg gtg tct gtg ctg aca gtg ctg<br>Glu Gln Tyr Asn Ser Thr Tyr Arg Val Val Ser Val Leu Thr Val Leu<br>145                           150                     155                160 | 480 |
| cat cag gac tgg ctg aac ggc aaa gag tac aag tgc aag gtg tcc aac<br>His Gln Asp Trp Leu Asn Gly Lys Glu Tyr Lys Cys Lys Val Ser Asn<br>                165                    170                    175 | 528 |
| aag gcc ctg cct gcc ccc atc gag aaa acc atc agc aag gcc aag ggc<br>Lys Ala Leu Pro Ala Pro Ile Glu Lys Thr Ile Ser Lys Ala Lys Gly<br>                     180                   185                  190 | 576 |
| cag ccc cgc gaa ccc cag gtg tac aca ctg ccc cct agc cgg gaa gag<br>Gln Pro Arg Glu Pro Gln Val Tyr Thr Leu Pro Pro Ser Arg Glu Glu<br>        195                    200                    205 | 624 |
| atg acc aag aac cag gtg tcc ctg acc tgt ctc gtg aaa ggc ttc tac<br>Met Thr Lys Asn Gln Val Ser Leu Thr Cys Leu Val Lys Gly Phe Tyr<br>210                           215                     220 | 672 |
| ccc agc gac att gcc gtg gaa tgg gag agc aac ggc cag ccc gag aac<br>Pro Ser Asp Ile Ala Val Glu Trp Glu Ser Asn Gly Gln Pro Glu Asn<br>225                         230                    235                240 | 720 |
| aac tac aag acc acc ccc cct gtg ctg gac agc gac ggc tca ttc ttc<br>Asn Tyr Lys Thr Thr Pro Pro Val Leu Asp Ser Asp Gly Ser Phe Phe<br>                     245                    250                  255 | 768 |
| ctg tac agc aag ctg acc gtg gac aag agc cgg tgg cag cag ggc aac<br>Leu Tyr Ser Lys Leu Thr Val Asp Lys Ser Arg Trp Gln Gln Gly Asn<br>             260                    265                  270 | 816 |
| gtg ttc agc tgc agc gtg atg cac gag gcc ctg cac aac cac tac acc<br>Val Phe Ser Cys Ser Val Met His Glu Ala Leu His Asn His Tyr Thr<br>        275                    280                    285 | 864 |
| cag aag tcc ctg agc ctg agc ccc ggc aaa tga<br>Gln Lys Ser Leu Ser Leu Ser Pro Gly Lys<br>290                           295 | 897 |

<210> SEQ ID NO 52
<211> LENGTH: 298
<212> TYPE: PRT
<213> ORGANISM: Artificial Sequence
<220> FEATURE:
<223> OTHER INFORMATION: Synthetic Construct

<400> SEQUENCE: 52

Asp Asp Asp Gly Pro Gln Phe Gly Leu Phe Ser Lys Tyr Arg Thr Pro
1                     5                    10                 15

Asn Cys Met Gln His Ala Arg Gln Gly Cys His Tyr Asp Tyr Asp Pro
                20                    25                    30

Val Cys Gly Ser Asp Met Ser Thr Tyr Ala Asn Glu Cys Thr Leu Cys
             35                    40                    45

Met Lys Ile Arg Glu Gly Gly His Asn Ile Lys Ile Ile Arg Asn Gly
     50                    55                    60

Pro Cys Glu Pro Lys Ser Cys Asp Lys Thr His Thr Cys Pro Pro Cys
65                      70                    75                    80

Pro Ala Pro Glu Leu Leu Gly Gly Pro Ser Val Phe Leu Phe Pro Pro
                     85                    90                    95

Lys Pro Lys Asp Thr Leu Met Ile Ser Arg Thr Pro Glu Val Thr Cys
                100                    105                  110

Val Val Val Asp Val Ser His Glu Asp Pro Glu Val Lys Phe Asn Trp
             115                    120                  125

Tyr Val Asp Gly Val Glu Val His Asn Ala Lys Thr Lys Pro Arg Glu
     130                    135                    140

Glu Gln Tyr Asn Ser Thr Tyr Arg Val Val Ser Val Leu Thr Val Leu
145                           150                     155                160

```
His Gln Asp Trp Leu Asn Gly Lys Glu Tyr Lys Cys Lys Val Ser Asn
            165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
            275                 280                 285

Gln Lys Ser Leu Ser Leu Ser Pro Gly Lys
        290                 295
```

<210> SEQ ID NO 53
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 53

```
gat gac gac ggc cct cag ttc ggc ctg ttc agc aag tac aga acc cct        48
Asp Asp Asp Gly Pro Gln Phe Gly Leu Phe Ser Lys Tyr Arg Thr Pro
1               5                   10                  15 aac tgc ggt gaa tac aaa ggt cgt ggt tgt tac tac cat tac gac cct        96
Asn Cys Gly Glu Tyr Lys Gly Arg Gly Cys Tyr Tyr His Tyr Asp Pro
            20                  25                  30 gtg tgc ggc agc gac atg agc acc tac gcc aat gag tgc acc ctg tgc       144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc       192
Met Lys Ile Arg Glu Gly Gly His Asn Ile Lys Ile Ile Arg Asn Gly
50                  55                  60 ccc tgc gaa ccc aag agc tgc gac aag acc cac acc tgt ccc cct tgt       240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca       288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc       336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg       384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag       432
Tyr Val Asp Gly Val Glu Val His Asn Ala Lys Thr Lys Pro Arg Glu
130                 135                 140 gaa cag tac aac tcc acc tac cgg gtg gtg tct gtg ctg aca gtg ctg       480
Glu Gln Tyr Asn Ser Thr Tyr Arg Val Val Ser Val Leu Thr Val Leu
```

```
                         145                 150                 155                 160
cat cag gac tgg ctg aac ggc aaa gag tac aag tgc aag gtg tcc aac        528
His Gln Asp Trp Leu Asn Gly Lys Glu Tyr Lys Cys Lys Val Ser Asn
                165                 170                 175 aag gcc ctg cct gcc ccc atc gag aaa acc atc agc aag gcc aag ggc        576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag        624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac        672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac        720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc        768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac        816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc        864
Val Phe Ser Cys Ser Val Met His Glu Ala Leu His Asn His Tyr Thr
        275                 280                 285 cag aag tcc ctg agc ctg agc ccc ggc aaa tga                            897
Gln Lys Ser Leu Ser Leu Ser Pro Gly Lys
    290                 295

<210> SEQ ID NO 54
<211> LENGTH: 298
<212> TYPE: PRT
<213> ORGANISM: Artificial Sequence
<220> FEATURE:
<223> OTHER INFORMATION: Synthetic Construct

<400> SEQUENCE: 54

Asp Asp Asp Gly Pro Gln Phe Gly Leu Phe Ser Lys Tyr Arg Thr Pro
1               5                   10                  15

Asn Cys Gly Glu Tyr Lys Gly Arg Gly Cys Tyr Tyr His Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
```

```
                       165                 170                 175
Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 55
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 55 gat gac gac ggc cct cag ttc ggc ctg ttc agc aag tac aga acc cct        48
Asp Asp Asp Gly Pro Gln Phe Gly Leu Phe Ser Lys Tyr Arg Thr Pro
1               5                   10                  15 aac tgc ggt act atg cag ggt tct ggt tgt act tac cat tac gaa cct        96
Asn Cys Gly Thr Met Gln Gly Ser Gly Cys Thr Tyr His Tyr Glu Pro
            20                  25                  30 gtg tgc ggc agc gac atg agc acc tac gcc aat gag tgc acc ctg tgc       144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc       192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt       240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca       288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc       336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg       384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag       432
Tyr Val Asp Gly Val Glu Val His Asn Ala Lys Thr Lys Pro Arg Glu
    130                 135                 140 gaa cag tac aac tcc acc tac cgg gtg gtg tct gtg ctg aca gtg ctg       480
Glu Gln Tyr Asn Ser Thr Tyr Arg Val Val Ser Val Leu Thr Val Leu
145                 150                 155                 160
```

| | |
|---|---|
| cat cag gac tgg ctg aac ggc aaa gag tac aag tgc aag gtg tcc aac<br>His Gln Asp Trp Leu Asn Gly Lys Glu Tyr Lys Cys Lys Val Ser Asn<br>              165                        170                  175 | 528 |
| aag gcc ctg cct gcc ccc atc gag aaa acc atc agc aag gcc aag ggc<br>Lys Ala Leu Pro Ala Pro Ile Glu Lys Thr Ile Ser Lys Ala Lys Gly<br>180                        185                        190 | 576 |
| cag ccc cgc gaa ccc cag gtg tac aca ctg ccc cct agc cgg gaa gag<br>Gln Pro Arg Glu Pro Gln Val Tyr Thr Leu Pro Pro Ser Arg Glu Glu<br>        195                        200                        205 | 624 |
| atg acc aag aac cag gtg tcc ctg acc tgt ctc gtg aaa ggc ttc tac<br>Met Thr Lys Asn Gln Val Ser Leu Thr Cys Leu Val Lys Gly Phe Tyr<br>210                        215                        220 | 672 |
| ccc agc gac att gcc gtg gaa tgg gag agc aac ggc cag ccc gag aac<br>Pro Ser Asp Ile Ala Val Glu Trp Glu Ser Asn Gly Gln Pro Glu Asn<br>225                        230                        235                  240 | 720 |
| aac tac aag acc acc ccc cct gtg ctg gac agc gac ggc tca ttc ttc<br>Asn Tyr Lys Thr Thr Pro Pro Val Leu Asp Ser Asp Gly Ser Phe Phe<br>              245                        250                        255 | 768 |
| ctg tac agc aag ctg acc gtg gac aag agc cgg tgg cag cag ggc aac<br>Leu Tyr Ser Lys Leu Thr Val Asp Lys Ser Arg Trp Gln Gln Gly Asn<br>        260                        265                        270 | 816 |
| gtg ttc agc tgc agc gtg atg cac gag gcc ctg cac aac cac tac acc<br>Val Phe Ser Cys Ser Val Met His Glu Ala Leu His Asn His Tyr Thr<br>275                        280                        285 | 864 |
| cag aag tcc ctg agc ctg agc ccc ggc aaa tga<br>Gln Lys Ser Leu Ser Leu Ser Pro Gly Lys<br>    290                        295 | 897 |

<210> SEQ ID NO 56
<211> LENGTH: 298
<212> TYPE: PRT
<213> ORGANISM: Artificial Sequence
<220> FEATURE:
<223> OTHER INFORMATION: Synthetic Construct

<400> SEQUENCE: 56

Asp Asp Asp Gly Pro Gln Phe Gly Leu Phe Ser Lys Tyr Arg Thr Pro
1               5                   10                  15

Asn Cys Gly Thr Met Gln Gly Ser Gly Cys Thr Tyr His Tyr Glu Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

```
Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

```
<210> SEQ ID NO 57
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 57
```

```
gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc ggc cag gtt gtt gaa act tac tgt aac cgt gac tac gac cct      96
Asn Cys Gly Gln Val Val Glu Thr Tyr Cys Asn Arg Asp Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
    50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc     336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg     384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag     432
Tyr Val Asp Gly Val Glu Val His Asn Ala Lys Thr Lys Pro Arg Glu
    130                 135                 140 gaa cag tac aac tcc acc tac cgg gtg gtg tct gtg ctg aca gtg ctg     480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac     528
His Gln Asp Trp Leu Asn Gly Lys Glu Tyr Lys Cys Lys Val Ser Asn
```

```
                    165                 170                 175
aag gcc ctg cct gcc ccc atc gag aaa acc atc agc aag gcc aag ggc       576
Lys Ala Leu Pro Ala Pro Ile Glu Lys Thr Ile Ser Lys Ala Lys Gly
        180                 185                 190 cag ccc cgc gaa ccc cag gtg tac aca ctg ccc cct agc cgg gaa gag       624
Gln Pro Arg Glu Pro Gln Val Tyr Thr Leu Pro Pro Ser Arg Glu Glu
    195                 200                 205 atg acc aag aac cag gtg tcc ctg acc tgt ctc gtg aaa ggc ttc tac       672
Met Thr Lys Asn Gln Val Ser Leu Thr Cys Leu Val Lys Gly Phe Tyr
210                 215                 220 ccc agc gac att gcc gtg gaa tgg gag agc aac ggc cag ccc gag aac       720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc       768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac       816
Leu Tyr Ser Lys Leu Thr Val Asp Lys Ser Arg Trp Gln Gln Gly Asn
        260                 265                 270 gtg ttc agc tgc agc gtg atg cac gag gcc ctg cac aac cac tac acc       864
Val Phe Ser Cys Ser Val Met His Glu Ala Leu His Asn His Tyr Thr
    275                 280                 285 cag aag tcc ctg agc ctg agc ccc ggc aaa tga                           897
Gln Lys Ser Leu Ser Leu Ser Pro Gly Lys
    290                 295

<210> SEQ ID NO 58
<211> LENGTH: 298
<212> TYPE: PRT
<213> ORGANISM: Artificial Sequence
<220> FEATURE:
<223> OTHER INFORMATION: Synthetic Construct

<400> SEQUENCE: 58

Asp Asp Asp Gly Pro Gln Phe Gly Leu Phe Ser Lys Tyr Arg Thr Pro
1               5                   10                  15

Asn Cys Gly Gln Val Val Glu Thr Tyr Cys Asn Arg Asp Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190
```

```
Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
        260                 265                 270

Val Phe Ser Cys Ser Val Met His Glu Ala Leu His Asn His Tyr Thr
            275                 280                 285

Gln Lys Ser Leu Ser Leu Ser Pro Gly Lys
        290                 295

<210> SEQ ID NO 59
<211> LENGTH: 897
<212> TYPE: DNA
<213> ORGANISM: Artificial Sequence
<220> FEATURE:
<223> OTHER INFORMATION: binder
<220> FEATURE:
<221> NAME/KEY: CDS
<222> LOCATION: (1)..(897)

<400> SEQUENCE: 59 gat gac gac ggc cct cag ttc ggc ctg ttc agc aag tac aga acc cct      48
Asp Asp Asp Gly Pro Gln Phe Gly Leu Phe Ser Lys Tyr Arg Thr Pro
1               5                   10                  15 aac tgc tac gac act act act cat tac tgt tct cgt gaa tac gac cct      96
Asn Cys Tyr Asp Thr Thr Thr His Tyr Cys Ser Arg Glu Tyr Asp Pro
            20                  25                  30 gtg tgc ggc agc gac atg agc acc tac gcc aat gag tgc acc ctg tgc     144
Val Cys Gly Ser Asp Met Ser Thr Tyr Ala Asn Glu Cys Thr Leu Cys
        35                  40                  45 atg aag atc aga gaa ggc ggc cac aac atc aag atc atc cgg aat ggc     192
Met Lys Ile Arg Glu Gly Gly His Asn Ile Lys Ile Ile Arg Asn Gly
50                  55                  60 ccc tgc gaa ccc aag agc tgc gac aag acc cac acc tgt ccc cct tgt     240
Pro Cys Glu Pro Lys Ser Cys Asp Lys Thr His Thr Cys Pro Pro Cys
65                  70                  75                  80 cct gcc ccc gaa ctg ctg gga gga cct agc gtg ttc ctg ttc ccc cca     288
Pro Ala Pro Glu Leu Leu Gly Gly Pro Ser Val Phe Leu Phe Pro Pro
                85                  90                  95 aag ccc aag gac acc ctg atg atc agc cgg acc ccc gaa gtg acc tgc     336
Lys Pro Lys Asp Thr Leu Met Ile Ser Arg Thr Pro Glu Val Thr Cys
            100                 105                 110 gtg gtg gtg gat gtg tcc cac gag gac cct gaa gtg aag ttc aat tgg     384
Val Val Val Asp Val Ser His Glu Asp Pro Glu Val Lys Phe Asn Trp
        115                 120                 125 tac gtg gac ggc gtg gaa gtg cac aac gcc aag acc aag cct aga gag     432
Tyr Val Asp Gly Val Glu Val His Asn Ala Lys Thr Lys Pro Arg Glu
    130                 135                 140 gaa cag tac aac tcc acc tac cgg gtg gtg tct gtg ctg aca gtg ctg     480
Glu Gln Tyr Asn Ser Thr Tyr Arg Val Val Ser Val Leu Thr Val Leu
145                 150                 155                 160 cat cag gac tgg ctg aac ggc aaa gag tac aag tgc aag gtg tcc aac     528
His Gln Asp Trp Leu Asn Gly Lys Glu Tyr Lys Cys Lys Val Ser Asn
                165                 170                 175
```

-continued

```
aag gcc ctg cct gcc ccc atc gag aaa acc atc agc aag gcc aag ggc      576
Lys Ala Leu Pro Ala Pro Ile Glu Lys Thr Ile Ser Lys Ala Lys Gly
            180                 185                 190 cag ccc cgc gaa ccc cag gtg tac aca ctg ccc cct agc cgg gaa gag      624
Gln Pro Arg Glu Pro Gln Val Tyr Thr Leu Pro Pro Ser Arg Glu Glu
        195                 200                 205 atg acc aag aac cag gtg tcc ctg acc tgt ctc gtg aaa ggc ttc tac      672
Met Thr Lys Asn Gln Val Ser Leu Thr Cys Leu Val Lys Gly Phe Tyr
    210                 215                 220 ccc agc gac att gcc gtg gaa tgg gag agc aac ggc cag ccc gag aac      720
Pro Ser Asp Ile Ala Val Glu Trp Glu Ser Asn Gly Gln Pro Glu Asn
225                 230                 235                 240 aac tac aag acc acc ccc cct gtg ctg gac agc gac ggc tca ttc ttc      768
Asn Tyr Lys Thr Thr Pro Pro Val Leu Asp Ser Asp Gly Ser Phe Phe
                245                 250                 255 ctg tac agc aag ctg acc gtg gac aag agc cgg tgg cag cag ggc aac      816
Leu Tyr Ser Lys Leu Thr Val Asp Lys Ser Arg Trp Gln Gln Gly Asn
            260                 265                 270 gtg ttc agc tgc agc gtg atg cac gag gcc ctg cac aac cac tac acc      864
Val Phe Ser Cys Ser Val Met His Glu Ala Leu His Asn His Tyr Thr
        275                 280                 285 cag aag tcc ctg agc ctg agc ccc ggc aaa tga                          897
Gln Lys Ser Leu Ser Leu Ser Pro Gly Lys
    290                 295
```

<210> SEQ ID NO 60
<211> LENGTH: 298
<212> TYPE: PRT
<213> ORGANISM: Artificial Sequence
<220> FEATURE:
<223> OTHER INFORMATION: Synthetic Construct

<400> SEQUENCE: 60

```
Asp Asp Asp Gly Pro Gln Phe Gly Leu Phe Ser Lys Tyr Arg Thr Pro
1               5                   10                  15

Asn Cys Tyr Asp Thr Thr Thr His Tyr Cys Ser Arg Glu Tyr Asp Pro
            20                  25                  30

Val Cys Gly Ser Asp Met Ser Thr Tyr Ala Asn Glu Cys Thr Leu Cys
        35                  40                  45

Met Lys Ile Arg Glu Gly Gly His Asn Ile Lys Ile Arg Asn Gly
    50                  55                  60

Pro Cys Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
```

```
            195                 200                 205
Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 61
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(22)
<223> OTHER INFORMATION: Wherein X at at each of positions 16 to 22 is
      defined as any amino acid
<220> FEATURE:
<221> NAME/KEY: MISC_FEATURE
<222> LOCATION: (24)..(28)
<223> OTHER INFORMATION: Wherein X at at each of positions 24 to 28 is
      defined as any amino acid

<400> SEQUENCE: 61

Gly Pro Gln Phe Gly Leu Phe Ser Lys Tyr Arg Thr Pro Asn Cys Xaa
1               5                   10                  15

Xaa Xaa Xaa Xaa Xaa Xaa Cys Xaa Xaa Xaa Xaa Xaa Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 62
<211> LENGTH: 45
<212> TYPE: DNA
<213> ORGANISM: Artificial Sequence
<220> FEATURE:
<223> OTHER INFORMATION: primer

<400> SEQUENCE: 62
aaaaggatcc ctggacaaac gtggcccgca gtttggtctg tttag              45

<210> SEQ ID NO 63
<211> LENGTH: 39
<212> TYPE: DNA
<213> ORGANISM: Artificial Sequence
<220> FEATURE:
<223> OTHER INFORMATION: Primer

<400> SEQUENCE: 63
aaaactcgag ttagccgccg cacggaccat tgcgaataa                     39

<210> SEQ ID NO 64
<211> LENGTH: 43
```

<212> TYPE: DNA
<213> ORGANISM: Artificial Sequence
<220> FEATURE:
<223> OTHER INFORMATION: Primer

<400> SEQUENCE: 64
ggcgattata aagatgacga tgataaacac catcaccacc atc         43

<210> SEQ ID NO 65
<211> LENGTH: 43
<212> TYPE: DNA
<213> ORGANISM: Artificial Sequence
<220> FEATURE:
<223> OTHER INFORMATION: Primer

<400> SEQUENCE: 65
gtttaaactc aatgatggtg gtgatggtgt ttatcatcgt cat         43

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
aaaatctaga gccgccacca tggccacagc tagacccccct         40

<210> SEQ ID NO 67
<211> LENGTH: 43
<212> TYPE: DNA
<213> ORGANISM: Artificial Sequence
<220> FEATURE:
<223> OTHER INFORMATION: Primer

<400> SEQUENCE: 67
cgtcatcttt ataatcgccg ctgttggcct ggatggtttc ctg         43

<210> SEQ ID NO 68
<211> LENGTH: 43
<212> TYPE: DNA
<213> ORGANISM: Artificial Sequence
<220> FEATURE:
<223> OTHER INFORMATION: Primer

<400> SEQUENCE: 68
aaaatctaga gccgccacca tggccagatc tctgctgctg ccc         43

<210> SEQ ID NO 69
<211> LENGTH: 43
<212> TYPE: DNA
<213> ORGANISM: Artificial Sequence
<220> FEATURE:
<223> OTHER INFORMATION: Primer

<400> SEQUENCE: 69
cgtcatcttt ataatcgccc cggtgtttct tcatggtgtc gtt         43

<210> SEQ ID NO 70
<211> LENGTH: 43
<212> TYPE: DNA
<213> ORGANISM: Artificial Sequence
<220> FEATURE:
<223> OTHER INFORMATION: Primer

<400> SEQUENCE: 70

-continued

```
aaaatctaga gccgccacca tgttcctcct cctcaccgcc ctc                    43

<210> SEQ ID NO 71
<211> LENGTH: 43
<212> TYPE: DNA
<213> ORGANISM: Artificial Sequence
<220> FEATURE:
<223> OTHER INFORMATION: Primer

<400> SEQUENCE: 71
cgtcatcttt ataatcgccc ttgtcgcgca tggtctcctc gat                    43

<210> SEQ ID NO 72
<211> LENGTH: 34
<212> TYPE: DNA
<213> ORGANISM: Artificial Sequence
<220> FEATURE:
<223> OTHER INFORMATION: Primer

<400> SEQUENCE: 72
aaaagtttaa actcaatgat ggtggtgatg gtgt                              34

<210> SEQ ID NO 73
<211> LENGTH: 43
<212> TYPE: DNA
<213> ORGANISM: Artificial Sequence
<220> FEATURE:
<223> OTHER INFORMATION: Primer

<400> SEQUENCE: 73
aaaatctaga gccgccacca tgggagtgtg gctgctgagc ctg                    43

<210> SEQ ID NO 74
<211> LENGTH: 58
<212> TYPE: DNA
<213> ORGANISM: Artificial Sequence
<220> FEATURE:
<223> OTHER INFORMATION: Primer

<400> SEQUENCE: 74
aaaagtttaa actcaatgat ggtggtgatg gtgccggtgg gtcttcatgg tttccatg    58

<210> SEQ ID NO 75
<211> LENGTH: 43
<212> TYPE: DNA
<213> ORGANISM: Artificial Sequence
<220> FEATURE:
<223> OTHER INFORMATION: Primer

<400> SEQUENCE: 75
aaaatctaga gccgccacca tgtttctgct gctgatcatc ctg                    43

<210> SEQ ID NO 76
<211> LENGTH: 56
<212> TYPE: DNA
<213> ORGANISM: Artificial Sequence
<220> FEATURE:
<223> OTHER INFORMATION: Primer

<400> SEQUENCE: 76
aaaagtttaa actcaatgat ggtggtgatg gtggttgctc tgcatggtcc gctgaa      56

<210> SEQ ID NO 77
<211> LENGTH: 10
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Wherein X at position 7 is defined as Nva

<400> SEQUENCE: 77

Arg Pro Lys Pro Val Glu Xaa Trp Arg Lys
1               5                   10

<210> SEQ ID NO 78
<211> LENGTH: 4
<212> TYPE: PRT
<213> ORGANISM: Artificial Sequence
<220> FEATURE:
<223> OTHER INFORMATION: Substrate

<400> SEQUENCE: 78

Leu Leu Val Tyr
1

<210> SEQ ID NO 79
<211> LENGTH: 4
<212> TYPE: PRT
<213> ORGANISM: Artificial Sequence
<220> FEATURE:
<223> OTHER INFORMATION: Substrate

<400> SEQUENCE: 79

Ala Ala Pro Val
1

<210> SEQ ID NO 80
<211> LENGTH: 4
<212> TYPE: PRT
<213> ORGANISM: Artificial Sequence
<220> FEATURE:
<223> OTHER INFORMATION: Substrate

<400> SEQUENCE: 80

Leu Ser Thr Arg
1

<210> SEQ ID NO 81
<211> LENGTH: 45
<212> TYPE: DNA
<213> ORGANISM: Artificial Sequence
<220> FEATURE:
<223> OTHER INFORMATION: Primer

<400> SEQUENCE: 81
agatgggtgt tgtctgatga cgacggccct cagttcggcc tgttc          45

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
gcaggggcca ttccggat          18

<210> SEQ ID NO 83
<211> LENGTH: 48
<212> TYPE: DNA
```

```
<213> ORGANISM: Artificial Sequence
<220> FEATURE:
<223> OTHER INFORMATION: Primer

<400> SEQUENCE: 83
aaaatctaga gccgccacca tgaagcacct gtggttcttt ctgctgct         48

<210> SEQ ID NO 84
<211> LENGTH: 44
<212> TYPE: DNA
<213> ORGANISM: Artificial Sequence
<220> FEATURE:
<223> OTHER INFORMATION: Primer

<400> SEQUENCE: 84
agacaacacc catctaggag cggccaccag cagcagaaag aacc             44

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85
atccggaatg gcccctgcga acccaagagc tgcgac                      36

<210> SEQ ID NO 86
<211> LENGTH: 30
<212> TYPE: DNA
<213> ORGANISM: Artificial Sequence
<220> FEATURE:
<223> OTHER INFORMATION: Primer

<400> SEQUENCE: 86
aaaagtttaa actcatttgc cggggctcag                             30

<210> SEQ ID NO 87
<211> LENGTH: 232
<212> TYPE: PRT
<213> ORGANISM: Homo sapiens

<400> SEQUENCE: 87
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 88
<211> LENGTH: 62
<212> TYPE: PRT
<213> ORGANISM: Homo sapiens

<400> SEQUENCE: 88

```
Glu Ala Ala Lys Glu Ile Cys Ser Glu Phe Arg Asp Gln Val Arg Asn
1               5                   10                  15

Gly Thr Leu Ile Cys Thr Arg Glu His Asn Pro Val Arg Gly Pro Asp
            20                  25                  30

Gly Lys Met His Gly Asn Lys Cys Ala Met Cys Ala Ser Val Phe Lys
        35                  40                  45

Leu Glu Glu Glu Glu Lys Lys Asn Asp Lys Glu Glu Lys Gly
    50                  55                  60
```

<210> SEQ ID NO 89
<211> LENGTH: 62
<212> TYPE: PRT
<213> ORGANISM: Homo sapiens

<400> SEQUENCE: 89

```
Glu Ala Val Gln Glu Leu Cys Ser Glu Tyr Arg His Tyr Val Arg Asn
1               5                   10                  15

Gly Arg Leu Pro Cys Thr Arg Glu Asn Asp Pro Ile Glu Gly Leu Asp
            20                  25                  30

Gly Lys Ile His Gly Asn Thr Cys Ser Met Cys Glu Ala Phe Phe Gln
        35                  40                  45

Gln Glu Ala Lys Glu Lys Glu Arg Ala Glu Pro Arg Ala Lys
    50                  55                  60
```

<210> SEQ ID NO 90
<211> LENGTH: 67
<212> TYPE: PRT
<213> ORGANISM: Homo sapiens

<400> SEQUENCE: 90

```
Ile Glu Cys Ala Lys Gln Thr Lys Gln Met Val Asp Cys Ser His Tyr
1               5                   10                  15

Lys Lys Leu Pro Pro Gly Gln Gln Arg Phe Cys His His Met Tyr Asp
            20                  25                  30

Pro Ile Cys Gly Ser Asp Gly Lys Thr Tyr Lys Asn Asp Cys Phe Phe
        35                  40                  45

Cys Ser Lys Val Lys Lys Thr Asp Gly Thr Leu Lys Phe Val His Phe
    50                  55                  60

Gly Lys Cys
```

<210> SEQ ID NO 91
<211> LENGTH: 227
<212> TYPE: PRT
<213> ORGANISM: Mus musculus

<400> SEQUENCE: 91

```
Arg Ile Val Asn Gly Ser Asp Cys Gln Lys Asp Ala Gln Pro Trp Gln
1               5                   10                  15

Gly Ala Leu Leu Leu Gly Pro Asn Lys Leu Tyr Cys Gly Ala Val Leu
            20                  25                  30

Ile Ser Pro Gln Trp Leu Leu Thr Ala Ala His Cys Arg Lys Pro Val
        35                  40                  45

Phe Arg Ile Arg Leu Gly His His Ser Met Ser Pro Val Tyr Glu Ser
    50                  55                  60

Gly Gln Gln Met Phe Gln Gly Ile Lys Ser Ile Pro His Pro Gly Tyr
65                  70                  75                  80

Ser His Pro Gly His Ser Asn Asp Leu Met Leu Ile Lys Met Asn Arg
                85                  90                  95

Lys Ile Arg Asp Ser His Ser Val Lys Pro Val Glu Ile Ala Cys Asp
            100                 105                 110

Cys Ala Thr Glu Gly Thr Arg Cys Met Val Ser Gly Trp Gly Thr Thr
        115                 120                 125

Ser Ser Ser His Asn Asn Phe Pro Lys Val Leu Gln Cys Leu Asn Ile
    130                 135                 140

Thr Val Leu Ser Glu Glu Arg Cys Lys Asn Ser Tyr Pro Gly Gln Ile
145                 150                 155                 160

Asp Lys Thr Met Phe Cys Ala Gly Asp Glu Glu Gly Arg Asp Ser Cys
                165                 170                 175

Gln Gly Asp Ser Gly Gly Pro Val Val Cys Asn Gly Lys Leu Gln Gly
            180                 185                 190

Leu Val Ser Trp Gly Asp Phe Pro Cys Ala Gln Arg Asn Arg Pro Gly
        195                 200                 205

Val Tyr Thr Asn Leu Cys Glu Phe Val Lys Trp Ile Lys Asp Thr Met
    210                 215                 220

Asn Ser Asn
225
```

<210> SEQ ID NO 92
<211> LENGTH: 225
<212> TYPE: PRT
<213> ORGANISM: Mus musculus

<400> SEQUENCE: 92

```
Arg Ile Ile Asp Gly Tyr Lys Cys Lys Glu Gly Ser His Pro Trp Gln
1               5                   10                  15

Val Ala Leu Leu Lys Gly Asn Gln Leu His Cys Gly Gly Val Leu Val
            20                  25                  30

Asp Lys Tyr Trp Val Leu Thr Ala Ala His Cys Lys Met Gly Gln Tyr
        35                  40                  45

Gln Val Gln Leu Gly Ser Asp Lys Ile Gly Asp Gln Ser Ala Gln Lys
    50                  55                  60

Ile Lys Ala Thr Lys Ser Phe Arg His Pro Gly Tyr Ser Thr Lys Thr
65                  70                  75                  80

His Val Asn Asp Ile Met Leu Val Arg Leu Asp Glu Pro Val Lys Met
```

```
                    85                  90                  95
Ser Ser Lys Val Glu Ala Val Gln Leu Pro Glu His Cys Glu Pro Pro
                100                 105                 110

Gly Thr Ser Cys Thr Val Ser Gly Trp Gly Thr Thr Ser Pro Asp
            115                 120                 125

Val Thr Phe Pro Ser Asp Leu Met Cys Ser Asp Val Lys Leu Ile Ser
            130                 135                 140

Ser Arg Glu Cys Lys Lys Val Tyr Lys Asp Leu Leu Gly Lys Thr Met
145                 150                 155                 160

Leu Cys Ala Gly Ile Pro Asp Ser Lys Thr Asn Thr Cys Asn Gly Asp
                165                 170                 175

Ser Gly Gly Pro Leu Val Cys Asn Asp Thr Leu Gln Gly Leu Val Ser
                180                 185                 190

Trp Gly Thr Tyr Pro Cys Gly Gln Pro Asn Asp Pro Gly Val Tyr Thr
                195                 200                 205

Gln Val Cys Lys Tyr Lys Arg Trp Val Met Glu Thr Met Lys Thr His
            210                 215                 220

Arg
225

<210> SEQ ID NO 93
<211> LENGTH: 227
<212> TYPE: PRT
<213> ORGANISM: Mus musculus

<400> SEQUENCE: 93

Ile Ile Gly Gly Tyr Arg Cys Val Arg Asn Ser Gln Pro Trp Gln Val
1               5                   10                  15

Ala Leu Gln Ala Gly Pro Gly His Arg Phe Leu Cys Gly Gly Val Leu
                20                  25                  30

Leu Ser Asp Gln Trp Val Ile Thr Ala Ala His Cys Ala Arg Pro Ile
            35                  40                  45

Leu His Val Ala Leu Gly Lys His Asn Ile Arg Arg Trp Glu Ala Thr
    50                  55                  60

Gln Gln Val Val Arg Val Ala Arg Gln Val Pro His Pro Gln Tyr Gln
65                  70                  75                  80

Pro Gln Ala His Asp Asn Asp Leu Met Leu Leu Lys Leu Gln Lys Lys
                85                  90                  95

Val Arg Leu Gly Arg Ala Val Lys Thr Ile Ser Val Ala Ser Ser Cys
                100                 105                 110

Ala Ser Pro Gly Thr Pro Cys Arg Val Ser Gly Trp Gly Thr Ile Ala
                115                 120                 125

Ser Pro Ile Ala Arg Tyr Pro Thr Ala Leu Gln Cys Val Asn Val Asn
            130                 135                 140

Ile Met Ser Glu Gln Ala Cys His Arg Ala Tyr Pro Gly Ile Ile Thr
145                 150                 155                 160

Ser Gly Met Val Cys Ala Gly Val Pro Glu Gly Gly Lys Asp Ser Cys
                165                 170                 175

Gln Gly Asp Ser Gly Gly Pro Leu Val Cys Gly Gly Gln Leu Gln Gly
            180                 185                 190

Leu Val Ser Trp Gly Met Glu Arg Cys Ala Met Pro Gly Tyr Pro Gly
            195                 200                 205

Val Tyr Ala Asn Leu Cys Asn Tyr His Ser Trp Ile Gln Arg Thr Met
    210                 215                 220
```

Gln Ser Asn
225

<210> SEQ ID NO 94
<211> LENGTH: 39
<212> TYPE: DNA
<213> ORGANISM: Artificial Sequence
<220> FEATURE:
<223> OTHER INFORMATION: primer

<400> SEQUENCE: 94
agatgggtgt tgtctgacgg ccctcagttc ggcctgttc                    39

<210> SEQ ID NO 95
<211> LENGTH: 891
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(891)

<400> SEQUENCE: 95

```
gac ggc cct cag ttc ggc ctg ttc agc aag tac aga acc cct aac tgc      48
Asp Gly Pro Gln Phe Gly Leu Phe Ser Lys Tyr Arg Thr Pro Asn Cys
1               5                   10                  15 gct aac act atg aaa cag gac tgt act cgt gaa tac gac cct gtg tgc      96
Ala Asn Thr Met Lys Gln Asp Cys Thr Arg Glu Tyr Asp Pro Val Cys
                20                  25                  30 ggc agc gac atg agc acc tac gcc aat gag tgc acc ctg tgc atg aag    144
Gly Ser Asp Met Ser Thr Tyr Ala Asn Glu Cys Thr Leu Cys Met Lys
            35                  40                  45 atc aga gaa ggc ggc cac aac atc aag atc atc cgg aat ggc ccc tgc    192
Ile Arg Glu Gly Gly His Asn Ile Lys Ile Ile Arg Asn Gly Pro Cys
        50                  55                  60 gaa ccc aag agc tgc gac aag acc cac acc tgt ccc cct tgt cct gcc    240
Glu Pro Lys Ser Cys Asp Lys Thr His Thr Cys Pro Pro Cys Pro Ala
65                  70                  75                  80 ccc gaa ctg ctg gga gga cct agc gtg ttc ctg ttc ccc cca aag ccc    288
Pro Glu Leu Leu Gly Gly Pro Ser Val Phe Leu Phe Pro Pro Lys Pro
                85                  90                  95 aag gac acc ctg atg atc agc cgg acc ccc gaa gtg acc tgc gtg gtg    336
Lys Asp Thr Leu Met Ile Ser Arg Thr Pro Glu Val Thr Cys Val Val
                100                 105                 110 gtg gat gtg tcc cac gag gac cct gaa gtg aag ttc aat tgg tac gtg    384
Val Asp Val Ser His Glu Asp Pro Glu Val Lys Phe Asn Trp Tyr Val
            115                 120                 125 gac ggc gtg gaa gtg cac aac gcc aag acc aag cct aga gag gaa cag    432
Asp Gly Val Glu Val His Asn Ala Lys Thr Lys Pro Arg Glu Glu Gln
        130                 135                 140 tac aac tcc acc tac cgg gtg gtg tct gtg ctg aca gtg ctg cat cag    480
Tyr Asn Ser Thr Tyr Arg Val Val Ser Val Leu Thr Val Leu His Gln
145                 150                 155                 160 gac tgg ctg aac ggc aaa gag tac aag tgc aag gtg tcc aac aag gcc    528
Asp Trp Leu Asn Gly Lys Glu Tyr Lys Cys Lys Val Ser Asn Lys Ala
                165                 170                 175 ctg cct gcc ccc atc gag aaa acc atc agc aag gcc aag ggc cag ccc    576
Leu Pro Ala Pro Ile Glu Lys Thr Ile Ser Lys Ala Lys Gly Gln Pro
                180                 185                 190 cgc gaa ccc cag gtg tac aca ctg ccc cct agc cgg gaa gag atg acc    624
Arg Glu Pro Gln Val Tyr Thr Leu Pro Pro Ser Arg Glu Glu Met Thr
            195                 200                 205
```

```
aag aac cag gtg tcc ctg acc tgt ctc gtg aaa ggc ttc tac ccc agc      672
Lys Asn Gln Val Ser Leu Thr Cys Leu Val Lys Gly Phe Tyr Pro Ser
    210                 215                 220 gac att gcc gtg gaa tgg gag agc aac ggc cag ccc gag aac aac tac      720
Asp Ile Ala Val Glu Trp Glu Ser Asn Gly Gln Pro Glu Asn Asn Tyr
225                 230                 235                 240 aag acc acc ccc cct gtg ctg gac agc gac ggc tca ttc ttc ctg tac      768
Lys Thr Thr Pro Pro Val Leu Asp Ser Asp Gly Ser Phe Phe Leu Tyr
                245                 250                 255 agc aag ctg acc gtg gac aag agc cgg tgg cag cag ggc aac gtg ttc      816
Ser Lys Leu Thr Val Asp Lys Ser Arg Trp Gln Gln Gly Asn Val Phe
            260                 265                 270 agc tgc agc gtg atg cac gag gcc ctg cac aac cac tac acc cag aag      864
Ser Cys Ser Val Met His Glu Ala Leu His Asn His Tyr Thr Gln Lys
        275                 280                 285 tcc ctg agc ctg agc ccc ggc aaa tga                                  891
Ser Leu Ser Leu Ser Pro Gly Lys
    290                 295
```

<210> SEQ ID NO 96
<211> LENGTH: 296
<212> TYPE: PRT
<213> ORGANISM: Artificial Sequence
<220> FEATURE:
<223> OTHER INFORMATION: Synthetic Construct

<400> SEQUENCE: 96

```
Asp Gly Pro Gln Phe Gly Leu Phe Ser Lys Tyr Arg Thr Pro Asn Cys
1               5                   10                  15

Ala Asn Thr Met Lys Gln Asp Cys Thr Arg Glu Tyr Asp Pro Val Cys
            20                  25                  30

Gly Ser Asp Met Ser Thr Tyr Ala Asn Glu Cys Thr Leu Cys Met Lys
        35                  40                  45

Ile Arg Glu Gly Gly His Asn Ile Lys Ile Ile Arg Asn Gly Pro Cys
    50                  55                  60

Glu Pro Lys Ser Cys Asp Lys Thr His Thr Cys Pro Pro Cys Pro Ala
65                  70                  75                  80

Pro Glu Leu Leu Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser His Glu Asp Pro Glu Val Lys Phe Asn Trp Tyr Val
        115                 120                 125

Asp Gly Val Glu Val His Asn Ala Lys Thr Lys Pro Arg Glu Glu Gln
    130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Glu Glu Met Thr
        195                 200                 205

Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240
```

```
Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 97
<211> LENGTH: 62
<212> TYPE: PRT
<213> ORGANISM: Homo sapiens

<400> SEQUENCE: 97

Pro Gln Phe Gly Leu Phe Ser Lys Tyr Arg Thr Pro Asn Cys Ser Gln
1               5                   10                  15

Tyr Arg Leu Pro Gly Cys Pro Arg His Phe Asn Pro Val Cys Gly Ser
            20                  25                  30

Asp Met Ser Thr Tyr Ala Asn Glu Cys Thr Leu Cys Met Lys Ile Arg
        35                  40                  45

Glu Gly Gly His Asn Ile Lys Ile Ile Arg Asn Gly Pro Cys
    50                  55                  60

<210> SEQ ID NO 98
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as Succinyl
      derivative of Leucine
<220> FEATURE:
<221> NAME/KEY: MISC_FEATURE
<222> LOCATION: (4)..(4)
<223> OTHER INFORMATION: Wherein X at position 4 is defined as 7-amido-
      4-methylcoumarin derivative of Tyrosine

<400> SEQUENCE: 98

Xaa Leu Val Xaa
1

<210> SEQ ID NO 99
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as Methoxy-
      succinyl derivative of Alanine
<220> FEATURE:
<221> NAME/KEY: MISC_FEATURE
<222> LOCATION: (4)..(4)
<223> OTHER INFORMATION: Wherein X at position 4 is defined as 7-amido-
      4-methylcoumarin derivative of Valine

<400> SEQUENCE: 99

Xaa Ala Pro Xaa
1
```

```
<210> SEQ ID NO 100
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      t-Butyloxycarbonyl derivative of Leucine
<220> FEATURE:
<221> NAME/KEY: MISC_FEATURE
<222> LOCATION: (4)..(4)
<223> OTHER INFORMATION: Wherein X at position 4 is defined as 7-amido-
      4-methylcoumarin derivative of Arginine

<400> SEQUENCE: 100

Xaa Ser Thr Xaa
1

<210> SEQ ID NO 101
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as 7-amido-
      4-methylcoumarin derivative of Arginine
<220> FEATURE:
<221> NAME/KEY: MISC_FEATURE
<222> LOCATION: (7)..(7)
<223> OTHER INFORMATION: Wherein X at position 7 is defined as Nva
<220> FEATURE:
<221> NAME/KEY: MISC_FEATURE
<222> LOCATION: (10)..(10)
<223> OTHER INFORMATION: Wherein X at position 10 is defined as
      2,4-dinitrophenol derivative of Lysine

<400> SEQUENCE: 101

Xaa Pro Lys Pro Val Glu Xaa Trp Arg Xaa
1               5                   10
```

KLK5 INHIBITORY PEPTIDE

CROSS REFERENCE TO RELATED APPLICATIONS

This application is a continuation of application Ser. No. 17/326,280, filed May 20, 2021, now U.S. Pat. No. 11,292,828, which is a continuation of application Ser. No. 17/064,543, filed Oct. 6, 2020, which is a continuation of International Application No. PCT/JP2019/043384, filed Nov. 6, 2019, which claims priority to Japanese Application No. 2018-209729, filed Nov. 7, 2018, each expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 1660-P100USCON3_Seq_List_FINAL_20220606_ST25.txt. The text file is 159,960 bytes in size; was created on Jun. 6, 2022; and has been submitted via EFS-Web.

TECHNICAL FIELD

The present invention relates to a peptide, a polynucleotide, a vector, a cell, a method for producing the peptide, a peptide obtained by such a method, a conjugate containing the peptide, a composition containing the peptide or the conjugate, a pharmaceutical composition, the pharmaceutical composition for treating or preventing various diseases, use of the peptide or the conjugate for treating or preventing various diseases, a method for treating various diseases that includes the step of administering the peptide or the conjugate, a composition for diagnosing or testing various diseases that contains the peptide or the conjugate, and the like.

BACKGROUND ART

Kallikrein 5 (KLK5) is a trypsin-like serine protease (Clan PA, family S1) and is also called a stratum corneum tryptic enzyme (SCTE). Kallikrein 7 (KLK7) is a chymotrypsin-like protease (Clan PA, family S1) and is also called a stratum corneum chymotryptic enzyme (SCCE). Further, kallikrein 14 (KLK14) is a trypsin-like protease (Clan PA, family S1). KLK5, KLK7, and KLK14 belong to a tissue kallikrein family composed of 15 types of highly conserved trypsin- or chymotrypsin-like serine proteases. KLK5 is expressed in cells and thereafter converted into active KLK5 by autoactivation, whereas KLK7 and KLK14 are expressed as inactive preproenzymes and converted into active forms by cleavage of their preprosequences by proteases represented by KLK5 (Non Patent Literature 1). Expression of KLK5 has been observed in the skin, and it is reported to degrade factors related to cell adhesion such as Desmoglein and Desmocollin (Non Patent Literature 2). KLK5, KLK7, and KLK14 are important for skin desquamation and are further involved in activation of proteinase-activated receptor 2 (PAR-2) (Non Patent Literature 3). Activation of PAR-2 induces cytokines and chemokines and enhances immunity, inflammation reactions, and the like.

Netherton syndrome is one of the ichthyosis syndromes with severe skin inflammation, desquamation, abnormal hair, and allergic symptoms such as asthma and allergic dermatitis due to autosomal recessive inheritance, and is a rare disease (OMIM256500) (Non Patent Literature 4). Since exfoliative dermatitis develops from the time of birth, dehydration, infection, or the like may be caused by significant damage to the skin barrier function and may be accompanied by developmental delay. Although detailed epidemiological data is not available, it is said that high postnatal mortality is exhibited. Netherton syndrome develops due to the loss of function of a serine protease inhibitor (LEKTI) following a mutation of a gene (SPINK5) encoding LEKTI expressed in skin epithelial cells. LEKTI is composed of 15 Kazal-like inhibitor domains. In patients with Netherton syndrome, a plurality of mutation sites has been found in SPINK5 across the sequence encoding each domain, and symptoms and severity change in association with the mutation sites (Non Patent Literatures 4 and 5).

SPINK5-deficient mice (Spink5$^{-/-}$) exhibit Netherton syndrome-like skin symptoms, and high protease activity of KLK5 and KLK7 is observed in the skin epithelium (Non Patent Literature 1). Although SPINK5-deficient mice die within several hours after birth, improvement of neonatal mortality is reported in mice (Spink5$^{-/-}$Klk5$^{-/-}$) obtained by crossing KLK5-deficient mice with SPINK5-deficient mice (Non Patent Literature 6). Further, in Spink5-/- Klk5$^{-/-}$ mice, severe skin barrier defects, epithelium structural defects, skin inflammation, and the like observed in Spink5$^{-/-}$ have been recovered. Likewise, mice with the SPINK5 mutation Spink5$^{A135X/A135X}$ observed in patients with Netherton syndrome show Netherton syndrome-like skin symptoms, and death is observed within 12 hours after birth, whereas skin barrier and severe skin symptoms are improved in Klk5$^{-/-}$Spink5$^{A135X/A135X}$ obtained by crossing with KLK5-deficient mice (Non Patent Literature 7). Further, abnormal skin symptoms are eliminated by crossing with KLK7-deficient mice (Klk5$^{-/-}$Klk7$^{-/-}$Spink5$^{A135X/A135X}$). It has been reported that KLK5 transgenic mice also show Netherton syndrome-like skin symptoms (Non Patent Literature 8). High protease activity like trypsin and chymotrypsin is observed in the stratum corneum of patients with Netherton syndrome and Netherton syndrome model mice, and it is suggested that the kallikrein family located downstream, such as KLK7 and KLK14, are related to the protease activity in the stratum corneum, in addition to KLK5. From the above, it is considered that Netherton syndrome is caused by a gene mutation of SPINK5 and develops with abnormally elevated KLK5, KLK7, or KLK14 protease activity in the corneum. Currently, there is no fundamental therapeutic agent but only symptomatic treatment such as application of humectants.

KLK5 has also been suggested to be associated with rosacea, which is a chronic inflammatory disease of the face. In rosacea patients, increased expressions of KLK5 and the antimicrobial peptide Cathelicidin have been reported. Although the details of its etiology are unknown, it is considered that KLK5 with elevated expression degrades Cathelicidin, thereby producing a peptide that causes rosacea (Non Patent Literature 9).

There are multiple reports that SPINK5 polymorphisms are associated with the severity of atopic dermatitis (Non Patent Literatures 10 to 14). It has been reported that, in the skin of atopic dermatitis patients having SPINK5 genes encoding LEKTI in which amino acid residue 420 is lysine in both alleles, the expression of Desmoglein1 is decreased at the protein level, and the activity of proteases, including KLK5 and KLK7, is increased, as compared with the case in which glutamic acid is encoded in both alleles (Non Patent Literature 15). It is considered that the activation of these proteases facilitates the invasion of allergens due to a decrease in skin barrier function and creates a condition where an inflammation reaction easily occurs.

SPINK2 (Serine Protease Inhibitor Kazal-type 2) is composed of a Kazal-like domain having three disulfide bonds and functions as a trypsin/acrosin inhibitor (Non Patent Literature 16), but the relationship of SPINK2 and its mutants to diseases such as Netherton syndrome, rosacea, and atopic dermatitis has not been clarified.

CITATION LIST

Non Patent Literatures

Non Patent Literature 1: Ovaere P, et al., published in 2009, Trends Biochem Sci., Vol. 34, No. 9: pp. 453-463
Non Patent Literature 2: Descargues P, et al., published in 2005, Nat Genet., Vol. 37, No. 1: pp. 56-65
Non Patent Literature 3: Rattenholl A, et al., published in 2008, Drug News Perspect., Vol. 21, No. 7: pp. 369-381
Non Patent Literature 4: Hovnanian A., published in 2013, Cell Tissue Res., Vol. 351, No. 2: pp. 289-300
Non Patent Literature 5: Sarri C A, et al., published in 2017, Mol Diagn Ther., Vol. 21, No. 2: pp. 137-152
Non Patent Literature 6: Furio L, et al., published in 2015, PLoS Genet., Vol. 11, No. 9: e1005389
Non Patent Literature 7: Kasparek P, et al., published in 2017, PLoS Genet., Vol. 13, No. 1: e1006566
Non Patent Literature 8: Furio L, et al., published in 2014, J Exp Med., Vol. 211, No. 3: pp. 499-513
Non Patent Literature 9: Yamasaki K, et al., published in 2007, Nat Med., Vol. 13, No. 8: pp. 975-980
Non Patent Literature 10: Nishio Y, et al., published in 2003, Genes Immun., Vol. 4, No. 7: pp. 515-517
Non Patent Literature 11: Kusunoki T, et al., published in 2005, J Allergy Clin Immunol., Vol. 4, No. 7: pp. 515-517
Non Patent Literature 12: Lan C C, et al., published in 2011, Exp Dermatol., Vol. 20, No. 12: pp. 975-979
Non Patent Literature 13: Kato A, et al., published in 2003, Br J Dermatol., Vol. 148, No. 4: pp. 665-669
Non Patent Literature 14: Zhao L P, et al., published in 2012, J Eur Acad Dermatol Venereol., Vol. 26, No. 5: pp. 572-577
Non Patent Literature 15: Fortugno P, et al., published in 2012, Hum Mol Genet., Vol. 21, No. 19: pp. 4187-4200
Non Patent Literature 16: Chen T, et al., published in 2009, Proteins., Vol. 77, No. 1: pp. 209-219

SUMMARY OF INVENTION

Technical Problem

An object of the present invention is to provide a novel KLK5 inhibitory peptide, a conjugate containing the peptide, a pharmaceutical composition containing the peptide or the conjugate, and the like.

Solution to Problem

The present invention relates to:
(1) A SPINK2 mutant peptide that comprises the amino acid sequence set forth in SEQ ID NO: 61 (FIG. 69) and inhibits the protease activity of active human KLK5;
(2) The peptide according to (1), wherein the peptide inhibits the protease activity of human KLK7 or human KLK14;
(3) The peptide according to (1), wherein the peptide selectively inhibits human KLK5 and optionally human KLK7 or KLK14;
(4) The peptide according to any one of (1) to (3), wherein Xaa16 ($X_1$) is Ala, Asp, Gly, Gln, Leu, Ser, or Thr;
(5) The peptide according to any one of (1) to (4), wherein Xaa17 ($X_2$) is Arg, Glu, Asn, Gln, or Ser;
(6) The peptide according to any one of (1) to (5), wherein Xaa18 ($X_3$) is Asp, Gln, Ile, Thr, Trp, or Tyr;
(7) The peptide according to any one of (1) to (6), wherein Xaa19 ($X_4$) is Arg, Gly, Met, Gln, or Thr;
(8) The peptide according to any one of (1) to (7), wherein Xaa20 ($X_5$) is Asp, Glu, Leu, Lys, Thr, or Tyr;
(9) The peptide according to any one of (1) to (8), wherein Xaa21 ($X_6$) is Glu, Gly, His, Leu, Ser, Gln, or Tyr;
(10) The peptide according to any one of (1) to (9), wherein Xaa22 ($X_7$) is Asp, Gly, Gln, Ser, or Tyr;
(11) The peptide according to any one of (1) to (10), wherein Xaa24 ($X_8$) is Ala, Asp, Glu, Gly, Asn, Ser, or Thr;
(12) The peptide according to any one of (1) to (11), wherein Xaa25 ($X_9$) is Arg or Lys;
(13) The peptide according to any one of (1) to (12), wherein Xaa26 ($X_{10}$) is Asp, Glu, Gln, Ser, or Val;
(14) The peptide according to any one of (1) to (13), wherein Xaa27 ($X_{11}$) is Phe or Tyr;
(15) The peptide according to any one of (1) to (14), wherein Xaa28 ($X_{12}$) is Asp or Glu;
(16) The peptide according to any one of (1) to (15), wherein the peptide comprises the amino acids at positions 1 to 63 in the amino acid sequence set forth in any one of SEQ ID NOs: 6, 8, 10, 12, 14, 16, 18, and 20 (FIGS. 14, 16, 18, 20, 22, 24, 26, and 28);
(17) The peptide according to any one of (1) to (3), wherein Xaa16 ($X_1$) is Gly, Met, or Tyr;
(18) The peptide according to any one of (1) to (3) and (17), wherein Xaa17 ($X_2$) is Glu, Gln, or Thr;
(19) The peptide according to any one of (1) to (3), (17), and (18), wherein Xaa18 ($X_3$) is His, Met, or Tyr;
(20) The peptide according to any one of (1) to (3) and (17) to (19), wherein Xaa19 ($X_4$) is Ala, Arg, Lys, or Gln;
(21) The peptide according to any one of (1) to (3) and (17) to (20), wherein Xaa20 ($X_5$) is Gly, Arg, or Ser;
(22) The peptide according to any one of (1) to (3) and (17) to (21), wherein Xaa21 ($X_6$) is Arg, Lys, Gln, or Ser;
(23) The peptide according to any one of (1) to (3) and (17) to (22), wherein Xaa22 ($X_7$) is Gly;
(24) The peptide according to any one of (1) to (3) and (17) to (23), wherein Xaa24 ($X_8$) is His, Thr, or Tyr;
(25) The peptide according to any one of (1) to (3) and (17) to (24), wherein Xaa25 ($X_9$) is His or Tyr;
(26) The peptide according to any one of (1) to (3) and (17) to (25), wherein Xaa26 ($X_{10}$) is Asp, Glu, or His;
(27) The peptide according to any one of (1) to (3) and (17) to (26), wherein Xaa27 ($X_{11}$) is Tyr;
(28) The peptide according to any one of (1) to (3) and (17) to (27), wherein Xaa28 ($X_{12}$) is Asp or Glu;
(29) The peptide according to any one of (1) to (3) and (17) to (28), wherein the peptide comprises the amino acids at positions 1 to 63 in the amino acid sequence set forth in any one of SEQ ID NOs: 22, 24, 26, and 28 (FIGS. 30, 32, 34, and 36);
(30) The peptide according to any one of (1) to (3), wherein Xaa16 ($X_1$) is Gly, Ser, or Tyr;

(31) The peptide according to any one of (1) to (3) and (30), wherein Xaa17 ($X_2$) is Asp or Gln;
(32) The peptide according to any one of (1) to (3), (30), and (31), wherein Xaa18 ($X_3$) is Thr or Val;
(33) The peptide according to any one of (1) to (3) and (30) to (32), wherein Xaa19 ($X_4$) is Thr or Val;
(34) The peptide according to any one of (1) to (3) and (30) to (33), wherein Xaa20 ($X_5$) is Glu or Thr;
(35) The peptide according to any one of (1) to (3) and (30) to (34), wherein Xaa21 ($X_6$) is His or Thr;
(36) The peptide according to any one of (1) to (3) and (30) to (35), wherein Xaa22 ($X_7$) is Tyr;
(37) The peptide according to any one of (1) to (3) and (30) to (36), wherein Xaa24 ($X_8$) is Asn or Ser;
(38) The peptide according to any one of (1) to (3) and (30) to (37), wherein Xaa25 ($X_9$) is Arg;
(39) The peptide according to any one of (1) to (3) and (30) to (38), wherein Xaa26 ($X_{10}$) is Asp or Glu;
(40) The peptide according to any one of (1) to (3) and (30) to (39), wherein Xaa27 ($X_{11}$) is Tyr;
(41) The peptide according to any one of (1) to (3) and (30) to (40), wherein Xaa28 ($X_{18}$) is Asp;
(42) The peptide according to any one of (1) to (3) and (30) to (41), wherein the peptide comprises the amino acids at positions 1 to 63 in the amino acid sequence set forth in any one of SEQ ID NOs: 30 and 32 (FIGS. 38 and 40);
(43) The peptide according to any one of (1) to (42), wherein the peptide has three disulfide bonds and has a three-dimensional structure characterized by including a loop structure, an α-helix, and a β-sheet;
(44) A polynucleotide comprising a nucleotide sequence encoding the amino acid sequence of the peptide according to any one of (1) to (43);
(45) A vector comprising the polynucleotide according to (44);
(46) A cell that comprises the polynucleotide according to (44) or the vector according to (45) or produces the peptide according to any one of (1) to (43);
(47) A method for producing a SPINK2 mutant peptide, comprising the steps (i) and (ii) below: (i) culturing the cell according to (46); and (ii) collecting the SPINK2 mutant peptide from the culture;
(48) A method for producing the peptide according to any one of (1) to (43), comprising a step of preparing the peptide by chemical synthesis or in-vitro translation;
(49) A SPINK2 mutant peptide obtained by the method according to (47) or (48);
(50) A conjugate comprising the peptide according to any one of (1) to (43) and (49) wherein the peptide is bound by one and optionally more than one moiety;
(51) The conjugate according to (50), wherein the one or more optional moiety comprises a second peptide that is not the SPINK2 mutant;
(52) The conjugate according to (51), wherein the second peptide is located on the amino terminal side of the SPINK2 mutant;
(53) The conjugate according to (51), wherein the second peptide is located on the carboxyl terminal side of the SPINK2 mutant;
(54) The conjugate according to any one of (51) to (53), wherein the second peptide is an antibody or a fragment thereof and comprises one or more Fc regions;
(55) The conjugate according to (54), wherein the or each Fc region is an Fc region of human immunoglobulin, or a fragment thereof;
(56) The conjugate according to (54) or (55), wherein the or each Fc region is an Fc region of IgG1, IgG2, IgG3, IgG4, IgM, IgA1, IgA2, IgD, and/or IgE, or a fragment thereof;
(57) The conjugate according to any one of (54) to (56), wherein the or each Fc region is an Fc region of human IgG1, or a fragment thereof;
(58) The conjugate according to (57), wherein the or each Fc region of human IgG1 comprises the amino acid sequence set forth in SEQ ID NO: 87 (FIG. 95);
(59) The conjugate according to any one of (54) to (57), wherein the or each Fc region is a wild type or a mutant Fc region;
(60) The conjugate according to any one of (51) to (59), wherein the conjugate comprises one to several aspartic acids and/or glutamic acids added to the amino terminus thereof;
(61) The conjugate according to any one of (50) to (60), wherein the conjugate comprises the amino acid sequence described in (i) or (ii) below: (i) the amino acid sequence set forth in any one of SEQ ID NOs: 34, 36, 38, 40, 42, 44, 46, 48, 50, 52, 54, 56, 58, 60, and 96 (FIGS. 42, 44, 46, 48, 50, 52, 54, 56, 58, 60, 62, 64, 66, 68, and 106); or (ii) the amino acid sequence of a conjugate that is 90% or more identical to the amino acid sequence described in (i) above and inhibits the protease activity of KLK5;
(62) The conjugate according to any one of (51) to (61), wherein the SPINK2 mutant and the second peptide are linked to each other via a linker;
(63) The conjugate according to (62), wherein the linker is a third peptide that is not the SPINK2 mutant or the second peptide;
(64) A method for producing the conjugate according to any one of (50) to (63), comprising the steps (i) and (ii) below: (i) culturing a cell comprising a polynucleotide comprising a nucleotide sequence encoding an amino acid sequence of the conjugate or a vector in which the polynucleotide is inserted; and (ii) collecting a SPINK2 mutant peptide conjugate or a peptide moiety comprised in the conjugate from the culture;
(65) A method for producing the SPINK2 mutant peptide conjugate according to any one of (50) to (63), comprising a step of preparing the conjugate or a peptide moiety comprised in the conjugate by chemical synthesis or in-vitro translation;
(66) A SPINK2 mutant peptide conjugate obtained by the method according to (64) or (65);
(67) An antibody or a binding fragment thereof that binds to the peptide according to any one of (1) to (43) and (49);
(68) A composition comprising the peptide according to any one of (1) to (43) and (49), the polynucleotide according to (44), the vector according to (45), the cell according to (46), the conjugate according to any one of (50) to (63) and (66), and/or the antibody or the binding fragment thereof according to (67);
(69) A pharmaceutical composition comprising the peptide according to any one of (1) to (43) and (49), the polynucleotide according to (44), the vector according to (45), the cell according to (46), and/or the conjugate according to any one of (50) to (63) and (66);
(70) The pharmaceutical composition according to (69), for treating or preventing a KLK5-related disease;
(71) The pharmaceutical composition according to (70), wherein the KLK5-related disease is Netherton syndrome, atopic dermatitis, rosacea, UV-induced skin injury, psoriasis, asthma, spinal cord injury, cancer, or Barrett's esophagus;

(72) The pharmaceutical composition according to any one of (69) to (71), for use in combination with an additional pharmaceutical product;

(73) A composition for testing or diagnosis comprising the peptide according to any one of (1) to (43) and (49), the polynucleotide according to (44), the vector according to (45), the cell according to (46), the conjugate according to any one of (50) to (63) and (66), and/or the antibody or the binding fragment thereof according to (67);

(74) The method according to any one of (47), (48), (64), and (65), comprising a step of performing affinity purification using the antibody or the binding fragment thereof according to (67);

(75) A method for identifying a KLK5 inhibitory SPINK2 mutant peptide, comprising the steps (i) to (iii) below: (i) incubating a KLK5 protease and a substrate in the presence and absence of a test SPINK2 mutant peptide; (ii) measuring the protease activity of KLK5 in the presence and absence of the test SPINK2 mutant peptide; and (iii) determining the peptide to be positive when the protease activity of KLK5 in the presence of the peptide is lower than the protease activity of KLK5 in the absence of the peptide;

(76) A method for identifying a KLK5 inhibitory compound, comprising the steps (i) to (iii) below, using a peptide comprising the amino acid sequence set forth in any one of SEQ ID NOs: 6, 8, 10, 12, 14, 16, 18, 20, 22, 24, 26, 28, 30, and 32 (FIGS. 14, 16, 18, 20, 22, 24, 26, 28, 30, 32, 34, 36, 38, and 40) or a conjugate comprising the peptide as a reference compound: (i) incubating a KLK5 protease and a substrate in the presence and absence of a test compound; (ii) measuring the protease activity of KLK5 in the presence and absence of the test compound; and (iii) determining the test compound to be positive when the protease activity of KLK5 in the presence of the test compound is lower than the protease activity of KLK5 in the absence of the test compound;

(77) A method for identifying a KLK5 inhibitory compound, comprising the steps (i) to (iii) below: (i) measuring a protease inhibitory activity against KLK5 of a test compound; (ii) measuring a protease inhibitory activity against KLK5 of a reference compound that is a peptide comprising the amino acid sequence set forth in any one of SEQ ID NOs: 6, 8, 10, 12, 14, 16, 18, 20, 22, 24, 26, 28, 30, and 32 (FIGS. 14, 16, 18, 20, 22, 24, 26, 28, 30, 32, 34, 36, 38, and 40) or a conjugate comprising the peptide; and (iii) determining the test compound to be positive when the protease inhibitory activity against KLK5 of the test compound is equivalent to or higher than the protease inhibitory activity against KLK5 of the reference compound;

(78) A method of measuring a KLK5 protease activity, comprising the steps (i) and (ii) below, using a peptide comprising the amino acid sequence set forth in any one of SEQ ID NOs: 6, 8, 10, 12, 14, 16, 18, 20, 22, 24, 26, 28, 30, and 32 (FIGS. 14, 16, 18, 20, 22, 24, 26, 28, 30, 32, 34, 36, 38, and 40) or a conjugate comprising the peptide as a reference compound: (i) incubating a KLK5 protease with a substrate, and optionally another component; and (ii) measuring an amount of the substrate and/or an amount of a product after step (i);

(79) A KLK5 inhibitory SPINK2 mutant peptide or a SPINK2 mutant peptide conjugate, having a dissociation constant ($K_D$) for KLK5, as measured by surface plasmon resonance analysis by immobilizing the peptide or the conjugate and adding KLK5 thereto, of $1 \times 10^{-9}$ M or less;

(80) A conjugate comprising the amino acid sequence set forth in SEQ ID NO: 34 (FIG. 42);

(81) A conjugate comprising the amino acid sequence set forth in SEQ ID NO: 36 (FIG. 44);

(82) A conjugate comprising the amino acid sequence set forth in SEQ ID NO: 38 (FIG. 46);

(83) A conjugate comprising the amino acid sequence set forth in SEQ ID NO: 40 (FIG. 48);

(84) A conjugate comprising the amino acid sequence set forth in SEQ ID NO: 42 (FIG. 50);

(85) A conjugate comprising the amino acid sequence set forth in SEQ ID NO: 44 (FIG. 52);

(86) A conjugate comprising the amino acid sequence set forth in SEQ ID NO: 46 (FIG. 54);

(87) A conjugate comprising the amino acid sequence set forth in SEQ ID NO: 48 (FIG. 56);

(88) A conjugate comprising the amino acid sequence set forth in SEQ ID NO: 50 (FIG. 58);

(89) A conjugate comprising the amino acid sequence set forth in SEQ ID NO: 52 (FIG. 60);

(90) A conjugate comprising the amino acid sequence set forth in SEQ ID NO: 54 (FIG. 62);

(91) A conjugate comprising the amino acid sequence set forth in SEQ ID NO: 56 (FIG. 64);

(92) A conjugate comprising the amino acid sequence set forth in SEQ ID NO: 58 (FIG. 66);

(93) A conjugate comprising the amino acid sequence set forth in SEQ ID NO: 60 (FIG. 68); and

(94) A conjugate comprising the amino acid sequence set forth in SEQ ID NO: 96 (FIG. 106).

Advantageous Effects of Invention

A peptide provided by the present invention, a conjugate containing the peptide, and a pharmaceutical composition containing the peptide or the conjugate have KLK5 inhibitory activity and are useful for treating or preventing KLK5-related diseases (which will be described below).

BRIEF DESCRIPTION OF DRAWINGS

FIG. 1 includes views for comparing the similarities in the amino acid sequences of human KLK5 (SEQ ID NO: 2), KLK7 (SEQ ID NO: 3), and KLK14 (SEQ ID NO: 4).

FIG. 3A includes graphs to evaluate the cross-reactivity of each inhibitory peptide with proteases, using the degradation of a peptide substrate as an index. For evaluating the Bovine trypsin inhibitory activity, trypsin (Pierce, 20233) with a final concentration of 5 nM and a substrate peptide Boc-Val-Pro-Arg-AMC (R&D Systems, Inc., ES011) with a final concentration of 100 μM were used. For evaluating the Human trypsin inhibitory activity, trypsin (Sigma-Aldrich Co. LLC, T6424) with a final concentration of 1 nM and a substrate peptide Boc-Val-Pro-Arg-AMC (R&D Systems, Inc., ES011) with a final concentration of 100 μM were used. For evaluating the Bovine α-chymotrypsin inhibitory activity, chymotrypsin (Worthington Biochemical Corporation, LS001434) with a final concentration of 10 nM and a substrate peptide Suc-Leu-Leu-Val-Tyr-MCA (SEQ ID NO: 98)(PEPTIDE INSTITUTE, INC., 3120-v) with a final concentration of 100 μM were used.

FIG. 3B includes graphs to evaluate the cross-reactivity of each inhibitory peptide with proteases, using the degradation of a peptide substrate as an index. For evaluating the Human chymotrypsin inhibitory activity, chymotrypsin (Sigma-Aldrich Co. LLC, C8946) with a final concentration of 10 nM and a substrate peptide Suc-Leu-Leu-Val-Tyr-MCA (SEQ ID NO: 98) (PEPTIDE INSTITUTE, INC., 3120-v) with a final concentration of 10 μM were used. For evaluating the Human tryptase inhibitory activity, tryptase (Sigma-Aldrich Co. LLC, T7063) with a final concentration of 1 nM and a substrate peptide Boc-Phe-Ser-Arg-MCA (PEPTIDE INSTITUTE, INC., 3107-v) with a final concentration of 100 μM were used. For evaluating the Human chymase inhibitory activity, chymase (Sigma-Aldrich Co. LLC, C8118) with a final concentration of 100 nM and a substrate peptide Suc-Leu-Leu-Val-Tyr-MCA (SEQ ID NO: 98) (PEPTIDE INSTITUTE, INC., 3120-v) with a final concentration of 100 μM were used.

FIG. 3C includes graphs to evaluate the cross-reactivity of each inhibitory peptide with proteases, using the degradation of a peptide substrate as an index. For evaluating the Human plasmin inhibitory activity, plasmin (Sigma-Aldrich Co. LLC, P1867) with a final concentration of 50 nM and a substrate peptide Boc-Val-Leu-Lys-MCA (PEPTIDE INSTITUTE, INC., 3104-v) with a final concentration of 100 μM were used. For evaluating the Human thrombin inhibitory activity, thrombin (Sigma-Aldrich Co. LLC, T6884) with a final concentration of 1 nM and a substrate peptide Boc-Val-Pro-Arg-AMC (R&D Systems, Inc., ES011) with a final concentration of 100 μM were used. For evaluating the Human neutrophil elastase inhibitory activity, neutrophil elastase (Enzo Life Sciences, BML-SE284) with a final concentration of 0.00001 U/μL and a substrate peptide Suc (OMe)-Ala-Ala-Pro-Val-MCA (SEQ ID NO: 99)(PEPTIDE INSTITUTE, INC., 3153-v) with a final concentration of 100 μM were used.

FIG. 3D includes graphs to evaluate the cross-reactivity of each inhibitory peptide with proteases, using the degradation of a peptide substrate as an index. For evaluating the Human matriptase inhibitory activity, matriptase (R&D Systems, Inc., 3946-SE) with a final concentration of 1 nM and a substrate peptide Boc-Gln-Ala-Arg-AMC (R&D Systems, Inc., ES014) with a final concentration of 100 μM were used. For evaluating the Human protein C inhibitory activity, protein C (Sigma-Aldrich Co. LLC, P2200) with a final concentration of 100 nM and a substrate peptide Boc-Leu-Ser-Thr-Arg-MCA (SEQ ID NO: 100)(PEPTIDE INSTITUTE, INC., 3112-v) with a final concentration of 100 μM were used. For evaluating the Human tPA inhibitory activity, tPA (Sigma-Aldrich Co. LLC, 10831) with a final concentration of 10 nM and a substrate peptide Pyr-Gly-Arg-MCA (PEPTIDE INSTITUTE, INC., 3145-v) with a final concentration of 100 μM were used.

FIG. 3F includes graphs to evaluate the cross-reactivity of each inhibitory peptide with proteases, using the degradation of a peptide substrate as an index. For evaluating the Human KLK1 inhibitory activity, hKLK1 (R&D Systems, Inc., 2337-SE) with a final concentration of 0.1 μg/mL and a substrate peptide Pro-Phe-Arg-MCA (PEPTIDE INSTITUTE, INC., 3096-v) with a final concentration of 100 μM were used. For evaluating the Human KLK2 inhibitory activity, hKLK2 (R&D Systems, Inc., 4104-SE) with a final concentration of 2 μg/mL and a substrate peptide Pro-Phe-Arg-MCA (PEPTIDE INSTITUTE, INC., 3096-v) with a final concentration of 100 μM were used. For evaluating the Human KLK4 inhibitory activity, hKLK4 (R&D Systems, Inc., 1719-SE) with a final concentration of 1 μg/mL and a substrate peptide Boc-Val-Pro-Arg-AMC (R&D Systems, Inc., ES011) with a final concentration of 100 μM were used.

FIG. 3G includes graphs to evaluate the cross-reactivity of each inhibitory peptide with proteases, using the degradation of a peptide substrate as an index. For evaluating the Human KLK7 inhibitory activity, hKLK7 with a final concentration of 1 μg/mL and a substrate peptide Mca-Arg-Pro-Lys-Pro-Val-Glu-Nval-Trp-Arg-Lys (Dnp)-$NH_2$ (SEQ ID NO: 101)(R&D Systems, Inc., ES002) with a final concentration of 20 μM were used. For evaluating the Human KLK8 inhibitory activity, hKLK8 (UniProt: O60259, prepared by the inventors) with a final concentration of 5 nM and a substrate peptide Boc-Val-Pro-Arg-AMC (R&D Systems, Inc., ES011) with a final concentration of 100 μM were used. For evaluating the Human KLK12 inhibitory activity, hKLK12 (R&D Systems, Inc., 3095-SE) with a final concentration of 0.1 μg/mL and a substrate peptide Boc-Val-Pro-Arg-AMC (R&D Systems, Inc., ES011) with a final concentration of 100 μM were used.

FIG. 3H includes graphs to evaluate the cross-reactivity of each inhibitory peptide with proteases, using the degradation of a peptide substrate as an index. For evaluating the Human KLK13 inhibitory activity, hKLK13 (R&D Systems, Inc., 2625-SE) with a final concentration of 0.5 μg/mL, a substrate peptide Boc-Val-Pro-Arg-AMC (R&D Systems, Inc., ES011) with a final concentration of 100 μM, and a fluorescence signal with excitation at 380 nm/emission at 460 nm were used. For evaluating the Human KLK14 inhibitory activity, hKLK14 with a final concentration of 0.2 μg/mL and a substrate peptide Boc-Val-Pro-Arg-AMC (R&D Systems, Inc., ES011) with a final concentration of 100 μM were used.

FIG. 6D includes graphs to evaluate the cross-reactivity of each inhibitory peptide Fc fusion with proteases, using the degradation of a peptide substrate as an index. For evaluating the Human matriptase, Human protein C, and Human tPA inhibitory activities, the same conditions as in FIG. 3D were used.

FIG. 6F includes graphs to evaluate the cross-reactivity of each inhibitory peptide Fc fusion with proteases, using the degradation of a peptide substrate as an index. For evaluating the Human KLK1, Human KLK2, and Human KLK4 inhibitory activities, the same conditions as in FIG. 3F were used.

FIG. 6G includes graphs to evaluate the cross-reactivity of each inhibitory peptide Fc fusion with proteases, using the degradation of a peptide substrate as an index. For evaluating the Human KLK7, Human KLK8, and Human KLK12 inhibitory activities, the same conditions as in FIG. 3G were used.

FIG. 6H includes graphs to evaluate the cross-reactivity of each inhibitory peptide Fc fusion with proteases, using the degradation of a peptide substrate as an index. For evaluating the Human KLK13 and Human KLK14 inhibitory activities, the same conditions as in FIG. 3H were used.

FIG. 8 includes views for comparing the sequence identities in human SPINK2 (SEQ ID NO: 1), D8 and D9 of human SPINK5 (SEQ ID NO: 88 and SEQ ID NO: 89, respectively), and human SPINK9 (SEQ ID NO: 90). It is known that D8 and D9 of human SPINK5, and human SPINK9 have human KLK5 inhibitory activities, but it is seen that the amino acid sequence identities with human SPINK2, for which there is no report on human KLK5 inhibitory activity, are low in all cases.

FIG. 9 is the amino acid sequence of human SPINK2 (SEQ ID NO: 1).

FIG. 10 is the amino acid sequence of human KLK5 (SEQ ID NO: 2).

FIG. 11 is the amino acid sequence of human KLK7 (SEQ ID NO: 3).

FIG. 12 is the amino acid sequence of human KLK14 (SEQ ID NO: 4).

FIG. 13 is the nucleotide sequence of the KLK5 inhibitory peptide K50032 (SEQ ID NO: 5).

FIG. 14 is the amino acid sequence of the KLK5 inhibitory peptide K50032 (SEQ ID NO: 6).

FIG. 15 is the nucleotide sequence of the KLK5 inhibitory peptide K50055 (SEQ ID NO: 7).

FIG. 16 is the amino acid sequence of the KLK5 inhibitory peptide K50055 (SEQ ID NO: 8).

FIG. 17 is the nucleotide sequence of the KLK5 inhibitory peptide K51072 (SEQ ID NO: 9).

FIG. 18 is the amino acid sequence of the KLK5 inhibitory peptide K51072 (SEQ ID NO: 10).

FIG. 19 is the nucleotide sequence of the KLK5 inhibitory peptide K50016 (SEQ ID NO: 11).

FIG. 20 is the amino acid sequence of the KLK5 inhibitory peptide K50016 (SEQ ID NO: 12).

FIG. 21 is the nucleotide sequence of the KLK5 inhibitory peptide K51034 (SEQ ID NO: 13).

FIG. 22 is the amino acid sequence of the KLK5 inhibitory peptide K51034 (SEQ ID NO: 14).

FIG. 23 is the nucleotide sequence of the KLK5 inhibitory peptide K50062 (SEQ ID NO: 15).

FIG. 24 is the amino acid sequence of the KLK5 inhibitory peptide K50062 (SEQ ID NO: 16).

FIG. 25 is the nucleotide sequence of the KLK5 inhibitory peptide K51090 (SEQ ID NO: 17).

FIG. 26 is the amino acid sequence of the KLK5 inhibitory peptide K51090 (SEQ ID NO: 18).

FIG. 27 is the nucleotide sequence of the KLK5 inhibitory peptide K50098 (SEQ ID NO: 19).

FIG. 28 is the amino acid sequence of the KLK5 inhibitory peptide K50098 (SEQ ID NO: 20).

FIG. 29 is the nucleotide sequence of the KLK5/KLK7 inhibitory peptide K51028 (SEQ ID NO: 21).

FIG. 30 is the amino acid sequence of the KLK5/KLK7 inhibitory peptide K51028 (SEQ ID NO: 22).

FIG. 31 is the nucleotide sequence of the KLK5/KLK7 inhibitory peptide K51005 (SEQ ID NO: 23).

FIG. 32 is the amino acid sequence of the KLK5/KLK7 inhibitory peptide K51005 (SEQ ID NO: 24).

FIG. 33 is the nucleotide sequence of the KLK5/KLK7 inhibitory peptide K50031 (SEQ ID NO: 25).

FIG. 34 is the amino acid sequence of the KLK5/KLK7 inhibitory peptide K50031 (SEQ ID NO: 26).

FIG. 35 is the nucleotide sequence of the KLK5/KLK7 inhibitory peptide K51057 (SEQ ID NO: 27).

FIG. 36 is the amino acid sequence of the KLK5/KLK7 inhibitory peptide K51057 (SEQ ID NO: 28).

FIG. 37 is the nucleotide sequence of the KLK5/KLK14 inhibitory peptide K51069 (SEQ ID NO: 29).

FIG. 38 is the amino acid sequence of the KLK5/KLK14 inhibitory peptide K51069 (SEQ ID NO: 30).

FIG. 39 is the nucleotide sequence of the KLK5/KLK14 inhibitory peptide K50015 (SEQ ID NO: 31).

FIG. 40 is the amino acid sequence of the KLK5/KLK14 inhibitory peptide K50015 (SEQ ID NO: 32).

FIG. 41 is the nucleotide sequence of the KLK5 inhibitory peptide Fc fusion D3-K50032dN-Fc (SEQ ID NO: 33).

FIG. 42 is the amino acid sequence of the KLK5 inhibitory peptide Fc fusion D3-K50032dN-Fc (SEQ ID NO: 34).

FIG. 43 is the nucleotide sequence of the KLK5 inhibitory peptide Fc fusion D3-K50055-Fc (SEQ ID NO: 35).

FIG. 44 is the amino acid sequence of the KLK5 inhibitory peptide Fc fusion D3-K50055-Fc (SEQ ID NO: 36).

FIG. 45 is the nucleotide sequence of the KLK5 inhibitory peptide Fc fusion D3-K51072-Fc (SEQ ID NO: 37).

FIG. 46 is the amino acid sequence of the KLK5 inhibitory peptide Fc fusion D3-K51072-Fc (SEQ ID NO: 38).

FIG. 47 is the nucleotide sequence of the KLK5 inhibitory peptide Fc fusion D3-K50016dN-Fc (SEQ ID NO: 39).

FIG. 48 is the amino acid sequence of the KLK5 inhibitory peptide Fc fusion D3-K50016dN-Fc (SEQ ID NO: 40).

FIG. 49 is the nucleotide sequence of the KLK5 inhibitory peptide Fc fusion D3-K51034-Fc (SEQ ID NO: 41).

FIG. 50 is the amino acid sequence of the KLK5 inhibitory peptide Fc fusion D3-K51034-Fc (SEQ ID NO: 42).

FIG. 51 is the nucleotide sequence of the KLK5 inhibitory peptide Fc fusion D3-K50062-Fc (SEQ ID NO: 43).

FIG. 52 is the amino acid sequence of the KLK5 inhibitory peptide Fc fusion D3-K50062-Fc (SEQ ID NO: 44).

FIG. 53 is the nucleotide sequence of the KLK5 inhibitory peptide Fc fusion D3-K51090-Fc (SEQ ID NO: 45).

FIG. 54 is the amino acid sequence of the KLK5 inhibitory peptide Fc fusion D3-K51090-Fc (SEQ ID NO: 46).

FIG. 55 is the nucleotide sequence of the KLK5 inhibitory peptide Fc fusion D3-K50098dN-Fc (SEQ ID NO: 47).

FIG. 56 is the amino acid sequence of the KLK5 inhibitory peptide Fc fusion D3-K50098dN-Fc (SEQ ID NO: 48).

FIG. 57 is the nucleotide sequence of the KLK5/KLK7 inhibitory peptide Fc fusion D3-K51028-Fc (SEQ ID NO: 49).

FIG. 58 is the amino acid sequence of the KLK5/KLK7 inhibitory peptide Fc fusion D3-K51028-Fc (SEQ ID NO: 50).

FIG. 59 is the nucleotide sequence of the KLK5/KLK7 inhibitory peptide Fc fusion D3-K51005-Fc (SEQ ID NO: 51).

FIG. 60 is the amino acid sequence of the KLK5/KLK7 inhibitory peptide Fc fusion D3-K51005-Fc (SEQ ID NO: 52).

FIG. 61 is the nucleotide sequence of the KLK5/KLK7 inhibitory peptide Fc fusion D3-K50031-Fc (SEQ ID NO: 53).

FIG. 62 is the amino acid sequence of the KLK5/KLK7 inhibitory peptide Fc fusion D3-K50031-Fc (SEQ ID NO: 54).

FIG. 63 is the nucleotide sequence of the KLK5/KLK7 inhibitory peptide Fc fusion D3-K51057-Fc (SEQ ID NO: 55).

FIG. 64 is the amino acid sequence of the KLK5/KLK7 inhibitory peptide Fc fusion D3-K51057-Fc (SEQ ID NO: 56).

FIG. 65 is the nucleotide sequence of the KLK5/KLK14 inhibitory peptide Fc fusion D3-K51069dN-Fc (SEQ ID NO: 57).

FIG. 66 is the amino acid sequence of the KLK5/KLK14 inhibitory peptide Fc fusion D3-K51069dN-Fc (SEQ ID NO: 58).

FIG. 67 is the nucleotide sequence of the KLK5/KLK14 inhibitory peptide Fc fusion D3-K50015-Fc (SEQ ID NO: 59).

FIG. 68 is the amino acid sequence of the KLK5/KLK14 inhibitory peptide Fc fusion D3-K50015-Fc (SEQ ID NO: 60).

FIG. 69 is the formula of the SPINK2 mutant peptide (SEQ ID NO: 61).

FIG. 70 is the nucleotide sequence of primer 1 (SEQ ID NO: 62).

FIG. 71 is the nucleotide sequence of primer 2 (SEQ ID NO: 63).

FIG. 72 is the nucleotide sequence of primer 3 (SEQ ID NO: 64).

FIG. 73 is the nucleotide sequence of primer 4 (SEQ ID NO: 65).

FIG. 74 is the nucleotide sequence of primer 5 (SEQ ID NO: 66).

FIG. 75 is the nucleotide sequence of primer 6 (SEQ ID NO: 67).

FIG. 76 is the nucleotide sequence of primer 7 (SEQ ID NO: 68).

FIG. 77 is the nucleotide sequence of primer 8 (SEQ ID NO: 69).

FIG. 78 is the nucleotide sequence of primer 9 (SEQ ID NO: 70).

FIG. 79 is the nucleotide sequence of primer 10 (SEQ ID NO: 71).

FIG. 80 is the nucleotide sequence of primer 11 (SEQ ID NO: 72).

FIG. 81 is the nucleotide sequence of primer 12 (SEQ ID NO: 73).

FIG. 82 is the nucleotide sequence of primer 13 (SEQ ID NO: 74).

FIG. 83 is the nucleotide sequence of primer 14 (SEQ ID NO: 75).

FIG. 84 is the nucleotide sequence of primer 15 (SEQ ID NO: 76).

FIG. 85 is the KLK7 substrate peptide (the amino acid sequence is shown in SEQ ID NO: 77).

FIG. 86 is the bovine α-chymotrypsin substrate peptide (the amino acid sequence is shown in SEQ ID NO: 78).

FIG. 87 is the neutrophil elastase substrate peptide (the amino acid sequence is shown in SEQ ID NO: 79).

FIG. 88 is the human protein C substrate peptide (the amino acid sequence is shown in SEQ ID NO: 80).

FIG. 89 is the nucleotide sequence of primer 16 (SEQ ID NO: 81).

FIG. 90 is the nucleotide sequence of primer 17 (SEQ ID NO: 82).

FIG. 91 is the nucleotide sequence of primer 18 (SEQ ID NO: 83).

FIG. 92 is the nucleotide sequence of primer 19 (SEQ ID NO: 84).

FIG. 93 is the nucleotide sequence of primer 20 (SEQ ID NO: 85).

FIG. 94 is the nucleotide sequence of primer 21 (SEQ ID NO: 86).

FIG. 95 is the amino acid sequence of Fc of human IgG1 (SEQ ID NO: 87).

FIG. 96 is the amino acid sequence of D8 of human SPINK5 (SEQ ID NO: 88).

FIG. 97 is the amino acid sequence of D9 of human SPINK5 (SEQ ID NO: 89).

FIG. 98 is the amino acid sequence of human SPINK9 (SEQ ID NO: 90).

FIG. 99 is the amino acid sequence of mouse KLK5 (SEQ ID NO: 91).

FIG. 100 is the amino acid sequence of mouse KLK7 (SEQ ID NO: 92).

FIG. 101 is the amino acid sequence of mouse KLK14 (SEQ ID NO: 93).

FIG. 104 is the nucleotide sequence of primer 22 (SEQ ID NO: 94).

FIG. 105 is the nucleotide sequence of the KLK5 inhibitory peptide Fc fusion D1-K50055-Fc (SEQ ID NO: 95).

FIG. 106 is the amino acid sequence of the KLK5 inhibitory peptide Fc fusion D1-K50055-Fc (SEQ ID NO: 96).

FIG. 107A is a graph showing the KLK5 inhibitory activity ($IC_{50}$) of the KLK5 inhibitory peptide Fc fusion D1-K50055-Fc, using the degradation rate of a peptide substrate as an index. For evaluating the KLK5 inhibitory activity, KLK5 with a final concentration of 10 nM and Boc-Val-Pro-Arg-AMC (R&D Systems, Inc., ES011) with a final concentration of 100 µM were used.

FIG. 107B is a graph to evaluate the cross-reactivity of the KLK5 inhibitory peptide Fc fusion D1-K50055-Fc with KLK7, using the degradation rate of a peptide substrate as an index. The same conditions as in FIG. 3G were used.

FIG. 107C is a graph to evaluate the cross-reactivity of the KLK5 inhibitory peptide Fc fusion D1-K50055-Fc with KLK14, using the degradation rate of a peptide substrate as an index. The same conditions as in FIG. 3H were used.

DESCRIPTION OF EMBODIMENTS

1. Definition

Figure 2:
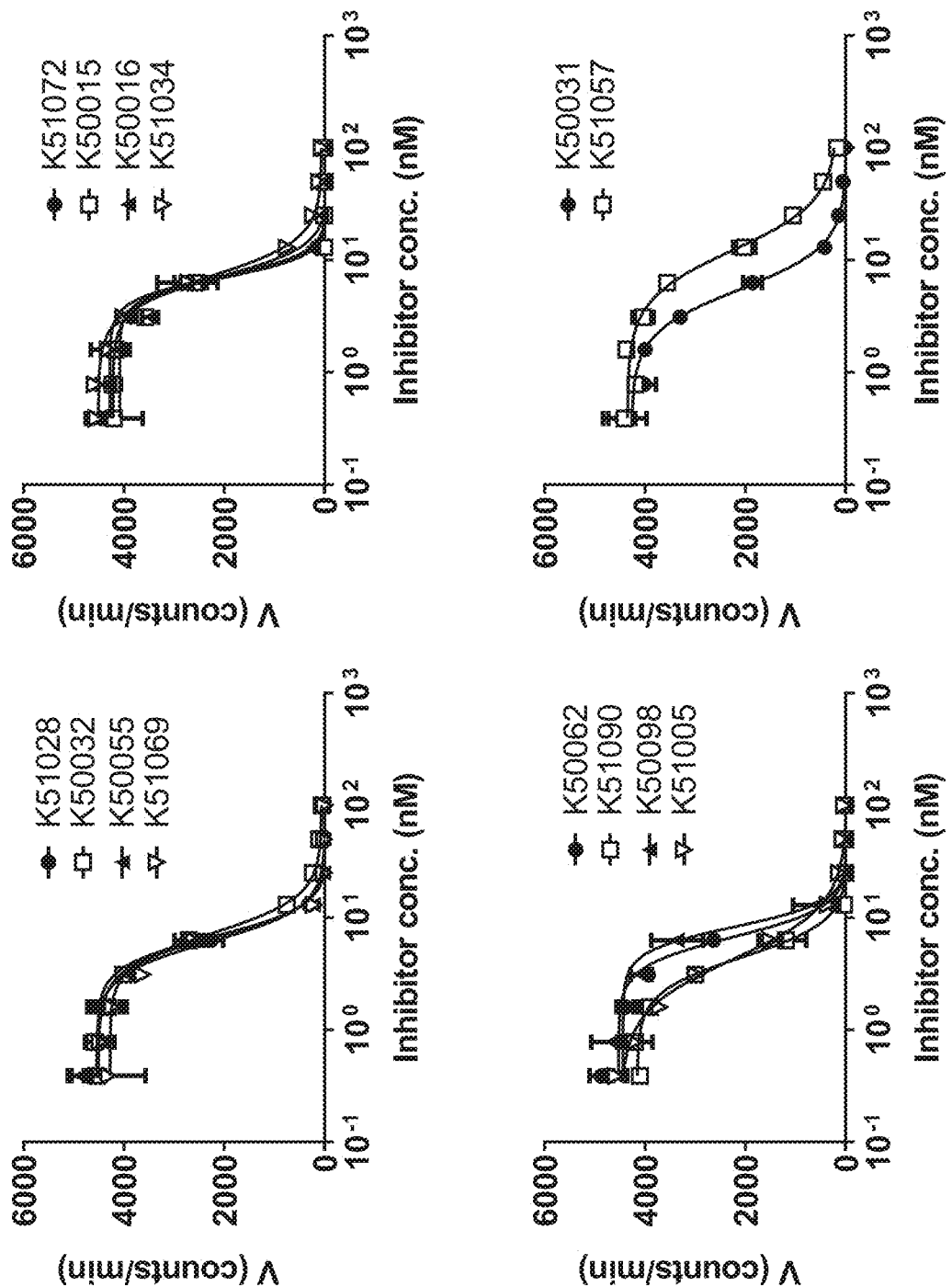
FIG. 2 includes graphs showing the KLK5 inhibitory activity (50% inhibitory concentration: $IC_{50}$) of each KLK5 inhibitory peptide, using the degradation rate of a peptide substrate as an index. For evaluating the KLK5 inhibitory activity, KLK5 with a final concentration of 10 nM and Boc-Val-Pro-Arg-AMC (R&D Systems, Inc., ES011) with a final concentration of 100 μM were used.

In the present invention, the term "gene" means a nucleic acid molecule containing a nucleotide sequence encoding the amino acid sequence of a protein or a complementary strand thereof. The meaning of "gene" includes a single-stranded, double-stranded, or triple-stranded or more association of a DNA strand and an RNA strand, and a mixture of ribonucleotides and deoxyribonucleotides on one strand, and double- or triple- or more stranded nucleic acid molecules containing such strands.

In the present invention, "gene", "polynucleotide", and "nucleic acid molecules" have the same meaning and are not limited at all by the number of ribonucleotides, deoxyribonucleotides, nucleotides, nucleosides, and the like, which are their constituent units. For example, DNA, RNA, mRNA, cDNA, cRNA, probe, oligonucleotide, primer, and the like, are also included within the scope of these terms. "Nucleic acid molecules" may be abbreviated as "nucleic acids".

In the present invention, "polypeptide", "peptide", and "protein" have the same meaning.

In the present invention, a peptide that recognizes target molecule X or binds to the target molecule X (hereinafter, the recognition or binding action will be collectively referred to as "X binding activity") can be referred to as an "X binding peptide". Further, a peptide that recognizes the target molecule X or binds to the target molecule X and inhibits or suppresses one or more activities or functions of the target molecule X (hereinafter, the inhibitory or suppressive action will be collectively referred to as "X inhibitory activity") can be referred to as an "X inhibitory peptide".

In the present invention, "SPINK2" means Serine Protease Inhibitor Kazal-type 2, which is a 7 kDa protein composed of a Kazal-like domain having three disulfide bonds. SPINK2 is preferably derived from humans. In the present invention, human SPINK2 (SEQ ID NO: 1, FIG. 9) will be simply referred to as "SPINK2", unless otherwise stated.

In the present invention, "KLK5" is a protein composed of an N-terminal propeptide and a protease active domain and having trypsin-like and chymotrypsin-like protease activities with N-type sugar chains added at three sites. KLK5 is preferably derived from humans. In the present invention, human KLK5 (SEQ ID NO: 2, FIG. 10) may be simply referred to as "KLK5", unless otherwise stated.

In the present invention, "KLK7" is a protein composed of an N-terminal propeptide and a trypsin-like domain having a protease activity, with an N-type sugar chain added. KLK7 is preferably derived from humans. In the present invention, human KLK7 (SEQ ID NO: 3, FIG. 11) may be simply referred to as "KLK7", unless otherwise stated.

In the present invention, "KLK14" is also called neuropsin and is a protein composed of an N-terminal propeptide and a trypsin-like domain having a protease activity, with an N-type sugar chain added. KLK14 is preferably derived from humans. In the present invention, human KLK14 (SEQ ID NO: 4, FIG. 12) may be simply referred to as "KLK14", unless otherwise stated.

In the present invention, "precursor-type KLK5" means pro-KLK5, which is composed of a propeptide and a domain having a protease activity. "Active KLK5" means active KLK5, which is composed of a domain having a protease activity. Active KLK5 is preferably derived from humans.

In the present invention, "precursor-type KLK7" means pro-KLK7, which is composed of a propeptide and a domain having a protease activity. "Active KLK7" means active KLK7, which is composed of a domain having a protease activity. Active KLK7 is preferably derived from humans.

In the present invention, "precursor-type KLK14" means pro-KLK14, which is composed of a propeptide and a domain having a protease activity. "Active KLK14" means active KLK14, which is composed of a domain having a protease activity. Active KLK14 is preferably derived from humans.

In the present invention, "KLK5 inhibitory peptide", "KLK5/KLK7 inhibitory peptide", or "KLK5/KLK14 inhibitory peptide" means a peptide that inhibits or suppresses one or more activities or functions of KLK5, KLK5 and KLK7, or KLK5 and KLK14, respectively.

The scope of the terms "KLK5 inhibitory peptide", "KLK5/7 inhibitory peptide", and "KLK5/KLK14 inhibitory peptide" include fragments of such a peptide, and conjugates formed by the addition or binding of other moieties to the peptide or fragments thereof that maintain the KLK5 inhibitory (binding) activity, the KLK5/KLK7 inhibitory (binding) activity, or the KLK5/KLK14 inhibitory (binding) activity, respectively. That is, "KLK5 inhibitory peptide", "KLK5/KLK7 inhibitory peptide", or "KLK5/KLK14 inhibitory peptide" includes fragments, adducts, and modified forms (such as conjugates) of such a peptide that maintain the KLK5 inhibitory (binding) activity, the KLK5 inhibitory (binding) activity and the KLK7 inhibitory (binding) activity, or the KLK5 inhibitory (binding) activity and the KLK14 inhibitory (binding) activity, respectively.

In the present invention, "sites" to which the peptide binds, that is, "sites" recognized by the peptide mean consecutive or intermittent partial amino acid sequences or partial higher-order structures on the target molecules to which the peptide binds or recognizes. In the present invention, such sites can be called epitopes or binding sites on the target molecules.

In the present invention, "cells" include various cells derived from animal individuals, subcultured cells, primary cultured cells, cell lines, recombinant cells, yeasts, and microorganisms.

In the present invention, "SPINK2 mutant" means a peptide containing an amino acid sequence formed by substituting one or more amino acids with amino acids different from those of the wild type, deleting one or more wild-type amino acids, or inserting one or more amino acids that are not found in the wild type (which will be hereinafter referred to collectively as "mutation"), in the amino acid sequence of wild-type SPINK2. "SPINK2 mutants" that have the KLK5 inhibitory activity, the KLK5 inhibitory activity and the KLK7 inhibitory activity (KLK5/KLK7 inhibitory activity), or the KLK5 inhibitory activity and the KLK14 inhibitory activity (KLK5/KLK14 inhibitory activity) are included within the KLK5 inhibitory peptides, KLK5/KLK7 inhibitory peptides, or KLK5/KLK14 inhibitory peptides. In the present invention, "insertion" can be included within the scope of "addition".

In the present invention, "several" in "one to several" means three to ten.

In the present invention, the phrase "hybridizing under stringent conditions" means hybridization in a solution containing 5×SSC at 65° C. and then washing in an aqueous solution containing 2×SSC-0.1% SDS at 65° C. for 20 minutes, in an aqueous solution containing 0.5×SSC-0.1% SDS at 65° C. for 20 minutes, and in an aqueous solution containing 0.2×SSC-0.1% SDS at 65° C. for 20 minutes, or hybridization under conditions equivalent to the above conditions. SSC means an aqueous solution of 150 mM NaCl-15 mM sodium citrate, and "n×SSC" means SSC of n-fold concentration.

In the present invention, the terms "specific" and "specificity" have the same meaning as "selective" and "selectivity", respectively, and are interchangeable. For example, a KLK5-specific inhibitory peptide has the same meaning as a KLK5-selective inhibitory peptide, and a KLK5- and KLK7-specific inhibitory peptide has the same meaning as a KLK5- and KLK7-selective inhibitory peptide, respectively.

2. Peptide
2-1. Amino Acid

The term "amino acid" means an organic compound containing an amino group and a carboxyl group, and preferably means an α-amino acid contained as a constituent unit in a protein, more preferably in a natural protein. In the present invention, more suitable examples of the amino acid include Ala, Arg, Asn, Asp, Cys, Gln, Glu, Gly, His, Ile, Leu, Lys, Met, Phe, Pro, Ser, Thr, Trp, Tyr, and Val, and the term "amino acid" means these 20 amino acids in total, unless otherwise noted. A total of these 20 amino acids can be called "natural amino acids". The KLK5 inhibitory peptide, the KLK5/KLK7 inhibitory peptide, or the KLK5/KLK14 inhibitory peptide of the present invention preferably contains a natural amino acid.

In the present invention, "amino acid residues" may be abbreviated as "amino acids".

Further, in the present invention, the amino acid may be an L-amino acid, a D-amino acid, or a mixture thereof (DL-amino acid) but means L-amino acid unless otherwise noted.

The natural amino acids can be classified, for example, into the following groups based on the properties of their common side chains:

(1) Hydrophobic amino acid group: Met, Ala, Val, Leu, and Ile;
(2) Neutral hydrophilic amino acid group: Cys, Ser, Thr, Asn, and Gln;
(3) Acidic amino acid group: Asp and Glu;
(4) Basic amino acid group: His, Lys, and Arg;
(5) Group of amino acids that affect the orientation of the main chain: Gly and Pro; and
(6) Aromatic amino acid group: Trp, Tyr, and Phe.

However, classification of natural amino acids is not limited to these groups.

In the present invention, natural amino acids can undergo a conservative amino acid substitution.

The term "conservative amino acid substitution" means a substitution with a functionally equivalent or similar amino acid. A conservative amino acid substitution in a peptide results in a static change in the amino acid sequence of the peptide. For example, one or more amino acids having the same polarity act functionally equivalently, resulting in a static change in the amino acid sequence of the peptide. In general, a substitution within a group can be considered to be conservative in structure and function. However, as will be obvious to those skilled in the art, the role played by a specific amino acid residue can be determined in the context of the three-dimensional structure of molecules containing the amino acid. For example, a cysteine residue can take a less polar oxidized (disulfide) form, as compared with the reduced (thiol) form. A long aliphatic moiety of an arginine side chain can form a structurally and functionally important feature. Further, a side chain containing an aromatic ring (such as tryptophan, tyrosine, and phenylalanine) can contribute to ion-aromatic interactions or cation-pi interactions. In such a case, even if amino acids having these side chains are substituted with amino acids belonging to the acidic or non-polar group, they can be structurally and functionally conservative. Residues such as proline, glycine, and cysteine (disulfide form) can have a direct effect on the three-dimensional structure of the main chain and often cannot be substituted without structural distortion.

The conservative amino acid substitution includes specific substitutions (L. Lehninger, Biochemistry, $2^{nd}$ edition, pp 73-75, Worth Publisher, New York (1975)) and typical substitutions based on the similarity in side chains, as shown below:

(1) Non-polar amino acid group: alanine (which will be hereinafter referred to as "Ala" or simply "A"), valine (which will be hereinafter referred to as "Val" or simply "V"), leucine (which will be hereinafter referred to as "Leu" or simply "L"), isoleucine (which will be hereinafter referred to as "Ile" or simply "I"), proline (which will be hereinafter referred to as "Pro" or simply "P"), phenylalanine ("Phe" or simply "F"), tryptophan (which will be hereinafter referred to as "Trp" or simply "W"), and methionine (which will be hereinafter referred to as "Met" or simply "M");

(2) Uncharged polar amino acid group: glycine (which will be hereinafter referred to as "Gly" or simply "G"), serine (which will be hereinafter referred to as "Ser" or simply "S"), threonine (which will be hereinafter referred to as "Thr" or simply "T"), cysteine (which will be hereinafter referred to as "Cys" or simply "C"), tyrosine (which will be hereinafter referred to as "Tyr" or simply "Y"), asparagine (which will be hereinafter referred to as "Asn" or simply "N"), and glutamine (which will be hereinafter referred to as "Gln" or simply "Q");

(3) Acidic amino acid group: aspartic acid (which will be hereinafter referred to as "Asp" or simply "D") and glutamic acid (which will be hereinafter referred to as "Glu" or simply "E"); and (4) Basic amino acid group: lysine (which will be hereinafter referred to as "Lys" or simply "K"), arginine (which will be hereinafter referred to as "Arg" or simply "R"), and histidine (which will be hereinafter referred to as "His" or simply "H").

In the present invention, the amino acid may be an amino acid other than a natural amino acid. Examples thereof can include amino acids found in natural peptides or proteins, such as selenocysteine, N-formylmethionine, pyrrolidine, pyroglutamic acid, cystine, hydroxyproline, hydroxylysine, thyroxine, O-phosphoserine, desmosin, β-alanine, sarcosine, ornithine, creatine, γ aminobutyric acid, opine, theanine, tricolominic acid, kainic acid, domoic acid, and acromelic acid, and other amino acids not found in the natural world, such as N-terminal protected amino acids including norleucine, Ac-amino acid, Boc-amino acid, Fmoc-amino acid, Trt-amino acid, and Z-amino acid, C-terminal protected amino acids including amino acid t-butyl ester, benzyl ester, cyclohexyl ester, and fluorenyl ester, diamine, ω amino acid, β amino acid, γ amino acid, Tic derivatives of amino acids, and aminophosphonic acid. However, there is no limitation to these, and amino acids other than the aforementioned 20 "natural amino acids" will be collectively referred to as "non-natural amino acids" in the present invention for convenience of description.

2-2. KLK5 Inhibitory Peptide, KLK5/KLK7 Inhibitory Peptide, and KLK5/KLK14 Inhibitory Peptide The peptide of the present invention has a KLK5 inhibitory activity, a KLK5/KLK7 inhibitory activity, or a KLK5/KLK14 inhibitory activity.

KLK5, KLK7, and KLK14 targeted by the KLK5 inhibitory peptide, the KLK5/KLK7 inhibitory peptide, and the KLK5/KLK14 inhibitory peptide of the present invention are preferably derived from vertebrate animals, more preferably mammals, furthermore preferably primates, optimally humans. KLK5, KLK7, and KLK14 can be purified from tissues or cells, or prepared by methods known to those skilled in the art as methods for preparing proteins such as gene recombination, in-vitro translation, and peptide synthesis. A signal sequence, an Fc region of an immunoglobulin, a tag, a label, and the like may be linked to KLK5, KLK7, and KLK14. The KLK5 inhibitory activity, the KLK5/KLK7 inhibitory activity, and the KLK5/KLK14 inhibitory activity can be evaluated using the protease activities of KLK5, KLK5 and KLK7, and KLK5 and KLK14, as indices. For example, when KLK5, KLK5 and KLK7, or KLK5 and KLK14, or a functional fragment thereof is allowed to coexist with a substrate and the KLK5 inhibitory peptide, the KLK5/KLK7 inhibitory peptide, or the KLK5/KLK14 inhibitory peptide of the present invention or a candidate thereof, KLK5 inhibition, KLK5/KLK7 inhibition, or KLK5/KLK14 inhibition occurs when the protease activity of KLK5, KLK5 and KLK7, or KLK5 and KLK14 is 70% or less, 50% or less, 30% or less, 20% or less, 10% or less, 5% or less, 1% or less, or 0%, as compared with that in the presence of the control or in the absence of the inhibitor or the candidate thereof. The inhibitory activity is 30% or more, 50% or more, 70% or more, 80% or more, 90% or more, 95% or more, 99% or more, or 100%, respectively. The KLK5 inhibitory activity, the KLK5/KLK7 inhibitory activity, and the KLK5/KLK14 inhibitory activity can vary depending on the reaction conditions, the type of substrate, the concentration, and the like. The reaction conditions can be exemplified by those described in the Examples, but they are not limited to these examples. The enzymatic activity can be evaluated by adding a substrate peptide or a substrate protein to KLK5, KLK5 and KLK7, or KLK5 and KLK14 at a certain concentration and allowing it to react for a certain time and thereafter detecting the fluorescence of the substrate peptide or the substrate protein by SDS-PAGE, Western blotting, liquid chromatography, or the like. As a buffer, phosphate buffer saline (which will be hereinafter referred to as "PBS"), tris buffer (50 mM tris, pH 7 to 8.5, for example, pH 7.5), and the like can be used, and salts such as NaCl (0 to 200 mM, for example, 200 mM), $CaCl_2$ (0 to 10 mM, for example, 2 mM), $ZnCl_2$, and Brij-35 can be added thereto. However, there is no limitation to these.

The KLK5 inhibitory activity, the KLK5/KLK7 inhibitory activity, and the KLK5/KLK14 inhibitory activity can each be represented by an inhibition constant $K_i$. The protease activity is measured by adding a substrate peptide to an enzyme at a certain concentration and allowing it to react for a certain time and thereafter detecting the fluorescence of the substrate peptide. From the protease activity at each substrate concentration, the maximum reaction rate $V_{max}$ and the Michaelis constant $K_m$ are calculated according to the Michaelis-Menten equation (Michaelis L, et al. (2011) Biochemistry., Vol. 50, No. 39, pp. 8264-8269). Further, the inhibition constant $K_i$ is calculated from the protease activity when each inhibitor is added to an enzyme at a certain concentration according to the Morrison equation (Morrison J F. (1969) Biochim Biophys Acta., Vol. 185, No. 2, pp. 269-286). Examples of the software used for the calculation can include GraphPad Prism (GraphPad Software Inc).

The protease substrate of KLK5, KLK7 and KLK5, or KLK5 and KLK14 is not specifically limited and may be an endogenous substrate, an exogenous substrate, a synthetic substrate, or the like. Examples of the human endogenous substrate of KLK5 can include low-molecular weight kininogen or kallistatin, collagen, Desmoglein, Desmocollin, and Cathelicidin. Examples of the human endogenous substrate of KLK7 can include Pro-KLK5, fibronectin, and collagen. Examples of the human endogenous substrate of KLK14 can include tPA, fibronectin, and collagen. Gelatin obtained by heat-denaturing collagen can also be used as a substrate. The synthetic substrate is not specifically limited, but examples thereof can include PFR-AMC and Boc-VPR-AMC. In the present invention, the KLK5 inhibitory activity ($IC_{50}$ or $K_i$) of the KLK5 inhibitory peptide, the KLK5 inhibitory activity of the KLK5/KLK7 inhibitory peptide, and the KLK5 inhibitory activity and the KLK14 inhibitory activity of the KLK5/KLK14 inhibitory peptide are each 1 µM or less, preferably 300 nM or less, more preferably 100 nM or less, further preferably 30 nM, furthermore preferably 10 nM or less. The KLK7 inhibitory activity of the KLK5/

KLK7 inhibitory peptide is preferably 1000 nM or less, more preferably 300 nM or less, further preferably 100 nM, furthermore preferably 30 nM or less. Further, classification of the KLK5/KLK7 inhibitory peptide or the KLK5/KLK14 inhibitory peptide can be made by the relative degree of the KLK5 inhibitory activity and the KLK7 inhibitory activity or the KLK14 inhibitory activity (each represented by $IC_{50}$ or $K_i$). Peptides are preferably classified into three groups: (i) the KLK5 inhibitory activity is less than 0.5 times the KLK7 inhibitory activity or the KLK14 inhibitory activity; (ii) the KLK5 inhibitory activity is more than 0.5 times and less than 2 times the KLK7 inhibitory activity or the KLK14 inhibitory activity; and (iii) the KLK5 inhibitory activity is 2 times or more the KLK7 inhibitory activity or the KLK14 inhibitory activity, and desired peptides can be selected from these groups according to their application, such as treatment.

Further, the KLK5 inhibitory peptide, the KLK5/KLK7 inhibitory peptide, or the KLK5/KLK14 inhibitory peptide of the present invention preferably does not inhibit or suppress protease activities other than KLK5, KLK5 and KLK7, or KLK5 and KLK14, respectively, or the degree of inhibition or suppression against the other protease activities is preferably relatively weak. In other words, the protease inhibitory activity of the KLK5 inhibitory peptide, the KLK5/KLK7 inhibitory peptide, or the KLK5/KLK14 inhibitory peptide of the present invention preferably has high KLK5 specificity, KLK5/KLK7 specificity, or KLK5/KLK14 specificity. The peptide of the present invention preferably does not inhibit or suppress the activities of proteases such as KLK1, KLK2, KLK3, KLK4, KLK6, KLK8, KLK9 to KLK13, KLK15, chymotrypsin, tryptase, chymase, plasmin, thrombin, elastase, matriptase, protein C, tissue plasminogen activator (tPA), urokinase plasminogen activator (uPA), and plasma kallikrein, or the degree of inhibition or suppression thereagainst is relatively weak. Such a preferred peptide of the present invention does not exhibit side effects caused by inhibiting or suppressing the activities of other proteases and is suitable to be used as a therapeutic or prophylactic agent for KLK5-related diseases (which will be described below). Further, the KLK5-specific inhibitory peptide of the present invention preferably does not inhibit or suppress the protease activities of KLK7 and KLK14, or the degree of inhibition or suppression thereagainst is relatively weak; the KLK5/KLK7-specific inhibitory peptide of the present invention preferably does not inhibit or suppress the protease activity of KLK14, or the degree of inhibition or suppression thereagainst is relatively weak; and the KLK5/KLK14 inhibitory peptide of the present invention preferably does not inhibit or suppress the protease activities of KLK7, or the degree of inhibition or suppression thereagainst is relatively weak.

Inhibitors that have low specificity for KLK5, KLK5 and KLK7, or KLK5 and KLK14 and inhibit the protease activities of other KLKs in addition to KLK5, KLK5 and KLK7, or KLK5 and KLK14, that is, non-selective inhibitors can cause side effects when administered to humans (Coussens, L M, et al., Science, Vol. 295, No. 5564, pp. 2387-2392 (2002); Bissett, D, et al., J. Clin. Oncol., Vol. 23, No. 4, pp. 842-849 (2005)). Meanwhile, inhibitors that have high specificity for KLK5, KLK5/KLK7, or KLK5/KLK14, that is, KLK5-specific inhibitory peptides, KLK5/KLK7-specific inhibitory peptides, or KLK5/KLK14-specific inhibitory peptides can avoid such side effects as described above and therefore are suitable to be used for treating and preventing KLK5-related diseases (which will be described below).

The KLK5 inhibitory peptide, the KLK5/KLK7 inhibitory peptide, or the KLK5/KLK14 inhibitory peptide of the present invention may be competitive in binding of the protease substrate to KLK5, KLK5 and/or KLK7, or KLK5 and/or KLK14.

As described above, KLK5, KLK7, and KLK14 targeted by the peptide of the present invention are derived from vertebrate animals, preferably mammals, more preferably primates, furthermore preferably humans but may be derived from nonhuman animals, for example, rodents such as rats and mice, and primates such as cynomolgus monkeys, common marmosets, and rhesus monkeys. Peptides with an inhibitory activity against nonhuman animal-derived KLK5, KLK5 and KLK7, or KLK5 and KLK14 can be used, for example, for diagnosing, testing, treating, or preventing diseases related to KLK5 in nonhuman animals. Further, when such peptides also inhibit human KLK5, KLK5 and KLK7, or KLK5 and KLK14, pharmacological tests and pharmacokinetic tests using such nonhuman animals as animal pathology models, safety tests and toxicity tests using them as healthy animals, and the like can be performed in non-clinical research and development of the peptides as therapeutic or prophylactic agents for KLK5-related diseases (which will be described below).

Further, the KLK5 inhibitory peptide, the KLK5/KLK7 inhibitory peptide, and the KLK5/KLK14 inhibitory peptide of the present invention have advantages such as low molecular weight, comparatively easy production (which will be described below), excellent physical properties such as storage stability and thermostability, and a wide range of choices for the administration route, administration method, formulation, etc., when used as pharmaceutical compositions (which will be described below), as compared with other biopolymers such as antibodies used in this field as pharmaceuticals and diagnostic agents. Further, the half-life in blood when used as a pharmaceutical composition can be adjusted to be longer by applying a known method such as the addition of biopolymers and polymers to increase the molecular weight of the peptide of the present invention. The KLK5 inhibitory peptide, the KLK5/KLK7 inhibitory peptide, and the KLK5/KLK14 inhibitory peptide of the present invention have a molecular weight of less than 10,000, preferably less than 8,000, more preferably about 7,000 to 7,200. Further, variable loop moieties composed of Cys15 to Cys31 in SEQ ID NO: 61 (FIG. 69) or moieties composed of Cys15 to Cys63 (hereinafter, referred to as "moieties containing six Cys residues") having a KLK5 inhibitory activity, KLK5/KLK7 inhibitory activity, or KLK5/KLK14 inhibitory activity are also included within the KLK5 inhibitory peptide, the KLK5/KLK7 inhibitory peptide, or the KLK5/KLK14 inhibitory peptide of the present invention, respectively. The variable loop moieties have a molecular weight of less than 2,500, preferably about 1,800 to 2,000, and the moieties containing six Cys have a molecular weight of less than 6,000, preferably about 5,300 to 5,500.

The KLK5 inhibitory peptide, the KLK5/KLK7 inhibitory peptide, or the KLK5/KLK14 inhibitory peptide of the present invention is a SPINK2 mutant (which may be hereinafter abbreviated as "SPINK2 mutant") in which the backbone of SPINK2 is at least partially maintained, and preferably recognizes a partial peptide, a partial higher-order structure, or the like of KLK5, KLK5 and KLK7, or KLK5 and KLK14 or binds thereto (hereinafter, the recognition or binding action will be collectively referred to as "target binding activity").

The binding of the SPINK2 mutant to KLK5, KLK7, or KLK14 in the present invention can be measured or determined using methods known to those skilled in the art such as ELISA, Surface Plasmon Resonance (hereinafter, referred to as "SPR") analysis, BioLayer Interferometry (hereinafter, referred to as "BLI"), Isothermal Titration Calorimetry (hereinafter, referred to as "ITC"), flow cytometry, and immunoprecipitation.

Examples of ELISA include a method of detecting the KLK5 inhibitory peptide, the KLK5/KLK7 inhibitory peptide, or the KLK5/KLK14 inhibitory peptide that recognizes and binds to KLK5, KLK5/KLK7, or KLK5/KLK14 immobilized on a plate. Antibodies for solid phase that recognize KLK5, KLK5/KLK7, or KLK5/KLK14, or a tag fused to KLK5, KLK5/KLK7, or KLK5/KLK14 can be used for immobilizing KLK5, KLK5/KLK7, or KLK5/KLK14, other than biotin-streptavidin. Labeled antibodies for detection that recognize the KLK5 inhibitory peptide, the KLK5/KLK7 inhibitory peptide, or the KLK5/KLK14 inhibitory peptide, or a tag fused to the KLK5 inhibitory peptide, the KLK5/KLK7 inhibitory peptide, or the KLK5/KLK14 inhibitory peptide can be used for detecting the KLK5 inhibitory peptide, the KLK5/KLK7 inhibitory peptide, or the KLK5/KLK14 inhibitory peptide, other than labeled streptavidin. Methods that can be performed for biochemical analysis such as HRP, alkaline phosphatase, and FITC can be used for labeling, other than biotin. For detection using an enzyme label, chromogenic substrates such as TMB (3,3',5,5'-tetramethylbenzidine), BCIP (5-bromo-4-chloro-3-indolyl phosphate), p-NPP (p-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific), fluorescence substrates such as QuantaBlu® Fluorogenic Peroxidase Substrate (Thermo Fisher Scientific), and chemiluminescence substrates can be used. Absorption plate readers, fluorescence plate readers, luminescence plate readers, RI liquid scintillation counters, and the like can be used for measuring detection signals.

The measurement method by SPR analysis may be any of: a method of immobilizing the SPINK2 mutant peptide on a sensor chip and adding a target molecule such as KLK5 to measure the binding between the two; and a method of immobilizing a target molecule such as KLK5 on a sensor chip and adding the SPINK2 mutant peptide to measure the binding between the two. The former is preferred. For immobilizing the SPINK2 mutant contained in the peptide of the present invention or the conjugate thereof, a direct method or a capture method can be used. The latter is preferred. In the direct method, the hydrophobicity of the SPINK2 mutant, the amino groups and carboxyl groups of SPINK2, and the like can be used for direct immobilization. In the capture method, antibodies that recognize the conjugate or a tag fused to the conjugate, protein A, protein G, or the like can be used for immobilization, other than biotin-streptavidin. A target molecule, such as KLK5 diluted using an assay buffer, is added to the sensor chip on which the SPINK2 mutant is immobilized, and the SPR signal is observed over time to obtain binding sensorgrams. Subsequently, an assay buffer, containing no target molecules such as KLK5, is added and the SPR signal is observed over time to obtain dissociation sensorgrams. The binding affinity is analyzed using the obtained sensorgrams, to calculate a dissociation constant $K_D$. Devices used for the SPR analysis can include BIAcore® (GE healthcare), ProteOn® (Bio-Rad), SPR-Navi® (BioNavisOy), Spreeta® (Texas Instruments), SPRi-PlexII® (HORIBA, Ltd.), and Autolab SPR® (Metrohm). Devices used for BLI can include Octet® (Pall).

Examples of immunoprecipitation include a method of detecting KLK5, KLK5 and KLK7, or KLK5 and KLK14 recognized by and bound to the KLK5 inhibitory peptide, the KLK5/KLK7 inhibitory peptide, or the KLK5/KLK14 inhibitory peptide immobilized on beads. As regards the beads, magnetic beads, agarose beads, and the like can be used. For immobilizing the KLK5 inhibitory peptide, the KLK5/KLK7 inhibitory peptide, or the KLK5/KLK14 inhibitory peptide, antibodies that recognize such a peptide or a tag fused to the peptide, protein A, protein G, or the like can be used, other than biotin-streptavidin. The beads are separated by a magnet, centrifugation or the like, and the KLK5, KLK5 and KLK7, or KLK5 and KLK14 precipitated together with the beads are detected by SDS-PAGE or Western blotting. For detecting KLK5, KLK5 and KLK7, or KLK5 and KLK14, labeled antibodies for detection that recognize a tag fused to KLK5, KLK7, or KLK14, or KLK5, KLK7, or KLK14 and the like can be used, other than labeled streptavidin. Methods that can be performed for biochemical analysis such as HRP, alkaline phosphatase, and FITC can be used for labeling, other than biotin. For detection using an enzyme label, the same substrate as used in ELISA can be used. For measuring detection signals, ChemiDoc® (BioRad), LuminoGraph (ATTO), and the like can be used.

In the present invention, "specific recognition", that is, "specific binding" means binding that is not non-specific adsorption. Examples of criteria to determine whether or not the binding is specific can include the binding activity $EC_{50}$ in ELISA. Examples of other criteria can include the dissociation constant (hereinafter, referred to as "$K_D$"). In the present invention, the $K_D$ value of the KLK5 inhibitory peptide for KLK5, the $K_D$ value of the KLK5/KLK7 inhibitory peptide for KLK5 and KLK7, or the $K_D$ value of the KLK5/KLK14 inhibitory peptide for KLK5 and KLK14 is $1 \times 10^{-5}$ M or less, $5 \times 10^{-6}$ M or less, $2 \times 10^{-6}$ M or less, or $1 \times 10^{-6}$ M or less, more preferably $5 \times 10^{-7}$ M or less, $2 \times 10^{-7}$ M or less, or $1 \times 10^{-7}$ M or less, further preferably $5 \times 10^{-8}$ M or less, $2 \times 10^{-8}$ M or less, or $1 \times 10^{-8}$ M or less, furthermore preferably $5 \times 10^{-9}$ M or less, $2 \times 10^{-9}$ M or less, or $1 \times 10^{-9}$ M or less. Examples of other criteria can include the analysis results of immunoprecipitation. In the case of immobilizing the KLK5 inhibitory peptide, the KLK5/KLK7 inhibitory peptide, or the KLK5/KLK14 inhibitory peptide on beads, which is preferred in the present invention, and adding KLK5, KLK5 and KLK7, or KLK5 and KLK14 thereto, followed by separation of the beads, to detect KLK5, KLK5 and KLK7, or KLK5 and KLK14 precipitated together with the beads, the signals of KLK5, KLK5 and KLK7, or KLK5 and KLK14 are detected.

The SPINK2 mutant as the KLK5 inhibitory peptide, the KLK5/KLK7 inhibitory peptide, or the KLK5/KLK14 inhibitory peptide of the present invention can have the protease inhibitory activity, target binding activity, other properties, functions, and features as described above, while its full-length amino acid sequence has a high sequence identity to the amino acid sequence of human wild-type SPINK2. The SPINK2 mutant of the present invention has a sequence identity of 60% or more, 70% or more, 75% or more, 80% or more, 85% or more, 90% or more, 95% or more, 98% or more or 99% or more, to the amino acid sequence of human SPINK2 (SEQ ID NO: 1, FIG. 9).

The term "identity" means a property that indicates the degree of similarity or the relationship between two sequences. The identity (%) of an amino acid sequence is calculated by dividing the number of amino acids or amino acid residues that are identical by the total number of amino acids or amino acid residues and multiplying the numerical value obtained by 100.

The term "gap" means a gap in the alignment between two or more sequences resulting from a deletion and/or addition in at least one of the sequences.

The identity between two amino acid sequences that have completely identical amino acid sequences is 100%, but when one of the amino acid sequences is compared with the other, and one or more amino acids or amino acid residues are substituted, deleted, or added, the identity between the two is less than 100%. Examples of algorithms or programs for determining the identity between two sequences in consideration of a gap can include techniques known to those skilled in the art using standard parameters, such as BLAST (Altschul, et al. Nucleic Acids Res., Vol. 25, pp. 3389-3402, 1997), BLAST2 (Altschul, et al., J. Mol. Biol., Vol. 215, pp. 403-410, 1990), and Smith-Waterman (Smith, et al., J. Mol. Biol., Vol. 147, pp. 195-197, 1981).

In the present invention, the term "mutated" means that one or more nucleotides, nucleotide residues, amino acids, or amino acid residues have been substituted, deleted, or inserted in a nucleotide sequence or an amino acid sequence, as compared with the naturally occurring nucleic acid molecule or peptide. The amino acid sequence of the SPINK2 mutant of the present invention has one or more amino acids or amino acid residues mutated, as compared with the amino acid sequence of human SPINK2.

In an aspect of the present invention, the amino acid sequence of the SPINK2 mutant may have: one, two, three, four, five, six, or seven amino acids out of Ser16 to Gly22 substituted with other amino acids or amino acid residues; one, two, three, four, or five amino acids out of Pro24 to Asn28 substituted with other amino acids or amino acid residues; and one, two, three, four, five, or six out of Cys15, Cys23, Cys31, Cys42, Cys45 and Cys63 substituted with other amino acids in order to delete natural disulfide bonds or to generate non-natural disulfide bonds, although they are preferably the same Cys as in the wild type in order to maintain the natural disulfide bonds, in the amino acid sequence of human SPINK2 (SEQ ID NO: 1, FIG. 9). In some preferred KLK5 inhibitory peptides, KLK5/KLK7 inhibitory peptides, or KLK5/KLK14 inhibitory peptides of the SPINK2 mutant of the present invention, Cys is maintained at the same 6 sites as in the natural type to retain the disulfide bonds. In some more preferred aspects of such peptides, Cys15 to Cys45, Cys23 to Cys42, and Cys31 to Cys63 each form a disulfide bond.

When the amino acid sequence of such a SPINK2 mutant is contained in the KLK5 inhibitory peptide, the KLK5/KLK7 inhibitory peptide, or the KLK5/KLK14 inhibitory peptide, a three-dimensional structure constituted by a loop structure composed of Ser16 to Val30 contained in the amino acid sequence of the wild-type SPINK2, a β-sheet composed of β strand (1) composed of Cys31 and Gly32 and β strand (2) composed of Ile57 to Arg59, and an α-helix composed of Glu41 to Gly51, or a loop structure, a β-sheet, and an α-helix that are similar to or at least partially correspond to the above (positions thereof) are preferably maintained, to the extent that the KLK5 inhibitory activity, the KLK5/KLK7 inhibitory activity, or the KLK5/KLK14 inhibitory activity can be exerted.

The amino acid sequence of the KLK5 inhibitory peptide, the KLK5/KLK7 inhibitory peptide, or the KLK5/KLK14 inhibitory peptide according to some aspects of the SPINK2 mutant of the present invention will be described below. As described above, "amino acid residues" may be simply expressed as "amino acids" in the present invention.

In the amino acid sequence (formula) set forth in SEQ ID NO: 61 (FIG. 69), $X_1$ to $X_{12}$ are not specifically limited, as long as they are any amino acid such that the resultant mutant inhibits KLK5, KLK5 and KLK7, or KLK5 and KLK14. Hereinafter, suitable amino acids of $X_1$ to $X_{12}$ will be described, but the amino acids may include the same amino acids as in the amino acid sequence of the natural-type, that is, the wild-type human SPINK2.

In the amino acid sequence set forth in SEQ ID NO: 61 (FIG. 69) contained in the KLK5 inhibitory peptide, it is suitable that: Xaa16 ($X_1$) be Ala, Asp, Gly, Gln, Leu, Ser, or Thr; Xaa17 ($X_2$) be Arg, Glu, Asn, Gln, or Ser; Xaa18 ($X_3$) be Asp, Gln, Ile, Thr, Trp, or Tyr; Xaa19 ($X_4$) be Arg, Gly, Met, Gln, or Thr; Xaa20 ($X_5$) be Asp, Glu, Leu, Lys, Thr, or Tyr; Xaa21 ($X_6$) be Glu, Gly, His, Leu, Ser, Gln, or Tyr; Xaa22 ($X_7$) be Asp, Gly, Gln, Ser, or Tyr; Xaa24 ($X_8$) be Ala, Asp, Glu, Gly, Asn, Ser, or Thr; Xaa25 ($X_9$) be Arg or Lys; Xaa26 ($X_{10}$) be Asp, Glu, Gln, Ser, or Val; Xaa27 ($X_{11}$) be Phe or Tyr; and Xaa28 ($X_{12}$) be Asp or Glu.

In the amino acid sequence set forth in SEQ ID NO: 61 (FIG. 69) contained in the KLK5/KLK7 inhibitory peptide, it is suitable that: Xaa16 ($X_1$) be Gly, Met, or Tyr; Xaa17 ($X_2$) be Glu, Gln, or Thr; Xaa18 ($X_3$) be His, Met, or Tyr; Xaa19 ($X_4$) be Ala, Arg, Lys, or Gln; Xaa20 ($X_5$) be Gly, Arg, or Ser; Xaa21 ($X_6$) be Arg, Lys, Gln, or Ser; Xaa22 ($X_7$) be Gly; Xaa24 ($X_8$) be His, Thr, or Tyr; Xaa25 ($X_9$) be His or Tyr; Xaa26 ($X_{12}$) be Asp, Glu, or His; Xaa27 ($X_{11}$) be Tyr; and Xaa28 ($X_{12}$) be Asp or Glu.

In the amino acid sequence set forth in SEQ ID NO: 61 (FIG. 69) contained in the KLK5/KLK14 inhibitory peptide, it is suitable that: Xaa16 ($X_1$) be Gly, Ser, or Tyr; Xaa17 ($X_2$) be Asp or Gln; Xaa18 ($X_3$) be Thr or Val; Xaa19 ($X_4$) be Thr or Val; Xaa20 ($X_5$) be Glu or Thr; Xaa21 ($X_6$) be His or Thr; Xaa22 ($X_7$) be Tyr; Xaa24 ($X_8$) be Asn or Ser; Xaa25 ($X_9$) be Arg; Xaa26 ($X_{10}$) be Asp or Glu; Xaa27 ($X_1$) be Tyr; and Xaa28 ($X_{12}$) be Asp.

Xaa16 to 22 and Xaa24 to 28 ($X_1$ to $X_{12}$) of the wild type are respectively Ser, Gln, Tyr, Arg, Leu, Pro, Gly, Pro, Arg, His, Phe, and Asn.

In the present invention, one to several or more, preferably 1 to 5 amino acids may be further added to the N-terminal side of the first amino acid. Examples of such an addition of amino acids can preferably include the addition of 1 to 5 Asp and/or Glu (both of Asp and Glu may be included), more preferably the addition of 1 to 5 Asp or the addition of 1 to 5 Glu.

In the present invention, a peptide that is formed by the substitution, addition, and/or deletion of one or more amino acids in, to or from an added moiety of an N-terminal and/or C-terminal adduct of the SPINK2 mutant peptide (which will be hereinafter referred to as a "parent peptide") and partially or fully maintains the activities of the SPINK2 mutant peptide may be referred to as a "derivative of the parent peptide" or a "parent peptide derivative". Such a "derivative" is also included within the scope of the "peptide" of the present invention.

The amino acid sequence of the SPINK2 mutant included within the scope of the KLK5 inhibitory peptide, the KLK5/KLK7 inhibitory peptide, or the KLK5/KLK14 inhibitory peptide of the present invention can contain natural amino acids or mutated amino acids or amino acid sequences in moieties other than $X_1$ to $X_{12}$, that is, at the positions of Pro2 to Cys15, Cys23, and Pro29 to Cys63 in the amino acid sequence of wild-type human SPINK2 (SEQ ID NO: 1, FIG. 9). For example, the SPINK2 mutant may be mutated at one or more positions as long as the mutations do not completely prevent or interfere with the KLK5 inhibitory activity, the KLK5/KLK7 inhibitory activity, or the KLK5/KLK14 inhibitory activity, or folding. Such mutations can be achieved using standard methods known to those skilled in the art. Examples of typical mutations in the amino acid sequence can include the substitution, deletion or insertion of one or more amino acids, and examples of a substitution can include a conservative substitution. As a result of a conservative substitution, an amino acid residue is substituted with another amino acid residue having similar chemical characteristics not only in bulkiness but also in polarity. Examples of conservative substitutions are described elsewhere in this description. Meanwhile, moieties other than $X_1$ to $X_{12}$ can allow the non-conservative substitution of one or more amino acids, as long as the substitutions do not completely prevent or interfere with the KLK5 inhibitory activity, the KLK5/KLK7 inhibitory activity, or the KLK5/KLK14 inhibitory activity, or folding.

In the amino acid sequence of the SPINK2 mutant serving as the KLK5 inhibitory peptide, the KLK5/KLK7 inhibitory peptide, or the KLK5/KLK14 inhibitory peptide of the present invention, $X_1$ to $X_{12}$ are preferably respectively the amino acids of $X_1$ to $X_{12}$ in any one of SEQ ID NOs: 6, 8, 10, 12, 14, 16, 18, and 20 (FIGS. 14, 16, 18, 20, 22, 24, 26, and 28), SEQ ID NOs: 22, 24, 26, and 28 (FIGS. 30, 32, 34, and 36), and SEQ ID NOs: 30 and 32 (FIGS. 38 and 40), and moieties other than $X_1$ to $X_{12}$ can have amino acids or amino acid sequences that do not completely prevent or interfere with the KLK5 inhibitory activity, the KLK5/KLK7 inhibitory activity, or the KLK5/KLK14 inhibitory activity, or folding.

Further, examples of the amino acid sequence of the SPINK2 mutant serving as the KLK5 inhibitory peptide, the KLK5/KLK7 inhibitory peptide, or the KLK5/KLK14 inhibitory peptide of the present invention can include any one of the amino acid sequences (a1) to (a4), (b1) to (b4), or (c1) to (c4) below:

- (a1) an amino acid sequence composed of the amino acids at positions 1 to 63 in the amino acid sequence set forth in any one of SEQ ID NOs: 6, 8, 10, 12, 14, 16, 18, and 20 (FIGS. 14, 16, 18, 20, 22, 24, 26, and 28);
- (a2) an amino acid sequence encoded by a nucleotide sequence that hybridizes with a nucleotide sequence complementary to the nucleotide sequence encoding the amino acid sequence described in (a1) under stringent conditions and encodes the amino acid sequence contained in a peptide having a KLK5 inhibitory activity;
- (a3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (a1) and contained in a peptide having a KLK5 inhibitory activity; and
- (a4) an amino acid sequence that is 60%, 70%, 80%, 85%, 90%, 92%, 94%, 96%, 97%, 98% or 99% or more identical to the amino acid sequence described in (a1) and contained in a peptide having a KLK5 inhibitory activity,
- (b1) an amino acid sequence composed of the amino acids at positions 1 to 63 in the amino acid sequence set forth in any one of SEQ ID NOs: 22, 24, 26, and 28 (FIGS. 30, 32, 34, and 36);
- (b2) an amino acid sequence encoded by a nucleotide sequence that hybridizes with a nucleotide sequence complementary to the nucleotide sequence encoding the amino acid sequence described in (b1) under stringent conditions and encodes the amino acid sequence contained in a peptide having a KLK5/KLK7 inhibitory activity;
- (b3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (b1) and contained in a peptide having a KLK5/KLK7 inhibitory activity; and
- (b4) an amino acid sequence that is 60%, 70%, 80%, 85%, 90%, 92%, 94%, 96%, 97%, 98% or 99% or more identical to the amino acid sequence described in (b1) and contained in a peptide having a KLK5/KLK7 inhibitory activity, or
- (c1) an amino acid sequence composed of the amino acids at positions 1 to 63 in the amino acid sequence set forth in any one of SEQ ID NOs: 30 and 32 (FIGS. 38 and 40);
- (c2) an amino acid sequence encoded by a nucleotide sequence that hybridizes with a nucleotide sequence complementary to the nucleotide sequence encoding the amino acid sequence described in (c1) under stringent conditions and encodes the amino acid sequence contained in a peptide having a KLK5/KLK14 inhibitory activity;
- (c3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (c1) and contained in a peptide having a KLK5/KLK14 inhibitory activity; and
- (c4) an amino acid sequence that is 60%, 70%, 80%, 85%, 90%, 92%, 94%, 96%, 97%, 98% or 99% or more identical to the amino acid sequence described in (c1) and contained in a peptide having a KLK5/KLK14 inhibitory activity.

The amino acids at positions 64 and 65 in SEQ ID NOs: 6, 8, 10, 12, 14, 16, 18, 20, 22, 24, 26, 28, 30, and 32 (FIGS. 14, 16, 18, 20, 22, 24, 26, 28, 30, 32, 34, 36, 38, and 40) are not amino acids corresponding to those in the wild-type human SPINK2 (SEQ ID NO: 1, FIG. 9: composed of 63 amino acids) but are added to express the peptide of the present invention in an aspect of the present invention.

Mutations can be introduced into the peptide of the present invention for the purpose of improving the folding stability, the thermostability, the storage stability, the half-life in blood, the water solubility, the biological activity, the pharmacological activity, the side effects, and the like. For example, new reactive groups such as Cys can be introduced by a mutation for conjugation to other substances such as polyethylene glycol (PEG), hydroxyethyl starch (HES), biotin, peptides, or proteins.

In the present invention, the KLK5 inhibitory peptide, the KLK5/KLK7 inhibitory peptide, or the KLK5/KLK14 inhibitory peptide may be linked or added to other moieties, and such conjugates are referred to as "KLK5 inhibitory peptide conjugates", "KLK5/KLK7 inhibitory peptide conjugates", or "KLK5/KLK14 inhibitory peptide conjugates", respectively. In the present invention, "conjugates" mean molecules formed by other moieties binding to the peptide of the present invention or a fragment thereof. The "conjugates" or "conjugation" include moieties linked or bound to the N-terminus and/or C-terminus of the peptide of the present invention via a chemical substance such as a cross-linking agent, or via an active substance or the like that is suitable for linking the moieties to an amino acid side chain, by a synthetic chemical method, or by a genetic engineering method or the like. Example of such "moieties" that improve the half-life in blood can include polyalkylene glycol molecules such as polyethylene glycol (PEG), hydroxyethyl starch (HES), fatty acid molecules such as palmitic acid, an Fc region of an immunoglobulin (for example, an Fc region of human immunoglobulin G1: its amino acid sequence is shown in SEQ ID NO: 87, FIG. 95), the CH3 domain of an immunoglobulin, the CH4 domain of an immunoglobulin, albumin or a fragment thereof, albumin binding peptides, albumin binding proteins such as streptococcal protein G, and transferrin. As regards other "moieties", the peptide of the present invention can be linked to such "moieties" via a linker such as a peptide linker.

In an aspect of the present invention, such a conjugate is a fusion of the SPINK2 mutant peptide of the present invention with an Fc region of an antibody or a fragment thereof. Examples of the origin of the antibody can include humans and nonhuman animals, including rodents such as mice, rats, and rabbits, other mammals such as bovines, pigs, dogs, cynomolgus monkeys, marmosets, and rhesus monkeys, and birds such as chickens, however, it is preferably from humans.

Examples of the antibody can include IgG1, IgG2, IgG3, IgG4, IgM, IgA1, IgA2, IgD, and IgE, preferably IgG1. More preferably, the conjugate is a fusion of the peptide of the present invention with an Fc region of human IgG1 or a fragment thereof. Although the fusion of the peptide of the present invention with the Fc region of the antibody or the fragment thereof may be referred to as "Fc fusion" or "conjugate", all have the same meaning.

Examples of the Fc region of human IgG1 can include a region containing or consisting of the amino acid sequence set forth in SEQ ID NO: 87 (FIG. 95), but there is no limitation to this. The Fc region of the antibody may be either the wild type or a mutant type.

Further, the KLK5 inhibitory peptide, the KLK5/KLK7 inhibitory peptide, or the KLK5/KLK14 inhibitory peptide of the present invention may be conjugated with another drug, in order to exert or enhance the pharmacological activity. Techniques and aspects known to those skilled in the art as antibody-drug conjugates (ADC) in the antibody field can constitute some aspects of the present invention by replacing the antibody with the peptide of the present invention.

The KLK5 inhibitory peptide, the KLK5/KLK7 inhibitory peptide, or the KLK5/KLK14 inhibitory peptide of the present invention may further contain one or more moieties exerting binding affinity, inhibitory activity, antagonist activity, and agonist activity to target molecules other than KLK5, KLK5 and KLK7, or KLK5 and KLK14, respectively, or may be conjugated with such moieties. Examples of such "moieties" can include antibodies or fragments thereof, and proteins having a backbone other than antibodies such as the SPINK2 mutant or fragments thereof. Techniques and aspects known to those skilled in the art as multispecific antibodies and bispecific antibodies in the antibody field fall within some aspects of the conjugate of the present invention by replacing at least one of the two or more "antibodies" contained therein with the peptide of the present invention.

The KLK5 inhibitory peptide, the KLK5/KLK7 inhibitory peptide, or the KLK5/KLK14 inhibitory peptide of the present invention, or its precursor can contain a signal sequence. A signal sequence that is present at the N-terminus of a polypeptide or its precursor or added thereto is useful for delivering the polypeptide to a specific compartment of a cell, such as the periplasm in the case of *Escherichia coli* and the endoplasmic reticulum in the case of eukaryotic cells. Many signal sequences are known to those skilled in the art and can be selected according to the host cells. Examples of the signal sequence for secreting a desired peptide into the periplasm of *Escherichia coli* can include OmpA. An embodiment containing such a signal sequence can also be included within the conjugate of the present invention as an aspect.

Further, the peptide can be purified by affinity chromatography by adding a tag to the KLK5 inhibitory peptide, the KLK5/KLK7 inhibitory peptide, or the KLK5/KLK14 inhibitory peptide of the present invention in advance.

The peptide of the present invention, for example, can contain biotin, Strep Tag®, Strep tag II®, oligohistidines such as His6, polyhistidines, immunoglobulin domains, maltose binding proteins, glutathione-S-transferases (GSTs), calmodulin binding peptides (CBPs), haptens such as digoxigenin and dinitrophenol, epitope tags such as FLAG®, myc tag, HA tag, and the like (hereinafter, collectively referred to as "affinity tags") at its C-terminus. The tag adducts can also be included within the conjugate of the present invention as some aspects. The conjugate of the present invention, as a whole, may be a peptide (polypeptide).

The KLK5 inhibitory peptide, the KLK5/KLK7 inhibitory peptide, or the KLK5/KLK14 inhibitory peptide of the present invention can contain labeling moieties, and can be specifically conjugated with labeling moieties such as enzyme labels, radioactive labels, colored labels, fluorescence labels, chromogenic labels, luminescent labels, haptens, digoxigenin, biotin, metal complexes, metals, and colloidal gold. The aspect containing labeling moieties can also be included within the conjugate of the present invention as some aspects.

Examples of the amino acid sequence of the KLK5 inhibitory peptide conjugate, the KLK5/KLK7 inhibitory peptide conjugate, or the KLK5/KLK14 inhibitory peptide conjugate of the present invention can include any one of the amino acid sequences (a1) to (a4), (b1) to (b4), or (c1) to (c4) below:

(a1) the amino acid sequence set forth in any one of SEQ ID NOs: 34, 36, 38, 40, 42, 44, 46, 48, and 96 (FIGS. 42, 44, 46, 48, 50, 52, 54, 56, and 106);

(a2) an amino acid sequence encoded by a nucleotide sequence that hybridizes with a nucleotide sequence complementary to the nucleotide sequence encoding the amino acid sequence described in (a1) under stringent conditions and encodes the amino acid sequence contained in a peptide having a KLK5 inhibitory activity;

(a3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (a1) and contained in a peptide having a KLK5 inhibitory activity; and (a4) an amino acid sequence that is 60%, 70%, 80%, 85%, 90%, 92%, 94%, 96%, 97%, 98% or 99% or more identical to the amino acid sequence described in (a1) and contained in a peptide having a KLK5 inhibitory activity, (b1) the amino acid sequence set forth in any one of SEQ ID NOs: 50, 52, 54, and 56 (FIGS. 58, 60, 62, and 64);

(b2) an amino acid sequence encoded by a nucleotide sequence that hybridizes with a nucleotide sequence complementary to the nucleotide sequence encoding the amino acid sequence described in (b1) under stringent conditions and encodes the amino acid sequence contained in a peptide having a KLK5/KLK7 inhibitory activity;

(b3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (b1) and contained in a peptide having a KLK5/KLK7 inhibitory activity; and (b4) an amino acid sequence that is 60%, 70%, 80%, 85%, 90%, 92%, 94%, 96%, 97%, 98% or 99% or more identical to the amino acid sequence described in (b1) and contained in a peptide having a KLK5/KLK7 inhibitory activity, or (c1) the amino acid sequence set forth in any one of SEQ ID NOs: 58 and 60 (FIGS. 66 and 68);

(c2) an amino acid sequence encoded by a nucleotide sequence that hybridizes with a nucleotide sequence complementary to the nucleotide sequence encoding the amino acid sequence described in (c1) under stringent conditions and encodes the amino acid sequence contained in a peptide having a KLK5/KLK14 inhibitory activity;

(c3) an amino acid sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 amino acid in the amino acid sequence described in (c1) and contained in a peptide having a KLK5/KLK14 inhibitory activity; and (c4) an amino acid sequence that is 60%, 70%, 80%, 85%, 90%, 92%, 94%, 96%, 97%, 98% or 99% or more identical to the amino acid sequence described in (c1) and contained in a peptide having a KLK5/KLK14 inhibitory activity.

The KLK5 inhibitory peptide, the KLK5/KLK7 inhibitory peptide, or the KLK5/KLK14 inhibitory peptide of the present invention (the amino acid sequence thereof) can contain both natural amino acids and non-natural amino acids. The natural amino acids can include both L-amino acids and D-amino acids.

The KLK5 inhibitory peptide, the KLK5/KLK7 inhibitory peptide, or the KLK5/KLK14 inhibitory peptide of the present invention can exist as a monomer, a dimer, a trimer or higher oligomer, or a multimer. The dimer, the trimer or higher oligomer, and the multimer may be either a homomer composed of a single type of monomer or a heteromer composed of two or more different types of monomers. The monomer may rapidly diffuse and be excellent in penetration into tissues, for example. The dimer, the oligomer, and the multimer can have excellent aspects such as high local affinity or binding activity to the target molecules, a low dissociation rate, or high KLK5 inhibitory activity, KLK5/KLK7 inhibitory activity, or KLK5/KLK14 inhibitory activity. In addition to spontaneous dimerization, oligomerization, and multimerization, intended dimerization, oligomerization, and multimerization can also be achieved by introducing a jun-fos domain, a leucine zipper, or the like into the peptide of the present invention.

The KLK5 inhibitory peptide, the KLK5/KLK7 inhibitory peptide, or the KLK5/KLK14 inhibitory peptide of the present invention can bind to one or more target molecules or inhibit the activities of the target molecules, in the form of a monomer, a dimer, a trimer or higher oligomer, or a multimer.

Examples of the form of the KLK5 inhibitory peptide, the KLK5/KLK7 inhibitory peptide, or the KLK5/KLK14 inhibitory peptide of the present invention can include isolated forms (such as freeze-dried preparations and solutions), the aforementioned conjugates, and forms bound to other molecules (such as immobilized forms, associations with foreign molecules, and forms bound to target molecules), but there is no limitation to these examples, and a form suitable for expression, purification, use, storage, or the like can be optionally selected.

3. Identification of KLK5 Inhibitory Peptide, KLK5/KLK7 Inhibitory Peptide, and KLK5/KLK14 Inhibitory Peptide A KLK5 inhibitory peptide, a KLK5/KLK7 inhibitory peptide, and a KLK5/KLK14 inhibitory peptide can be identified by methods known to those skilled in the art, using the amino acid sequence of SPINK2 or the amino acid sequence of the KLK5 inhibitory peptide, the KLK5/KLK7 inhibitory peptide, and the KLK5/KLK14 inhibitory peptide of the present invention (for example, the amino acid sequences according to (a1), (b1), or (c1) above), a nucleotide sequence encoding such an amino acid sequence, nucleic acid molecules containing such a nucleotide sequence, and the like as starting materials. As a suitable example, such identification can be made from a human SPINK2 mutant library, using the KLK5 inhibitory activity, the KLK5/KLK7 inhibitory activity, or the KLK5/KLK14 inhibitory activity, respectively, as an index, and the binding activity to KLK5, KLK5/KLK7, or KLK5/KLK14 may be combined for use, respectively, as an index.

For example, the nucleic acid molecules serving as the starting material can be subjected to mutagenesis and introduced into an appropriate bacterial or eukaryotic host using recombinant DNA technology. The SPINK2 mutant library is known as a technique for identifying a binder or an inhibitor of a target molecule. For example, the disclosure in International Publication No. WO 2014/024914 is also incorporated within the disclosure of the present invention by reference in its entirety. After the nucleotide sequence subjected to mutagenesis is expressed in the appropriate host, a clone formed by linking the SPINK2 mutant having the desired properties, activities, functions, and the like with its genetic trait can be concentrated and/or selected from the library to be identified. For concentrating and/or selecting the clone, methods known to those skilled in the art can be used, such as the bacterial display method (Francisco, J. A., et al. (1993) Proc. Natl. Acad. Sci., USA, Vol. 90, pp. 10444-10448), the yeast display method (Boder, E. T., et al. (1997) Nat. Biotechnol., Vol. 15, pp. 553-557), the mammalian cell display method (Ho M, et al. (2009) Methods Mol Biol., Vol. 525, pp. 337-352), the phage display method (Smith, G. P. (1985) Science., Vol. 228, pp. 1315-1317), the ribosome display method (Mattheakis L C, et al. (1994) Proc. Natl. Acad. Sci., USA, Vol. 91, No. 19, pp. 9022-9029), the nucleic acid display method (Nemoto N, et al. (1997) FEBS Lett., Vol. 414, No. 2, pp. 405-408) such as mRNA display, and the colony screening method (Pini, A. et al. (2002) Comb. Chem. High Throughput Screen., Vol. 5, pp. 503-510). The nucleotide sequence of the SPINK2 mutant contained in the clone thus selected and identified is determined. Thereby, an amino acid sequence encoded by the nucleotide sequence can be determined as the amino acid sequence of the SPINK2 mutant, that is, the KLK5 inhibitory peptide, the KLK5/KLK7 inhibitory peptide, or the KLK5/KLK14 inhibitory peptide contained in the clone.

The SPINK2 mutant of the present invention can be obtained, for example, by mutagenesis of the natural SPINK2. "Mutagenesis" means enabling substitution or deletion of one or more amino acids present at some positions in an amino acid sequence with other amino acids, or insertion of amino acids that are not present in the amino acid sequence. Such deletion or insertion can change the sequence length. In the SPINK2 mutant of the present invention, mutagenesis can preferably occur at one or more positions of $X_1$ to $X_{12}$ in the amino acid sequence set forth in SEQ ID NO: 61 (FIG. 69).

However, the scope of the mutant also includes those with the same amino acids as present at specific positions in the natural amino acid sequence, that is, a natural amino acid sequence is maintained at one or more positions of $X_1$ to $X_{12}$ after such suitable mutagenesis, as long as at least one amino acid is mutated overall. Likewise, in an aspect of the present invention, the scope of the mutant also includes those with the same amino acids as present at specific positions in the natural amino acid sequence, that is, a natural amino acid sequence is maintained at one or more positions in moieties other than $X_1$ to $X_{12}$ after mutation is induced at the positions, as long as at least one amino acid is mutated overall.

The term "random mutagenesis" means that one or more different amino acids are introduced at specific positions within a sequence by mutagenesis with a certain probability, but not all the probabilities of introducing the amino acids may be the same. Further, in the present invention, the inclusion of the naturally-occurring amino acid (as one of the amino acids) in the at least two different amino acids cannot be prevented, and the scope of "random mutagenesis" also includes such a case.

As regards a method for random mutagenesis at specific positions, standard methods known to those skilled in the art can be used. For example, mutations can be induced at specific positions in a sequence by PCR (polymerase chain reaction) using a mixture of synthetic oligonucleotides containing a degenerate nucleotide composition. For example, use of a codon NNK or NNS (N=adenine, guanine, cytosine, or thymine; K=guanine or thymine; S=adenine or cytosine) induces a mutation to introduce a stop codon in addition to all 20 natural amino acids, whereas use of a codon VVS (V=adenine, guanine, or cytosine) eliminates the possibility of introducing Cys, Ile, Leu, Met, Phe, Trp, Tyr, and Val and induces a mutation to introduce the other 12 natural amino acids. Further, use of a codon NMS (M=adenine or cytosine) eliminates the possibility of introducing Arg, Cys, Gly, Ile, Leu, Met, Phe, Trp, and Val and induces a mutation to introduce the other 11 natural amino acids, for example. Special codons, artificial codons, or the like can be used to induce a mutation to introduce non-natural amino acids.

Site-specific mutagenesis can also be performed using structural information containing a higher-order structure of a target and/or a peptide against the target or a wild-type peptide from which the peptide is derived. In the present invention, site-specific mutation can be introduced using structural information containing higher-order information on the target KLK5, KLK7, or KLK14, and/or the SPINK2 mutant, the wild-type SPINK2 or a complex of the two, with respect to KLK5, KLK5 and KLK7, or KLK5 and KLK14. There may cases where a correlation can be found between the KLK5 inhibitory activity, the KLK5/KLK7 inhibitory activity, or the KLK5/KLK14 inhibitory activity and the structural information obtained, for example, through identifying a SPINK2 mutant having the KLK5 inhibitory activity, the KLK5/KLK7 inhibitory activity, or the KLK5/KLK14 inhibitory activity, then obtaining crystals of KLK5, KLK7, or KLK14 and the SPINK2 mutant complex to perform X-ray crystal structure analysis, and specifying an epitope on the KLK5, KLK7, or KLK14 molecule to which the SPINK2 mutant binds and a paratope on the SPINK2 mutant corresponding to the epitope based on the analysis results. Based on the structure-activity correlation, substitution with specific amino acids at specific positions, or insertion or deletion of amino acids at specific positions or the like is designed, so that the KLK5 inhibitory activity, the KLK5/KLK7 inhibitory activity, or the KLK5/KLK14 inhibitory activity can be actually confirmed.

Further, mutations can be induced, for example, using a nucleotide constituent unit that modifies the specificity of a base pair, such as inosine.

Further, mutations can be induced at random positions, for example, by the error-prone PCR method using a DNA polymerase with a high error rate without a proofreading function, such as Taq DNA polymerase, or chemical mutagenesis, and the like.

The KLK5 inhibitory peptide, the KLK5/KLK7 inhibitory peptide, or the KLK5/KLK14 inhibitory peptide can be concentrated and/or selected from suitable libraries, such as a phage library and a colony library, known to those skilled in the art for the respective screening method using bacterial display, yeast display, mammalian cell display, phage display, ribosome display, nucleic acid display, colony screening, or the like. Using vectors and methods known to those skilled in the art that are suitable for the respective libraries, such as a phagemid for the phage library and a cosmid for colony screening in these libraries, construction of the libraries can be achieved. The vectors may be viruses that infect prokaryotic or eukaryotic cells or viral vectors. Such recombinant vectors can be prepared by methods known to those skilled in the art such as genetic engineering.

Bacterial display is, for example, a technique of fusing a desired protein with a part of the outer membrane lipoprotein (Lpp) of *Escherichia coli* and the outer membrane protein OmpA to present the desired protein on the surface of *Escherichia coli*. A DNA group obtained by random mutagenesis of a nucleotide sequence encoding an amino acid sequence of a protein is introduced into vectors suitable for bacterial display to transform bacterial cells with the vectors. Thus, a library presenting a randomly mutagenized protein group can be obtained on the surface of the transformed bacterial cells (Francisco, J. A., et al. (1993) Proc. Natl. Acad. Sci., USA, Vol. 90, pp. 10444-10448).

Yeast display is a technique of fusing a desired protein with a protein such as α-agglutinin on the outer shell of the surface of a yeast cell to present it on the yeast surface. The α-agglutinin contains a C-terminal hydrophobic region, which is thought to be a glycosylphosphatidylinositol (GPI) anchor attachment signal, a signal sequence, an active domain, a cell wall domain, and the like, and the desired protein can be displayed on the surface of the yeast cell by manipulation of them. A DNA group obtained by random mutagenesis of a nucleotide sequence encoding an amino acid sequence of a protein is introduced into vectors suitable for yeast display to transform yeast cells with the vectors. Thus, a library presenting a randomly mutagenized protein group can be obtained on the surface of the transformed yeast cells (Ueda, M. & Tanaka, A., Biotechnol. Adv., Vol. 18, pp. from 121, Published in 2000; Ueda, M. & Tanaka, A., J. Biosci. Bioeng., Vol. 90, pp. from 125, Published in 2000).

Animal cell display is, for example, a technique of fusing a desired protein with a transmembrane region of a membrane protein typified by a platelet-derived growth factor receptor (PDGFR) to present the desired protein on the surface of a mammalian cell, such as HEK293 and Chinese hamster ovary (CHO) cells. A DNA group obtained by random mutagenesis of a nucleotide sequence encoding an amino acid sequence of a protein is introduced into vectors suitable for animal cell display to transfect animal cells with the vectors. Thus, a library presenting a randomly mutagenized protein group can be obtained on the surface of the transfected animal cells (Ho M, et al. (2009) Methods Mol Biol., Vol. 525, pp. 337-352).

The desired library presented on cells such as yeast, bacteria, and animal cells can be incubated in the presence of the target molecules or brought into contact with the target molecules. For example, after a cell containing the library and KLK5, KLK7, or KLK14 modified with biotin or the like are incubated for a certain time, a carrier such as magnetic beads is added thereto, the cell is separated from the carrier, and then the carrier is washed to remove non-specific adsorbates and binders. Thus, a cell group presenting a peptide bound to the carrier (or KLK5, KLK7, or KLK14 bound to the carrier), an assembly of the peptides, or the concentrated peptide assembly can be collected. Likewise, a cell group presenting a peptide bound to the carrier (or KLK5, KLK7, or KLK14 bound to the carrier) or KLK5, KLK7, or KLK14, an assembly of the peptides, or the concentrated peptide assembly can be collected by performing magnetic cell separation (MACS) after addition of the magnetic beads or FACS after cell staining using an anti-KLK5 antibody, an anti-KLK7 antibody, or an anti-KLK14 antibody. Non-specific adsorbate sites and/or binding sites can be subjected, for example, to blocking treatment, and a blocking step can be incorporated as long as it is an appropriate method. A vector expressing the peptide, the peptide assembly, or the concentrated peptide assembly thus obtained is collected, and a nucleotide sequence of the polynucleotide inserted into the vector is determined, so that an amino acid sequence encoded by the nucleotide sequence can be determined. Further, the peptide assembly binding to the target molecules can be more highly concentrated by introducing the vector into the host cell again and repeating the aforementioned operation as a cycle once to several times.

In the case of phage display, a phagemid is, for example, a bacterial plasmid containing a second origin of replication derived from a single-stranded bacteriophage other than the origin of plasmid replication. A cell containing a phagemid can replicate the phagemid via a single-stranded replication mode by superinfection with M13 or a similar helper bacteriophage. That is, single-stranded phagemid DNA is packaged in infectious particles coated with a bacteriophage coat protein. Thus, phagemid DNA can be formed in infected bacteria as a cloned double-stranded DNA plasmid, and a phagemid can be formed as bacteriophage-like particles from the culture supernatant of the superinfected cell. The particles themselves can be reformed as plasmids by injecting the bacteriophage-like particles into bacteria having an F-pilus in order to infect the bacteria with such DNA.

A fusion gene containing a polynucleotide having a nucleotide sequence encoding the amino acid sequence of the test peptide and a bacteriophage coat protein gene is inserted into the phagemid to infect the bacteria, and such cells are cultured. Thus, the peptide can be expressed or presented (the same meaning as displayed) on the bacteria or the phage-like particles or can be produced as a fusion protein with the coat protein in the phage particles or the culture supernatant of the bacteria.

For example, the peptide can be produced in the culture supernatant of *Escherichia coli* as a fusion protein containing the peptide and the coat protein by inserting a fusion gene containing the polynucleotide and the bacteriophage coat protein gene gpIII into a phagemid for superinfection of *Escherichia coli* with M13 or a similar helper phage.

In the case of using various cyclic or non-cyclic vectors such as a viral vector instead of the phagemid, a peptide having an amino acid sequence encoded by the nucleotide sequence of the polynucleotide inserted into such a vector can be expressed or presented on the cell in which the vector is introduced or on virus-like particles, or can be produced in the culture supernatant of the cell according to methods known to those skilled in the art.

The library expressing the peptide thus obtained can be incubated in the presence of the target molecules or brought into contact with the target molecules. For example, a carrier to which KLK5, KLK5 and/or KLK7, or KLK5 and/or KLK14 is immobilized is incubated for a certain time together with a mobile phase containing the library, thereafter the mobile phase is separated from the carrier, and then the carrier is washed to remove non-specific adsorbates and binders. Thus, a peptide bound to the carrier (or KLK5, KLK5 and/or KLK7, or KLK5 and/or KLK14 bound to the carrier), an assembly of the peptides, or the concentrated peptide assembly can be collected by elution. The elution can be non-selectively performed under relatively high ionic strength, low pH, and moderate denaturing conditions, in the presence of chaotropic salts, and the like, or can be selectively performed by adding soluble target molecules such as KLK5, KLK7, and KLK14, antibodies that bind to the target molecules, natural ligands, substrates, and the like to allow the mixture to compete with the immobilized target molecules. Non-specific adsorbate sites and/or binding sites can be subjected, for example, to blocking treatment, and a blocking step can be incorporated as long as it is an appropriate method.

A vector expressing the peptide, the peptide assembly, or the concentrated peptide assembly thus obtained is collected, and a nucleotide sequence of the polynucleotide inserted into the vector is determined, so that an amino acid sequence encoded by the nucleotide sequence can be determined. Further, the peptide assembly binding to the target molecules can be more highly concentrated by introducing the vector into the host cell again and repeating the aforementioned operation as a cycle once to several times.

Ribosome display is a technique of synthesizing a desired protein and mRNA corresponding thereto, and a ribosome-linked molecule within a test tube, for example, using mRNA encoding the desired protein free from a termination codon and a cell-free protein synthesis system. A library presenting a randomly mutagenized protein group on ribosomes can be obtained, using the mRNA group obtained by random mutagenesis of a nucleotide sequence encoding an amino acid sequence of a protein and a cell-free protein synthesis system (Mattheakis L C, et al. (1994) Proc. Natl. Acad. Sci., USA, Vol. 91, No. 19, pp. 9022-9029).

Nucleic acid display is also called mRNA display and is a technique of synthesizing a desired protein, mRNA encoding the protein, and a ribosome-linked molecule, for example, using a linker such as puromycin which has a similar structure to the 3' end of tyrosyl tRNA. Since such a technique uses a cell-free protein synthesis system instead of living cells, synthesis within a test tube is possible. A library presenting a randomly mutagenized protein group on ribosomes can be obtained, using an mRNA group obtained by random mutagenesis of a nucleotide sequence encoding an amino acid sequence of a protein, a linker such as puromycin, and a cell-free protein synthesis system (Nemoto N, et al. (1997) FEBS Lett., Vol. 414, No. 2, pp. 405-408).

The library obtained through a cell-free synthesis system such as ribosome display or nucleic acid display and expressing the peptide can be incubated in the presence of the target molecules or brought into contact with the target molecules. For example, a carrier to which KLK5, KLK5 and/or KLK7, or KLK5 and/or KLK14 is immobilized is incubated for a certain time together with a mobile phase containing the library, thereafter the mobile phase is separated from the carrier, and then the carrier is washed to remove non-specific adsorbates and binders. Thus, a peptide bound to the carrier (or KLK5, KLK5 and/or KLK7, or KLK5 and/or KLK14 bound to the carrier), an assembly of the peptides, or the concentrated peptide assembly can be collected by elution. The elution can be non-selectively performed under relatively high ionic strength, low pH, and moderate denaturing conditions, in the presence of chaotropic salts, and the like, or can be selectively performed by adding soluble target molecules such as KLK5, KLK7, and KLK14, antibodies that bind to the target molecules, natural ligands, substrates, and the like to allow the mixture to compete with the immobilized target molecules. Non-specific adsorbate sites and/or binding sites can be subjected, for example, to blocking treatment, and a blocking step can be incorporated as long as it is an appropriate method.

Nucleic acids expressing the peptide, the peptide assembly, or the concentrated peptide assembly thus obtained are collected, and the nucleotide sequence is determined after reverse transcription to cDNA in the case of mRNA, so that an amino acid sequence encoded by the nucleotide sequence can be determined. Further, the peptide assembly binding to the target molecules can be more highly concentrated by transcribing mRNA from the nucleic acids thus collected and repeating the aforementioned operation as a cycle once to several times.

The peptide or its assembly can be efficiently purified by conjugating an affinity tag to the peptide, the peptide assembly, or the concentrated peptide assembly in advance. For example, the peptide can be eluted by conjugating a substrate of a protease as a tag to the peptide assembly in advance and then cleaving it through the protease activity.

Based on the sequence information obtained and the functions or the like of the peptide, further mutations are induced in the clone or the library obtained, so that a peptide with functions (for example, the KLK5 inhibitory activity, the KLK5/KLK7 inhibitory activity, or the KLK5/KLK14 inhibitory activity), physical properties (such as thermostability and storage stability), pharmacokinetics (such as distribution and half-life in blood), and the like which are improved can be obtained from the library to which the mutation has been introduced.

The KLK5 inhibitory peptide, the KLK5/KLK7 inhibitory peptide, or the KLK5/KLK14 inhibitory peptide can be identified by determining whether or not the obtained peptide has the KLK5 inhibitory activity, the KLK5/KLK7 inhibitory activity, or the KLK5/KLK14 inhibitory activity, respectively.

Further, the KLK5 inhibitory peptide, the KLK5/KLK7 inhibitory peptide, or the KLK5/KLK14 inhibitory peptide can preferably maintain a three-dimensional structure constituted by a loop structure composed of Ser16 to Val30 contained in the amino acid sequence of the wild-type SPINK2, a β-sheet composed of β strand (1) composed of Cys31 and Gly32 and β strand (2) composed of Ile57 to Arg59, and an α-helix composed of Glu41 to Gly51, or a loop structure, a β-sheet, and an α-helix that are similar to or at least partially correspond to the above (positions thereof), to the extent that the KLK5 inhibitory activity, the KLK5/KLK7 inhibitory activity, or the KLK5/KLK14 inhibitory activity can be exerted. It is also possible to identify a more suitable KLK5 inhibitory peptide, KLK5/KLK7 inhibitory peptide, or KLK5/KLK14 inhibitory peptide using such a three-dimensional structure (the entire structure or a partial structure) as a part of the index.

Further, the present invention relates to a method for identifying a KLK5 inhibitory peptide, a KLK5/KLK7 inhibitory peptide, or a KLK5/KLK14 inhibitory peptide using a SPINK2 mutant library, and examples thereof can include the method described in (75) above. Further, the present invention relates to a method for identifying a KLK5 inhibitory compound, a KLK5/KLK7 inhibitory compound, or a KLK5/KLK14 inhibitory compound, using various compound libraries. In such a method, the peptide of the present invention or the conjugate thereof can be used as a reference compound, a control, or the like, and such a method can be exemplified by (76) above. In such a method, a test compound may be determined to be positive when the enzyme inhibitory activity of the compound is equivalent to or stronger than the enzyme inhibitory activity of the reference compound or the control, whereas the compound may be determined to be negative when the enzyme inhibitory activity is weaker. A method involving such a comparison can be exemplified by (77) above. Meanwhile, the peptide of the present invention or the conjugate thereof can be used as a reference compound, a control, or the like, in any test involving a step of measuring the protease activity of KLK5 and optionally KLK7 or KLK14, and such a test method is also included in the present invention. Such a test is not specifically limited and can be exemplified by (78) above. Suitable examples thereof can include a diagnostic method, a test method, a detection method, and a method for identifying an individual to whom a pharmaceutical composition is to be administered of the present invention (all will be described below).

4. Nucleic Acid Molecules Encoding Peptide of Present Invention or Conjugate thereof, Vector Containing the Same, Cell Containing the Same, and Method for Producing Recombinant Peptide or Conjugate.

The present invention also provides a polynucleotide containing the nucleotide sequence encoding the amino acid sequence contained in the KLK5 inhibitory peptide, the KLK5/KLK7 inhibitory peptide, or the KLK5/KLK14 inhibitory peptide (which will be hereinafter referred to as "nucleic acid molecules encoding the KLK5 inhibitory peptide", "nucleic acid molecules encoding the KLK5/KLK7 inhibitory peptide", or "nucleic acid molecules encoding the KLK5/KLK14 inhibitory peptide"), a recombinant vector with such a gene inserted, a cell with the gene or the vector introduced (which will be hereinafter referred to as a "cell containing nucleic acid molecules encoding the KLK5 inhibitory peptide", a "cell containing nucleic acid molecules encoding the KLK5/KLK7 inhibitory peptide", or a "cell containing nucleic acid molecules encoding the KLK5/KLK14 inhibitory peptide"), a cell that produces the KLK5 inhibitory peptide, the KLK5/KLK7 inhibitory peptide, or the KLK5/KLK14 inhibitory peptide (which will be hereinafter referred to as a "cell producing the KLK5 inhibitory peptide", a "cell producing the KLK5/KLK7 inhibitory peptide", or a "cell producing the KLK5/KLK14 inhibitory peptide").

Suitable examples of the nucleic acid molecules encoding the KLK5 inhibitory peptide, the nucleic acid molecules encoding the KLK5/KLK7 inhibitory peptide, or the nucleic acid molecules encoding the KLK5/KLK14 inhibitory peptide of the present invention can include those containing the nucleotide sequence described in any one of (a1) to (a4), (b1) to (b4), or (c1) to (c4) below (which will be hereinafter referred to as the "nucleotide sequence of the KLK5 inhibitory peptide", the "nucleotide sequence of the KLK5/KLK7 inhibitory peptide", or the "nucleotide sequence of the KLK5/KLK14 inhibitory peptide", respectively), those composed of a nucleotide sequence containing the nucleotide sequence of the KLK5 inhibitory peptide, the nucleotide sequence of the KLK5/KLK7 inhibitory peptide, or the nucleotide sequence of the KLK5/KLK14 inhibitory peptide, or those composed of the nucleotide sequence of the KLK5 inhibitory peptide, the nucleotide sequence of the KLK5/KLK7 inhibitory peptide, or the nucleotide sequence of the KLK5/KLK14 inhibitory peptide:

(a1) a nucleotide sequence composed of nucleotides 1 to 189 in a nucleotide sequence encoding an amino acid sequence composed of the amino acids at positions 1 to 63 in the amino acid sequence set forth in any one of SEQ ID NOs: 6, 8, 10, 12, 14, 16, 18, and 20 (FIGS. 14, 16, 18, 20, 22, 24, 26, and 28) or the nucleotide sequence described in any one of SEQ ID NOs: 5, 7, 9, 11, 13, 15, 17, and 19 (FIGS. 13, 15, 17, 19, 21, 23, 25, and 27);

(a2) a nucleotide sequence that hybridizes with a nucleotide sequence complementary to the nucleotide sequence described in (a1) under stringent conditions and encodes the amino acid sequence contained in a peptide having a KLK5 inhibitory activity;

(a3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (a1) and encodes the amino acid sequence contained in a peptide having a KLK5 inhibitory activity; and (a4) a nucleotide sequence that is 60%, 70%, 80%, 85%, 90%, 92%, 94%, 96%, 97%, 98% or 99% or more identical to the nucleotide sequence described in (a1) and encodes the amino acid sequence contained in a peptide having a KLK5 inhibitory activity:

(b1) a nucleotide sequence encoding an amino acid sequence composed of the amino acids at positions 1 to 63 in the amino acid sequence set forth in any one of SEQ ID NOs: 22, 24, 26, and 28 (FIGS. 30, 32, 34, and 36) or a nucleotide sequence composed of nucleotides 1 to 189 in the nucleotide sequence described in any one of SEQ ID NOs: 21, 23, 25, and 27 (FIGS. 29, 31, 33, and 35);

(b2) a nucleotide sequence that hybridizes with a nucleotide sequence complementary to the nucleotide sequence described in (b1) under stringent conditions and encodes the amino acid sequence contained in a peptide having a KLK5/KLK7 inhibitory activity;

(b3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (b1) and encodes the amino acid sequence contained in a peptide having a KLK5/KLK7 inhibitory activity; and (b4) a nucleotide sequence that is 60%, 70%, 80%, 85%, 90%, 92%, 94%, 96%, 97%, 98% or 99% or more identical to the nucleotide sequence described in (b1) and encodes the amino acid sequence contained in a peptide having a KLK5/KLK7 inhibitory activity:

(c1) a nucleotide sequence encoding an amino acid sequence composed of the amino acids at positions 1 to 63 in the amino acid sequence set forth in any one of SEQ ID NOs: 30 and 32 (FIGS. 38 and 40), or a nucleotide sequence composed of nucleotides 1 to 189 in the nucleotide sequence described in SEQ ID NO: 29 or 31 (FIG. 37 or 39);

(c2) a nucleotide sequence that hybridizes with a nucleotide sequence complementary to the nucleotide sequence described in (c1) under stringent conditions and encodes the amino acid sequence contained in a peptide having a KLK5/KLK14 inhibitory activity;

(c3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (c1) and encodes the amino acid sequence contained in a peptide having a KLK5/KLK14 inhibitory activity; and (c4) a nucleotide sequence that is 60%, 70%, 80%, 85%, 90%, 92%, 94%, 96%, 97%, 98% or 99% or more identical to the nucleotide sequence described in (c1) and encodes the amino acid sequence contained in a peptide having a KLK5/KLK14 inhibitory activity.

A SPINK2 mutant peptide composed of an amino acid sequence encoded by the nucleotide sequence described in any one of (a1) to (a4), (b1) to (b4), or (c1) to (c4) above or containing an amino acid sequence that inhibits the protease activity of KLK5, KLK5 and KLK7, or KLK5 and KLK14, preferably that specifically inhibits the protease activity thereof.

Nucleotides 190 to 195 in SEQ ID NOs: 5, 7, 9, 11, 13, 15, 17, 19, 21, 23, 25, 27, 29, and 31 (FIGS. 13, 15, 17, 19, 21, 23, 25, 27, 29, 31, 33, 35, 37, and 39) are not nucleotides corresponding to those in the nucleotide sequence encoding the wild-type human SPINK2 (SEQ ID NO: 1, FIG. 9: composed of 63 amino acids) but are added in order to express the peptide of the present invention in an aspect of the present invention.

However, the nucleic acid molecules encoding the KLK5 inhibitory peptide, the KLK5/KLK7 inhibitory peptide, or the KLK5/KLK14 inhibitory peptide are not limited to those described in (a1) to (a4), (b1) to (b4), or (c1) to (c4), and nucleic acid molecules containing a nucleotide sequence encoding an amino acid sequence contained in a SPINK2 mutant having a KLK5 inhibitory activity, KLK5/KLK7 inhibitory activity, or KLK5/KLK14 inhibitory activity, preferably, having the amino acid sequence set forth in SEQ ID NO: 61 (FIG. 69) are all included within the scope of the nucleic acid molecules encoding the KLK5 inhibitory peptide, the KLK5/KLK7 inhibitory peptide, or the KLK5/KLK14 inhibitory peptide.

Further, the present invention also provides a polynucleotide containing the nucleotide sequence encoding the amino acid sequence contained in a KLK5 inhibitory peptide conjugate, a KLK5/KLK7 inhibitory peptide conjugate, or a KLK5/KLK14 inhibitory peptide conjugate (which will be hereinafter referred to as "nucleic acid molecules encoding the KLK5 inhibitory conjugate", "nucleic acid molecules encoding the KLK5/KLK7 inhibitory conjugate", or "nucleic acid molecules encoding the KLK5/KLK14 inhibitory conjugate", respectively), a recombinant vector with such a gene inserted, a cell with the gene or the vector introduced (which will be hereinafter referred to as a "cell containing nucleic acid molecules encoding the KLK5 inhibitory conjugate", a "cell containing nucleic acid molecules encoding the KLK5/KLK7 inhibitory conjugate", or a "cell containing nucleic acid molecules encoding the KLK5/KLK14 inhibitory conjugate"), and a cell producing the KLK5 inhibitory peptide conjugate, the KLK5/KLK7 inhibitory peptide conjugate, or the KLK5/KLK14 inhibitory peptide conjugate (which will be hereinafter referred to as a "cell producing the KLK5 inhibitory conjugate", a "cell producing the KLK5/KLK7 inhibitory conjugate", or a "cell producing the KLK5/KLK14 inhibitory conjugate", respectively).

Suitable examples of the nucleic acid molecules encoding the KLK5 inhibitory conjugate, the nucleic acid molecules encoding the KLK5/KLK7 inhibitory conjugate, or the nucleic acid molecules encoding the KLK5/KLK14 inhibitory conjugate of the present invention can respectively include those containing the nucleotide sequence described in any one of (a1) to (a4), (b1) to (b4), or (c1) to (c4) below (which will be hereinafter referred to as "the nucleotide sequence of the KLK5 inhibitory conjugate", "the nucleotide sequence of the KLK5/KLK7 inhibitory conjugate", or "the nucleotide sequence of the KLK5/KLK14 inhibitory conjugate", respectively), those composed of a nucleotide sequence containing the nucleotide sequence of the KLK5 inhibitory conjugate, the nucleotide sequence of the KLK5/KLK7 inhibitory conjugate, or the nucleotide sequence of the KLK5/KLK14 inhibitory conjugate, or those composed of the nucleotide sequence of the KLK5 inhibitory conjugate, the nucleotide sequence of the KLK5/KLK7 inhibitory conjugate, or the nucleotide sequence of the KLK5/KLK14 inhibitory peptide:

(a1) a nucleotide sequence encoding the amino acid sequence set forth in any one of SEQ ID NOs: 34, 36, 38, 40, 42, 44, 46, 48, and 96 (FIGS. 42, 44, 46, 48, 50, 52, 54, 56, and 106) or the nucleotide sequence described in any one of SEQ ID NOs: 33, 35, 37, 39, 41, 43, 45, 47, and 95 (FIGS. 41, 43, 45, 47, 49, 51, 53, 55, and 105);

(a2) a nucleotide sequence that hybridizes with a nucleotide sequence complementary to the nucleotide sequence described in (a1) under stringent conditions and encodes the amino acid sequence contained in a peptide or a conjugate having a KLK5 inhibitory activity;

(a3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (a1) and encodes the amino acid sequence contained in a peptide or a conjugate having a KLK5 inhibitory activity; and (a4) a nucleotide sequence that is 60%, 70%, 80%, 85%, 90%, 92%, 94%, 96%, 97%, 98% or 99% or more identical to the nucleotide sequence described in (a1) and encodes the amino acid sequence contained in a peptide or a conjugate having a KLK5 inhibitory activity:

(b1) a nucleotide sequence encoding the amino acid sequence set forth in any one of SEQ ID NOs: 50, 52, 54, and 56 (FIGS. 58, 60, 62, and 64) or the nucleotide sequence described in any one of SEQ ID NOs: 49, 51, 53, and 55 (FIGS. 57, 59, 61, and 63);

(b2) a nucleotide sequence that hybridizes with a nucleotide sequence complementary to the nucleotide sequence described in (b1) under stringent conditions and encodes the amino acid sequence contained in a peptide or a conjugate having a KLK5/KLK7 inhibitory activity;

(b3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (b1) and encodes the amino acid sequence contained in a peptide or a conjugate having a KLK5/KLK7 inhibitory activity; and (b4) a nucleotide sequence that is 60%, 70%, 80%, 85%, 90%, 92%, 94%, 96%, 97%, 98% or 99% or more identical to the nucleotide sequence described in (b1) and encodes the amino acid sequence contained in a peptide or a conjugate having a KLK5/KLK7 inhibitory activity:

(c1) a nucleotide sequence encoding the amino acid sequence set forth in any one of SEQ ID NOs: 58 and 60 (FIGS. 66 and 68) or the nucleotide sequence described in SEQ ID NO: 57 or 59 (FIG. 65 or 67);

(c2) a nucleotide sequence that hybridizes with a nucleotide sequence complementary to the nucleotide sequence described in (c1) under stringent conditions and encodes the amino acid sequence contained in a peptide or a conjugate having a KLK5/KLK14 inhibitory activity;

(c3) a nucleotide sequence that is formed by substituting, deleting, adding, and/or inserting 1 to 20, 1 to 15, 1 to 10, 1 to 8, 1 to 6, 1 to 5, 1 to 4, 1 to 3, 1 or 2, or 1 nucleotide or nucleotide residue in the nucleotide sequence described in (c1) and encodes the amino acid sequence contained in a peptide or a conjugate having a KLK5/KLK14 inhibitory activity; and (c4) a nucleotide sequence that is 60%, 70%, 80%, 85%, 90%, 92%, 94%, 96%, 97%, 98% or 99% or more identical to the nucleotide sequence described in (c1) and encodes the amino acid sequence contained in a peptide or a conjugate having a KLK5/KLK14 inhibitory activity.

A SPINK2 mutant peptide composed of an amino acid sequence encoded by the nucleotide sequence described in any one of (a1) to (a4), (b1) to (b4), or (c1) to (c4) above or containing an amino acid sequence that inhibits the protease activity of KLK5, KLK5 and KLK7, or KLK5 and KLK14, preferably that specifically inhibits the protease activity thereof.

However, the nucleic acid molecules encoding the KLK5 inhibitory peptide, the KLK5/KLK7 inhibitory peptide, or the KLK5/KLK14 inhibitory peptide are not limited to those described in (a1) to (a4), (b1) to (b4), or (c1) to (c4), and nucleic acid molecules containing a nucleotide sequence encoding an amino acid sequence contained in a conjugate containing the amino acid sequence contained in a SPINK2 mutant having a KLK5 inhibitory activity, KLK5/KLK7 inhibitory activity, or KLK5/KLK14 inhibitory activity, preferably, having the amino acid sequence set forth in SEQ ID NO: 61 (FIG. 69) are all included within the scope of the nucleic acid molecules encoding the KLK5 inhibitory conjugate, the nucleic acid molecules encoding the KLK5/KLK7 inhibitory conjugate, or the nucleic acid molecules encoding the KLK5/KLK14 inhibitory conjugate.

For designing a nucleotide sequence encoding an amino acid sequence, one or more codons corresponding to the respective amino acids can be used. Therefore, a base sequence encoding a single amino acid sequence of a peptide may have multiple variations. When selecting such codons, codons can be appropriately selected corresponding to the codon usage of a host cell for expression, into which a polynucleotide containing the nucleotide sequence or a vector containing the same is to be introduced, or the frequency or proportion of use of a plurality of codons can be appropriately adjusted. For example, in the case of using *Escherichia coli* as a host cell, the nucleotide sequence may be designed using codons that are frequently used in *Escherichia coli*.

The nucleic acid molecules encoding the peptide of the present invention or the conjugate thereof may be functionally linked to one or more regulatory sequences. Being "functionally linked" means enabling the linked nucleic acid molecules to be expressed or enabling the nucleotide sequence contained in the molecules to be expressed. Such a regulatory sequence contains sequence elements including information on transcriptional regulation and/or translational regulation. The regulatory sequence varies depending on the species but generally contains a promoter and a 5' non-coding sequence involved in the initiation of transcription and translation such as a prokaryotic −35/−10 box, Shine-Dalgarno sequence, a eukaryotic TATA box, CAAT sequence, and 5' capping sequence. Such a sequence may include an enhancer element and/or a repressor element, and a translatable signal sequence, a leader sequence, and the like for delivering a natural or mature peptide to a specific compartment inside or outside the host cell. Further, such a regulatory sequence may include a 3' non-coding sequence, and the sequence can include elements involved in transcription termination, polyadenylation, or the like. However, when a sequence relating to transcription termination does not sufficiently function in a specific host cell, the sequence can be substituted with a sequence suitable for the cell.

Examples of the promoter sequence can include a tet promoter, a lacUV5 promoter, and a T7 promoter for prokaryotic cells, and an SV40 promoter and a CMV promoter for eukaryotic cells.

The nucleic acid molecules encoding the peptide of the present invention or the conjugate thereof may be isolated or contained in a vector or other cloning vehicles (which will be hereinafter referred to simply as a "vector" such as a plasmid, phagemid, phage, baculovirus, and cosmid), or a chromosome, but there is no limitation to such forms. The vector may contain a replication sequence and a control sequence that are suitable for the host cell to be used for expression, and a selectable marker that gives a phenotype capable of selecting a cell into which the nucleic acid molecules have been introduced by transformation or the like, in addition to the regulatory sequence.

The nucleic acid molecules encoding the peptide of the present invention or the conjugate thereof, and the vector containing the nucleotide sequence of the peptide of the present invention or the conjugate thereof can be introduced by methods known to those skilled in the art, such as transformation into a host cell capable of expressing the peptide, the conjugate, or the nucleotide sequence. The host cell with the nucleic acid molecules or the vector introduced therein can be cultured under conditions suitable for expression of the peptide or the nucleotide sequence. The host cell may be either prokaryotic or eukaryotic. Examples of the prokaryotic cell can include *Escherichia coli* and *Bacillus subtilis*, and examples of the eukaryotic cell can include yeasts such as *Saccharomyces cerevisiae* and *Pichia pastoris*, insect cells such as SF9 and High5, and animal cells such as HeLa cells, CHO cells, COS cells, and NSO. The peptide of the present invention which is expressed can be subjected to desired post-translational modification using a eukaryotic cell or the like as the host cell. Examples of the post-translational modification can include the addition of functional groups such as sugar chains, the addition of peptides or proteins, the conversion of chemical properties of amino acids, and the like. Further, desired modifications can be artificially applied to the peptide of the present invention or the conjugate thereof. Such modified peptides or conjugates are also included within the scope of the "peptide" or "conjugate" of the present invention.

The present invention also provides a method for producing a peptide or a conjugate. The method includes step 1 of culturing a cell containing nucleic acid molecules encoding a KLK5 inhibitory peptide (or a KLK5 inhibitory conjugate) or a cell producing a KLK5 inhibitory peptide (or a KLK5 inhibitory conjugate), a cell containing nucleic acid molecules encoding a KLK5/KLK7 inhibitory peptide (or a KLK5/KLK7 inhibitory conjugate) or a cell producing a KLK5/KLK7 inhibitory peptide (or a KLK5/KLK7 inhibitory conjugate), or a cell containing nucleic acid molecules encoding a KLK5/KLK14 inhibitory peptide (or a KLK5/KLK14 inhibitory conjugate) or a cell producing a KLK5/KLK14 inhibitory peptide (or a KLK5/KLK14 inhibitory conjugate), and/or step 2 of collecting a SPINK2 mutant from the culture obtained in step 1. Operations known to those skilled in the art such as fractionation, chromatography, and purification can be applied to step 2. For example, purification by affinity chromatography using an antibody of the present invention or a binding fragment thereof, which will be described below, can be applied thereto.

In some aspects of the invention, the peptide or a peptide included in the conjugate has intramolecular disulfide bonds. It may be preferable to deliver the peptide having intramolecular disulfide bonds to a cell compartment having an oxidative redox environment using a signal sequence or the like. The oxidative environment can be provided by the periplasm of gram-negative bacteria such as *Escherichia coli*, the extracellular environment of gram-positive bacteria, the lumen of the endoplasmic reticulum of eukaryotic cells, or the like, and formation of structural disulfide bonds can be promoted under such an environment. Further, it is also possible to produce a peptide having intramolecular disulfide bonds in the cytoplasm of a host cell such as *Escherichia coli*. In such a case, the peptide can be directly acquired in a soluble and folded state or can be collected in the form of an inclusion body and then reconstituted in vitro. Further, it is also possible to select a host cell having an oxidative intracellular environment to produce a peptide having intramolecular disulfide bonds in the cytoplasm thereof. Meanwhile, when the peptide has no intramolecular disulfide bond, the peptide can be produced in a cell compartment having a reducing redox environment, such as the cytoplasm of gram-negative bacteria.

The peptide of the present invention or the conjugate thereof (the peptide moiety contained therein) can be produced by other methods known to those skilled in the art, such as the solid-phase peptide synthesis method of Merrifield, et al., and chemical synthesis exemplified by an organic synthetic chemical peptide synthesis method using t-butoxycarbonyl (Boc), 9-fluorenylmethoxycarbonyl (Fmoc), or the like, and in-vitro translation.

In some aspects, the present invention provides an antibody binding to the peptide of the present invention or a peptide contained in the conjugate, and a binding fragment thereof. The antibody may be either a polyclonal antibody or a monoclonal antibody, and the monoclonal antibody is not specifically limited, as long as it is an immunoglobulin or a derivative thereof. The binding fragment of the antibody is not limited, as long as it has an antigen-binding activity, that is, a binding activity to the peptide. Both or one of the heavy chains and light chains or fragments thereof, those lacking a constant region or Fc region, and conjugates with other proteins or labeling substances are also included therein. Such an antibody and a binding fragment thereof can be prepared by methods known to those skilled in the art and are useful for purification of the peptide by affinity chromatography, detection of the peptide in clinical tests, diagnoses, or the like related to a pharmaceutical composition containing the peptide or use thereof, immunological assay, and the like. The antibody of the present invention or the binding fragment thereof can be purified by affinity chromatography using the peptide of the present invention to which the antibody or the fragment binds.

5. Pharmaceutical Composition

The present invention also provides a pharmaceutical composition containing the peptide of the present invention or the conjugate thereof.

The pharmaceutical composition containing the peptide of the present invention or the conjugate thereof is useful for treating and/or preventing various diseases which are induced or exacerbated by KLK5 (which will be hereinafter referred to as "diseases related to KLK5" or "KLK5-related diseases") and in which suppression of such induction or exacerbation, recovery, maintenance or amelioration of symptoms, avoidance of secondary diseases, or the like is possible by inhibiting or suppressing the expression or functions of KLK5. Examples of the diseases related to KLK5 can include Netherton syndrome (Furio, L., et al. (2015) PLoS. Genet., Vol. 11, p. e1005389), atopic dermatitis (Fortugno, P., et al. (2012) Hum. Mol. Genet., Vol. 21, pp. 4187-4200), rosacea (Yamasaki, K., et al. (2007) Nat. Med., Vol. 13, pp. 975-980), UV-induced skin injury (Nin, M., et al. (2009) J. Dermatol. Sci., Vol. 54, pp. 17-24), psoriasis (Komatsu, N., et al. (2007) Br. J. Dermatol., Vol. 156, pp. 875-883), asthma (Grunberg, M., et al. (2018) Eur. J. Immunol., Vol. 48, pp. 1592-1594), spinal cord injury (Radulovic, M., et al. (2013) J. Neuropathol. Exp. Neurol., Vol. 72, pp. 1072-1089), cancer (such as uterine cancer, bladder urothelial cancer, colorectal cancer, oral squamous cell carcinoma, breast cancer, head and neck cancer, melanoma, prostate cancer, and glioma) (Emami, N., et al. (2007) Mol. Oncol., Vol. 1, pp. 269-287), and Barrett's esophagus (Gene Expression Omnibus, based on accession #GSE13083), but there is no limitation to these examples.

KLK5 is considered to be the main factor in the development of Netherton syndrome-like skin symptoms. KLK5 is an autoactivated protease and is also involved in activation of KLK7 and KLK14. Meanwhile, in the stratum corneum of Netherton syndrome patients and Netherton syndrome model mice, high protease activities like trypsin and chymotrypsin are observed, and it is suggested that the kallikrein family located downstream, such as KLK7 and KLK14, are related to the protease activity in the stratum corneum, in addition to KLK5. It is expected that there may be cases where the Netherton syndrome-like skin symptoms can be more strongly suppressed by inhibiting KLK7 or KLK14 in addition to KLK5. 70 or more examples of mutations in SPINK5 associated with Netherton syndrome are listed in Human Gene Mutation Database (HGMD) and reported to be related to the severity of Netherton syndrome. Mutations in exons 1 to 9 of SPINK5 are related to more severe pathologies of Netherton syndrome. Whether or not the pharmaceutical composition containing the peptide of the present invention or the conjugate thereof should be used for treating or preventing Netherton syndrome can be determined by investigating the mutations in SPINK5.

The pharmaceutical composition of the present invention can contain a therapeutically or prophylactically effective amount of the peptide or the conjugate and pharmaceutically acceptable diluents, carriers, solubilizers, emulsifiers, preservatives, and/or auxiliary agents.

The term "therapeutically or prophylactically effective amount" means an amount that exerts a therapeutic or prophylactic effect for a specific disease, administration form, or administration route, and has the same meaning as a "pharmacologically effective amount".

The pharmaceutical composition of the present invention can contain materials for changing, maintaining, or retaining the pH, the osmotic pressure, the viscosity, the transparency, the color, the isotonicity, the sterility, or the stability, the solubility, the sustained release, the absorbability, the permeability, the dosage form, the strength, the properties, the shape, etc., of the composition or the peptide, the conjugate, or the like contained in the composition (which will be hereinafter referred to as "pharmaceutical materials"). The pharmaceutical materials are not specifically limited, as long as they are pharmacologically acceptable materials. For example, no or low toxicity is a property preferably possessed by the pharmaceutical materials.

Examples of the pharmaceutical materials can include, but are not limited to, the following: amino acids such as glycine, alanine, glutamine, asparagine, histidine, arginine, or lysine, antibacterial agents, antioxidants such as ascorbic acid, sodium sulfate, or sodium bisulfite, buffers such as phosphate, citrate, or borate buffers, sodium bicarbonate, or tris-hydrochloric acid (Tris-HCl) solution, fillers such as mannitol and glycine, chelating agents such as ethylenediaminetetraacetic acid (EDTA), complexing agents such as caffeine, polyvinyl pyrrolidine, β-cyclodextrin, or hydroxypropyl-β-cyclodextrin, bulking agents such as glucose, mannose, or dextrin, monosaccharides, disaccharides, other carbohydrates such as glucose, mannose, or dextrin, colorants, flavoring agents, diluents, emulsifiers, hydrophilic polymers such as polyvinyl pyrrolidine, preservatives such as low-molecular weight polypeptides, salt-forming counterions, benzalkonium chloride, benzoic acid, salicylic acid, thimerosal, phenethyl alcohol, methylparaben, propylparaben, chlorhexidine, sorbic acid, or hydrogen peroxide, solvents such as glycerin, propylene glycol, or polyethylene glycol (PEG), sugar alcohols such as mannitol or sorbitol, suspending agents, polysorbates such as sorbitan ester, polysorbate 20, or polysorbate 80, surfactants such as triton, tromethamine, lecithin, or cholesterol, stability enhancers such as sucrose or sorbitol, elasticity enhancers such as sodium chloride, potassium chloride, mannitol, or sorbitol, transport agents, diluents, excipients, and/or pharmaceutical auxiliary agents.

The amount of these pharmaceutical materials to be added is 0.001 to 1000 times, preferably 0.01 to 100 times, more preferably 0.1 to 10 times, the weight of the peptide of the present invention or the peptide contained in the conjugate.

A liposome containing the peptide of the present invention or the conjugate and a pharmaceutical composition containing a modified form formed by binding the peptide to the liposome are also included within the pharmaceutical composition of the present invention.

The excipients or carriers are not particularly limited as long as they are liquid or solid materials usually used for oral or parenteral administration, such as injectable water, saline, artificial cerebrospinal fluids, and other preparations. Examples of saline can include neutral saline and serum albumin-containing saline.

Examples of the buffers can include a Tris buffer adjusted to bring the final pH of the pharmaceutical composition to 7.0 to 8.5, an acetate buffer adjusted to bring the final pH thereof to 4.0 to 5.5, a citrate buffer adjusted to bring the final pH thereof to 5.0 to 8.0, and a histidine buffer adjusted to bring the final pH thereof to 5.0 to 8.0.

The pharmaceutical composition of the present invention is a solid, a liquid, a suspension, or the like. Another example of the pharmaceutical composition of the present invention can include a freeze-dried preparation. The freeze-dried preparation can be formed using an excipient such as sucrose.

The administration route of the pharmaceutical composition of the present invention may be any of eye drops, enteral administration, topical administration, and parenteral administration. Examples thereof can include eye drops on the conjunctiva, intravitreal administration, intravenous administration, intraarterial administration, intramuscular administration, intradermal administration, subcutaneous administration, intraperitoneal administration, transdermal administration, intraosseous administration, and intraarticular administration.

The composition of the pharmaceutical composition can be determined depending on the administration method, the inhibitory activity of the peptide of the present invention or the peptide contained in the conjugate to KLK5, KLK5 and KLK7, or KLK5 and KLK14, the binding affinity, or the like. The stronger the inhibitory activity (the smaller the $IC_{50}$ value or $K_i$ value) or the higher the affinity (the smaller the $K_D$ value) to the target of the inhibitory peptide of the present invention, then the efficacy can be exerted with a lower dose.

The dose of the peptide of the present invention or the conjugate thereof is not limited, as long as it is a pharmacologically effective amount, and can be appropriately determined depending on the species of the individual, the type of disease, the symptom, the gender, the age, the chronic disease, the inhibitory activity against the target of the peptide, the binding affinity, and other factors, but the peptide of the present invention or the conjugate thereof is generally administered at 0.01 to 1000 mg/kg, preferably 0.1 to 100 mg/kg, once, twice, or more per day for 1 to 180 days.

Examples of the form of the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The pharmaceutical composition containing the peptide of the present invention or the conjugate thereof as an active ingredient can be administered simultaneously or separately with other drugs. For example, the pharmaceutical composition containing the peptide of the present invention or the conjugate thereof as an active ingredient may be administered after administration of other drugs, other drugs may be administered after administration of the pharmaceutical composition, or the pharmaceutical composition may be administered simultaneously with other drugs. In the case of simultaneous administration, the peptide of the present invention or the conjugate thereof and other drugs may be contained in either a single preparation or separate preparations (a plurality of preparations).

One, two, three, or more of such other drugs can be administered or received. These are collectively referred to as "combined use of other drugs" with or "combination with other drugs" of the pharmaceutical composition of the present invention. The pharmaceutical composition of the present invention containing other drugs in addition to the peptide of the present invention or the conjugate thereof or used in combination with other therapies is also included within the present invention as an aspect of "combined use of other drugs" or "combination with other drugs".

Examples thereof against Netherton syndrome can include humectants, steroid drugs, and antibacterial agents. Examples thereof against atopic dermatitis can include steroid drugs, calcineurin inhibitors, PDE4 inhibitors, immunosuppressive drugs, IL-4/IL-13 inhibitors, and phototherapy. Examples thereof against rosacea can include doxycycline, minocycline, azelaic acid, and brimonidine. Examples thereof against psoriasis can include TNFα inhibitors, IL-12/23 inhibitors, IL-17 inhibitors, PDE4 inhibitors, antimetabolites, calcineurin inhibitors, fumarate ester, retinoid preparations, steroid drugs, vitamin D3 analogs, and phototherapy. Examples thereof against asthma can include steroid drugs and β2 agonists. Examples thereof against cancers such as uterine cancer, bladder urothelial cancer, colorectal cancer, oral squamous cell carcinoma, breast cancer, head and neck cancer, melanoma, prostate cancer, and glioma can include various anticancer agents.

The present invention also provides a method for treating or preventing diseases related to KLK5, the method comprising a step of administering the peptide of the present invention or the conjugate thereof, use of the peptide of the present invention or the conjugate thereof for preparing a pharmaceutical composition for treating or preventing the diseases, and use of the peptide or the conjugate for treating and preventing the diseases. A treatment or prevention kit containing the peptide or the conjugate is also included within the present invention.

Further, a pharmaceutical composition containing a polynucleotide containing the nucleotide sequence encoding the amino acid sequence of the peptide of the present invention or the conjugate thereof, a vector containing the polynucleotide, a cell containing the polynucleotide or the vector, or a cell expressing the peptide of the present invention or the conjugate thereof is also provided. For example, the polynucleotide and the vector can be applied to gene therapy of the diseases related to KLK5, and the cells can be applied to cell therapy of the diseases related to KLK5, respectively, using known methods. Further, the cells for cell therapy can be prepared, for example, by introducing the polynucleotide or the vector into autologous cells or allogeneic cells (the same kind of cells). The polynucleotide and the vector are included within the present invention also as compositions for preparing cell therapeutic agents. However, the aspect of the pharmaceutical composition containing the polynucleotide, the vector, the cell, or the like of the present invention is not limited to the above.

An animal model can be used as a means for evaluating the therapeutic effect, against diseases related to KLK5, of the peptide or the conjugate thereof contained in the pharmaceutical composition of the present invention as an active ingredient. Examples of a Netherton syndrome model having a mutation in the SPINK5 gene that is the causative gene of Netherton syndrome can include SPINK5 gene-deficient mice (Descargues, P., et al. (2004) Nat. Genet., Vol. 37, pp. 56-65), SPINK5 gene conditional knockout mice (Petrova, E., et al. (2019) oral presentation in the 8th International Symposium on Kallikreins and Kallikrein-Related Peptidases: Abstract Book, p. 28), and Crusty2 mice (Mutagenetix database), but there is no limitation to these examples.

6. Diagnostic Composition

A composition for testing or diagnosis containing the peptide of the present invention or the conjugate thereof (which will be hereinafter referred to collectively as the "diagnostic composition") is provided.

The diagnostic composition of the present invention is useful for testing or diagnosing diseases related to KLK5, KLK5 expression, KLK7 expression, KLK14 expression, or the like. In the present invention, examples of the test or diagnosis include determination or measurement of morbidity risk, determination of morbidity, measurement of the degree of progression or exacerbation, measurement or determination of the effect of drug treatment with the pharmaceutical composition containing the peptide of the present invention or the conjugate thereof, measurement or determination of the effect of treatments other than the drug treatment, measurement of recurrence risk, and determination of recurrence. However, there is no limitation to these examples, as long as they are tests or diagnoses.

The diagnostic composition of the present invention is useful for identifying an individual to whom the peptide of the present invention or the conjugate thereof, the composition containing the same, or the pharmaceutical composition containing the same is to be administered.

Such a diagnostic composition can contain pH buffers, osmoregulators, salts, stabilizers, preservatives, developers, sensitizers, aggregation inhibitors, and the like.

The present invention also provides a method for testing or diagnosing diseases related to KLK5, use of the peptide of the present invention for preparing a diagnostic composition for the diseases, and use of the peptide of the present invention for testing or diagnosing the diseases. A kit for testing or diagnosis containing the peptide of the present invention is also included within the present invention.

As regards a method for testing or diagnosis using the peptide of the present invention, sandwich ELISA is desirable, but detection methods such as conventional ELISA or RIA, ELISPOT (Enzyme-Linked ImmunoSpot), dot blotting, the Ouchterlony method, CIE (Counterimmunoelectrophoresis), CLIA (Chemiluminescent immunoassay), and FCM (Flow Cytometry) can be used. For detection, antibodies or binding fragments thereof, or those labeled with the peptide of the present invention or the conjugate thereof are used. For labeling, labeling methods that can be used for biochemical analysis such as labeling with fluorophores such as HRP, alkaline phosphatase, and FITC, radioisotopes, or the like can be used, in addition to biotin. For detection using an enzyme label, chemiluminescence substrates can be used, in addition to chromogenic substrates such as TMB (3, 3', 5, 5'-tetramethylbenzidine), BCIP (5-bromo-4-chloro-3-indolyl phosphate), p-NPP (p-nitrophenyl phosphate), OPD (o-Phenylenediamine), ABTS (3-Ethylbenzothiazoline-6-sulfonic acid), and SuperSignal ELISA Pico Chemiluminescent Substrate (Thermo Fisher Scientific), and fluorescence substrates such as QuantaBlu (R) Fluorogenic Peroxidase Substrate (Thermo Fisher Scientific). Samples derived from humans or non-human animals as well as artificially treated samples such as recombinant proteins can be subjected to this assay. Examples of test samples derived from individual organisms can include, but are not limited to, blood, synovial fluids, ascites, lymph, cerebrospinal fluids, bronchoalveolar lavage, saliva, phlegm, tissue homogenate supernatants, and tissue sections.

A sandwich ELISA kit for testing or diagnosis containing the peptide of the present invention may contain coloring reagents, buffers for dilution, proteins for solid phase, proteins for detection, washing solutions, or the like as well as protein standard solutions which comprise the peptide of the present invention or the conjugate thereof. As a method for measuring the amount of protein bound to an antigen, an absorption method, a fluorescence method, a luminescence method, an RI (Radioisotope) method, or the like is suitably applied, and for the measurement, an absorption plate reader, a fluorescence plate reader, a luminescence plate reader, an RI liquid scintillation counter, or the like is preferably used.

Further, the tests or diagnoses can be performed by methods using immunoprecipitation.

Further, the present invention also provides a method for detecting or measuring KLK5, KLK5 and KLK7, or KLK5 and KLK14 in a test sample. The diagnostic composition of the present invention can be used for such a detection or measurement method. KLK5, KLK5 and KLK7, or KLK5 and KLK14 in the test sample can be detected by bringing the peptide of the present invention or the conjugate thereof into contact with the test sample (step 1) and then measuring the amount of KLK5, KLK5 and KLK7, or KLK5 and KLK14 bound to the peptide or the conjugate (step 2). Examples of step 1 can include immobilizing an Fc region of an immunoglobulin conjugated to the peptide of the present invention on magnetic beads via protein G and adding the test sample thereto, and examples of step 2 can include separating the magnetic beads and analyzing the soluble proteins precipitated together with the beads by SDS-PAGE or Western blotting to detect KLK5, KLK5 and KLK7, or KLK5 and KLK14. Artificially treated samples such as recombinant proteins can be subjected to this measurement, in addition to human- or nonhuman animal-derived samples. Examples of test samples derived from individual organisms can include, but are not limited to, blood, synovial fluids, ascites, lymph, cerebrospinal fluids, bronchoalveolar lavage, saliva, phlegm, tissue homogenate supernatants, and tissue sections.

The detection of KLK5, KLK5 and KLK7, or KLK5 and KLK14 can be performed not only in vitro but also in vivo. In the case of diagnostic imaging, the peptide of the present invention or the conjugate thereof labeled with a pharmaceutically acceptable radionuclide or luminescent material can be used. Examples of step 1 can include administering the labeled peptide or the conjugate thereof to a test subject, and examples of step 2 can include capturing an image using a diagnostic imaging technique such as PET/CT and determining or testing for the presence of KLK5, KLK5 and/or KLK7, or KLK5 and/or KLK14.

The peptide or the conjugate thereof contained in the diagnostic composition of the present invention binds to KLK5, KLK5 and KLK7, or KLK5 and KLK14, and preferably has KLK5-, KLK5 and KLK7-, or KLK5 and KLK14-specific binding activity.

A method for identifying an individual to whom the pharmaceutical composition of the present invention is to be administered is also included within the present invention. In such an identification method, KLK5, KLK5 and/or KLK7, or KLK5 and/or KLK14 in a sample derived from the individual is measured, and the individual can be determined to be positive when KLK5, KLK5 and/or KLK7, or KLK5 and/or KLK14 is detected in the sample, or KLK5, KLK5 and/or KLK7, or KLK5 and/or KLK14 is detected in an amount larger than the amount of KLK5, KLK5 and/or KLK7, or KLK5 and/or KLK14 detected in another sample derived from a healthy individual. For this method, the diagnostic composition of the present invention can be used.

Further, in a suitable aspect of the identification method, the individual has or is at risk of KLK5-related diseases.

Further, in one aspect, the pharmaceutical composition of the present invention can be administered to an individual determined to be positive in the identification method.

7. Method for Separating KLK5, KLK5 and KLK7, or KLK5 and KLK14

The peptide of the present invention or the conjugate thereof preferably has a binding activity specific to KLK5, KLK5 and/or KLK7, or KLK5 and/or KLK14. Accordingly, KLK5, KLK5 and/or KLK7, or KLK5 and/or KLK14 can be specifically separated from a sample in which KLK5, KLK5 and/or KLK7, or KLK5 and/or KLK14 is mixed with other KLKs, using the peptide of the present invention or the conjugate thereof. The release of KLK5, KLK5 and/or KLK7, or KLK5 and/or KLK14 from the peptide or the conjugate can be performed non-selectively, for example, under a relatively high ionic strength, a low pH, moderate denaturing conditions, in the presence of chaotropic salts, or the like, but is preferably performed within a range in which the protease activity of KLK5, KLK5 and/or KLK7, or KLK5 and/or KLK14 is not attenuated.

EXAMPLES

In the following examples, some aspects of the present invention will be described more specifically. However, the present invention is not limited to them.

In the following examples, operations relating to genetic engineering were performed according to the methods described in "Molecular Cloning" (Sambrook, J., Fritsch, E. F., and Maniatis, T., Cold Spring Harbor Laboratory Press, published in 1982 or published in 1989) and other methods described in experimental manuals used by those skilled in the art, or according to the instructions of commercially available products in the cases where commercially available reagents or kits were used, unless otherwise indicated.

Example 1. Preparation of KLK5 Inhibitory Peptide (1-1) Construction of KLK5 Inhibitory Peptide Expression Vector Using the nucleotide sequence of each inhibitory peptide (SEQ ID NO: 5, 7, 9, 11, 13, 15, 17, 19, 21, 23, 25, 27, 29, or 31) and the nucleotide sequence of SPINK2 as templates, inhibitory peptide fragments were amplified by PCR ((at 94° C. for 15 seconds, at 60° C. for 30 seconds, and at 68° C. for 20 seconds)×30 cycles) using the following primers and KOD-plus-(TOYOBO).

```
Primer 1:
                            (SEQ ID NO: 62, FIG. 70)
5'-AAAAGGATCCCTGGACAAACGTGGCCCGCAGTTTGGTCTGTTTAG-3'

Primer 2:
                            (SEQ ID NO: 63, FIG. 71)
5'-AAAACTCGAGTTAGCCGCCGCACGGACCATTGCGAATAA-3'
```

The amplified fragments were subjected to agarose gel electrophoresis, and then the desired DNA fragments were cut out, to prepare DNA using a QIAquick Gel Extraction Kit (QIAGEN). The prepared DNA fragments and pET 32a (Novagen) were treated using restriction enzymes BamHI (NEB) and XhoI (NEB) at 37° C. for 1 hour or more, and after agarose gel electrophoresis, the desired DNA fragments were cut out, followed by purification using a QIAquick PCR Purification Kit (QIAGEN). Using a LigaFast Rapid DNA Ligation System (Promega), each purified fragment was reacted at room temperature for 10 minutes to conduct a ligation reaction. The ligation solution was added to Escherichia coli JM109 (TOYOBO), left standing on ice for 30 minutes, then heat-treated at 42° C. for 45 seconds, further left standing on ice for 5 minutes, seeded on a 2YT plate containing 0.1 mg/mL ampicillin, and thereafter statically cultured at 37° C. overnight, to transform the Escherichia coli. The next day, the transformed Escherichia coli was inoculated on a Terrific Broth medium (Invitrogen) containing 0.1 mg/mL ampicillin and cultured at 37° C. overnight. Thereafter, plasmid DNA was collected using a QIAprep 96 Turbo Miniprep Kit (Qiagen) (which will be hereinafter referred to as "miniprep treatment"), and a sequence analysis was conducted, to construct a pET 32a_Kex2_KLK5 inhibitory peptide vector.

(1-2) Preparation of KLK5 Inhibitory Peptide

Escherichia coli Origami B (DE3) (Novagen) was transformed with the vector constructed in (1-1) and cultured at 37° C. using a 2YT medium containing 0.1 mg/mL ampicillin. Thereafter, IPTG (with a final concentration of 1 mM) was added thereto, followed by culture at 16° C. overnight. The next day, after collecting the cells by centrifugation (3,000 g, 20 minutes, and 4° C.), a lysate was prepared using BugBuster Master Mix (Novagen), and a His tag fusion target protein was purified using TALON Metal Affinity Resin (Clontech). Thereafter, a thioredoxin tag was cleaved from the desired protein using Kex2 (*Saccharomyces cerevisiae*: Accession CAA96143) and purified using TALON. Further, gel filtration chromatography (Superdex75 10/300 GL) or reverse phase chromatography (YMC-Pack ODS-AM) was applied, to prepare 14 kinds of KLK5 inhibitory peptides. The amino acid sequences of the derivatives are shown in SEQ ID NOs: 6, 8, 10, 12, 14, 16, 18, 20, 22, 24, 26, 28, 30, and 32 (FIGS. 14, 16, 18, 20, 22, 24, 26, 28, 30, 32, 34, 36, 38, and 40).

Example 2. Preparation of KLK5, KLK7, and KLK14

(2-1) Construction of Human KLK5, Human KLK7, and Human KLK14 Expression Vectors The primers and PCR conditions used for cloning human pro-KLK5, human pro-KLK7, and human pro-KLK14 were as follows. Fragment A was amplified by PCR ((at 94° C. for 15 seconds, at 60° C. for 30 seconds, and at 68° C. for 10 seconds)×30 cycles) using the following primers and KOD-plus-(TOYOBO).

```
Primer 3:
                            (SEQ ID NO: 64, FIG. 72)
5'-GGCGATTATAAAGATGACGATGATAAACACCATCACCACCATC-3'

Primer 4:
                            (SEQ ID NO: 65, FIG. 73)
5'-GTTTAAACTCAATGATGGTGGTGATGGTGTTTATCATCGTCAT-3'
```

Next, using nucleotide sequences encoding human pro-KLK5 (Uniprot: Q9Y337), human pro-KLK7 (Uniprot: P49862), and human pro-KLK14 (Uniprot: Q9P0G3) respectively as templates, fragments were amplified by PCR ((at 94° C. for 15 seconds, at 60° C. for 30 seconds, and at 68° C. for 60 seconds)×30 cycles) using the following primers and KOD-plus-(TOYOBO).

```
Human pro-KLK5 amplification primer
Primer 5:
                            (SEQ ID NO: 66, FIG. 74)
5'-AAAATCTAGAGCCGCCACCATGGCCACAGCTAGACCCCCT-3'

Primer 6:
                            (SEQ ID NO: 67, FIG. 75)
5'-CGTCATCTTTATAATCGCCGCTGTTGGCCTGGATGGTTTCCTG-3'

Human pro-KLK7 amplification primer
Primer 7:
                            (SEQ ID NO: 68, FIG. 76)
5'-AAAATCTAGAGCCGCCACCATGGCCAGATCTCTGCTGCTGCCC-3'

Primer 8:
                            (SEQ ID NO: 69, FIG. 77)
5'-CGTCATCTTTATAATCGCCCCGGTGTTTCTTCATGGTGTCGTT-3'
```

-continued

Human pro-KLK14 amplification primer
Primer 9:
(SEQ ID NO: 70, FIG. 78)
5'-AAAATCTAGAGCCGCCACCATGTTCCTCCTCCTCACCGCCCTC-3'

Primer 10:
(SEQ ID NO: 71, FIG. 79)
5'-CGTCATCTTTATAATCGCCCTTGTCGCGCATGGTCTCCTCGAT-3'

Desired DNA fragments were amplified by overlapping PCR using the fragments amplified above and fragment A, the following primers, and KOD-plus-(TOYOBO). Primer 5 (SEQ ID NO: 66, FIG. 74) or primer 7 (SEQ ID NO: 68, FIG. 76) or primer 9 (SEQ ID NO: 70, FIG. 78) and Primer 11:
(SEQ ID NO: 72, FIG. 80)
5'-AAAAGTTTAAACTCAATGATGGTGGTGATGGTGT-3'

Next, using nucleotide sequences encoding mouse pro-KLK7 (Uniprot: Q91VE3) or mouse pro-KLK14 (Uniprot: Q8CGR5) respectively as templates, fragments were amplified by PCR ((at 94° C. for 15 seconds, at 60° C. for 30 seconds, and at 68° C. for 60 seconds)×30 cycles) using the following primers and KOD-plus-(TOYOBO).

Mouse pro-KLK7 amplification primer
Primer 12:
(SEQ ID NO: 73, FIG. 81)
5'-AAAATCTAGAGCCGCCACCATGGGAGTGTGGCTGCTGAGCCTG-3'

Primer 13:
(SEQ ID NO: 74, FIG. 82)
5'-AAAAGTTTAAACTCAATGATGGTGGTGATGGTGCCGGTGGGTCTTCATGGTTTCCATG-3'

Mouse pro-KLK14 amplification primer
Primer 14:
(SEQ ID NO: 75, FIG. 83)
5'-AAAATCTAGAGCCGCCACCATGTTTCTGCTGCTGATCATCCTG-3'

Primer 15:
(SEQ ID NO: 76, FIG. 84)
5'-AAAAGTTTAAACTCAATGATGGTGGTGATGGTGGTTGCTCTGCATGGTCCGCTGAA-3'

Mammalian cell expression vectors pCMA_pro-hKLK5, pCMA_pro-hKLK7, pCMA_pro-hKLK14, pCMA_pro-mKLK7, and pCMA_pro-mKLK14 with a His tag added at the C-terminus encoded by each gene were constructed by cloning using the desired DNA fragments thus amplified and restriction enzymes XbaI (NEB) and PmeI (NEB). The operation was performed according to the method described in (1-1).

(2-2) Expression and Purification of Human KLK5, Human Pro-KLK7, Human Pro-KLK14, Mouse Pro-KLK7, and Mouse Pro-KLK14

Each expression vector constructed in (2-1) was transfected into Expi293F cells (Thermo Fisher Scientific) using PEI MAX 40000 (Polysciences), and the culture supernatant was collected after 3 days of culturing the cells. The desired His tag fusion protein was collected from the culture supernatant using HisTrap excel (GE healthcare), and the buffer was replaced with PBS using Amicon Ultra NMWL 10,000 (Merck KGaA Millipore), to purify KLK5, human pro-KLK7, human pro-KLK14, mouse pro-KLK7, and mouse pro-KLK14, respectively.

(2-3) Preparation of Human KLK5, Human KLK7, Human KLK14, Mouse KLK5, Mouse KLK7, and Mouse KLK14

To 200 µg/mL pro-KLK7 or 14 prepared using a KLK activation buffer (50 mM Tris-HCl, 150 mM NaCl, 10 mM CaCl$_2$, 0.05% (w/w) Brij-35, pH 7.5), was added an equal amount of 20 µg/mL thermolysin, followed by reaction for a certain time at 37° C. Thereafter, an equal amount of 100 mM EDTA was mixed therein to prepare activated human KLK7, activated human KLK14, activated mouse KLK7, and activated mouse KLK14.

Further, 200 µg/mL mouse KLK5 (R&D Systems, Inc., 7236-SE) and 2 µg/mL human KLK5 prepared using an activation buffer (50 mM Tris-HCl, 0.005% (w/w) Brij-35, pH 8.0) were mixed in equal amounts, followed by reaction at 37° C. for 24 hours, to prepare activated mouse KLK5.

Example 3. Evaluation of KLK5 Inhibitory Peptide (3-1) Evaluation of Human/Mouse KLK5, Human/Mouse KLK7, and Human/Mouse KLK14 Inhibitory Activities of KLK5 Inhibitory Peptide The substrate peptide was dissolved in DMSO to 10 mM and diluted with an assay buffer (50 mM Tris-HCl, 150 mM NaCl, pH 8.0) for use. 25 µL each of human/mouse KLK5, human/mouse KLK7, or human/mouse KLK14 and the inhibitory peptide diluted with the assay buffer were mixed, followed by a reaction at 37° C. for 20 minutes. Thereafter, 50 µL of a substrate diluted with the assay buffer was added thereto, and the fluorescence signal was measured using Enspire (PerkinElmer). The combinations of the enzyme and the substrate used were as follows. Each inhibitory peptide had a final concentration of 0.098 to 1,000 nM, and a PROTEOSAVE® SS96F black plate (Sumitomo Bakelite Co., Ltd.) was used for the reaction and the measurement.

Evaluation of Human KLK5 inhibitory activity: hKLK5 with a final concentration of 10 nM, a substrate peptide Boc-Val-Pro-Arg-AMC (R&D Systems, Inc.) with a final concentration of 100 µM, and a fluorescence signal with excitation at 380 nm/emission at 460 nm Evaluation of Human KLK7 inhibitory activity: hKLK7 with a final concentration of 1 µg/mL, a substrate peptide Mca-Arg-Pro-Lys-Pro-Val-Glu-Nval-Trp-Arg-Lys (Dnp)-NH$_2$ (SEQ ID NO: 101) (R&D Systems, Inc., FIG. 85, and the amino acid sequence shown in SEQ ID NO: 77) with a final concentration of 20 µM, and a fluorescence signal with excitation at 320 nm/emission at 405 nm Evaluation of Human KLK14 inhibitory activity: hKLK14 with a final concentration of 0.2 µg/mL, a substrate peptide Boc-Val-Pro-Arg-AMC with a final concentration of 100 µM (R&D Systems, Inc.), and a fluorescence signal with excitation at 380 nm/emission at 460 nm Evaluation of Mouse KLK5 inhibitory activity: mouse KLK5 with a final concentration of 0.25 µg/mL, a substrate peptide Boc-Val-Pro-Arg-AMC with a final concentration of 100 µM (R&D Systems, Inc.), and a fluorescence signal with excitation at 380 nm/emission at 460 nm Evaluation of Mouse KLK7 inhibitory activity: mouse KLK7 with a final concentration of 0.5 µg/mL, a substrate peptide Mca-Arg-Pro-Lys-Pro-Val-Glu-Nval-Trp-Arg-Lys (Dnp)-NH$_2$ (SEQ ID NO: 101) with a final concentration of 7 µM (R&D Systems, Inc., FIG. 85, and the amino acid sequence shown in SEQ ID NO: 77), and a fluorescence signal with excitation at 320 nm/emission at 405 nm Evaluation of Mouse KLK14 inhibitory activity: mouse KLK14 with a final concentration of 0.1 µg/mL, a substrate peptide Boc-Val-Pro-Arg-AMC with a final concentration of 100 µM (R&D Systems, Inc.), and a fluorescence signal with excitation at 380 nm/emission at 460 nm As a result of calculating the degradation rate of the substrate peptide by each inhibitory peptide at each concentration and calculating the 50% inhibitory concentration ($IC_{50}$) using GraphPad Prism (version 5.0; GraphPad Software Inc.) with the degradation rate of the inhibitory peptide at a concentration of 0 nM taken as 100%, it was revealed that all of the inhibitory peptides inhibited human KLK5 enzymatic activity at low concentrations (Table 1, FIG. 2). Some of the inhibitory peptides inhibited human KLK7 or human KLK14 enzymatic activity at low concentrations, and some of the inhibitory peptides exhibited weak inhibitory activities against these proteases (Table 1). The inhibitory peptides also exhibited a similar activity against mouse KLK5, KLK7, or KLK14 (Table 2). The average value of three independent experiments was used to calculate the $IC_{50}$ value.

TABLE 1

Human KLK5, human KLK7, or human KLK14 inhibitory activity of each KLK5 inhibitory peptide

| ID | $IC_{50}$(nM) for hKLK5 | $IC_{50}$(nM) for hKLK7 | $IC_{50}$(nM) for hKLK14 |
| --- | --- | --- | --- |
| K51028 | 6.1 ± 0.5 | 249 ± 25 | >1,000 |
| K50032 | 7.1 ± 0.4 | >1,000 | >1,000 |
| K50055 | 6.7 ± 0.2 | >1,000 | >1,000 |
| K51069 | 6.8 ± 0.4 | >1,000 | 72 ± 23 |
| K51072 | 7.0 ± 0.2 | >1,000 | 434 ± 18 |
| K50015 | 6.8 ± 0.3 | >1,000 | 17 ± 1 |
| K50016 | 6.9 ± 1.1 | >1,000 | >1,000 |
| K51034 | 6.4 ± 0.3 | >1,000 | >1,000 |
| K50062 | 7.5 ± 0.7 | >1,000 | 499 ± 27 |
| K51090 | 4.5 ± 0.3 | >1,000 | >1,000 |
| K50098 | 8.3 ± 0.9 | >1,000 | 268 ± 31 |
| K51005 | 5.8 ± 2.1 | 17 ± 0.2 | >1,000 |
| K50031 | 5.4 ± 0.1 | 13 ± 0.3 | >1,000 |
| K51057 | 12 ± 1 | 24 ± 0.7 | >1,000 |

TABLE 2

Mouse KLK5, mouse KLK7, or mouse KLK14 inhibitory activity of each KLK5 inhibitory peptide

| ID | $IC_{50}$(nM) for mKLK5 | $IC_{50}$(nM) for mKLK7 | $IC_{50}$(nM) for mKLK14 |
| --- | --- | --- | --- |
| K51028 | <0.5 | 77 | >1,000 |
| K50032 | 127 | >1,000 | >1,000 |
| K50055 | <0.5 | >1,000 | >1,000 |
| K51069 | <0.5 | 181 | 40 |
| K51072 | 2 | 512 | >1,000 |
| K50015 | <0.5 | 248 | 108 |
| K50016 | 15 | >1,000 | >1,000 |
| K51034 | 54 | >1,000 | >1,000 |
| K50062 | 10 | >1,000 | >1,000 |
| K51090 | 2 | 658 | >1,000 |
| K50098 | 14 | >1,000 | 547 |
| K51005 | 48 | 23 | 214 |
| K50031 | 40 | 4 | 244 |
| K51057 | 149 | 27 | 437 |

(3-2) Evaluation of Cross-Reactivity of KLK5 Inhibitory Peptide

The specificities for other proteases were evaluated using the degradation of a substrate peptide as an index. As in the method described in (3-1), 25 µL each of a protease and a sample diluted with an assay buffer were mixed (to a final concentration of sample of 1 µM), followed by a reaction at 37° C. for 20 minutes. Thereafter, 50 µL of a substrate diluted with an assay buffer was added thereto, and the fluorescence signal was measured using Enspire (PerkinElmer). An assay buffer (50 mM Tris, 150 mM NaCl, pH 8.0) was used for the evaluation of the protease activity, and a PROTEOSAVE® SS96F black plate (Sumitomo Bakelite Co., Ltd.) was used for the reaction and the measurement. The combinations of the protease and the substrate used for the evaluation of the specificity were as follows.

Figure 3E:
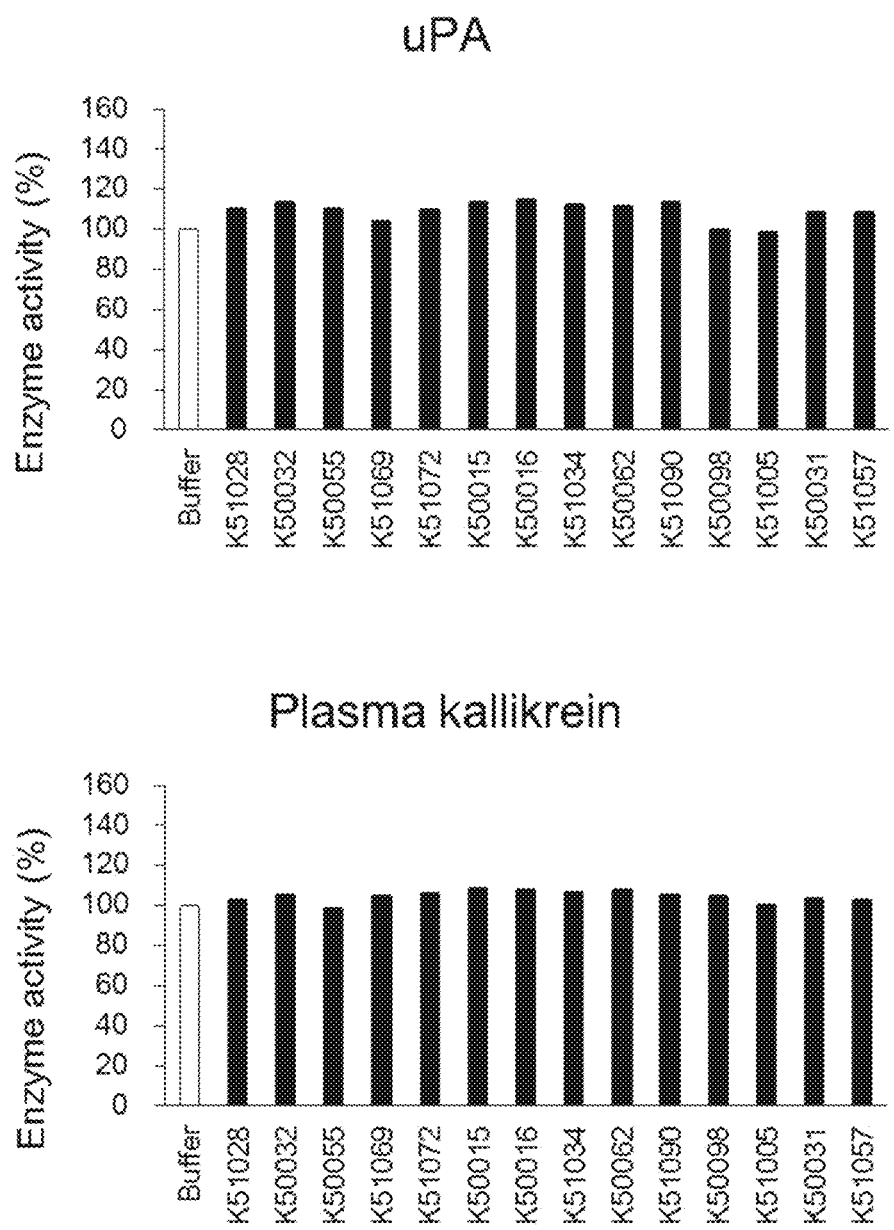
FIG. 3E includes graphs to evaluate the cross-reactivity of each inhibitory peptide with proteases, using the degradation of a peptide substrate as an index. For evaluating the Human uPA inhibitory activity, uPA (Sigma-Aldrich Co. LLC, U0633) with a final concentration of 2 nM and a substrate peptide Pyr-Gly-Arg-MCA (PEPTIDE INSTITUTE, INC., 3145-v) with a final concentration of 100 μM were used. For evaluating the Human plasma kallikrein inhibitory activity, plasma kallikrein (R&D Systems, Inc., 2497-SE) with a final concentration of 0.125 μg/mL and a substrate peptide Z-Phe-Arg-MCA (PEPTIDE INSTITUTE, INC., 3095-v) with a final concentration of 100 μM were used.

Evaluation of Bovine trypsin inhibitory activity: trypsin (Pierce; 20233) with a final concentration of 5 nM and a substrate peptide Boc-Val-Pro-Arg-AMC with a final concentration of 100 µM (R&D Systems, Inc., ES011), and a fluorescence signal with excitation at 380 nm/emission at 460 nm Evaluation of Human trypsin inhibitory activity: trypsin with a final concentration of 1 nM (Sigma-Aldrich Co. LLC, T6424) and a substrate peptide Boc-Val-Pro-Arg-AMC with a final concentration of 100 µM (R&D Systems, Inc., ES011), and a fluorescence signal with excitation at 380 nm/emission at 460 nm Evaluation of Bovine α-chymotrypsin inhibitory activity: chymotrypsin with a final concentration of 10 nM (Worthington Biochemical Corporation; LS001434) and a substrate peptide Suc-Leu-Leu-Val-Tyr-MCA (SEQ ID NO: 98) with a final concentration of 100 µM (PEPTIDE INSTITUTE, INC., 3120-v, FIG. 86, and the amino acid sequence shown in SEQ ID NO: 78), and a fluorescence signal with excitation at 380 nm/emission at 460 nm Evaluation of Human chymotrypsin inhibitory activity: chymotrypsin with a final concentration of 10 nM (Sigma-Aldrich Co. LLC, C8946), a substrate peptide Suc-Leu-Leu-Val-Tyr-MCA (SEQ ID NO: 98) with a final concentration of 10 µM (PEPTIDE INSTITUTE, INC., 3120-v, FIG. 86, and the amino acid sequence shown in SEQ ID NO: 78), and a fluorescence signal with excitation at 380 nm/emission at 460 nm Evaluation of Human tryptase inhibitory activity: tryptase with a final concentration of 1 nM (Sigma-Aldrich Co. LLC, T7063) and a substrate peptide Boc-Phe-Ser-Arg-MCA with a final concentration of 100 µM (PEPTIDE INSTITUTE, INC., 3107-v), and a fluorescence signal with excitation at 380 nm/emission at 460 nm Evaluation of Human chymase inhibitory activity: chymase with a final concentration of 100 nM (Sigma-Aldrich Co. LLC, C8118) and a substrate peptide Suc-Leu-Leu-Val-Tyr-MCA (SEQ ID NO: 98) with a final concentration of 100 µM (PEPTIDE INSTITUTE, INC., 3120-v, FIG. 86, and the amino acid sequence shown in SEQ ID NO: 78), and a fluorescence signal with excitation at 380 nm/emission at 460 nm Evaluation of Human plasmin inhibitory activity: Plasmin with a final concentration of 50 nM (Sigma-Aldrich Co. LLC, P1867) and a substrate peptide Boc-Val-Leu-Lys-MCA with a final concentration of 100 µM (PEPTIDE INSTITUTE, INC., 3104-v), and a fluorescence signal with excitation at 380 nm/emission at 460 nm Evaluation of Human thrombin inhibitory activity: thrombin with a final concentration of 1 nM (Sigma-Aldrich Co. LLC, T6884) and a substrate peptide Boc-Val-Pro-Arg-AMC with a final concentration of 100 µM (R&D Systems, Inc., ES011), and a fluorescence signal with excitation at 380 nm/emission at 460 nm Human neutrophil elastase inhibitory activity: Neutrophil elastase with a final concentration of 0.00001 U/µL (Enzo Life Sciences) and a substrate peptide Suc (OMe)-Ala-Ala-Pro-Val-MCA (SEQ ID NO: 99) with a final concentration of 100 µM (PEPTIDE INSTITUTE, INC., 3153-v, FIG. 87, and the amino acid sequence shown in SEQ ID NO: 79), and a fluorescence signal with excitation at 380 nm/emission at 460 nm Evaluation of Human matriptase inhibitory activity: matriptase with a final concentration of 1 nM (R&D Systems, Inc., 3946-SE) and a substrate peptide Boc-Gln-Ala-Arg-AMC with a final concentration of 100 μM (R&D Systems, Inc., ES014), and a fluorescence signal with excitation at 380 nm/emission at 460 nm Evaluation of Human protein C inhibitory activity: protein C with a final concentration of 100 nM (Sigma-Aldrich Co. LLC, P2200) and a substrate peptide Boc-Leu-Ser-Thr-Arg-MCA (SEQ ID NO: 100) with a final concentration of 100 μM (PEPTIDE INSTITUTE, INC., 3112-v, FIG. 88, and the amino acid sequence shown in SEQ ID NO: 80) a fluorescence signal with excitation at 380 nm/emission at 460 nm Evaluation of Human tPA inhibitory activity: tPA with a final concentration of 10 nM (Sigma-Aldrich Co. LLC, 10831) and a substrate peptide Pyr-Gly-Arg-MCA with a final concentration of 100 μM (PEPTIDE INSTITUTE, INC., 3145-v), and a fluorescence signal with excitation at 380 nm/emission at 460 nm Evaluation of Human uPA inhibitory activity: uPA with a final concentration of 2 nM (Sigma-Aldrich Co. LLC, U0633) and a substrate peptide Pyr-Gly-Arg-MCA with a final concentration of 100 μM (PEPTIDE INSTITUTE, INC., 3145-v), and a fluorescence signal with excitation at 380 nm/emission at 460 nm Evaluation of Human plasma kallikrein inhibitory activity: plasma kallikrein with a final concentration of 0.125 μg/mL (R&D Systems, Inc., 2497-SE) and a substrate peptide Z-Phe-Arg-MCA with a final concentration of 100 μM (PEPTIDE INSTITUTE, INC., 3095-v), and a fluorescence signal with excitation at 380 nm/emission at 460 nm Evaluation of Human KLK1 inhibitory activity: KLK1 with a final concentration of 0.1 μg/mL (R&D Systems, Inc., 2337-SE) and a substrate peptide Pro-Phe-Arg-MCA with a final concentration of 100 μM (PEPTIDE INSTITUTE, INC., 3096-v), and a fluorescence signal with excitation at 380 nm/emission at 460 nm Evaluation of Human KLK2 inhibitory activity: KLK2 with a final concentration of 2 μg/mL (R&D Systems, Inc., 4104-SE) and a substrate peptide Pro-Phe-Arg-MCA with a final concentration of 100 μM (PEPTIDE INSTITUTE, INC., 3096-v), and a fluorescence signal with excitation at 380 nm/emission at 460 nm Evaluation of Human KLK4 inhibitory activity: KLK4 with a final concentration of 1 μg/mL (R&D Systems, Inc., 1719-SE) and a substrate peptide Boc-Val-Pro-Arg-AMC with a final concentration of 100 μM (R&D Systems, Inc., ES011), and a fluorescence signal with excitation at 380 nm/emission at 460 nm Evaluation of Human KLK7 inhibitory activity: KLK7 with a final concentration of 1 μg/mL, a substrate peptide Mca-Arg-Pro-Lys-Pro-Val-Glu-Nval-Trp-Arg-Lys (Dnp)-NH2 (SEQ ID NO: 101) with a final concentration of 20 μM (R&D Systems, Inc., FIG. 85, and the amino acid sequence shown in SEQ ID NO: 77), and a fluorescence signal with excitation at 320 nm/emission at 405 nm Evaluation of Human KLK8 inhibitory activity: KLK8 with a final concentration of 5 nM (UniProt: O60259, prepared by the inventors) and a substrate peptide Boc-Val-Pro-Arg-AMC with a final concentration of 100 μM (R&D Systems, Inc., ES011), and a fluorescence signal with excitation at 380 nm/emission at 460 nm Evaluation of Human KLK12 inhibitory activity: KLK12 with a final concentration of 0.1 μg/mL (R&D Systems, Inc., 3095-SE) and a substrate peptide Boc-Val-Pro-Arg-AMC with a final concentration of 100 μM (R&D Systems, Inc., ES011), and a fluorescence signal with excitation at 380 nm/emission at 460 nm Evaluation of Human KLK13 inhibitory activity: KLK13 with a final concentration of 0.5 μg/mL (R&D Systems, Inc., 2625-SE) and a substrate peptide Boc-Val-Pro-Arg-AMC with a final concentration of 100 μM (R&D Systems, Inc., ES011), and a fluorescence signal with excitation at 380 nm/emission at 460 nm Evaluation of Human KLK14 inhibitory activity: hKLK14 with a final concentration of 0.2 μg/mL, a substrate peptide Boc-Val-Pro-Arg-AMC with a final concentration of 100 μM (R&D Systems, Inc.), and a fluorescence signal with excitation at 380 nm/emission at 460 nm In the same manner as in (3-1), the cross-reactivities of each KLK5 inhibitory peptide to proteases other than KLK5 were evaluated using the degradation of a peptide substrate as an index. Some of the inhibitory peptides exhibited weak cross-reactivity to Chymotrypsin with a final concentration of the inhibitory peptide of 1 μM (where the $IC_{50}$ value was less than 1 μM), but most of the inhibitory peptides exhibited no inhibitory activity to any protease other than KLKn (n=1, 2, 4, 5, 7, 8, 12, or 14) (FIG. 3). Meanwhile, some of the inhibitory peptides exhibited inhibitory activity to KLK4 or KLK12 with a final concentration of the inhibitory peptide of 1 μM (where the $IC_{50}$ value was less than 1 μM), but many of the inhibitory peptides exhibited no protease inhibitory activity against KLKn except KLK5, KLK7, and KLK14, and thus it was found that the inhibitory peptides had high specificity.

(3-3) Evaluation of KLK5 Binding Activity of KLK5 Inhibitory Peptide

In order to measure the binding affinity of the KLK5 inhibitory peptides, surface plasmon resonance analysis was conducted using BIAcore T 200 (GE healthcare). A complementary strand of DNA of a streptavidin conjugate was captured by hybridization on Sensor Chip CAP (GE healthcare) on which single-stranded DNA immobilized. Next, KLK5 biotinylated using EZ-Link NHS-PEG4-Biotin (Thermo Fisher Scientific) was captured at a flow rate of 10 μL/min to immobilize about 10 RU. Thereafter, the KLK5 inhibitory peptide, serially diluted 2-fold with HBS-EP (0.625 to 10 nM), was added thereto as an analyte at a flow rate of 30 μL/min. In the BIAcore T 200 Evaluation software (version 2.0), kon and koff were calculated by analysis using Single cycle kinetics in a simple one-to-one Langmuir binding model. The dissociation constant $K_D$ was calculated as a ratio of $k_{off}/k_{on}$. Further, multiple KLK5 inhibitory peptides were measured by regenerating Sensor Chip CAP using a Regeneration buffer attached to a Biotin CAPture Kit (GE healthcare) and repeatedly capturing biotinylated KLK5.

All of the 14 kinds of KLK5 inhibitory peptides measured exhibited $K_D$ values below 1 nM, revealing that their binding activities were very strong (Table 3A).

TABLE 3A

KLK5 binding activity of each KLK5 inhibitory peptide

| ID | Kon(1/M · s) | Koff(1/s) | $K_D$(M) |
|---|---|---|---|
| K51028 | $1.5 \times 10^6$ | $2.0 \times 10^{-5}$ | $1.4 \times 10^{-11}$ |
| K50032 | $2.0 \times 10^6$ | $2.7 \times 10^{-4}$ | $1.3 \times 10^{-10}$ |

TABLE 3A-continued

KLK5 binding activity of each KLK5 inhibitory peptide

| ID | Kon(1/M · s) | Koff(1/s) | $K_D$(M) |
|---|---|---|---|
| K50055 | $9.8 \times 10^5$ | $1.8 \times 10^{-5}$ | $1.9 \times 10^{-11}$ |
| K51069 | $9.4 \times 10^5$ | $1.0 \times 10^{-6}$ | $1.0 \times 10^{-12}$ |
| K51072 | $8.4 \times 10^5$ | $2.2 \times 10^{-5}$ | $2.6 \times 10^{-11}$ |
| K50015 | $9.4 \times 10^5$ | $1.0 \times 10^{-6}$ | $1.1 \times 10^{-12}$ |
| K50016 | $7.0 \times 10^6$ | $2.9 \times 10^{-4}$ | $4.2 \times 10^{-11}$ |
| K51034 | $5.2 \times 10^5$ | $3.5 \times 10^{-5}$ | $6.8 \times 10^{-11}$ |
| K50062 | $1.2 \times 10^6$ | $2.9 \times 10^{-6}$ | $2.5 \times 10^{-12}$ |
| K51090 | $2.1 \times 10^6$ | $5.7 \times 10^{-5}$ | $2.7 \times 10^{-11}$ |
| K50098 | $1.0 \times 10^6$ | $1.8 \times 10^{-5}$ | $1.8 \times 10^{-11}$ |
| K51005 | $3.5 \times 10^6$ | $1.2 \times 10^{-3}$ | $3.4 \times 10^{-10}$ |
| K50031 | $8.2 \times 10^5$ | $5.0 \times 10^{-5}$ | $6.1 \times 10^{-11}$ |
| K51057 | $6.0 \times 10^6$ | $1.5 \times 10^{-3}$ | $2.6 \times 10^{-10}$ |

(3-4) Evaluation of KLK5 Binding Activity of KLK5 Inhibitory Peptide Fc Fusion

In order to measure the binding affinity of a KLK5 inhibitory peptide Fc fusion prepared in (5-2), which will be described below, surface plasmon resonance analysis was conducted using BIAcore T 200 (GE healthcare).

The KLK5 inhibitory peptide Fc fusion was captured at a flow rate of 20 μL/min by Sensor Chip CM5 (GE healthcare) on which an anti-human IgG (Fc) antibody was immobilized to immobilize about 30 to 50 RU. Thereafter, KLK5, serially diluted 2-fold with HBS-EP (0.625 to 10 nM), was added thereto as an analyte at a flow rate of 30 μL/min. In the BIAcore T 200 Evaluation software (version 2.0), kon and koff were calculated by analysis using Single cycle kinetics in a simple one-to-one Langmuir binding model. The dissociation constant $K_D$ was calculated as a ratio of $k_{off}/k_{on}$. Further, the binding activity of KLK5 to multiple KLK5 inhibitory peptide Fc fusions was measured by regenerating Sensor Chip CM5 on which the anti-human IgG (Fc) antibody was immobilized using a Regeneration buffer attached to a Human Antibody Capture Kit (GE healthcare) and repeatedly capturing the KLK5 inhibitory peptide Fc fusion.

All of the 14 kinds of KLK5 inhibitory peptide Fc fusions measured exhibited $K_D$ values below 1 nM, revealing that their binding activities were very strong (Table 3B).

TABLE 3B

KLK5 binding activity of each KLK5 inhibitory peptide Fc fusion

| ID | Kon(1/M · s) | Koff(1/s) | $K_D$(M) |
|---|---|---|---|
| D3-K51028-Fc | $5.39 \times 10^5$ | $1.81 \times 10^{-6}$ | $3.35 \times 10^{-12}$ |
| D3-K50032dN-Fc | $1.08 \times 10^6$ | $5.69 \times 10^{-6}$ | $5.25 \times 10^{-12}$ |
| D3-K50055-Fc | $5.49 \times 10^5$ | $2.32 \times 10^{-6}$ | $4.22 \times 10^{-12}$ |
| D3-K51069dN-Fc | $7.14 \times 10^5$ | $2.81 \times 10^{-6}$ | $3.93 \times 10^{-12}$ |
| D3-K51072-Fc | $2.25 \times 10^5$ | $1.68 \times 10^{-6}$ | $7.48 \times 10^{-12}$ |
| D3-K50015-Fc | $1.04 \times 10^6$ | $3.52 \times 10^{-6}$ | $3.38 \times 10^{-12}$ |
| D3-K50016dN-Fc | $7.18 \times 10^5$ | $5.60 \times 10^{-6}$ | $7.81 \times 10^{-12}$ |
| D3-K51034-Fc | $2.83 \times 10^5$ | $2.93 \times 10^{-6}$ | $1.03 \times 10^{-11}$ |
| D3-K50062-Fc | $5.66 \times 10^5$ | $6.52 \times 10^{-6}$ | $1.15 \times 10^{-11}$ |
| D3-K51090-Fc | $7.00 \times 10^5$ | $7.86 \times 10^{-6}$ | $1.12 \times 10^{-11}$ |
| D3-K50098dN-Fc | $9.22 \times 10^5$ | $<1.62 \times 10^{-6}$ | $<1.76 \times 10^{-12}$ |
| D3-K51005-Fc | $1.47 \times 10^5$ | $1.96 \times 10^{-5}$ | $1.33 \times 10^{-10}$ |
| D3-K50031-Fc | $8.81 \times 10^4$ | $<1.00 \times 10^{-6}$ | $<1.14 \times 10^{-11}$ |
| D3-K51057-Fc | $8.69 \times 10^4$ | $1.79 \times 10^{-5}$ | $2.06 \times 10^{-10}$ |

Example 4. Analysis of Klk5 Inhibitory Peptide Using X-Ray Crystal Structure (4-1) Preparation of KLK5/KLK5 Inhibitory Peptide Complex According to the methods described in (1-2) and (2-2), KLK5 inhibitory peptides K51034 and KLK5 having the amino acid sequences shown by the SEQ ID numbers were prepared. After mixing the two under conditions of 50 mM Tris-HCl, 150 mM NaCl, and pH 8.0, a complex was isolated and purified by gel filtration chromatography (Superdex 200 10/300 GL).

(4-2) Analysis of X-Ray Crystal Structure

Figure 4:
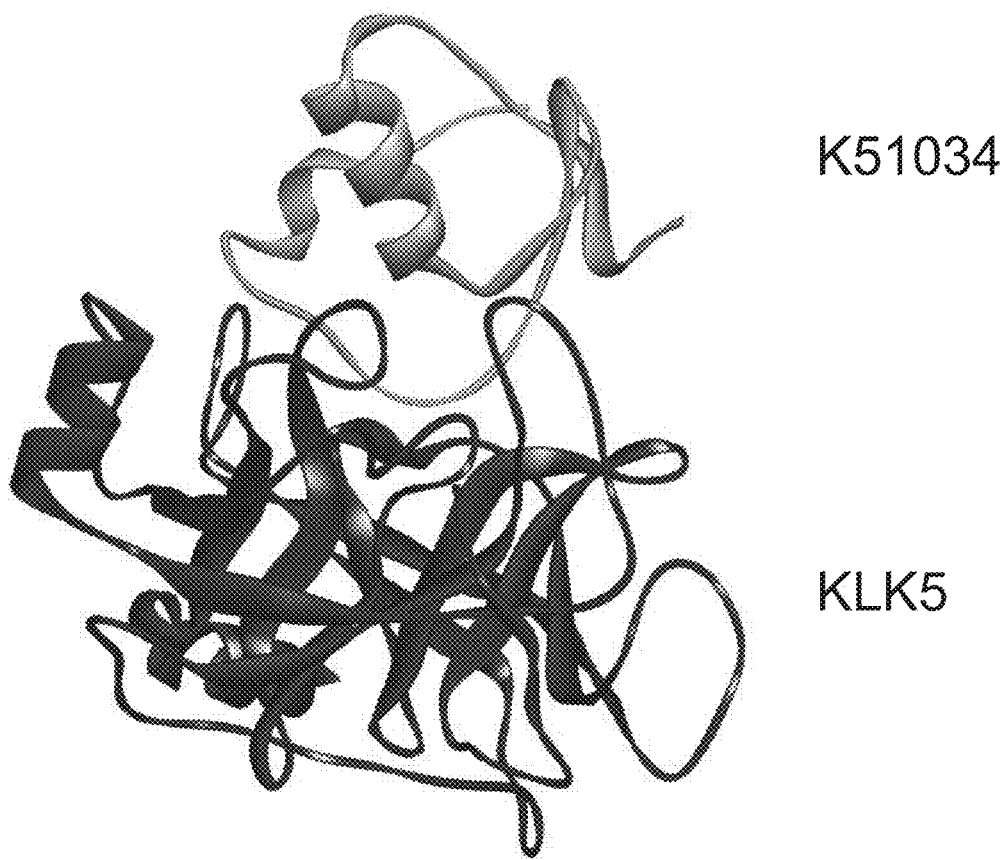
FIG. 4 is a view showing a KLK5/KLK5 inhibitory peptide complex obtained by X-ray crystal structure analysis. The inhibitory peptide K51034 is bound to a region containing the KLK5 active site.

The complex solution prepared in (4-1) was concentrated to 12 mg/mL, thereafter mixed with a reservoir solution (0.2 M Magnesium Chloride hexahydrate, 20% PEG3350) at a ratio of 1:1, and crystallized by a vapor diffusion method. The obtained cubic single crystal was immersed in a reservoir solution containing 20% glycerol and thereafter frozen in liquid nitrogen. The frozen crystals were irradiated with X-rays in a cryo-stream to obtain a diffraction image (Hypixel 6000HE/MicroMax007). Scaling data with a maximum resolution of 1.7 Å was obtained by analysis using CrysAlisPro. The phase was determined by the molecular replacement method using KLK5 alone (PDB ID: 2PSX) and SPINK2 alone (PDB ID: 2JXD) as templates. After structural refinement, complex crystals of KLK5/the peptide K51034 were determined at a resolution of 1.8 Å. One molecule each of KLK5 and SPINK2 was contained in a unit cell. For the SPINK2 molecule, a partial molecular model containing an interaction site with KLK5 was constructed based on the sequence information and the electron density observed. It was confirmed that the KLK5 inhibitory peptide K51034 was bound to a region containing the KLK5 enzyme's active site (FIG. 4).

Example 5. Preparation of KLK5 Inhibitory Peptide Fc Fusion (5-1) Construction of KLK5 Inhibitory Peptide Fc Fusion Expression Vector Using the nucleotide sequence of each inhibitory peptide (SEQ ID NO: 5, 7, 9, 11, 13, 15, 17, 19, 21, 23, 25, 27, 29, or 31) as a template, inhibitory peptide fragments were amplified by PCR ((at 94° C. for 15 seconds, at 60° C. for 30 seconds, and at 68° C. for 20 seconds)×30 cycles) using the following primers and KOD-plus-(TOYOBO).

Primer 16:

(SEQ ID NO: 81, FIG. 89)

5'-AGATGGGTGTTGTCTGATGACGACGGCCCTCAGTTCGGCCTGTTC-3'

Primer 17:

(SEQ ID NO: 82, FIG. 90)

5'-GCAGGGGCCATTCCGGAT-3'

Fragment B was amplified by PCR ((at 94° C. for 15 seconds, at 60° C. for 30 seconds, and at 68° C. for 10 seconds)×30 cycles) using the following primers and KOD-plus-(TOYOBO).

Primer 18:
(SEQ ID NO: 83, FIG. 91)
5'-AAAATCTAGAGCCGCCACCATGAAGCACCTGTGGTTCTTTCTGCTGCT-3'

Primer 19:
(SEQ ID NO: 84, FIG. 92)
5'-AGACAACACCCATCTAGGAGCGGCCACCAGCAGCAGAAAGAACC-3'

Using an Fc region of human IgG1 (SEQ ID NO: 87) as a template, fragment C containing an Fc region of human IgG1 was amplified by PCR ((at 94° C. for 15 seconds, at 60° C. for 30 seconds, at 68° C. for 30 seconds)×30 cycle) using the following primers and KOD-plus-(TOYOBO).

Primer 20:
(SEQ ID NO: 85, FIG. 93)
5'-ATCCGGAATGGCCCCTGCGAACCCAAGAGCTGCGAC-3'

Primer 21:
(SEQ ID NO: 86, FIG. 94)
5'-AAAAGTTTAAACTCATTTGCCGGGGCTCAG-3'

Desired DNA fragments were amplified by overlapping PCR using the inhibitory peptide fragments amplified above, fragment B, fragment C, primer 18, primer 21, and KOD-plus-(TOYOBO).

Further, a mammalian cell expression vector, pCMA_KLK5 inhibitory peptide Fc fusion, was constructed by cloning using restriction enzymes XbaI (NEB) and PmeI (NEB). The operation was performed according to the method described in (1-1).

(5-2) Preparation of KLK5 Inhibitory Peptide Fc Fusion

The expression vector constructed in (5-1) was transfected into Expi293F cells (Thermo Fisher Scientific) using PEI MAX 40000 (Polysciences), and the culture supernatant was collected after 6 days of culturing the cells. The desired Fc fusion was collected from the culture supernatant using MabSelect SuRe (GE healthcare), and the buffer was replaced with PBS using Amicon Ultra NMWL 10,000 (Merck KGaA Millipore), to prepare a KLK5 inhibitory peptide Fc fusion. From each clone having a glycosylation sequence in the KLK5 inhibitory peptide, the glycosylation sequence was removed by substitution of one residue, and "dN" was added thereto as an ID showing a deglycosylated form. The modification of the glycosylation sequence does not affect the activity such as KLK5 inhibitory activity or cross-reactivity at all.

(5-3) Construction of KLK5 Inhibitory Peptide Fc Fusion D1-K50055-Fc Expression Vector Using the nucleotide sequence of the KLK5 inhibitory peptide K50055 (SEQ ID NO: 7) as a template, inhibitory peptide fragments were amplified by PCR ((at 94° C. for 15 seconds, at 60° C. for 30 seconds, and at 68° C. for 20 seconds)×30 cycles) using the following primers and KOD-plus-(TOYOBO).

Primer 22:
(SEQ ID NO: 94, FIG. 104)
5'-AGATGGGTGTTGTCTGACGGCCCTCAGTTCGGCCTGTTC-3'

Primer 17:
(SEQ ID NO: 82, FIG. 90)
5'-GCAGGGGCCATTCCGGAT-3'

Desired DNA fragments were amplified by overlapping PCR using the inhibitory peptide fragments amplified above and fragment B, fragment C, primer 18, and primer 21, which were amplified in (5-1), and KOD-plus-(TOYOBO).

Further, a mammalian cell expression vector, pCMA_KLK5 inhibitory peptide Fc fusion, was constructed by cloning using restriction enzymes XbaI (NEB) and PmeI (NEB). The operation was performed according to the method described in (1-1).

(5-4) Preparation of KLK5 Inhibitory Peptide Fc Fusion D1-K50055-Fc

The expression vector constructed in (5-3) was transfected into Expi293F cells (Thermo Fisher Scientific) using PEI MAX 40000 (Polysciences), and the culture supernatant was collected after 6 days of culturing the cells. The desired Fc fusion was collected from the culture supernatant using MabSelect SuRe (GE healthcare), and the buffer was replaced with PBS using Amicon Ultra NMWL 10,000 (Merck KGaA Millipore), to prepare the KLK5 inhibitory peptide Fc fusion D1-K50055-Fc.

Figure 5:
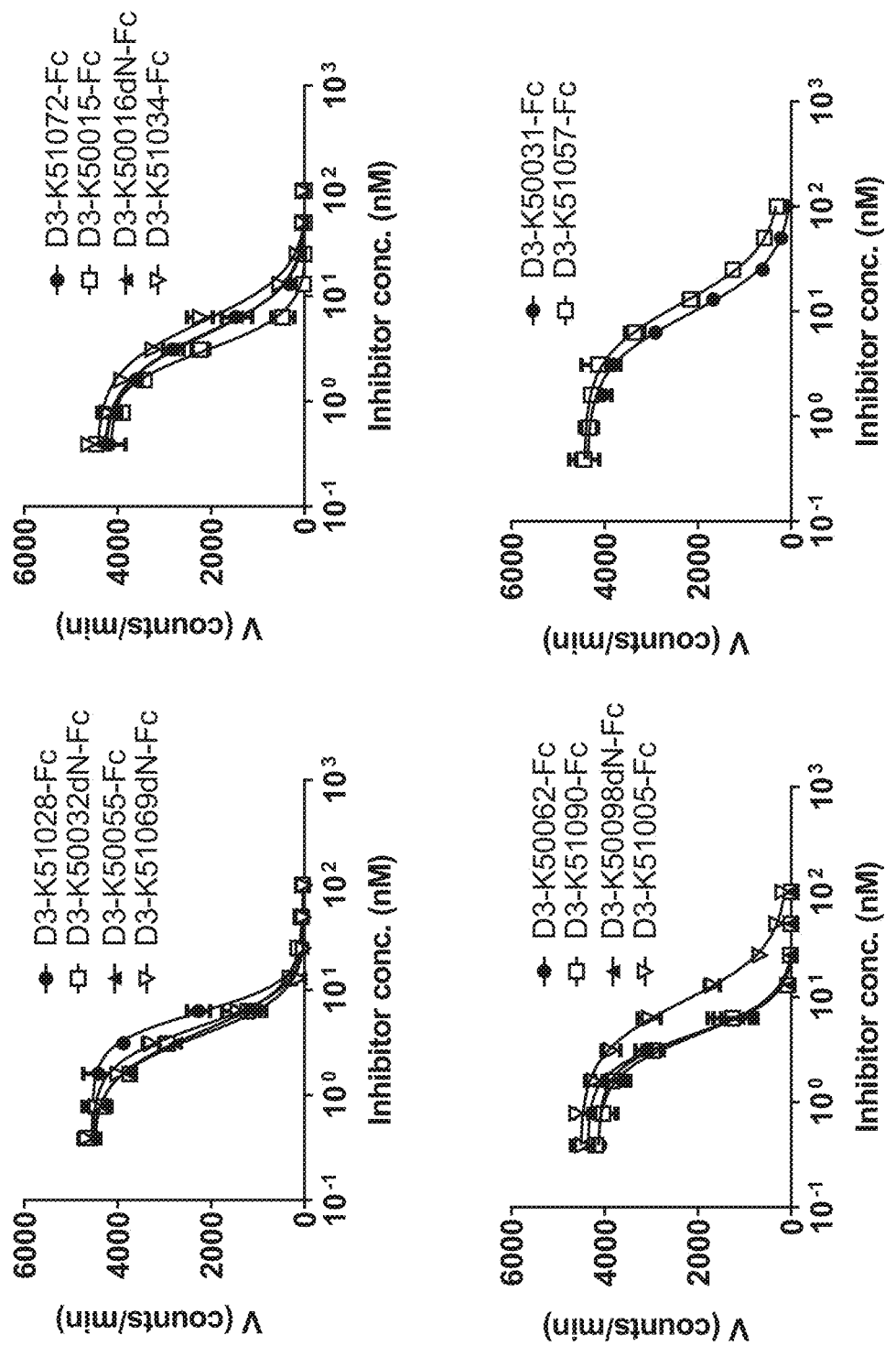
FIG. 5 includes graphs showing the KLK5 inhibitory activity ($IC_{50}$) of each KLK5 inhibitory peptide Fc fusion, using the degradation rate of a peptide substrate as an index. For evaluating the KLK5 inhibitory activity, KLK5 with a final concentration of 10 nM and Boc-Val-Pro-Arg-AMC (R&D Systems, Inc., ES011) with a final concentration of 100 μM were used.
Figure 6A:
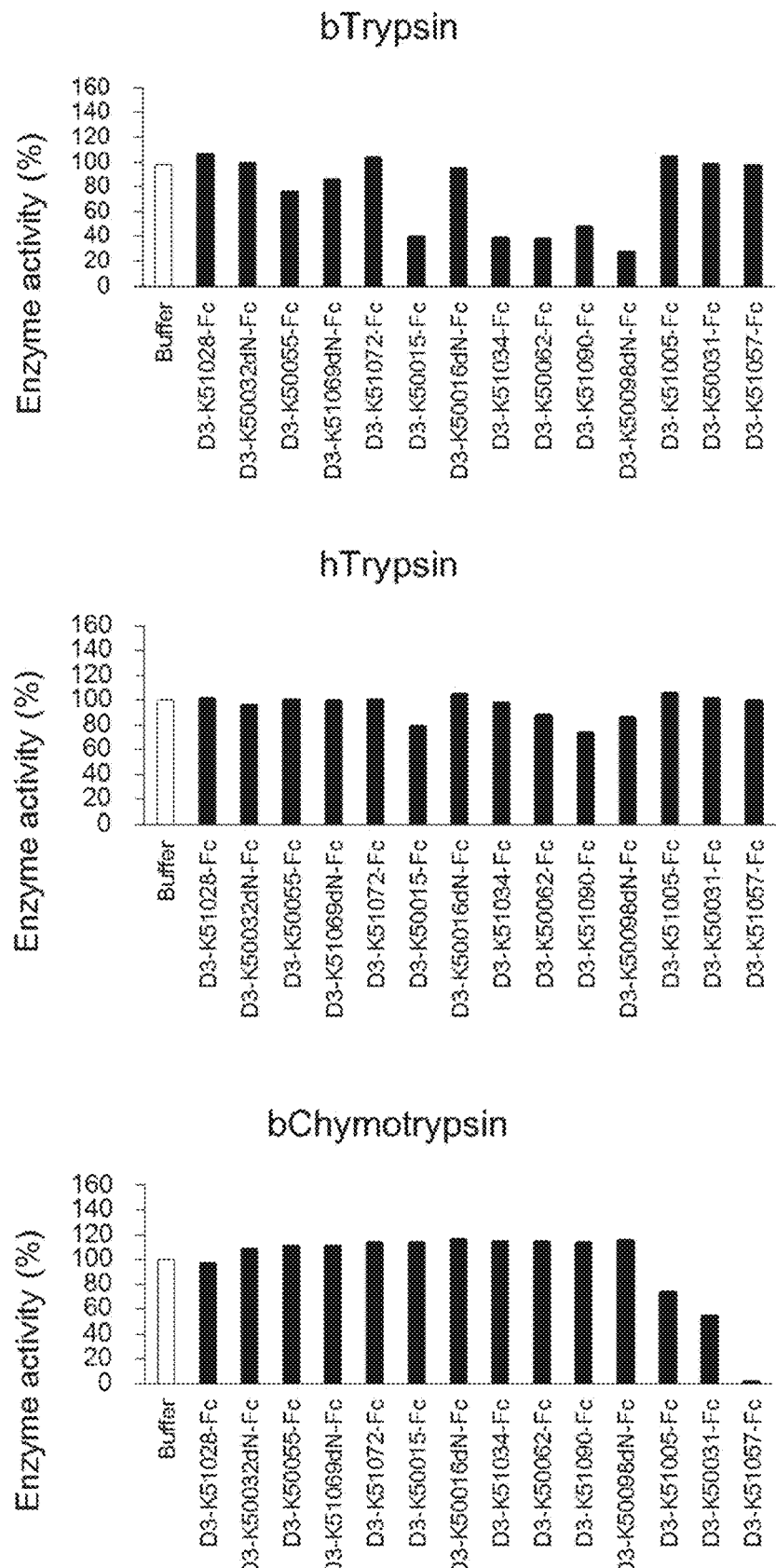
FIG. 6A includes graphs to evaluate the cross-reactivity of each inhibitory peptide Fc fusion with proteases, using the degradation of a peptide substrate as an index. For evaluating the Bovine trypsin, Human trypsin, and Bovine α-chymotrypsin inhibitory activities, the same conditions as in FIG. 3A were used.
Figure 6B:
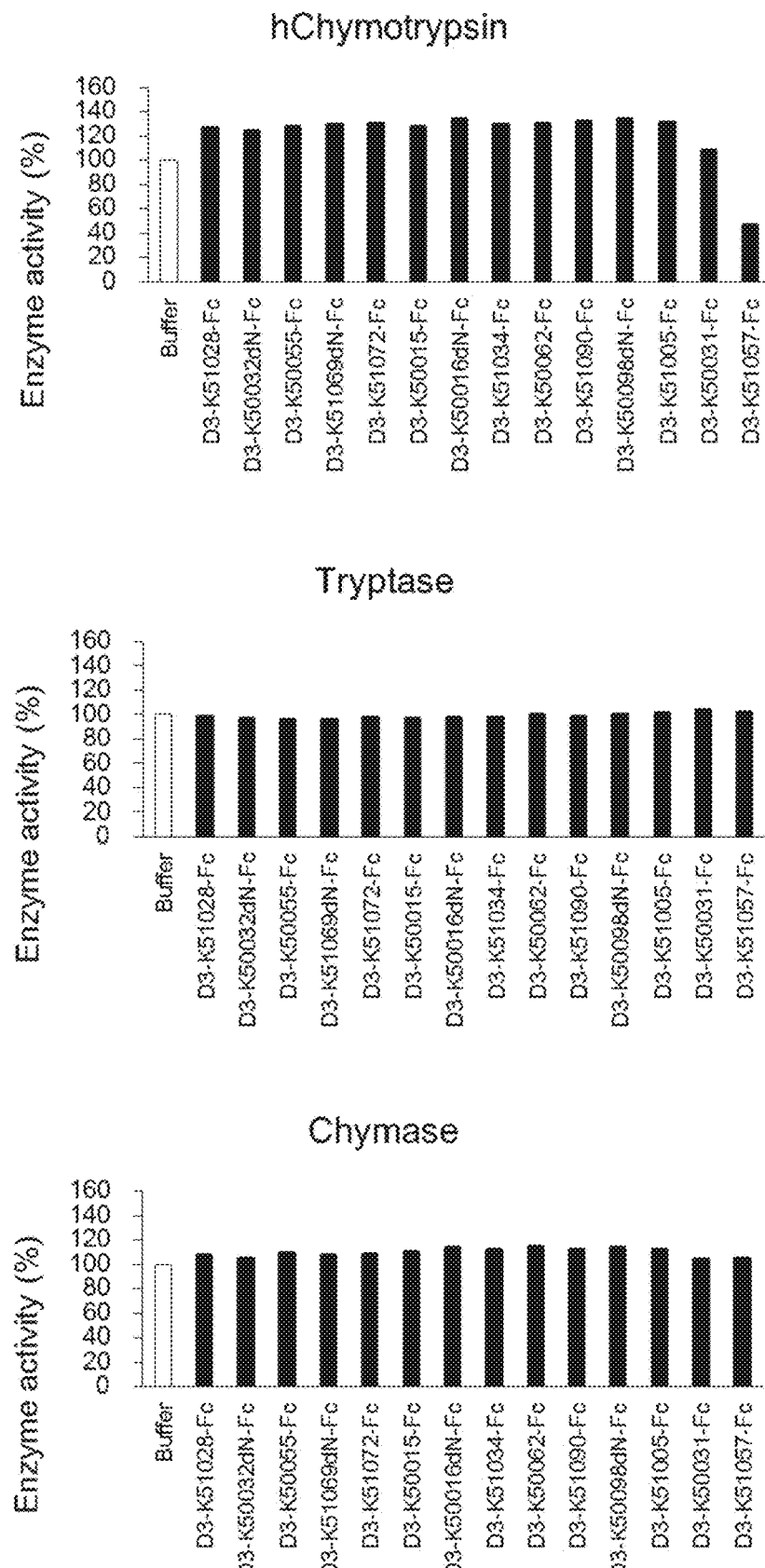
FIG. 6B includes graphs to evaluate the cross-reactivity of each inhibitory peptide Fc fusion with proteases, using the degradation of a peptide substrate as an index. For evaluating the Human chymotrypsin, Human tryptase, and Human chymase inhibitory activities, the same conditions as in FIG. 3B were used.
Figure 6C:
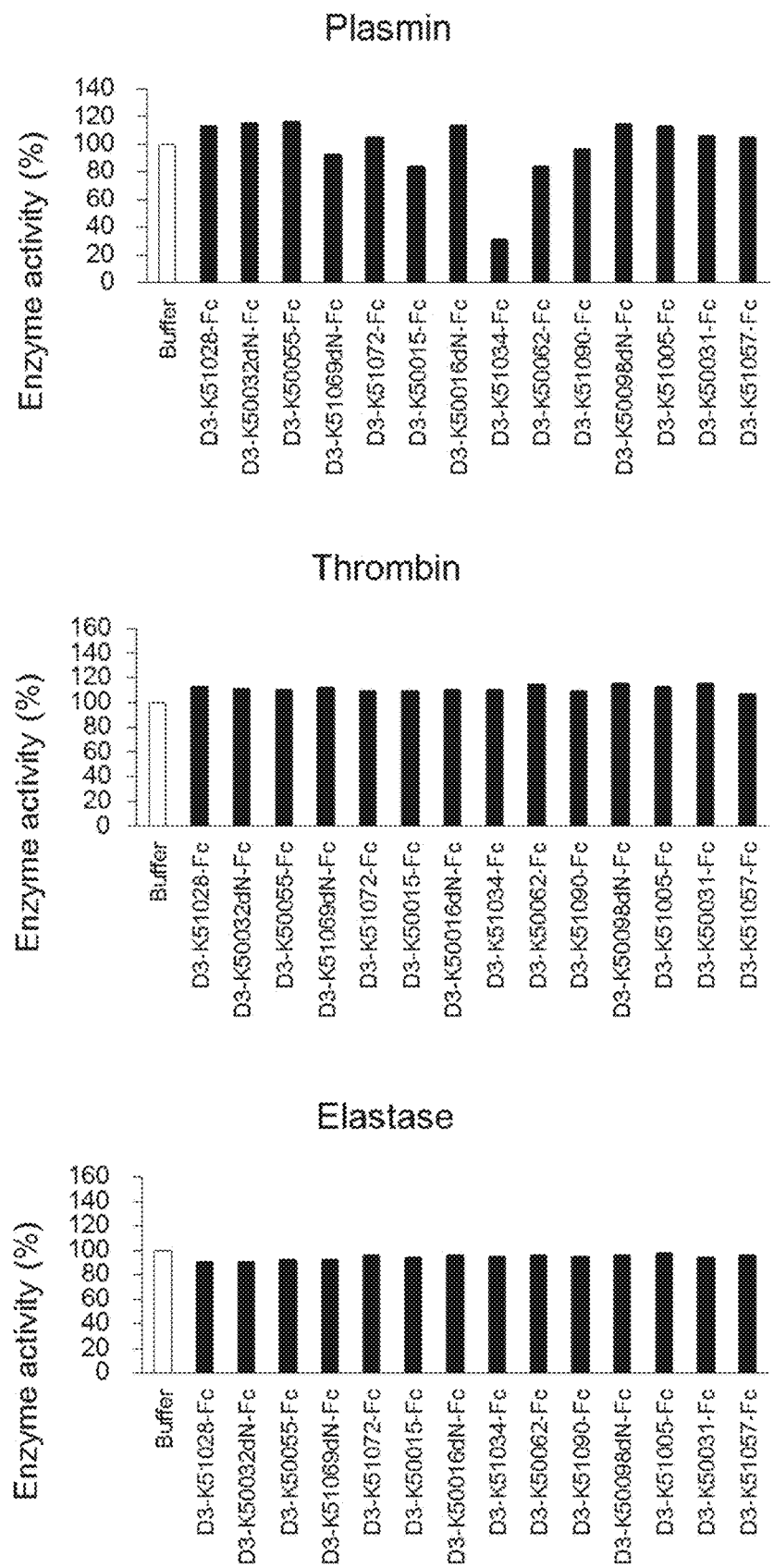
FIG. 6C includes graphs to evaluate the cross-reactivity of each inhibitory peptide Fc fusion with proteases, using the degradation of a peptide substrate as an index. For evaluating the Human plasmin, Human thrombin, and Human neutrophil elastase inhibitory activities, the same conditions as in FIG. 3C were used.
Figure 6E:
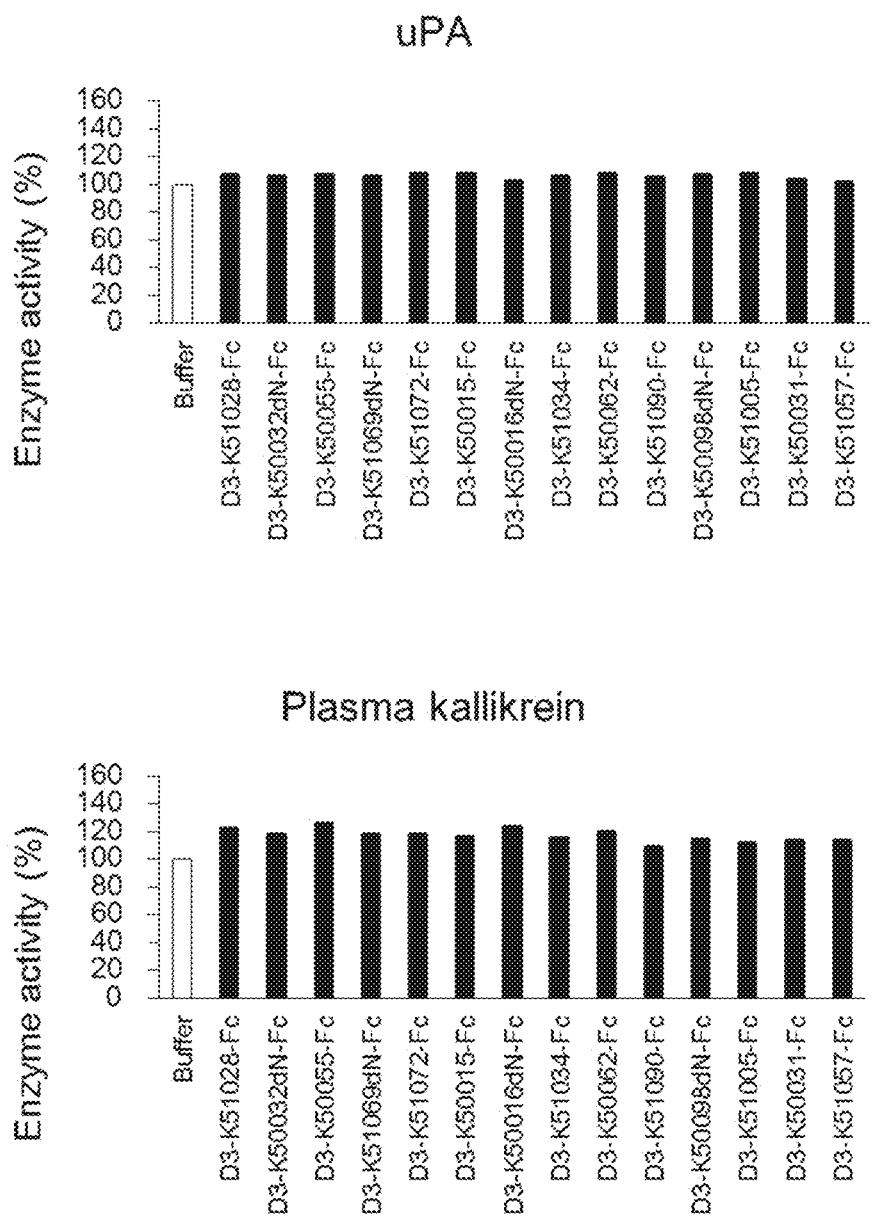
FIG. 6E includes graphs to evaluate the cross-reactivity of each inhibitory peptide Fc fusion with proteases, using the degradation of a peptide substrate as an index. For evaluating the Human uPA and Human plasma kallikrein inhibitory activities, the same conditions as in FIG. 3E were used.

Example 6. Evaluation of KLK5 Inhibitory Peptide Fc Fusion (6-1) Evaluation of Human/Mouse KLK5, Human/Mouse KLK7, and Human/Mouse KLK14 Inhibitory Activities of KLK5 Inhibitory Peptide Fc Fusion According to the method described in Example 3-1, the inhibitory activities of each KLK5 inhibitory peptide Fc fusion against human/mouse KLK5, human/mouse KLK7, and human/mouse KLK14 were evaluated. As a result of calculating the degradation rate of a substrate peptide by each inhibitory peptide Fc fusion at each concentration and calculating the 50% inhibitory concentration ($IC_{50}$) using GraphPad Prism (version 5.0; GraphPad Software Inc.) with the degradation rate of the inhibitory peptide Fc fusion at a concentration of 0 nM taken as 100%, it was revealed that all of the inhibitory peptide Fc fusions inhibited human KLK5 enzymatic activity at low concentrations (Table 4, FIG. 5, and FIG. 107). Some of the inhibitory peptide Fc fusions inhibited human KLK7 or human KLK14 enzymatic activity at low concentrations, and some of the inhibitory peptide Fc fusions exhibited weak inhibitory activities against these proteases. The inhibitory peptide Fc fusions also exhibited similar activity against mouse KLK5, KLK7, or KLK14 (Table 5). The average value of three independent experiments was used to calculate the $IC_{50}$ value.

TABLE 4

Human KLK5, human KLK7, or human KLK14 inhibitory activity of each KLK5 inhibitory peptide Fc fusion

| ID | $IC_{50}$(nM) for hKLK5 | $IC_{50}$(nM) for hKLK7 | $IC_{50}$(nM) for hKLK14 |
|---|---|---|---|
| D3-K51028-Fc | 4.5 ± 0.1 | 220 ± 10 | >1,000 |
| D3-K50032dN-Fc | 3.9 ± 0.3 | >1,000 | >1,000 |
| D3-K50055-Fc | 3.7 ± 0.1 | >1,000 | 340 ± 120 |
| D3-K51069dN-Fc | 4.5 ± 0.4 | >1,000 | 42 ± 11 |
| D3-K51072-Fc | 4.5 ± 0.3 | >1,000 | 260 ± 60 |

TABLE 4-continued

Human KLK5, human KLK7, or human KLK14 inhibitory activity of each KLK5 inhibitory peptide Fc fusion

| ID | IC$_{50}$(nM) for hKLK5 | IC$_{50}$(nM) for hKLK7 | IC$_{50}$(nM) for hKLK14 |
|---|---|---|---|
| D3-K50015-Fc | 3.1 ± 0.2 | >1,000 | 4.5 ± 1.3 |
| D3-K50016dN-Fc | 4.3 ± 0.7 | >1,000 | >1,000 |
| D3-K51034-Fc | 5.7 ± 0.8 | >1,000 | 960 ± 320 |
| D3-K50062-Fc | 4.3 ± 0.1 | >1,000 | 190 ± 50 |
| D3-K51090-Fc | 4.6 ± 0.5 | >1,000 | 350 ± 30 |
| D3-K50098dN-Fc | 4.3 ± 0.3 | >1,000 | 210 ± 60 |
| D3-K51005-Fc | 8.6 ± 1.4 | 28 ± 3 | >1,000 |
| D3-K50031-Fc | 9.5 ± 0.4 | 9.3 ± 1.3 | >1,000 |
| D3-K51057-Fc | 12 ± 1 | 18 ± 1 | >1,000 |
| D1-K50055-Fc | 5.8 ± 0.6 | >1,000 | >1,000 |

TABLE 5

Mouse KLK5, mouse KLK7, or mouse KLK14 inhibitory activity of each KLK5 inhibitory peptide Fc fusion

| ID | IC$_{50}$(nM) for mKLK5 | IC$_{50}$(nM) for mKLK7 | IC$_{50}$(nM) for mKLK14 |
|---|---|---|---|
| D3-K51028-Fc | 16 | 110 | >1,000 |
| D3-K50032dN-Fc | 26 | >1,000 | >1,000 |
| D3-K50055-Fc | 6.8 | >1,000 | >1,000 |
| D3-K51069dN-Fc | 6.8 | 410 | 24 |
| D3-K51072-Fc | 50 | >1,000 | >1,000 |
| D3-K50015-Fc | 4.4 | 340 | 48 |
| D3-K50016dN-Fc | 35 | >1,000 | >1,000 |
| D3-K51034-Fc | 39 | >1,000 | >1,000 |
| D3-K50062-Fc | 5.4 | >1,000 | >1,000 |
| D3-K51090-Fc | 5.1 | 730 | 510 |
| D3-K50098dN-Fc | 6.8 | >1,000 | 350 |
| D3-K51005-Fc | 330 | 37 | 240 |
| D3-K50031-Fc | 270 | 6.3 | 300 |
| D3-K51057-Fc | 600 | 24 | 380 |
| D1-K50055-Fc | 6.3 | >1,000 | >1,000 |

(6-2) Evaluation of Cross-Reactivity of KLK5 Inhibitory Peptide Fc Fusion

Like the results in (3-2), some of the inhibitory peptide Fc fusions exhibited weak cross-reactivity to bovine trypsin, chymotrypsin, and plasmin with a final concentration of the inhibitory peptide of 1 µM (where the IC$_{50}$ value was less than 1 µM), but most of the inhibitory peptides exhibited no inhibitory activity to any protease other than KLKs (FIG. 6). Some of the inhibitory peptide Fc fusions exhibited inhibitory activity to KLK4 or KLK12 with a final concentration of 1 µM (where the IC$_{50}$ value was less than 1 µM), but many of the inhibitory peptide Fc fusions exhibited no protease inhibitory activity against KLKs except KLK7 or KLK14. Accordingly, it was found that the inhibitory peptide Fc fusions had high specificity like the inhibitory peptides.

(6-3) Evaluation of KLK5 Inhibitory Activity of KLK5 Inhibitory Peptide Fc Fusion Using Peptide Substrate (Calculation of Inhibition Constant K$_i$)

The inhibitory activity of the KLK5 inhibitory peptide Fc fusions against human KLK5 was evaluated, and the inhibition constant K$_i$ was calculated. A substrate peptide Boc-Val-Pro-Arg-AMC (R&D Systems, Inc., ES011) was dissolved in DMSO to 10 mM and diluted with an assay buffer (50 mM Tris-HCl, 150 mM NaCl, pH 8.0) for use at a final concentration of 25 to 200 µM. 25 µL each of human KLK5 and the KLK5 inhibitory peptide Fc fusion diluted with the assay buffer were mixed, followed by a reaction at 37° C. for 20 minutes. Thereafter, 50 µL of a substrate diluted with the assay buffer was added thereto, and the fluorescence signal (excitation at 380 nm/emission at 460 nm) was measured using Enspire. The human KLK5 had a final concentration of 10 nM, the KLK5 inhibitory peptide Fc fusion had a final concentration of 0.5 to 25 nM, and a PROTEOSAVE® SS96F black plate (Sumitomo Bakelite Co., Ltd.) was used for the reaction and the measurement.

Figure 102:
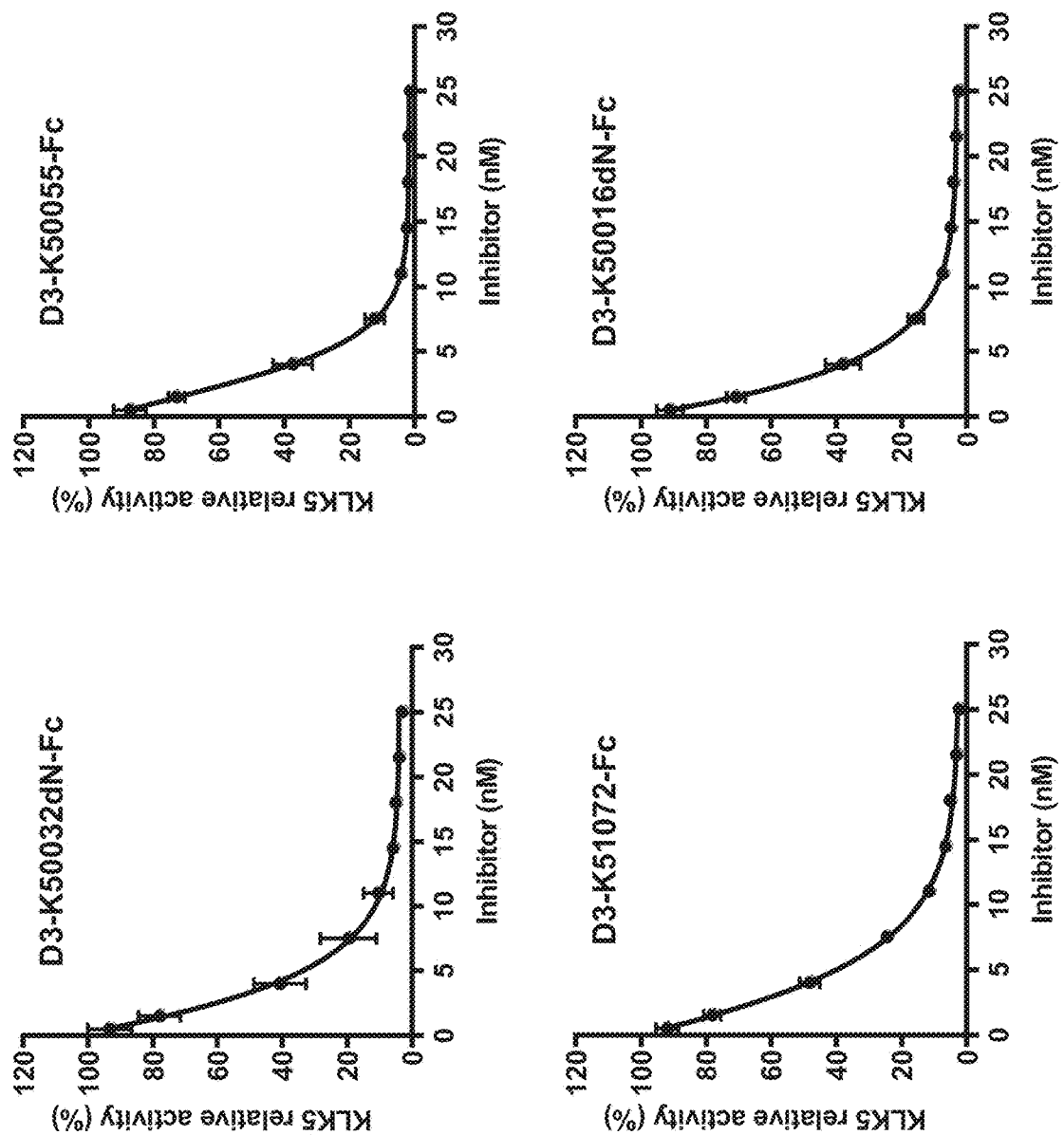
FIG. 102 includes graphs to evaluate the KLK5 inhibitory activity of each KLK5 inhibitory peptide Fc fusion (n=3, Mean±SD), using the degradation rate of a peptide substrate as an index, in order to calculate inhibition constants $K_i$. For evaluating the KLK5 inhibitory activity, KLK5 with a final concentration of 10 nM and Boc-Val-Pro-Arg-AMC (R&D Systems, Inc., ES011) with a final concentration of 100 µM were used.

The degradation rate of the substrate peptide by each inhibitory peptide Fc fusion at each concentration was calculated, and the human KLK5 inhibitory activity of each inhibitory peptide Fc fusion was evaluated, with the degradation rate of the inhibitory peptide Fc fusion at a concentration of 0 nM taken as 100% (FIG. 102). Using GraphPad Prism (version 5.0; GraphPad Software Inc.), the maximum reaction rate V. and the Michaelis constant K$_m$ were calculated according to the Michaelis-Menten equation at an enzyme concentration of 10 nM. Further, as a result of calculating the inhibition constant K$_i$ at a substrate concentration of 100 µM using GraphPad Prism according to the Morrison equation, it was revealed that all of the KLK5 inhibitory peptide Fc fusions inhibited human KLK5 enzymatic activity at low concentrations (Table 6). The average value of three independent experiments was used to calculate the K$_i$ value.

TABLE 6

Human KLK5 inhibition constant K$_i$ of each KLK5 inhibitory peptide Fc fusion

| ID | K$_i$(pM) |
|---|---|
| D3-K50032dN-Fc | 440 ± 10 |
| D3-K50055-Fc | 190 ± 60 |
| D3-K51072-Fc | 360 ± 70 |
| D3-K50016dN-Fc | 360 ± 40 |

(6-4) Evaluation of KLK5 Inhibitory Activity of KLK5 Inhibitory Peptide Fc Fusion Using Protein Substrate Using human Desmoglein1 and human Desmocollin1 as protein substrates, the KLK5 inhibitory activity of each KLK5 inhibitory peptide Fc fusion was evaluated. Human KLK5 and each KLK5 inhibitory peptide Fc fusion (D3-K50032dN-Fc, D3-K50055-Fc, D3-K51072-Fc, or D3-K50016dN-Fc) diluted with an assay buffer were mixed, followed by a reaction at 37° C. for 1 hour. Next, each protein substrate diluted with an assay buffer was added thereto, followed by a reaction at 37° C. for 4 hours. Thereafter, an SDS sample buffer containing a reductant was added thereto, and the enzymatic reaction was stopped by treatment at 99° C. for 5 minutes. Thereafter, the degradation of the protein substrate was evaluated using SDS-PAGE (reduction conditions) and Western blot analysis. The combinations of the substrate and enzyme, the inhibitory peptide Fc fusion, and the antibody for Western blot analysis were as follows.

Evaluation using Human Desmoglein1: hKLK5 with a final concentration of 1 µM, an inhibitory peptide Fc fusion with a final concentration of 0.001 to 10 µM, Recombinant Human Desmoglein-1 Fc Chimera Protein with a final concentration of 1 µM (R&D Systems, Inc.), Desmoglein 1 Antibody (aa471-499) (LSBio), and Anti-Rabbit IgG, HRP-Linked F (ab') 2 Fragment Donkey (GE healthcare)

Evaluation using Human Desmocollin1: hKLK5 with a final concentration of 0.2 µM, an inhibitory peptide Fc fusion with a final concentration of 0.0002 to 2 µM, Recombinant Human Desmocollin-1 Protein with a C-terminal His tag with a final concentration of 2 µM (R&D Systems, Inc.), and Penta His HRP Conjugate (QIAGEN)

Figure 103A:
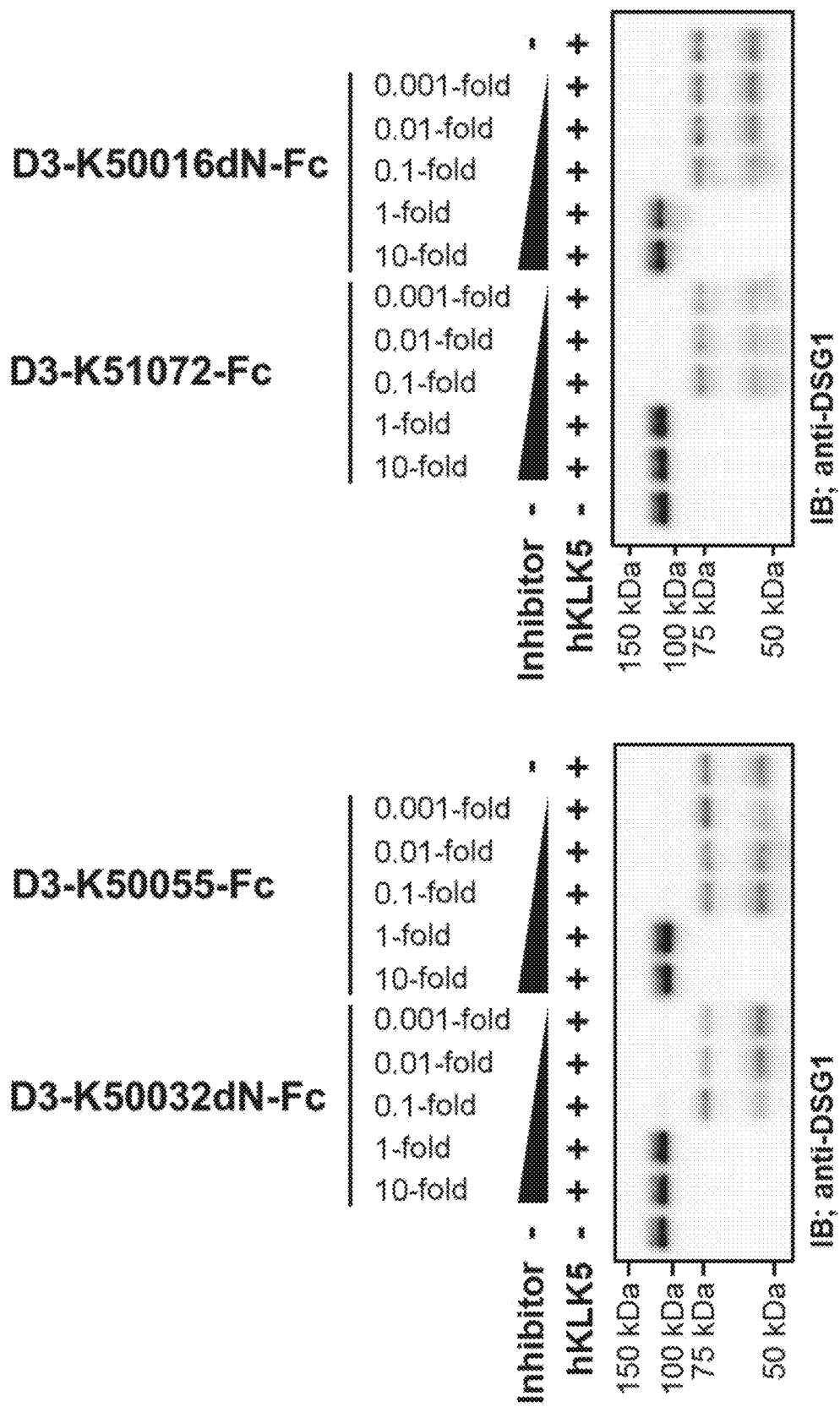
FIG. 103A includes diagrams to evaluate the KLK5 inhibitory activity of each KLK5 inhibitory peptide Fc fusion, using the degradation of human Desmoglein1 as an index. For evaluating the KLK5 inhibitory activity, KLK5 with a final concentration of 1 µM and Recombinant Human Desmoglein-1 Fc Chimera Protein (R&D Systems, Inc., 944-DM-100) with a final concentration of 1 µM were used. Analysis was performed by Western blotting using Desmoglein 1 Antibody (aa471-499) (LSBio, LS-C167542) and Anti-Rabbit IgG, HRP-Linked F (ab') 2 Fragment Donkey (GE healthcare, NA9340V).
Figure 103B:
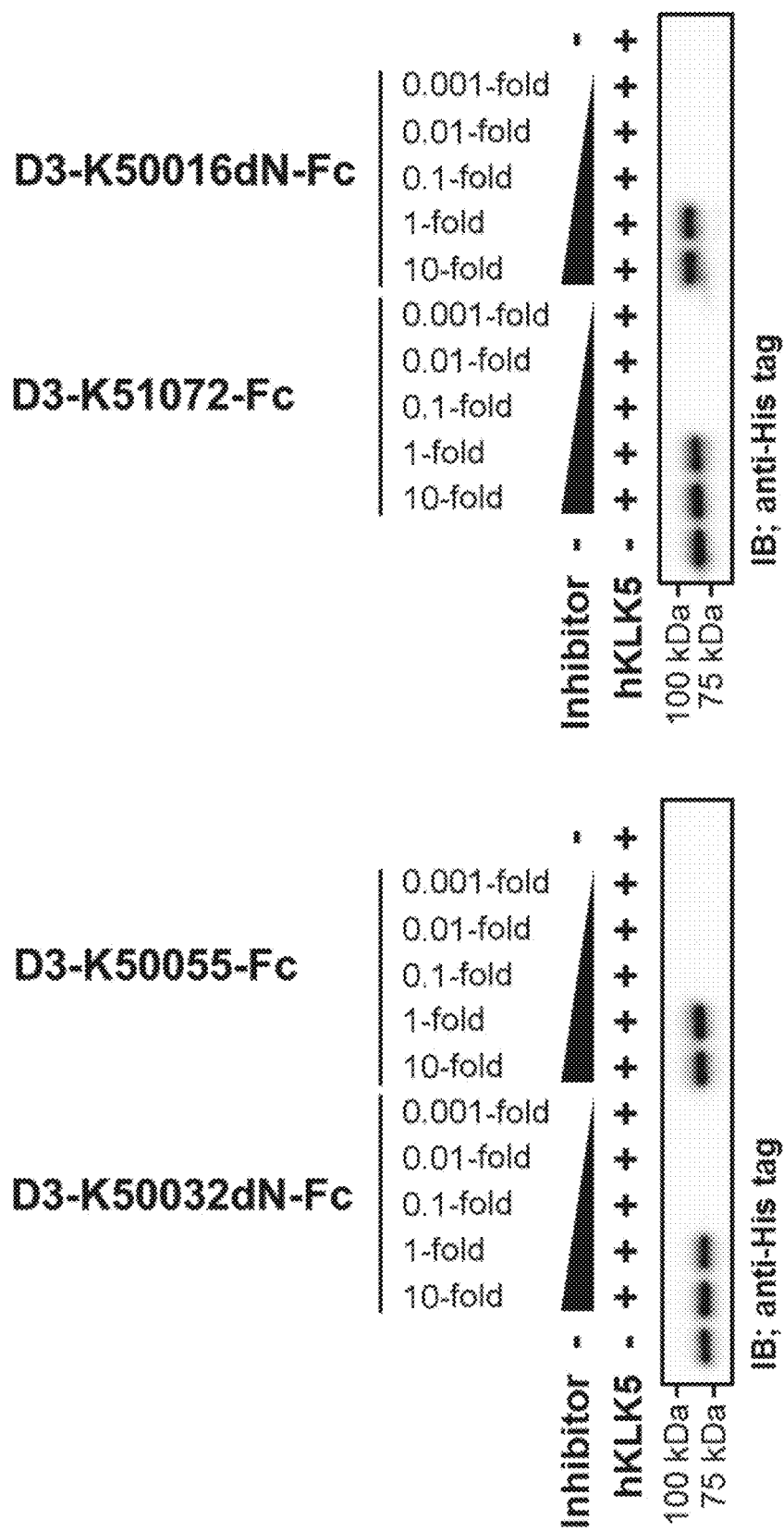
FIG. 103B includes diagrams to evaluate the KLK5 inhibitory activity of each KLK5 inhibitory peptide Fc fusion, using the degradation of human Desmocollin1 as an index. For evaluating the KLK5 inhibitory activity, KLK5 with a final concentration of 0.2 µM and Recombinant Human Desmocollin-1 Protein with a C-terminal His tag (R&D Systems, Inc., 4955-DC-050) with a final concentration of 2 µM were used. Analysis was performed by Western blotting using Penta His HRP Conjugate (QIAGEN, 34460).

Human Desmoglein1 and human Desmocollin1 were not degraded in the absence of human KLK5 but were completely degraded in the presence of human KLK5. As a result of evaluating human KLK5 preincubated with each KLK5 inhibitory peptide Fc fusion, it was revealed that each of the inhibitory peptide Fc fusions inhibited the human Desmoglein1 and human Desmocollin1 degradation activities of the human KLK5 enzyme. Under conditions where the human KLK5 concentration and the inhibitory peptide Fc fusion concentration were the same, the degradation of human Desmoglein1 and human Desmocollin1 was completely inhibited (FIG. 103).

Example 7. Effect of KLK5 Inhibitory Peptide Fc Fusion on Suppression of Transepidermal Water Loss (TEWL) Increase in Netherton Syndrome Model Mice (7-1) Netherton Syndrome Model Mice Crusty2 mice having a mutation in SPINK5 that is the causative gene of Netherton syndrome are known as Netherton syndrome model mice, and Crusty2 homomice (+/+) exhibit skin symptoms (Mutagenetix database).

Figure 7:
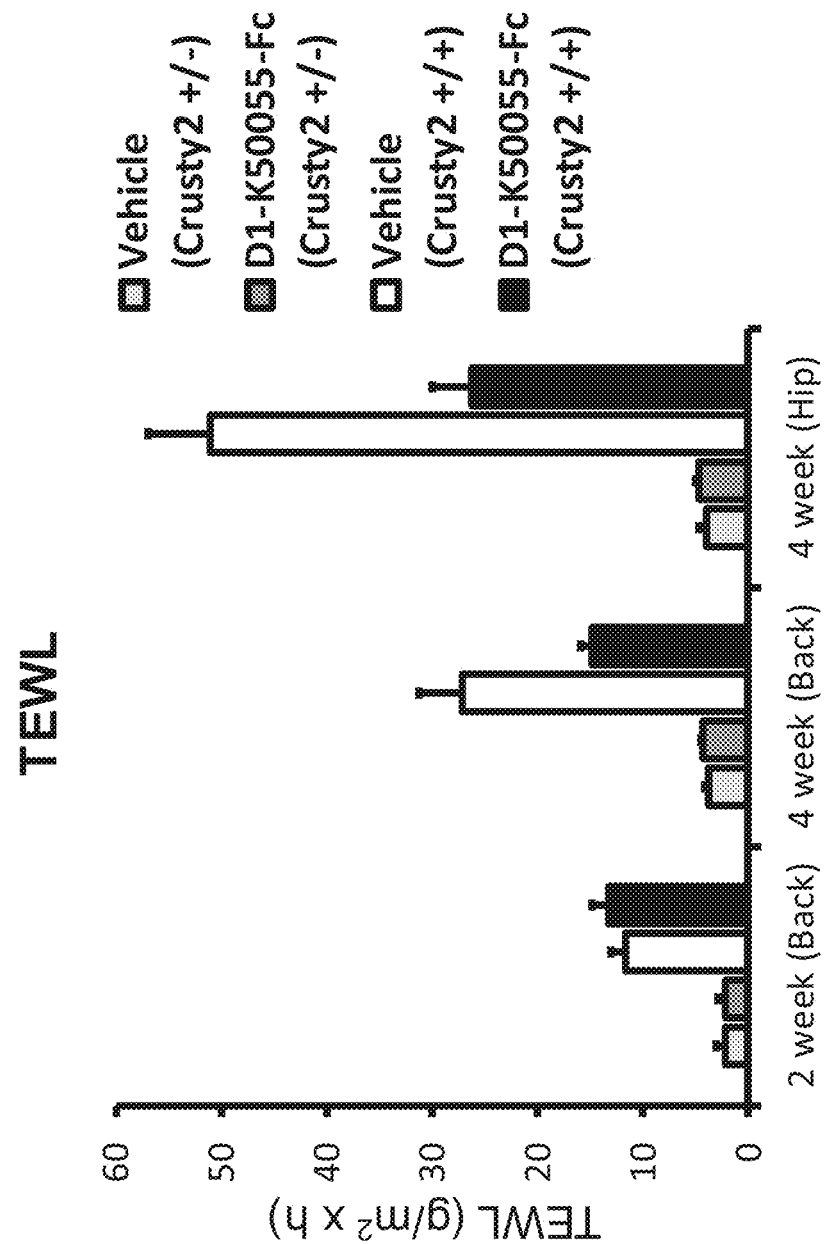
FIG. 7 is a graph showing a KLK5 inhibitory peptide Fc fusion-administered group suppressing the transepidermal water loss (TEWL) in Crusty2 model mice. With hetero (+/−) SPINK5 mutation, skin inflammation did not develop, but with homo (+/+) SPINK5 mutation, skin inflammation strongly developed, which elevated the TEWL. Administration of the peptide Fc fusion to the Crusty2 mice with homo (+/+) SPINK5 mutation improved dermatitis and reduced the TEWL. The number of cases of Crusty2 (+/−) mice was 9, and the number of cases of Crusty2 (+/+) mice was 12, in each of the PBS-administered group and the D1-K50055-Fc-administered group. The error bars in the figure show standard errors.

(7-2) Effect of KLK5 Inhibitory Peptide Fc Fusion on Suppression of TEWL Increase in Netherton Syndrome Model Mice Crusty2 (+/−) mice and Crusty2 (+/+) mice were crossed by artificial insemination, and the KLK5 inhibitory peptide Fc fusion D1-K50055-Fc produced in (5-4) was evaluated using the resulting offspring (Crusty2 (+/−) mice or Crusty2 (+/+) mice). From 0 or 1 day after birth, PBS or 100 mg/kg of D1-K50055-Fc was subcutaneously administered every other day for 4 weeks. At the first administration only, a 3-fold amount of D1-K50055-Fc was administered as a loading dose. Using VAPO SCAN (AS-VT100RS, Asahi Techno Lab. Ltd.), TEWL on the skin of the back or hip of the mice was measured at 2 and 4 weeks after administration (FIG. 7). The number of Crusty2 (+/−) mice was 9, and the number of Crusty2 (+/+) mice was 12, in each of the PBS-administered group and the D1-K50055-Fc-administered group.

A statistically significant increase in TEWL was observed in Crusty2 (+/+) mice as compared with Crusty2 (+/−) mice and was more remarkable in 4 week-old mice as compared with 2 week-old mice. After 4 weeks from the administration, a statistically significant decrease in TEWL was observed in both the back and the more severely affected hips in the D1-K50055-Fc-administered group as compared with the PBS-administered group. From the above, it was revealed that an increase in TEWL caused by the mutation in SPINK5 was observed in the mice, and D1-K50055-Fc exhibited an inhibitory action. Further, it was shown that the peptides of the present invention and their conjugates, including D1-K50055-Fc, are useful for reducing skin symptoms of Netherton syndrome.

INDUSTRIAL APPLICABILITY

The peptide and the conjugate provided by the present invention, and a pharmaceutical composition containing the same are useful for treating various diseases.

Sequence Listing Free Text

SEQ ID NO: 1: Amino acid sequence of human SPINK2 (FIG. 9)
SEQ ID NO: 2: Amino acid sequence of human KLK5 (FIG. 10)
SEQ ID NO: 3: Amino acid sequence of human KLK7 (FIG. 11)
SEQ ID NO: 4: Amino acid sequence of human KLK14 (FIG. 12)
SEQ ID NO: 5: Nucleotide sequence of the KLK5 inhibitory peptide K50032 (FIG. 13)
SEQ ID NO: 6: Amino acid sequence of the KLK5 inhibitory peptide K50032 (FIG. 14)
SEQ ID NO: 7: Nucleotide sequence of the KLK5 inhibitory peptide K50055 (FIG. 15)
SEQ ID NO: 8: Amino acid sequence of the KLK5 inhibitory peptide K50055 (FIG. 16)
SEQ ID NO: 9: Nucleotide sequence of the KLK5 inhibitory peptide K51072 (FIG. 17)
SEQ ID NO: 10: Amino acid sequence of the KLK5 inhibitory peptide K51072 (FIG. 18)
SEQ ID NO: 11: Nucleotide sequence of the KLK5 inhibitory peptide K50016 (FIG. 19)
SEQ ID NO: 12: Amino acid sequence of the KLK5 inhibitory peptide K50016 (FIG. 20)
SEQ ID NO: 13: Nucleotide sequence of the KLK5 inhibitory peptide K51034 (FIG. 21)
SEQ ID NO: 14: Amino acid sequence of the KLK5 inhibitory peptide K51034 (FIG. 22)
SEQ ID NO: 15: Nucleotide sequence of the KLK5 inhibitory peptide K50062 (FIG. 23)
SEQ ID NO: 16: Amino acid sequence of the KLK5 inhibitory peptide K50062 (FIG. 24)
SEQ ID NO: 17: Nucleotide sequence of the KLK5 inhibitory peptide K51090 (FIG. 25)
SEQ ID NO: 18: Amino acid sequence of the KLK5 inhibitory peptide K51090 (FIG. 26)
SEQ ID NO: 19: Nucleotide sequence of the KLK5 inhibitory peptide K50098 (FIG. 27)
SEQ ID NO: 20: Amino acid sequence of the KLK5 inhibitory peptide K50098 (FIG. 28)
SEQ ID NO: 21: Nucleotide sequence of the KLK5/KLK7 inhibitory peptide K51028 (FIG. 29)
SEQ ID NO: 22: Amino acid sequence of the KLK5/KLK7 inhibitory peptide K51028 (FIG. 30)
SEQ ID NO: 23: Nucleotide sequence of the KLK5/KLK7 inhibitory peptide K51005 (FIG. 31)
SEQ ID NO: 24: Amino acid sequence of the KLK5/KLK7 inhibitory peptide K51005 (FIG. 32)
SEQ ID NO: 25: Nucleotide sequence of the KLK5/KLK7 inhibitory peptide K50031 (FIG. 33)
SEQ ID NO: 26: Amino acid sequence of the KLK5/KLK7 inhibitory peptide K50031 (FIG. 34)
SEQ ID NO: 27: Nucleotide sequence of the KLK5/KLK7 inhibitory peptide K51057 (FIG. 35)
SEQ ID NO: 28: Amino acid sequence of the KLK5/KLK7 inhibitory peptide K51057 (FIG. 36)
SEQ ID NO: 29: Nucleotide sequence of the KLK5/KLK14 inhibitory peptide K51069 (FIG. 37)
SEQ ID NO: 30: Amino acid sequence of the KLK5/KLK14 inhibitory peptide K51069 (FIG. 38)
SEQ ID NO: 31: Nucleotide sequence of the KLK5/KLK14 inhibitory peptide K50015 (FIG. 39)
SEQ ID NO: 32: Amino acid sequence of the KLK5/KLK14 inhibitory peptide K50015 (FIG. 40)
SEQ ID NO: 33: Nucleotide sequence of the KLK5 inhibitory peptide Fc fusion D3-K50032dN-Fc (FIG. 41)
SEQ ID NO: 34: Amino acid sequence of the KLK5 inhibitory peptide Fc fusion D3-K50032dN-Fc (FIG. 42)

SEQ ID NO: 35: Nucleotide sequence of the KLK5 inhibitory peptide Fc fusion D3-K50055-Fc (FIG. 43)

SEQ ID NO: 36: Amino acid sequence of the KLK5 inhibitory peptide Fc fusion D3-K50055-Fc (FIG. 44)

SEQ ID NO: 37: Nucleotide sequence of the KLK5 inhibitory peptide Fc fusion D3-K51072-Fc (FIG. 45)

SEQ ID NO: 38: Amino acid sequence of the KLK5 inhibitory peptide Fc fusion D3-K51072-Fc (FIG. 46)

SEQ ID NO: 39: Nucleotide sequence of the KLK5 inhibitory peptide Fc fusion D3-K50016dN-Fc (FIG. 47)

SEQ ID NO: 40: Amino acid sequence of the KLK5 inhibitory peptide Fc fusion D3-K50016dN-Fc (FIG. 48)

SEQ ID NO: 41: Nucleotide sequence of the KLK5 inhibitory peptide Fc fusion D3-K51034-Fc (FIG. 49)

SEQ ID NO: 42: Amino acid sequence of the KLK5 inhibitory peptide Fc fusion D3-K51034-Fc (FIG. 50)

SEQ ID NO: 43: Nucleotide sequence of the KLK5 inhibitory peptide Fc fusion D3-K50062-Fc (FIG. 51)

SEQ ID NO: 44: Amino acid sequence of the KLK5 inhibitory peptide Fc fusion D3-K50062-Fc (FIG. 52)

SEQ ID NO: 45: Nucleotide sequence of the KLK5 inhibitory peptide Fc fusion D3-K51090-Fc (FIG. 53)

SEQ ID NO: 46: Amino acid sequence of the KLK5 inhibitory peptide Fc fusion D3-K51090-Fc (FIG. 54)

SEQ ID NO: 47: Nucleotide sequence of the KLK5 inhibitory peptide Fc fusion D3-K50098dN-Fc (FIG. 55)

SEQ ID NO: 48: Amino acid sequence of the KLK5 inhibitory peptide Fc fusion D3-K50098dN-Fc (FIG. 56)

SEQ ID NO: 49: Nucleotide sequence of the KLK5/KLK7 inhibitory peptide Fc fusion D3-K51028-Fc (FIG. 57)

SEQ ID NO: 50: Amino acid sequence of the KLK5/KLK7 inhibitory peptide Fc fusion D3-K51028-Fc (FIG. 58)

SEQ ID NO: 51: Nucleotide sequence of the KLK5/KLK7 inhibitory peptide Fc fusion D3-K51005-Fc (FIG. 59)

SEQ ID NO: 52: Amino acid sequence of the KLK5/KLK7 inhibitory peptide Fc fusion D3-K51005-Fc (FIG. 60)

SEQ ID NO: 53: Nucleotide sequence of the KLK5/KLK7 inhibitory peptide Fc fusion D3-K50031-Fc (FIG. 61)

SEQ ID NO: 54: Amino acid sequence of the KLK5/KLK7 inhibitory peptide Fc fusion D3-K50031-Fc (FIG. 62)

SEQ ID NO: 55: Nucleotide sequence of the KLK5/KLK7 inhibitory peptide Fc fusion D3-K51057-Fc (FIG. 63)

SEQ ID NO: 56: Amino acid sequence of the KLK5/KLK7 inhibitory peptide Fc fusion D3-K51057-Fc (FIG. 64)

SEQ ID NO: 57: Nucleotide sequence of the KLK5/KLK14 inhibitory peptide Fc fusion D3-K51069dN-Fc (FIG. 65)

SEQ ID NO: 58: Amino acid sequence of the KLK5/KLK14 inhibitory peptide Fc fusion D3-K51069dN-Fc (FIG. 66)

SEQ ID NO: 59: Nucleotide sequence of the KLK5/KLK14 inhibitory peptide Fc fusion D3-K50015-Fc (FIG. 67)

SEQ ID NO: 60: Amino acid sequence of the KLK5/KLK14 inhibitory peptide Fc fusion D3-K50015-Fc (FIG. 68)

SEQ ID NO: 61: Formula of the SPINK2 mutant peptide (FIG. 69)

SEQ ID NO: 62: Nucleotide sequence of primer 1 (FIG. 70)

SEQ ID NO: 63: Nucleotide sequence of primer 2 (FIG. 71)

SEQ ID NO: 64: Nucleotide sequence of primer 3 (FIG. 72)

SEQ ID NO: 65: Nucleotide sequence of primer 4 (FIG. 73)

SEQ ID NO: 66: Nucleotide sequence of primer 5 (FIG. 74)

SEQ ID NO: 67: Nucleotide sequence of primer 6 (FIG. 75)

SEQ ID NO: 68: Nucleotide sequence of primer 7 (FIG. 76)

SEQ ID NO: 69: Nucleotide sequence of primer 8 (FIG. 77)

SEQ ID NO: 70: Nucleotide sequence of primer 9 (FIG. 78)

SEQ ID NO: 71: Nucleotide sequence of primer 10 (FIG. 79)

SEQ ID NO: 72: Nucleotide sequence of primer 11 (FIG. 80)

SEQ ID NO: 73: Nucleotide sequence of primer 12 (FIG. 81)

SEQ ID NO: 74: Nucleotide sequence of primer 13 (FIG. 82)

SEQ ID NO: 75: Nucleotide sequence of primer 14 (FIG. 83)

SEQ ID NO: 76: Nucleotide sequence of primer 15 (FIG. 84)

SEQ ID NO: 77: Amino acid sequence in the KLK7 substrate peptide (FIG. 85)

SEQ ID NO: 78: Amino acid sequence in the bovine α-chymotrypsin substrate peptide (FIG. 86)

SEQ ID NO: 79: Amino acid sequence in the neutrophil elastase substrate peptide (FIG. 87)

SEQ ID NO: 80: Amino acid sequence in the human protein C substrate peptide (FIG. 88)

SEQ ID NO: 81: Nucleotide sequence of primer 16 (FIG. 89)

SEQ ID NO: 82: Nucleotide sequence of primer 17 (FIG. 90)

SEQ ID NO: 83: Nucleotide sequence of primer 18 (FIG. 91)

SEQ ID NO: 84: Nucleotide sequence of primer 19 (FIG. 92)

SEQ ID NO: 85: Nucleotide sequence of primer 20 (FIG. 93)

SEQ ID NO: 86: Nucleotide sequence of primer 21 (FIG. 94)

SEQ ID NO: 87: Amino acid sequence of Fc of human IgG1 (FIG. 95)

SEQ ID NO: 88: Amino acid sequence of D8 of human SPINK5 (FIG. 96)

SEQ ID NO: 89: Amino acid sequence of D9 of human SPINK5 (FIG. 97)

SEQ ID NO: 90: Amino acid sequence of human SPINK9 (FIG. 98)

SEQ ID NO: 91: Amino acid sequence of mouse KLK5 (FIG. 99)

SEQ ID NO: 92: Amino acid sequence of mouse KLK7 (FIG. 100)

SEQ ID NO: 93: Amino acid sequence of mouse KLK14 (FIG. 101)
SEQ ID NO: 94: Nucleotide sequence of primer 22 (FIG. 104)
SEQ ID NO: 95: Nucleotide sequence of the KLK5 inhibitory peptide Fc fusion D1-K50055-Fc (FIG. 105)
SEQ ID NO: 96: Amino acid sequence of the KLK5 inhibitory peptide Fc fusion D1-K50055-Fc (FIG. 106)

The invention claimed is:

1. A method for treating or preventing a KLK5-related disease, comprising administering to a subject in need thereof a therapeutically effective amount of a SPINK2 mutant peptide that inhibits the protease activity of active human KLK5, wherein the peptide comprises: (i) the amino acid sequence set forth in any one of SEQ ID Nos: 6, 8, 10, 12, 14, 16, 18, and 20; or (ii) the amino acid sequence consisting of amino acids 4 to 66 of the amino acid sequence set forth in any one of SEQ ID Nos: 34, 40, and 48.

2. The method according to claim 1, wherein the KLK5-related disease is Netherton syndrome, atopic dermatitis, rosacea, UV-induced skin injury, psoriasis, asthma, spinal cord injury, cancer, or Barrett's esophagus.

3. The method according to claim 1, further comprising administering the SPINK2 mutant peptide in combination with an additional pharmaceutical product.

4. A method for treating or preventing a KLK5-related disease, comprising administering to a subject in need thereof a therapeutically effective amount of a conjugate comprising the peptide according to claim 1, wherein the peptide has at least one moiety attached to the peptide.

5. The method according to claim 4, wherein the at least one moiety comprises a second peptide that is not the SPINK2 mutant.

6. The method according to claim 5, wherein the second peptide is located on the amino terminal side of the SPINK2 mutant.

7. The method according to claim 5, wherein the second peptide is located on the carboxyl terminal side of the SPINK2 mutant.

8. The method according to claim 7, wherein the second peptide is an antibody or a fragment thereof and comprises one or more Fc regions.

9. The method according to claim 8, wherein each Fc region is an Fc region of human immunoglobulin, or a fragment thereof.

10. The method according to claim 8, wherein each Fc region is an Fc region of IgG1, IgG2, IgG3, IgG4, IgM, IgA1, IgA2, IgD, or IgE, or a fragment thereof.

11. The method according to claim 8, wherein each Fc region is an Fc region of human IgG1, or a fragment thereof.

12. The method according to claim 11, wherein each Fc region of human IgG1 comprises the amino acid sequence set forth in SEQ ID NO: 87.

13. The method according to claim 8, wherein each Fc region is a wild type Fc region.

14. The method according to claim 8, wherein each Fc region is a mutant Fc region.

15. The method according to claim 4, wherein the conjugate comprises one or more aspartic acids and/or glutamic acids added to the amino terminus thereof.

16. The method according to claim 5, wherein the SPINK2 mutant and the second peptide are linked to each other via a linker.

17. The method according to claim 16, wherein the linker is a third peptide that is not the SPINK2 mutant or the second peptide.

18. The method according to claim 4, wherein the conjugate comprises:
(a) a peptide having an amino acid sequence set forth in any one of SEQ ID Nos: 34, 36, 38, 40, 42, 44, 46, 48, 50, 52, 54, 56, 58, 60, and 96; or
(b) a peptide having an amino acid sequence formed by the deletion of one amino acid from the amino acid sequence according to (a);
wherein the conjugate inhibits the protease activity of KLK5.

19. The method according to claim 4, wherein the conjugate comprises a peptide having the amino acid sequence set forth in SEQ ID No: 34 or the amino acid sequence formed by the deletion of one amino acid from the amino acid sequence set forth in SEQ ID No: 34.

20. The method according to claim 4, wherein the conjugate comprises a peptide having the amino acid sequence set forth in SEQ ID No: 36 or the amino acid sequence formed by the deletion of one amino acid from the amino acid sequence set forth in SEQ ID No: 36.

21. The method according to claim 4, wherein the conjugate comprises a peptide having the amino acid sequence set forth in SEQ ID No: 38 or the amino acid sequence formed by the deletion of one amino acid from the amino acid sequence set forth in SEQ ID No: 38.

22. The method according to claim 4, wherein the KLK5-related disease is Netherton syndrome, atopic dermatitis, rosacea, UV-induced skin injury, psoriasis, asthma, spinal cord injury, cancer, or Barrett's esophagus.

23. The method according to claim 4, further comprising administering the SPINK2 mutant peptide in combination with an additional pharmaceutical product.

* * * * *